United States Patent
Ye et al.

(10) Patent No.: US 10,745,384 B2
(45) Date of Patent: Aug. 18, 2020

(54) INDAZOLE DERIVATIVES AS αV INTEGRIN ANTAGONISTS

(71) Applicant: BRISTOL-MYERS SQUIBB COMPANY, Princeton, NJ (US)

(72) Inventors: Xiang-Yang Ye, Princeton, NJ (US); Christian L. Morales, Ewing, NJ (US); Mendi A. Higgins, Newtown, PA (US); Eric Mull, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/347,831

(22) PCT Filed: Nov. 7, 2017

(86) PCT No.: PCT/US2017/060386
§ 371 (c)(1),
(2) Date: May 7, 2019

(87) PCT Pub. No.: WO2018/089357
PCT Pub. Date: May 17, 2018

(65) Prior Publication Data
US 2019/0256496 A1      Aug. 22, 2019

Related U.S. Application Data

(60) Provisional application No. 62/418,842, filed on Nov. 8, 2016.

(51) Int. Cl.
| | | |
|---|---|---|
| C07D 401/14 | (2006.01) |
| A61P 35/00 | (2006.01) |
| C07D 471/04 | (2006.01) |
| C07D 498/04 | (2006.01) |
| A61K 31/404 | (2006.01) |

(52) U.S. Cl.
CPC ............ *C07D 401/14* (2013.01); *A61P 35/00* (2018.01); *C07D 471/04* (2013.01); *C07D 498/04* (2013.01)

(58) Field of Classification Search
None
See application file for complete search history.

(56) References Cited

U.S. PATENT DOCUMENTS

| | | |
|---|---|---|
| 5,760,029 A | 6/1998 | Jadhav et al. |
| 6,090,944 A | 7/2000 | Hutchinson |
| 6,114,328 A | 9/2000 | Wityak et al. |
| 2008/0045521 A1 | 2/2008 | Arnould et al. |
| 2008/0255183 A1 | 10/2008 | Arnould et al. |
| 2016/0264566 A1 | 9/2016 | DeGrado et al. |

FOREIGN PATENT DOCUMENTS

| | | |
|---|---|---|
| WO | WO1999/26945 A1 | 6/1999 |
| WO | WO199930709 A1 | 6/1999 |
| WO | WO2002060438 A1 | 8/2002 |
| WO | WO2006108040 A1 | 10/2006 |
| WO | WO2007141473 A1 | 12/2007 |
| WO | WO2011098603 A1 | 8/2011 |
| WO | WO2014154725 A1 | 10/2014 |
| WO | WO2015091426 A1 | 6/2015 |
| WO | WO2016046225 A1 | 3/2016 |
| WO | WO2016046226 A1 | 3/2016 |
| WO | WO2016046230 A1 | 3/2016 |
| WO | WO2016046241 A1 | 3/2016 |
| WO | WO2016134223 A2 | 8/2016 |

OTHER PUBLICATIONS

Fludzinski et al, J. Med. Chem, 30 (9), pp. 1535-1537, Sep. 1987.*
International Search Report Written Opinion of the International Searching Authority for PCT/US2017/060383, dated Jan. 24, 2018.
Kapp et al., "Integrin Modulators: a patent review", Expert Opinion on Therapeutic Patents, vol. 23(10), pp. 1273-1295 (2013).
Piras, M. et al., "High-Affinity "Click" RGD Peptidomimetics as Radiolabeled Probes for Imaging αvβ3 Integrin", ChemMedChem, vol. 12, pp. 1142-1151 (2017).
Raboisson, P. et al., "Identification of novel short chain 4-substituted indoles as potent αvβ3 antagonist using structure-based drug design", European Journal of Medicinal Chemistry, vol. 42, pp. 334-343 (2007).

(Continued)

*Primary Examiner* — Zinna Northington Davis
(74) *Attorney, Agent, or Firm* — Gary Greenblatt

(57) ABSTRACT

The present invention provides compounds of Formula (Ia) or (Ib): or stereoisomers, tautomers, or pharmaceutically acceptable salts or solvates thereof, wherein all the variables are as defined herein. These compounds are antagonists to αV-containing integrins. This invention also relates to pharmaceutical compositions comprising these compounds and methods of treating a disease, disorder, or condition associated with dysregulation of αV-containing integrins, such as pathological fibrosis, transplant rejection, cancer, osteoporosis, and inflammatory disorders, by using the compounds and pharmaceutical compositions.

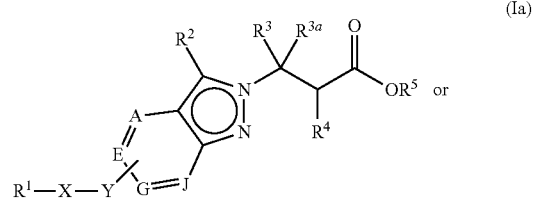

(Ia)

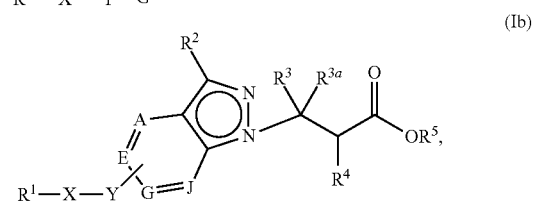

(Ib)

18 Claims, No Drawings

(56) References Cited

OTHER PUBLICATIONS

Hajduk, Philip J., et al., "Statistical Analysis of the Effects of Common Chemical Substituents on Ligand Potency", J. Med. Chem. 2008, vol. 51, pp. 553-564.

Pennington, Lewis D., et al., "Quinolinone-based agonists of S1P1: Use of a N-scan SAR strategy to optimize in vitro and in vivo activity", Bioorganic & Medicinal Chemistry Letters, 2012, vol. 22, pp. 527-531.

* cited by examiner

INDAZOLE DERIVATIVES AS αV INTEGRIN ANTAGONISTS

CROSS REFERENCE TO RELATED APPLICATION

This application is a national phase application under 35 U.S.C. § 371 of International Patent Application No. PCT/US2017/060386, filed Nov. 7, 2017, which claims priority to U.S. Provisional Application Ser. No. 62/418,842 filed Nov. 8, 2016, which are expressly incorporated fully herein by reference.

FIELD OF THE INVENTION

The present invention relates to substituted azole amides and amines as αV integrin antagonists, pharmaceutical compositions comprising such compounds and to their use in therapy, especially in the treatment or prophylaxis of diseases, disorders, and conditions for which an αV integrin antagonist is indicated in a human.

BACKGROUND OF THE INVENTION

Integrins belong to a large family of α/β heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Interactions in Cancer*, 2010). In mammals, there are 24 α/β integrin heterodimers known from various combinations of 18 alpha and 8 beta subunits. Transforming Growth Factor-β (TGF-β) has a central role in driving a number of pathological processes underlying fibrosis, cell growth, and autoimmune diseases. Alpha V (αV) Integrins, that include αVβ1, αVβ3, αVβ5, αVβ6, and αVβ8, are involved in a critical pathway that leads to the conversion of latent TGF-β to its active form (Henderson, N. C.; Sheppard, D. *Biochim, Biophys. Acta* 2013, 1832, 891). Thus, antagonism of such αV integrin-mediated activation of latent TGF-β provides a viable therapeutic approach to intervene in TGF-β-driven pathological states (Sheppard, D. *Eur. Resp. Rev.* 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five αV integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of $\alpha_V$ integrin subtypes varies significantly. For example, $\alpha_V\beta6$ is expressed on epithelial cells at very low levels in healthy tissue but is significantly upregulated during inflammation and wound healing. $\alpha_V\beta3$ and $\alpha_V\beta5$ are expressed on osteoclasts, endothelial, smooth muscle, and solid tumor cells, as well as on pericytes and podocytes, while $\alpha_V\beta1$ is expressed on activated fibroblasts and mesangial cells.

Common fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone and nintedanib, that act by non-integrin-mediated mechanisms, have recently been approved for treatment of IPF. The present invention relates to compounds that inhibit or antagonize the action of one or more of the $\alpha_V$ integrins in the treatment of pathological conditions, such as fibrosis and cancer, mediated by these integrins.

A number of selective or nonselective small molecule, peptidic, and antibody-based antagonists of $\alpha_V$ integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

SUMMARY OF THE INVENTION

In one aspect, the present invention provides compounds of Formula (Ia), (Ib), (IIa), (IIb), (IIc), (IId), (IIIa), (IIIb), (IIIc), (IIId), (IVa), (IVb), (IVc), (IVd), (IVe) and (IVf) as well as the subgenus and species thereof, including stereoisomers, tautomers, pharmaceutically acceptable salts, or solvates thereof, which are useful as $\alpha_V$ integrin antagonists.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with dysregulation of $\alpha_v$-containing integrins in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used for the manufacture of a medicament for the treatment of a disease, disorder, or condition associated with dysregulation of $\alpha_v$-containing integrins in a patient.

Other features and advantages of the invention will be apparent from the following detailed description and claims.

DETAILED DESCRIPTION OF THE INVENTION

The present application provides compounds, including all stereoisomers, solvates, prodrugs and pharmaceutically acceptable salt and solvate forms thereof, according to Formula (Ia) or (Ib). The present application also provides pharmaceutical compositions containing at least one compound according to Formula (Ia) or (Ib), or a stereoisomer, a tautomer, or a pharmaceutically acceptable salt or a solvate thereof, and optionally at least one additional therapeutic agent. Additionally, the present application provides methods for treating a patient suffering from an αV Integrin-modulated disease or disorder such as for example, Idiopathic Pulmonary Fibrosis (IPF), liver and kidney fibrosis, Non-Alcoholic Fatty Liver Disease (NAFLD), Non-Alcoholic Steato-Hepatitis (NASH), cardiac fibrosis, and systemic sclerosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

In one embodiment, the present invention provides, inter alia, a compound of Formula (Ia) or (Ib):

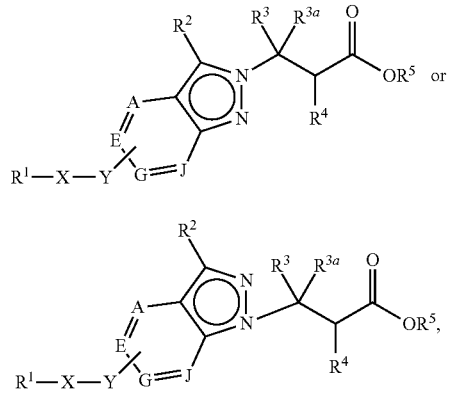

(Ia)

(Ib)

or a stereoisomer, a tautomer, or a pharmaceutically acceptable salt or a solvate thereof, wherein:

A, E, G, and J are independently N, C or CH; with the proviso that at least one of A, E, G, and J is C attached to Y;

X is a $C_{1-4}$ alkylene substituted with 0, 1, or 2 $R^{8a}$;

Y is a covalent bond, O, S, NH, —O—($C_{1-3}$ alkylene)-, —S—($C_{1-3}$ alkylene)-, or —NH—($C_{1-3}$ alkylene)-, wherein the $C_{1-3}$ alkylene is each independently substituted with 0, 1, or 2 $R^{8b}$;

$R^1$ is an Arginine mimetic moiety selected from the group consisting of

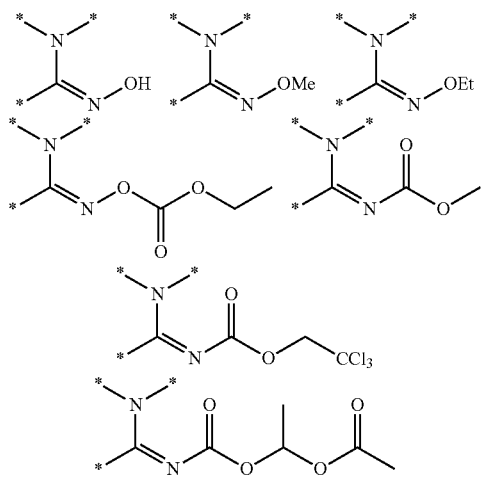

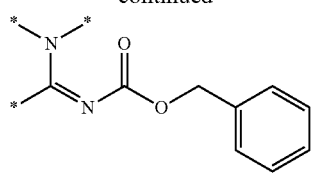

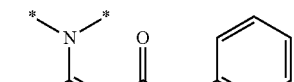

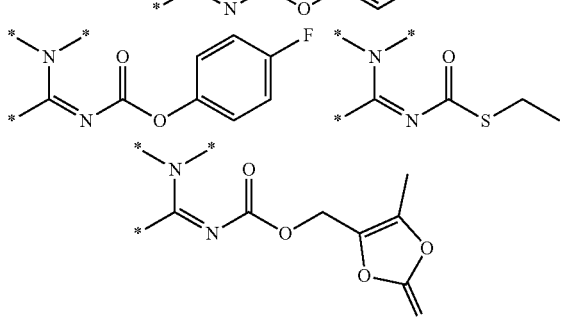

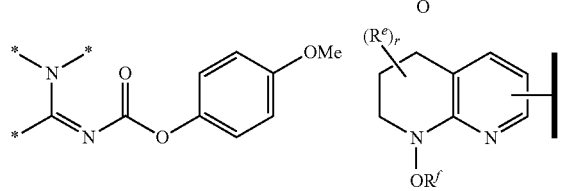

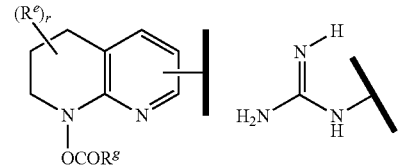

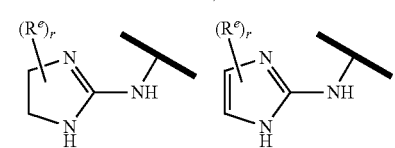

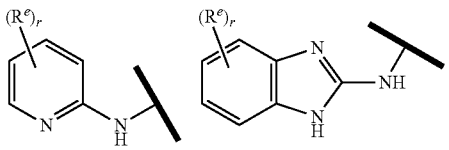

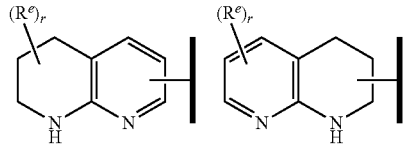

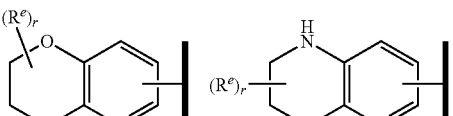

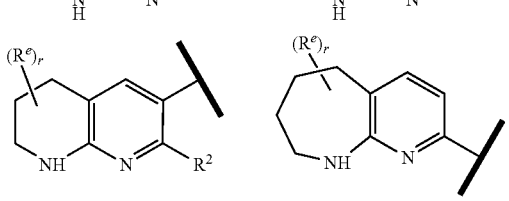

-continued

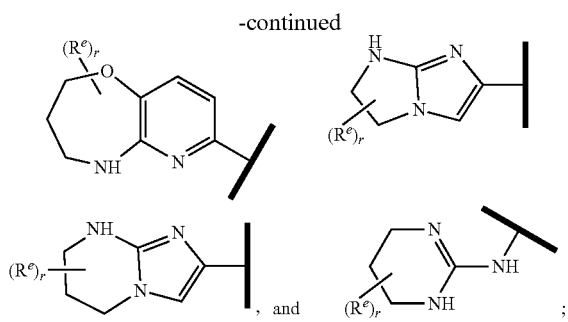

, and one of the asterisks in each of the arginine mimetics moiety is an attachment point to X and the other two asterisks are hydrogen;

$R^e$ is OH, amino, amido, carbamate, sulfonamide, $C_{1-4}$ alkyl, halo, $C_{1-4}$ haloalkyl, or $C_{3-6}$ cycloalkyl;

$R^f$=H, $CH_3$, $CH_2CH_3$, $C(O)OCH_2CH_3$;

$R^g$=$CH_3$, $CH_2CCl_3$, phenyl, 4-fluorophenyl, 4-methoxyphenyl, benzyl,

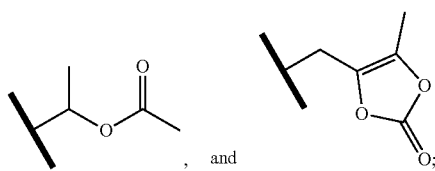

, and r is an integer of 0, 1, 2, or 3;

$R^2$ is hydrogen, halo, or $C_{1-6}$ alkyl;

$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^6$;

$R^{3a}$ is hydrogen; or alternatively, $R^{3a}$ and $R^3$, together with the atom or atoms to which they are attached, form a 3- to 6-membered carbocyclic or heterocyclic ring which is optionally substituted with one or more groups independently selected from halo, cyano, hydroxyl, amino, $C_{1-6}$ alkyl, haloalkyl, hydroxyalkyl, aminoalkyl, alkoxy, haloalkoxy, amido, carbamate, or sulfonamide;

$R^4$ is hydrogen, $C_{1-6}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, —S(O)$_m$R$^7$, —C(O)NR$^a$R$^b$, —NHC(O)OR$^a$, —NHC(O)NR$^a$R$^b$, —NHC(O)R$^7$, —OC(O)NR$^a$R$^b$, —OC(O)R$^7$, —NHS(O)$_m$NR$^a$R$^b$, or —NHS(O)$_m$R$^7$; wherein the alkyl, carbocyclyl, heterocyclyl, aryl, and heteroaryl, by themselves or as part of another group, are each independently substituted with 0, 1, 2, or 3 $R^9$;

$R^6$ is halo, cyano, hydroxyl, amino, oxo, nitro, —S(O)$_m$R$^{12}$, $C_{1-6}$ alkyl, alkoxy, haloalkyl, haloalkoxy, haloaminoalkyl, hydroxyalkyl, aminoalkyl, alkoxycarbonyl, 6- to 10-membered aryl, aryloxy, arylalkoxy, 5- to 10-membered heteroaryl, 3- to 6-membered carbocyclyl, or 3- to 7-membered heterocyclyl; wherein the alkyl, aryl, heteroaryl, carbocyclyl, or heterocyclyl, by themselves or as part of another group, are each independently substituted with 0, 1, or 2 $R^{10}$;

$R^7$ is each independently $C_{1-6}$ alkyl, $C_{1-6}$ alkoxy, $C_{1-6}$ aminoalkyl, $C_{1-6}$ haloalkyl, 6- to 10-membered aryl, arylalkyl, 5- to 10-membered heteroaryl, cycloalkyl, or heterocycloalkyl; wherein the alkyl, aryl, heteroaryl, cycloalkyl, and heterocycloalkyl, by themselves or as part of another group, are each independently substituted with 0, 1, 2, or 3 $R^{11}$;

$R^{8a}$, $R^{8b}$, and $R^{11}$, at each occurrence, are independently halo, cyano, hydroxyl, amino, oxo, $C_{1-6}$ alkyl, haloalkyl, hydroxyalkyl, aminoalkyl, alkoxy, or haloalkoxy;

$R^9$ is each independently halo, cyano, hydroxyl, amino, oxo, nitro, $C_{1-6}$ alkyl, alkoxy, haloalkyl, haloalkoxy, haloaminoalkyl, hydroxyalkyl, aminoalkyl, alkoxycarbonyl, 6- to 10-membered aryl, aryloxy, arylalkoxy, 5- to 10-membered heteroaryl, 3- to 6-membered carbocyclyl, or 3- to 7-membered heterocyclyl; wherein the alkyl, aryl, heteroaryl, carbocyclyl, or heterocyclyl, by themselves or as part of another group, are each independently substituted with 0, 1, or 2 $R^{13}$;

$R^{10}$ and $R^{13}$ are each independently halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;

$R^{12}$ is —N(R$^x$R$^y$), $C_{1-6}$ alkyl, $C_{1-6}$ haloalkyl, $C_{1-6}$ alkoxy, $C_{1-6}$ haloalkoxy, $C_{1-6}$ hydroxyalkyl, or $C_{1-6}$ aminoalkyl; and $R^x$ and $R^y$ are each independently hydrogen or $C_{1-6}$ alkyl;

$R^a$ and $R^b$, at each occurrence, are independently hydrogen, $C_{1-6}$ alkyl, $C_{1-6}$ haloalkyl, $C_{3-6}$ cycloalkyl, 6- to 10-membered aryl, 5- to 10-membered heteroaryl, cycloalkylalkyl, arylalkyl, heteroarylalkyl, or alkoxyalkyl; or alternatively, $R^a$ and $R^b$, taken together with the atoms to which they are attached, form a 3- to 8-membered carbocyclic or heterocyclic ring which is optionally substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, and sulfonamide;

m is an integer of 1 or 2;

$R^5$ is hydrogen, $R^{5a}$, or a structural moiety selected from

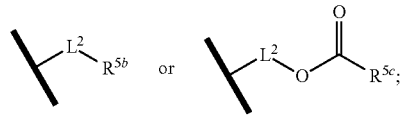

$L^1$ and $L^2$ are each independently $C_{1-4}$ alkylene;

$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;

$R^{5c}$ is $C_{1-6}$ alkyl or 5- to 7-membered carbocyclyl; wherein the $C_{1-6}$ alkyl, phenyl, and heterocyclyl are each independently substituted with 0 to 3 $R^{5d}$; and $R^{5d}$, at each occurrence, is independently halo, OH, alkoxy, oxo, or alkyl; or alternatively, two adjacent $R^{5d}$, together with the atoms to which they are attached, form a carbocyclyl moiety.

In one embodiment of Formula (Ia) or (Ib), $R^9$ is halo, cyano, hydroxyl, amino, oxo, or $C_{1-6}$ alkyl.

In one embodiment of Formula (Ia) or (Ib), A, E, G, and J, together with the two carbon atoms, form a ring moiety selected from the following structural formula:

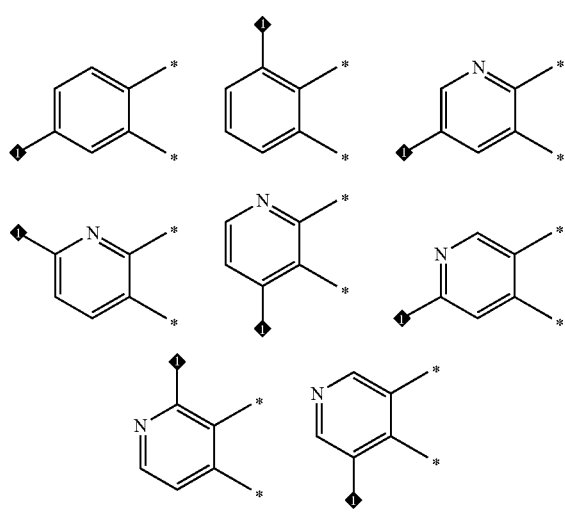

◆ Attachment point for Y.
* Attachment points to form the fused ring.

In one embodiment of Formula (Ia) or (Ib), $R^1$ is an Arginine mimetic moiety selected from the group consisting of

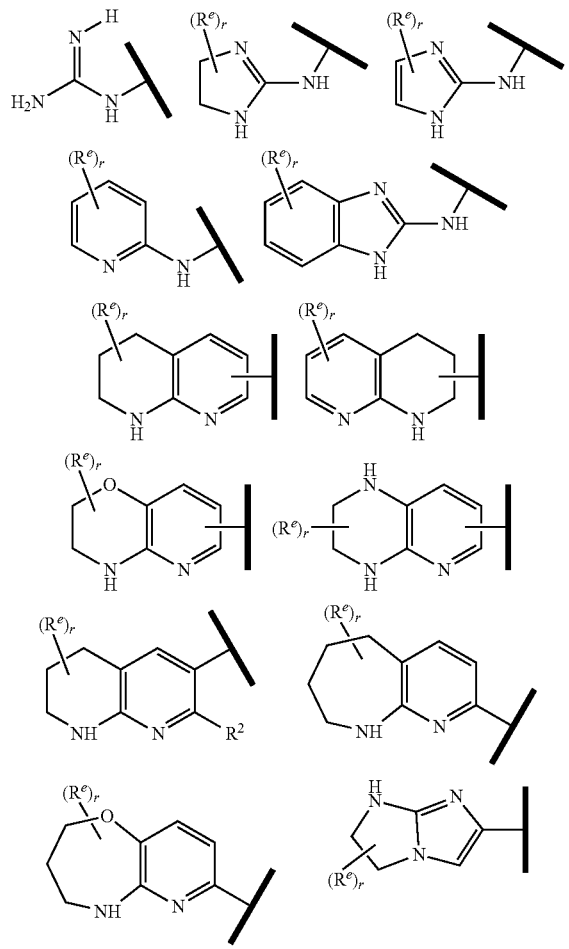

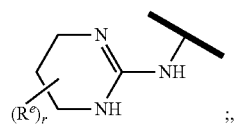

$R^e$ is OH, $C_{1-4}$ alkyl, halo, haloalkyl, or $C_{1-4}$ cycloalkyl; and r is an integer of 0, 1, 2, or 3.

In one embodiment of Formula (Ia) or (Ib), $R^1$ is an Arginine mimetic moiety selected from the group consisting of

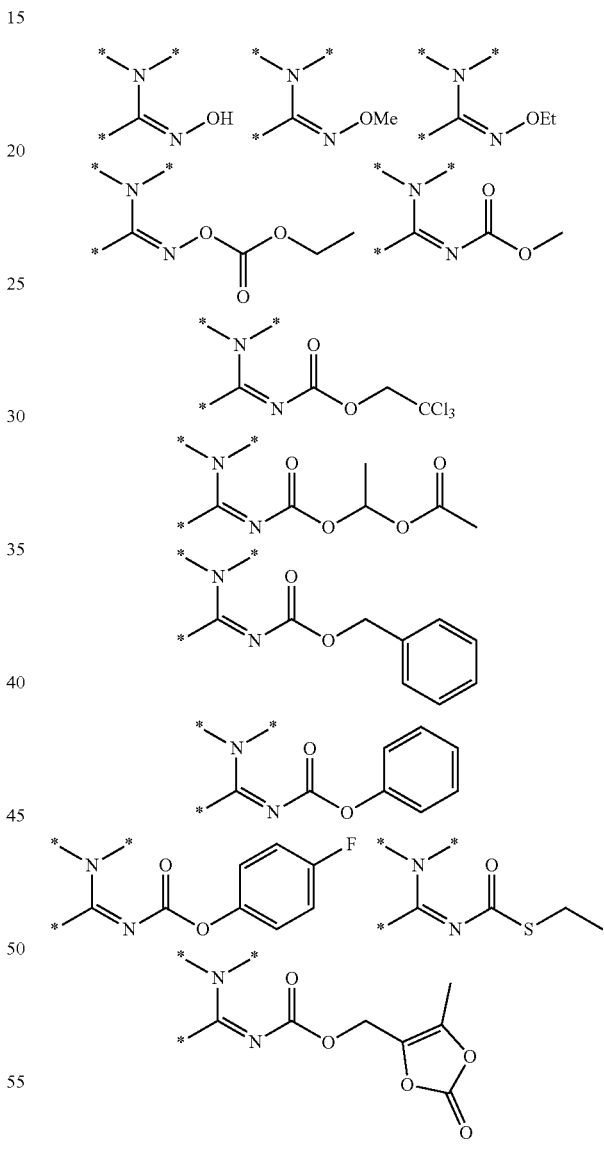

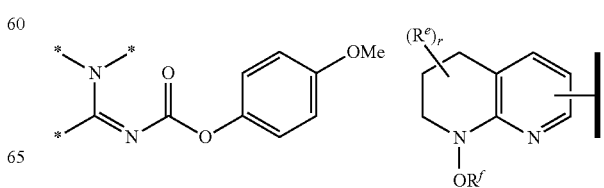

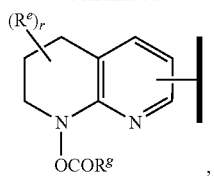

one of the asterisks in each of the arginine mimetics moiety is an attachment point to X and the other two asterisks are hydrogen;

$R^f$=H, Me, Et, COOEt;

$R^g$=CH$_3$, CH$_2$CH$_3$, CH$_2$CCl$_3$, phenyl, 4-fluorophenyl, 4-methoxyphenyl, benzyl,

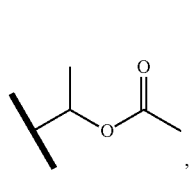, and 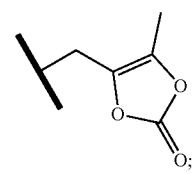;

$R^e$ is OH, C$_{1-4}$ alkyl, halo, haloalkyl, or C$_{1-4}$ cycloalkyl; and r is an integer of 0, 1, 2, or 3.

In one embodiment of Formula (Ia) or (Ib), $R^{3a}$ is hydrogen; and $R^3$ is hydrogen or a structural moiety selected from the group consisting of

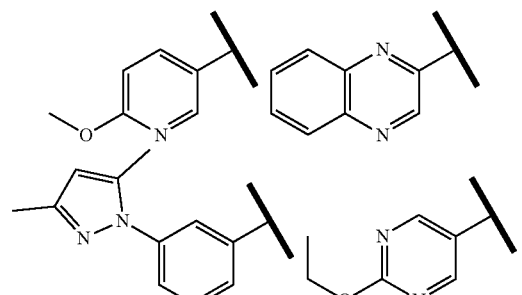
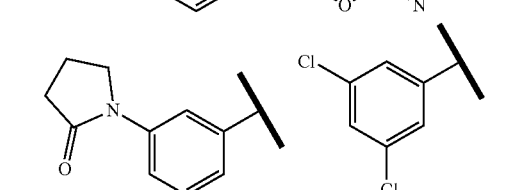
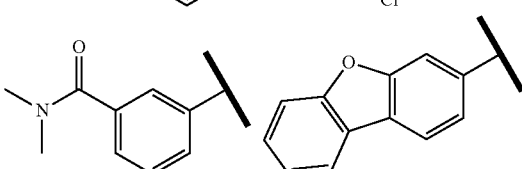
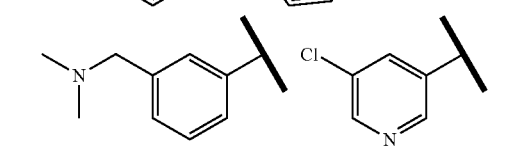
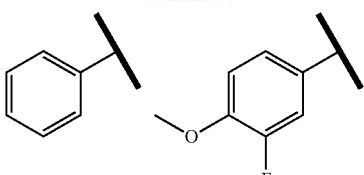
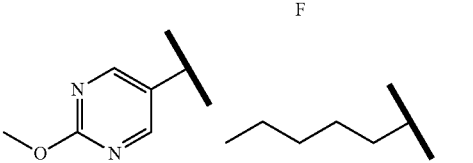
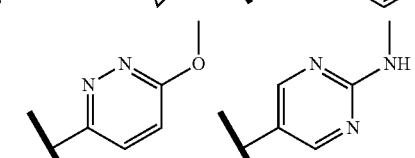
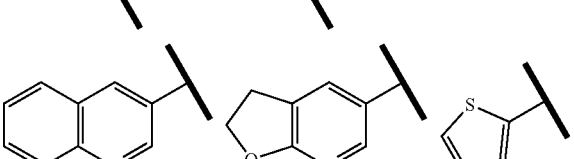
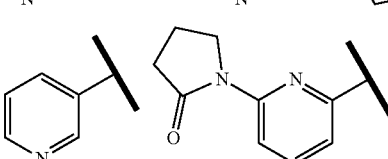
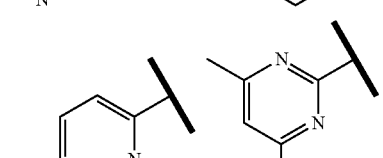
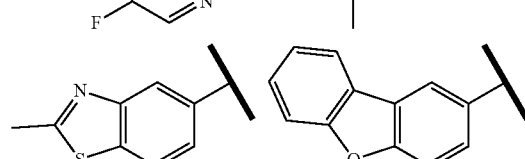
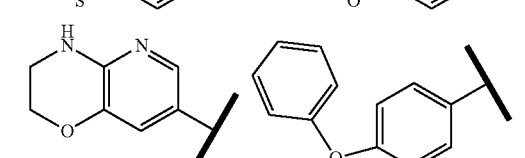
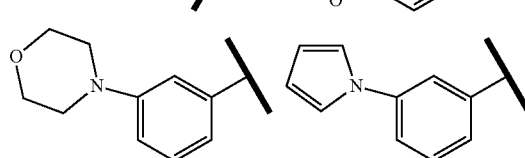
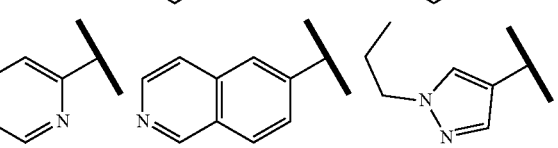

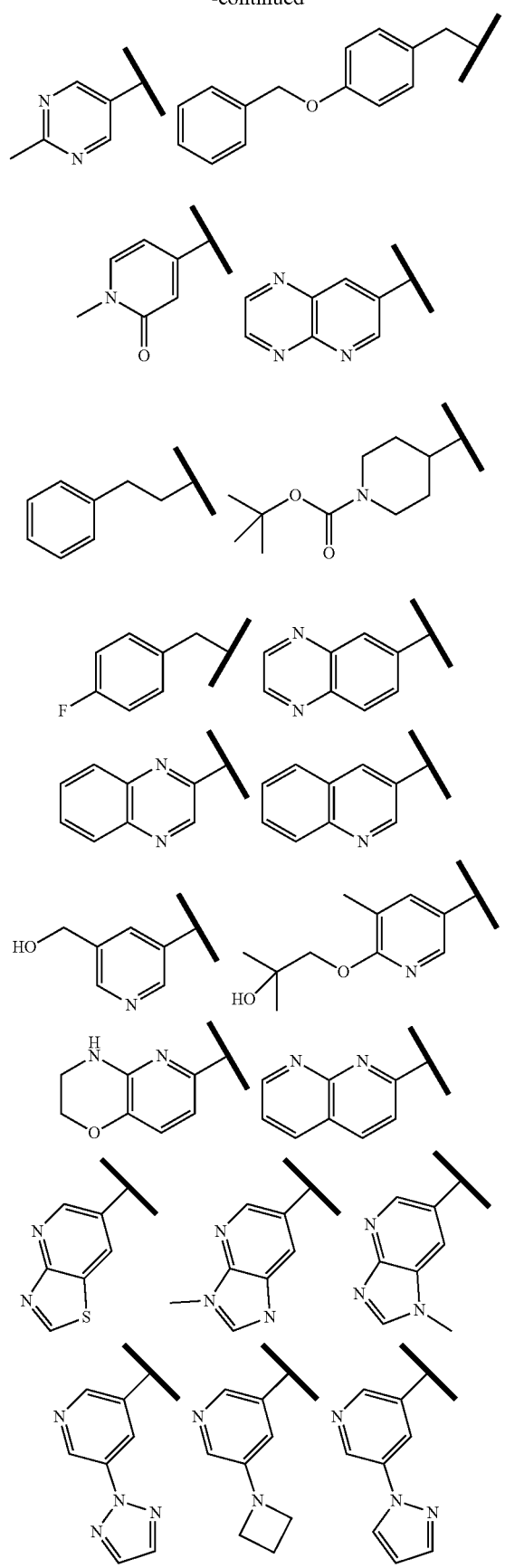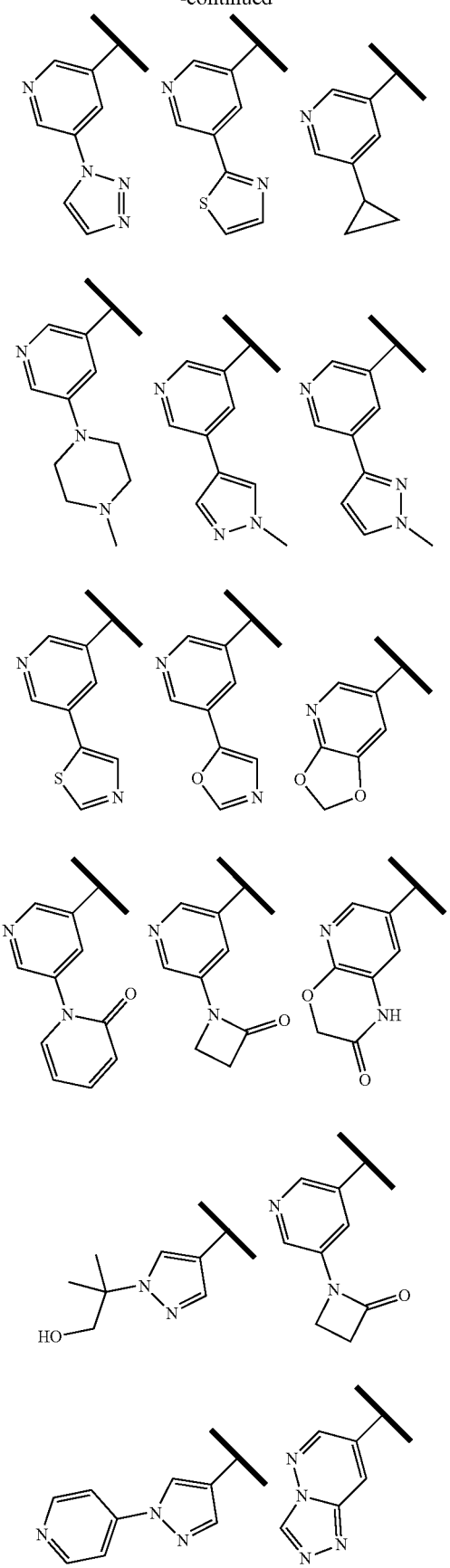

-continued

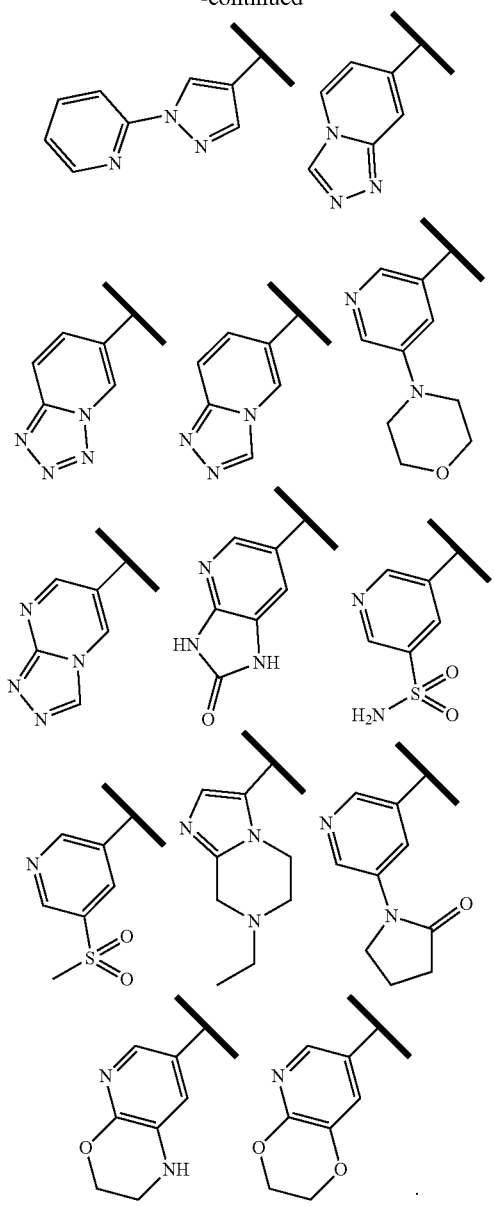

In one embodiment of Formula (Ia) or (Ib), $R^{3a}$ and $R^3$, taken together with the atoms to which they are attached, form a $C_{3-6}$ cycloalkyl moiety.

In one embodiment of Formula (Ia) or (Ib), $R^4$ is hydrogen or a structural moiety selected from the group consisting of

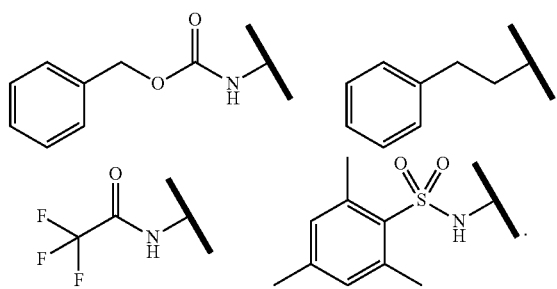

In one embodiment of Formula (Ia) or (Ib), $R^4$ is H, and $R^3$ is not H; or alternatively, $R^3$ is H, and $R^4$ is not H.

In one embodiment of Formula (Ia) or (Ib), $R^5$ is H or $R^{5a}$; and $R^{5a}$ is methyl, ethyl, isopropyl, n-butyl, isopentyl, or a structural moiety selected from

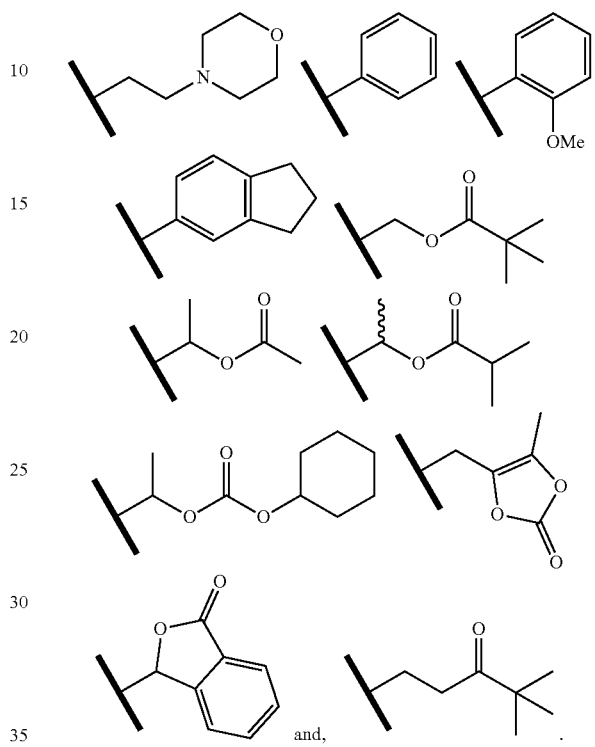

and,

In one embodiment of Formula (Ia) or (Ib), the compound is represented by structural Formula (IIa), (IIb), (IIc), or (IId):

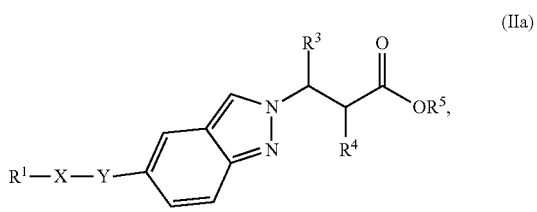

(IIa)

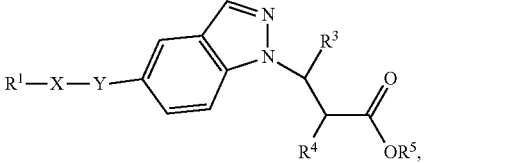

(IIb)

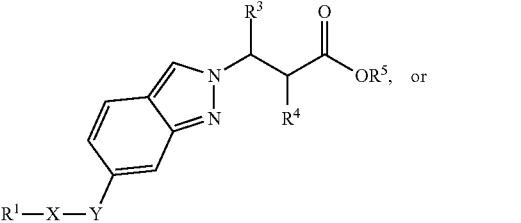

(IIc)

-continued (IId)

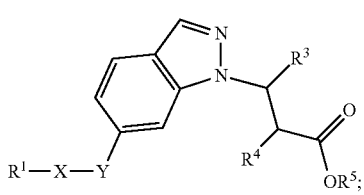

wherein R¹, X, Y, R³, R⁴, and R⁵ are the same as defined above.

In one embodiment of Formula (IIa), (IIb), (IIc), or (IId), R¹ is selected from a structural formula selected from the group consisting of

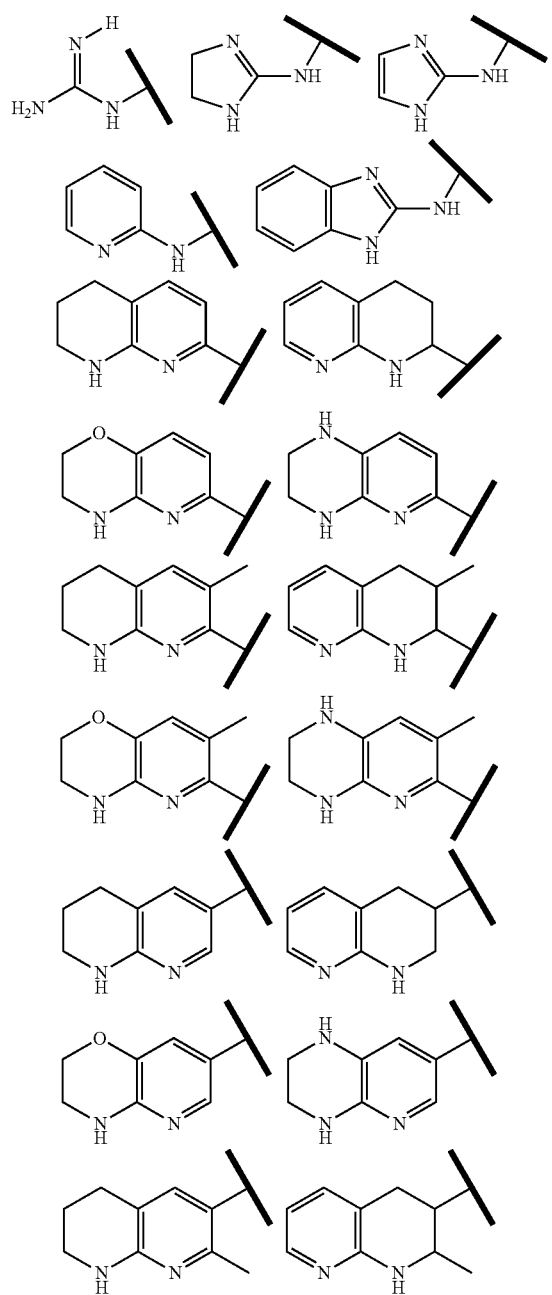

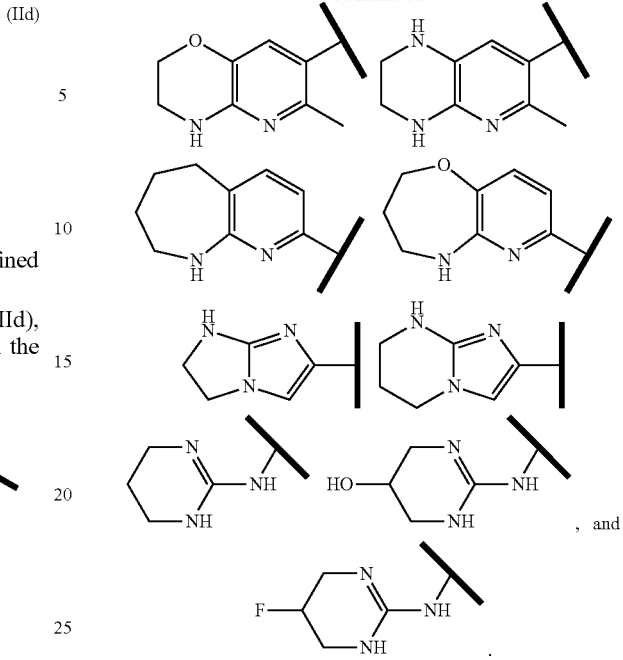

, and

In one embodiment of Formula (IIa), (IIb), (IIc), or (IId), X is $C_{1-4}$ alkylene; and Y is a covalent bond or O.

In one embodiment of Formula (IIa), (IIb), (IIc), or (IIId), R³ is hydrogen, $C_{1-6}$ alkyl, 3- to 6-membered carbocyclyl, carbocyclylalkyl, 6- to 10-membered aryl, arylalkyl, 3- to 6-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^6$;

$R^{3a}$ is hydrogen;

$R^4$ is hydrogen;

$R^6$ is halo, cyano, hydroxyl, amino, oxo, $C_{1-6}$ alkyl, alkoxy, haloalkyl, hydroxyalkyl, aminoalkyl, an amide moiety, an ester moiety, 6- to 10-membered aryl, aryloxy, arylalkoxy, 5- to 10-membered heteroaryl, 3- to 6-membered cycloalkyl, or 3- to 6-membered heterocycloalkyl; wherein the alkyl, alkoxy, aminoalkyl, haloalkyl, aryl, aryloxy, heteroaryl, cycloalkyl, or heterocycloalkyl, by themselves or as part of another group, are each independently substituted with 0, 1, or 2 $R^{10}$; and $R^{10}$, at each occurrence, is independently halo, cyano, hydroxyl, amino, oxo, or $C_{1-6}$ alkyl.

In one embodiment of Formula (IIa), (IIb), (IIc), or (IId), $R^4$ is hydrogen; $R^{3a}$ and $R^3$, together with the atom or atoms to which they are attached, form a 3- to 6-membered carbocyclic ring.

In one embodiment of Formula (IIa), (IIb), (IIc), or (IId), $R^3$ is hydrogen;

$R^{3a}$ is hydrogen;

$R^4$ is $C_{1-6}$ alkyl, arylalkyl, —S(O)$_m$R⁷, —C(O)NR$^a$R$^b$, —NHC(O)OR$^a$, —NHC(O)NR$^a$R$^b$, —NHC(O)R⁷, —OC(O)NR$^a$R$^b$, —OC(O)R⁷, —NHS(O)$_m$NR$^a$R$^b$, or —NHS(O)$_m$R⁷; wherein the alkyl and arylalkyl are each independently substituted with 0, 1, 2, or 3 $R^9$;

$R^7$ is each independently $C_{1-6}$ alkyl, $C_{1-6}$ alkoxy, $C_{1-6}$ aminoalkyl, $C_{1-6}$ haloalkyl, 6- to 10-membered aryl, arylalkyl, 5- to 10-membered heteroaryl, cycloalkyl, or heterocycloalkyl; wherein the alkyl, aryl, heteroaryl, cycloalkyl, and heterocycloalkyl, by themselves or as part of another group, are each independently substituted with 0, 1, 2, or 3 $R^1$;

$R^9$ and $R^{11}$, at each occurrence, are independently halo, cyano, hydroxyl, amino, oxo, or $C_{1-6}$ alkyl.

In one embodiment of Formula (IIa), (IIb), (IIc), or (IId), $R^5$ is hydrogen.

In one embodiment of Formula (Ia) or (Ib), the compound is represented by structural Formula (IIIa), (IIIb), (IIIc), or (IIId):

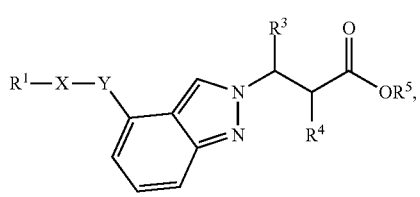

(IIIa)

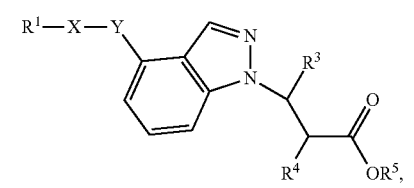

(IIIb)

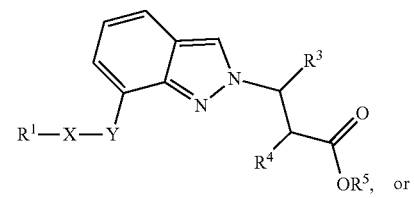

(IIIc)

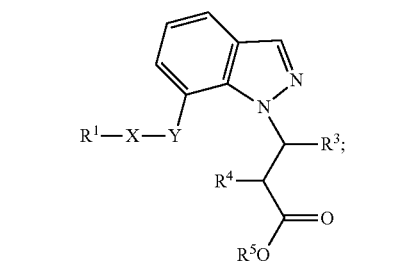

(IIId)

wherein $R^1$, X, Y, $R^3$, $R^4$, and $R^5$ are the same as defined above.

In one embodiment of Formula (IIIa), (IIIb), (IIIc), or (IIId), X is $C_{2-4}$ alkylene; and Y is a covalent bond or O.

In one embodiment of Formula (IIIa), (IIIb), (IIIc), or (IIId), $R^3$ is $C_{1-6}$ alkyl, 3- to 6-membered carbocyclyl, carbocyclylalkyl, 6- to 10-membered aryl, arylalkyl, 3- to 6-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 $R^6$;

$R^{3a}$ is hydrogen;

$R^4$ is hydrogen;

$R^6$ is halo, cyano, hydroxyl, amino, oxo, $C_{1-6}$ alkyl, alkoxy, haloalkyl, hydroxyalkyl, aminoalkyl, an amide moiety, an ester moiety, 6- to 10-membered aryl, aryloxy, arylalkoxy, 5- to 10-membered heteroaryl, 3- to 6-membered cycloalkyl, or 3- to 6-membered heterocycloalkyl; wherein the alkyl, alkoxy, aminoalkyl, haloalkyl, aryl, aryloxy, heteroaryl, cycloalkyl, or heterocycloalkyl, by themselves or as part of another group, are each independently substituted with 0, 1, or 2 $R^{10}$; and $R^{10}$, at each occurrence, is independently halo, cyano, hydroxyl, amino, oxo, or $C_{1-6}$ alkyl.

In one embodiment of Formula (IIIa), (IIIb), (IIIc), or (IIId), $R^3$ is hydrogen;

$R^{3a}$ is hydrogen;

$R^4$ is $C_{1-6}$ alkyl, arylalkyl, —S(O)$_m$R$^7$, —C(O)NR$^a$R$^b$, —NHC(O)OR$^a$, —NHC(O)NR$^a$R$^b$, —NHC(O)R$^7$, —OC(O)NR$^a$R$^b$, —OC(O)R$^7$, —NHS(O)$_m$NR$^a$R$^b$, or —NHS(O)$_m$R$^7$; wherein the alkyl and arylalkyl are each independently substituted with 0, 1, 2, or 3 $R^9$;

$R^7$ is each independently $C_{1-6}$ alkyl, $C_{1-6}$ alkoxy, $C_{1-6}$ aminoalkyl, $C_{1-6}$ haloalkyl, 6- to 10-membered aryl, arylalkyl, 5- to 10-membered heteroaryl, cycloalkyl, or heterocycloalkyl; wherein the alkyl, aryl, heteroaryl, cycloalkyl, and heterocycloalkyl, by themselves or as part of another group, are each independently substituted with 0, 1, 2, or 3 $R^{11}$; and $R^9$ and $R^{11}$, at each occurrence, are independently halo, cyano, hydroxyl, amino, oxo, or $C_{1-6}$ alkyl.

In one embodiment of Formula (IIIa), (IIIb), (IIIc), or (IIId), $R^5$ is hydrogen.

In one embodiment of Formula (Ia) or (Ib), the compound is represented by structural Formula (IVa), (IVb), (IVc), (IVd), (IVe) or (IVf):

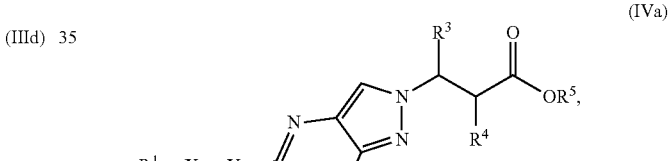

(IVa)

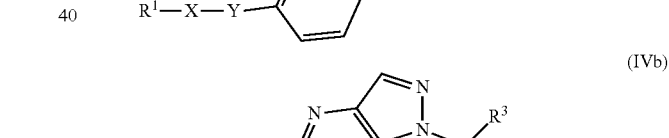

(IVb)

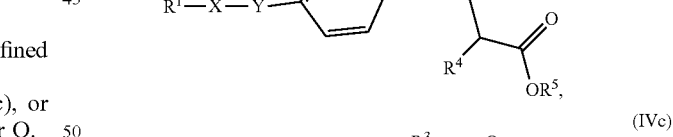

(IVc)

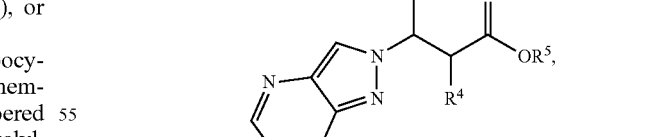

(IVd)

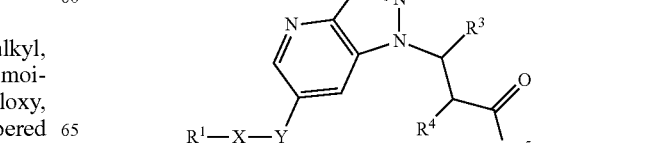

-continued (IVe)

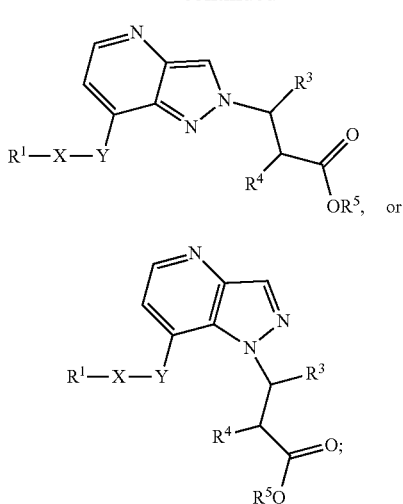

(IVf)

wherein R¹, X, Y, R³, R⁴, and R⁵ are the same as defined above.

In one embodiment of Formula (IVa), (IVb), (IVc), (IVd), (IVe) or (IVf), X is $C_{2-4}$ alkylene; and Y is a covalent bond or O.

In one embodiment of Formula (IVa), (IVb), (IVc), (IVd), (IVe) or (IVf),

R³ is $C_{1-6}$ alkyl, 3- to 6-membered carbocyclyl, carbocyclylalkyl, 6- to 10-membered aryl, arylalkyl, 3- to 6-membered heterocyclyl, heterocyclylalkyl, 5- to 14-membered heteroaryl, heteroarylalkyl, wherein the alkyl, carbocyclyl, heterocyclyl, aryl, and heteroaryl, by themselves or as part of another group, are each independently substituted with 0, 1, 2, or 3 R⁶;

$R^{3a}$ is hydrogen;

R⁴ is hydrogen;

R⁶ is halo, cyano, hydroxyl, amino, oxo, $C_{1-6}$ alkyl, alkoxy, haloalkyl, hydroxyalkyl, aminoalkyl, an amide moiety, an ester moiety, 6- to 10-membered aryl, aryloxy, arylalkoxy, 5- to 10-membered heteroaryl, 3- to 6-membered cycloalkyl, or 3- to 6-membered heterocycloalkyl; wherein the alkyl, alkoxy, aminoalkyl, haloalkyl, aryl, aryloxy, heteroaryl, cycloalkyl, or heterocycloalkyl, by themselves or as part of another group, are each independently substituted with 0, 1, or 2 $R^{10}$; and $R^{10}$, at each occurrence, is independently halo, cyano, hydroxyl, amino, oxo, or $C_{1-6}$ alkyl.

In one embodiment of Formula (IVa), (IVb), (IVc), (IVd), (IVe) or (IVf),

R³ is hydrogen;

$R^{3a}$ is hydrogen;

R⁴ is $C_{1-6}$ alkyl, arylalkyl, —S(O)$_m$R⁷, —C(O)NR$^a$R$^b$, —NHC(O)OR$^a$, —NHC(O)NR$^a$R$^b$, —NHC(O)R⁷, —OC(O)NR$^a$R$^b$, —OC(O)R⁷, —NHS(O)$_m$NR$^a$R$^b$, or —NHS(O)$_m$ R⁷; wherein the alkyl and arylalkyl are each independently substituted with 0, 1, 2, or 3 R⁹;

R⁷ is each independently $C_{1-6}$ alkyl, $C_{1-6}$ alkoxy, $C_{1-6}$ aminoalkyl, $C_{1-6}$ haloalkyl, 6- to 10-membered aryl, arylalkyl, 5- to 10-membered heteroaryl, cycloalkyl, or heterocycloalkyl; wherein the alkyl, aryl, heteroaryl, cycloalkyl, and heterocycloalkyl, by themselves or as part of another group, are each independently substituted with 0, 1, 2, or 3 $R^{11}$; and R⁹ and $R^{11}$, at each occurrence, are independently halo, cyano, hydroxyl, amino, oxo, or $C_{1-6}$ alkyl.

In one embodiment of Formula (IVa), (IVb), (IVc), (IVd), (IVe) or (IVf), R⁵ is hydrogen.

In any one embodiment of Formula (Ia) or (Ib), the compound is selected from any one of the Examples as described in this specification, or a stereoisomer, a tautomer, or a pharmaceutically acceptable salt or solvate thereof.

Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of $\alpha_V$ integrins in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of $\alpha_V\beta6$, $\alpha_V\beta1$, $\alpha_V\beta3$, $\alpha_V\beta5$, and $\alpha_V\beta8$; or a combination of one or more of $\alpha_V\beta6$, $\alpha_V\beta1$, $\alpha_V\beta3$, $\alpha_V\beta5$, and $\alpha_V\beta8$. For example, the integrin receptor antagonizing effect can be an $\alpha_V\beta6$, $\alpha_V\beta1$, $\alpha_V\beta3$, $\alpha_V\beta5$, and $\alpha_V\beta8$ antagonizing effect.

In some embodiments, the disease, disorder, or condition is associated with fibrosis, including pulmonary, liver, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma. Examples of diseases, disorders, or conditions associated with the activity of $\alpha_V$ integrins that can be prevented, modulated, or treated according to the present invention include, but are not limited to, transplant injection, fibrotic disorders (e. g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, vascular fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$\alpha_V\beta6$ monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, Sar$^9$, Met $(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic 32 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of NALFD, NASH, or systemic sclerosis, such as FXR agonists (for example OCA, GS-9674, and LJN452), LOXL2 inhibitors (for example simtuzumab), LPA1 antagonists (for example SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example, LY2405319), caspase inhibitors (for example, emricasan), NOX4 inhibitors (for example, GKT137831), MGAT2 inhibitor, and bile acid/fatty acid conjugates (for example aramchol). The $\alpha_V$ inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196).

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., FXR agonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the $\alpha_V$ integrins. Such compounds may be provided in a commercial kit, for example, for use in pharmaceutical research involving $\alpha_V$ integrins activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by Formula (Ia), (Ib), (IIa), (IIb), (IIc), (IId), (IIIa), (IIIb), (IIIc), (IIId), (IVa), (IVb), (IVc), (IVd), (IVe), or (IVf), or a stereoisomer, a tautomer, or a pharmaceutically acceptable salt or solvate thereof.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkyl amine (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulphur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide", as used herein alone or as part of another group, refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^c$R$^d$, wherein R$^c$ and R$^d$ are independently hydrogen or $C_{1-6}$ alkyl; or alternatively, R$^c$ and R$^d$, taken together with the atoms to which they are attached, form a 3- to 8-membered carbocyclic or heterocyclic ring which is optionally substituted with one or more groups independently selected from halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide. When R$^c$ or R$^d$ (or both of them) is $C_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^c$R$^d$)-alkylene-. "$C_1$ to $C_6$" or "$C_{1-6}$" aminoalkyl", is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, $CF_3CH_2$, $CF_3$ or $CF_3CF_2CH_2$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or Cl, preferably F, such as polyfluoroalkoxy, for example, $CF_3CH_2O$, $CF_3O$ or $CF_3CF_2CH_2O$.

"Hydroxyalkyl" are intended to include both branched and straight-chain saturated aliphatic hydrocarbon groups having the specified number of carbon atoms, substituted with 1 or more hydroxyl (OH) or amino, respectively. "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2] bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

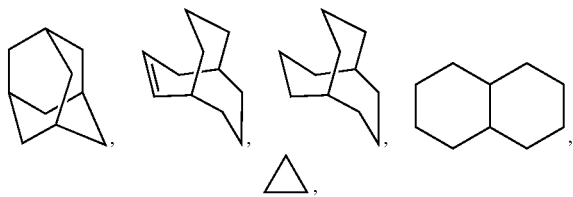

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N—O and S(O)p, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, dihydrofuro[2,3-b] tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolo-pyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

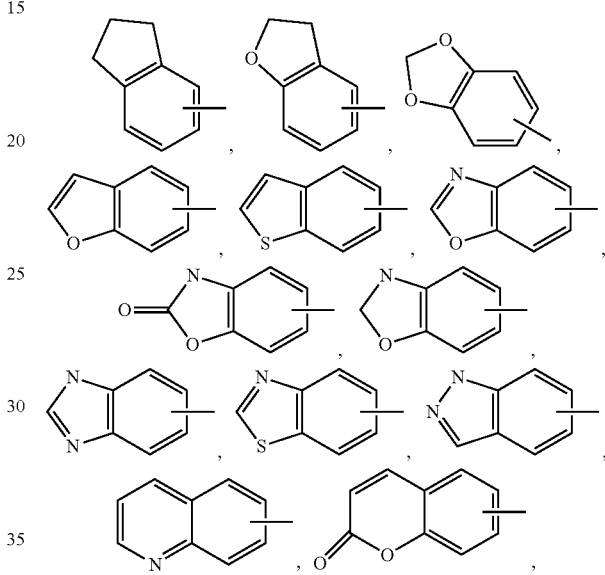

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, aminoalkylcarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy bond in a structural formula, such as

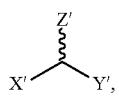

is used to depict a stereogenic center of the carbon atom to which X', Y', and Z' are attached and is intended to represent both enantiomers in a single figure. That is, a structural formula with such as wavy bond denotes each of the enantiomers individually, such as

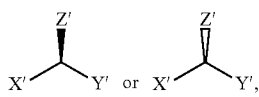

as we as a racemic mixture thereof.

It is understood herein that if a carbocyclic, aryl, heterocyclic, or heteroaryl moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a dotted ring is used within a ring structure, this indicates that the ring structure may be saturated, partially saturated or unsaturated.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule For example, one skilled in the art would readily understand that a 1,2,3-triazole exists in two tautomeric forms as defined above:

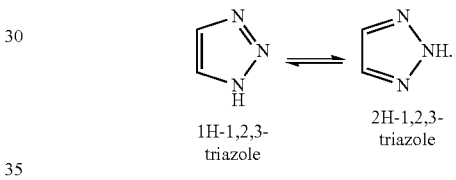

1H-1,2,3-triazole    2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Examples of such prodrug esters include:

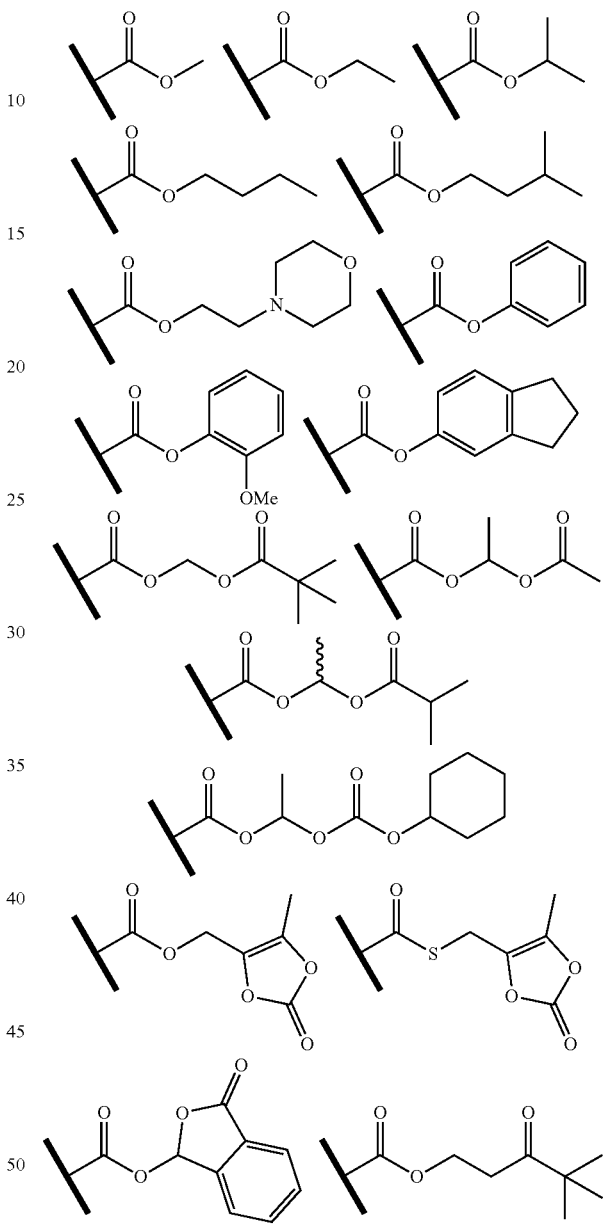

The compounds of the present invention contain an arginine mimetics moiety which can form physiologically hydrolyzable esters that serve as prodrugs, i.e., "prodrugs of arginine mimetics", by being hydrolyzed in the body to yield the compounds of the present invention per se. Representative examples of prodrugs of arginine mimetics include:

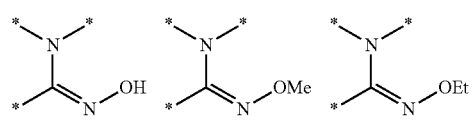

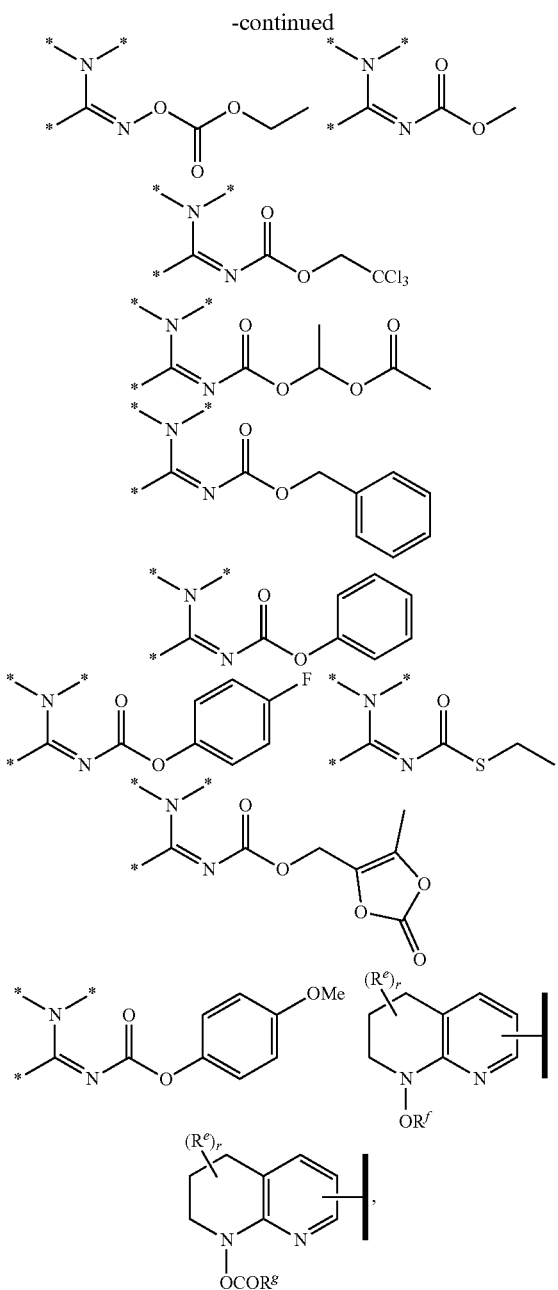

wherein, one of the asterisks in each of the arginine mimetics moiety is an attachment point to the parent molecule and the other two asterisks are hydrogen; $R^f$=H, Me, Et, COOEt; $R^g$=$CH_3$, $CH_2CCl_3$, phenyl, 4-fluorophenyl, 4-methoxyphenyl, benzyl,

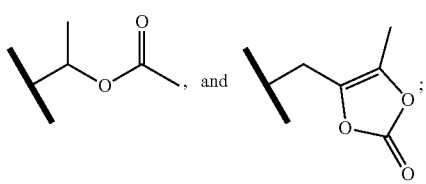

$R^e$ is OH, $C_{1-4}$ alkyl, halo, haloalkyl, or $C_{1-4}$ cycloalkyl; and r is an integer of 0, 1, 2, or 3.

Furthermore, various forms of prodrugs are well known in the art. For examples of such prodrug derivatives, see:

Bundgaard, H., ed., Design of Prodrugs, Elsevier (1985), and Widder, K. et al., eds., Methods in Enzymology, 112:309-396, Academic Press (1985);

Bundgaard, H., Chapter 5, "Design and Application of Prodrugs", Krosgaard-Larsen, P. et al., eds., A Textbook of Drug Design and Development, pp. 113-191, Harwood Academic Publishers (1991);

Bundgaard, H., Adv. Drug Deliv. Rev., 8:1-38 (1992);
Bundgaard, H. et al., J. Pharm. Sci., 77:285 (1988); and
Kakeya, N. et al., Chem. Pharm. Bull., 32:692 (1984).

Preparation of prodrugs is well known in the art and described in, for example, King, F. D., ed., Medicinal Chemistry: Principles and Practice, The Royal Society of Chemistry, Cambridge, UK (1994); Testa, B. et al., Hydrolysis in Drug and Prodrug Metabolism. Chemistry, Biochemistry and Enzymology, VCHA and Wiley-VCH, Zurich, Switzerland (2003); Wermuth, C. G., ed., The Practice of Medicinal Chemistry, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS"

or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The compounds of the present invention can be prepared as shown in the following reaction schemes and description thereof, as well as relevant published literature procedures that may be used by one skilled in the art. Exemplary reagents and procedures for these reactions appear hereinafter and in the working Examples.

Abbreviations

The following abbreviations are employed herein:
Bn=benzyl
t-Bu=tertiary butyl
Boc=tert-Butyloxycarbonyl
Boc$_2$O=di-tert-butyl dicarbonate
Cs$_2$CO$_3$=cesium carbonate
DBU=1,8-Diazabicyclo[5.4.0]undec-7-ene
DCM or CH$_2$Cl$_2$=dichloromethane
DIAD=diisopropyl azodicarboxylate
Dess-Martin periodinane or DMP=1,1,1-Triacetoxy-1,1-dihydro-1,2-benziodoxol-3(1H)-one
DIPEA or i-Pr$_2$NEt=diisopropylethylamine
DMAP=4-dimethylaminopyridine
DMF=dimethyl formamide
Et=ethyl
Et$_3$N=triethylamine
EtOH=ethanol
Et$_2$O=diethyl ether
EtOAc=ethyl acetate
HOAc or AcOH=acetic acid
K$_2$CO$_3$=potassium carbonate
LiCl=lithium chloride
LiOAc=lithium acetate
LiOH=lithium hydroxide
Me=methyl
MeCN or ACN=acetonitrile
MeOH=methanol
MgSO$_4$=magnesium sulfate
NaBH$_4$=sodium borohydride
NaOH=sodium hydroxide
NaHCO$_3$=sodium bicarbonate
PBu$_3$=tributylphosphine
Ph=phenyl
Pd/C=palladium on carbon
Pd(OAc)$_2$=palladium(II) acetate
Ph$_3$P=triphenylphosphine
PtO$_2$=platinum dioxide
TBAF=tetra-n-butylammonium fluoride
TBDMS=tert-butyldimethylsilyl
TMS=trimethylsilyl
THF=tetrahydrofuran
TFA=trifluoroacetic acid
min=minute(s)
hr or hrs=hour(s)
L=liter
mL=milliliter
μL=microliter
g=gram(s)
mg=milligram(s)
mol=moles
mmol=millimole(s)
meq=milliequivalent
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point IV. Methods of Preparation The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, 4th Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. 6th Edition, Wiley & Sons, New York, N.Y. (2007); Katritzky, A. R. et al., eds., *Comprehensive Organic Functional Groups Transformations II,* 2nd Edition, Elsevier Science Inc., Tarrytown, N.Y. (2004); Larock, R. C., *Comprehensive Organic Transformations*, VCH Publishers, Inc., New York, N.Y. (1999), and references therein.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Scheme 1

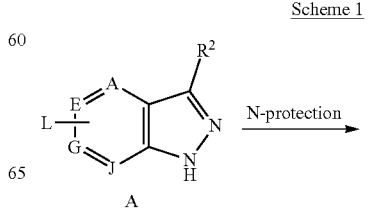

A

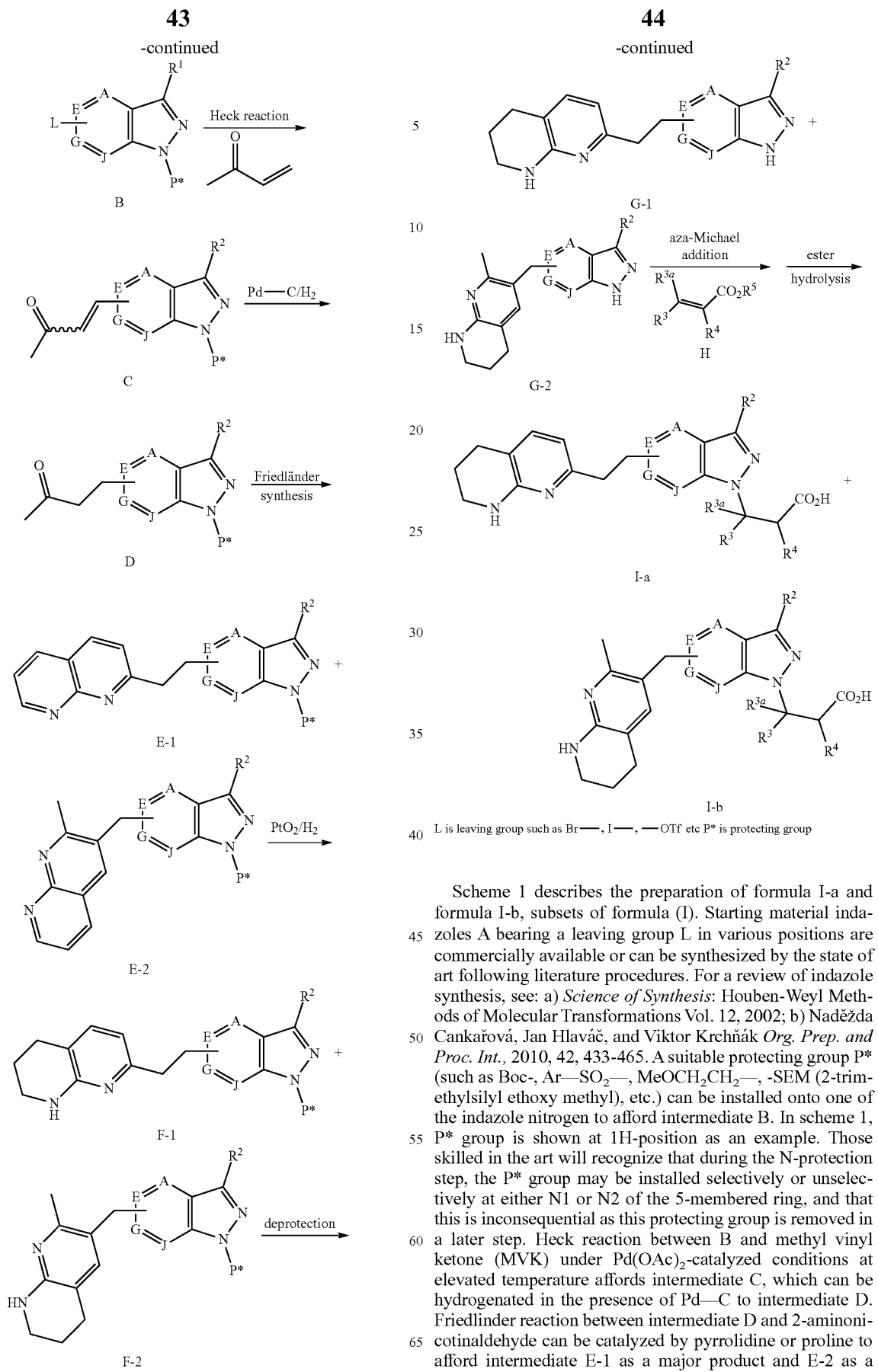

L is leaving group such as Br—, I—, —OTf etc P* is protecting group

Scheme 1 describes the preparation of formula I-a and formula I-b, subsets of formula (I). Starting material indazoles A bearing a leaving group L in various positions are commercially available or can be synthesized by the state of art following literature procedures. For a review of indazole synthesis, see: a) *Science of Synthesis*: Houben-Weyl Methods of Molecular Transformations Vol. 12, 2002; b) Naděžda Cankařová, Jan Hlaváč, and Viktor Krchňák *Org. Prep. and Proc. Int.,* 2010, 42, 433-465. A suitable protecting group P* (such as Boc-, Ar—SO$_2$—, MeOCH$_2$CH$_2$—, -SEM (2-trimethylsilyl ethoxy methyl), etc.) can be installed onto one of the indazole nitrogen to afford intermediate B. In scheme 1, P* group is shown at 1H-position as an example. Those skilled in the art will recognize that during the N-protection step, the P* group may be installed selectively or unselectively at either N1 or N2 of the 5-membered ring, and that this is inconsequential as this protecting group is removed in a later step. Heck reaction between B and methyl vinyl ketone (MVK) under Pd(OAc)$_2$-catalyzed conditions at elevated temperature affords intermediate C, which can be hydrogenated in the presence of Pd—C to intermediate D. Friedlinder reaction between intermediate D and 2-aminonicotinaldehyde can be catalyzed by pyrrolidine or proline to afford intermediate E-1 as a major product and E-2 as a minor product. Hydrogenation of E-1 and E-2 in the presence of Adams's catalyst ($PtO_2$) can afford the corresponding tetrahydronaphthyridine F-1 and F-2, where the protecting group P* can be removed to afford G-1 and G-2. Indazoles are reported to be capable of aza-Michael addition to 2-propenamide, α,β-unstaturated ketone, or alkyl acrylate (for the references, see: a) Han, X. *Tetrahedron Lett.* 2007, 48, 2845-2849; b) Yang, J. et al. *Synthesis* 2016, 48, 1139-1146; c) An, Y.-L. et al. *Synthesis,* 2015, 47, 1581-1592). However, no report has been documented about 3-substituted α,β-unsaturated ester. We report here that the fully elaborated indazole intermediates such as G-1 and G-2 can react with various Michael addition acceptors such as intermediate H (where $R^3$ and $R^{3a}$ can be H or aryl or alkyl, $R^4$ can be alkyl or $N(Boc)_2$). The typical reaction condition for such aza-Michael addition is mediated by base (such as DBU, $K_2CO_3$, $Cs_2CO_3$ etc) or Lewis acid (such as $BF_3$ etherate). Upon ester hydrolysis, formula I-a and I-b can be obtained after preparative HPLC purification or reversed phase chromatography purification.

Scheme 2 details the preparation of formula I-c and formula I-d, subsets of formula I. Under Heck reaction condition, intermediate B can react with a suitable terminal alkene or alkyne to form intermediate I-1 and 1-2. After hydrogenation, the secondary alcohol J can be oxidized to methyl ketone K. The transformation of K to formula I-c and I-d can be achieved by following the reaction sequences in Scheme 1.

Scheme 3

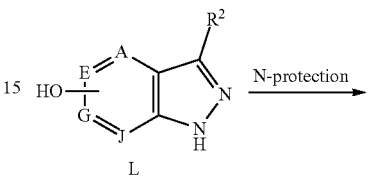

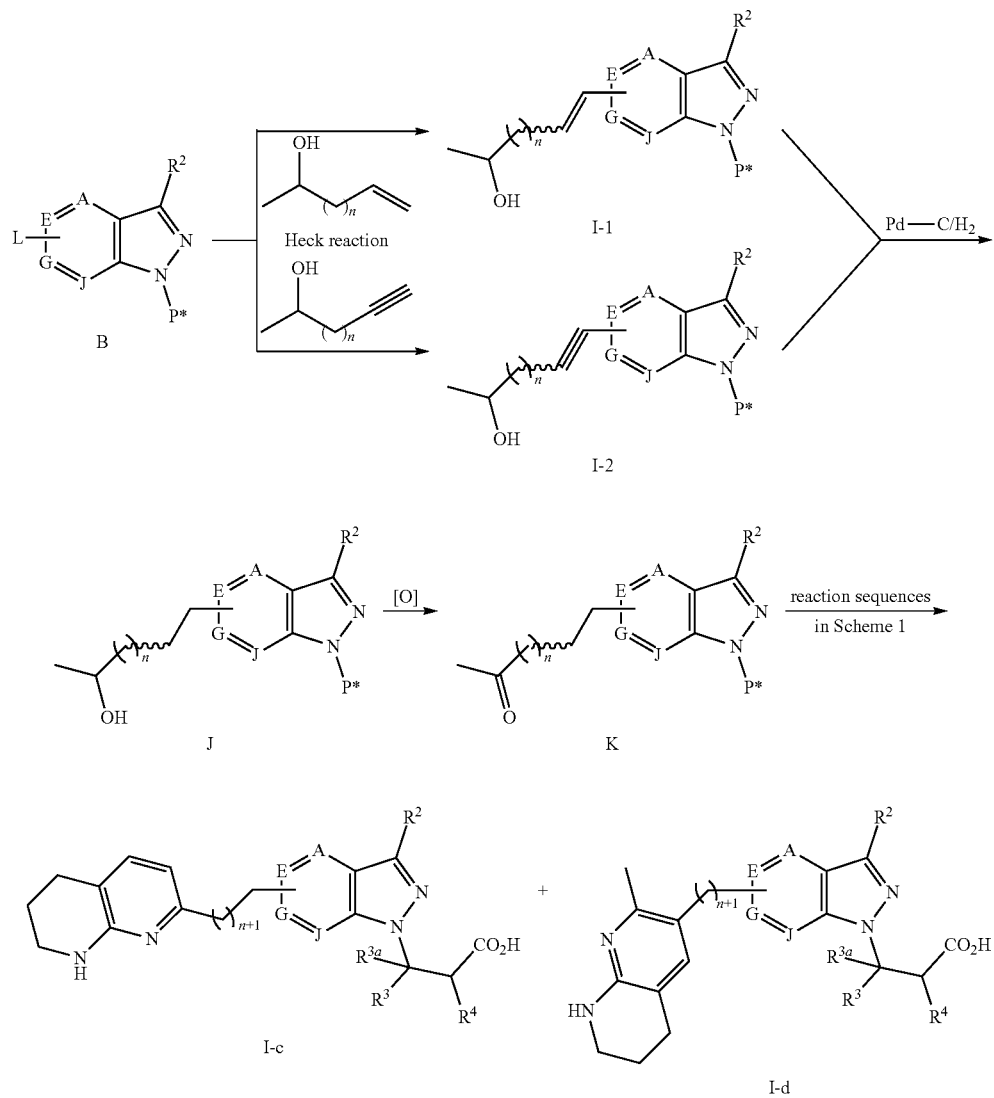

n = 1, 2, 3 L is leaving group such as Br——, I——, ——OTf etc P* is protecting group

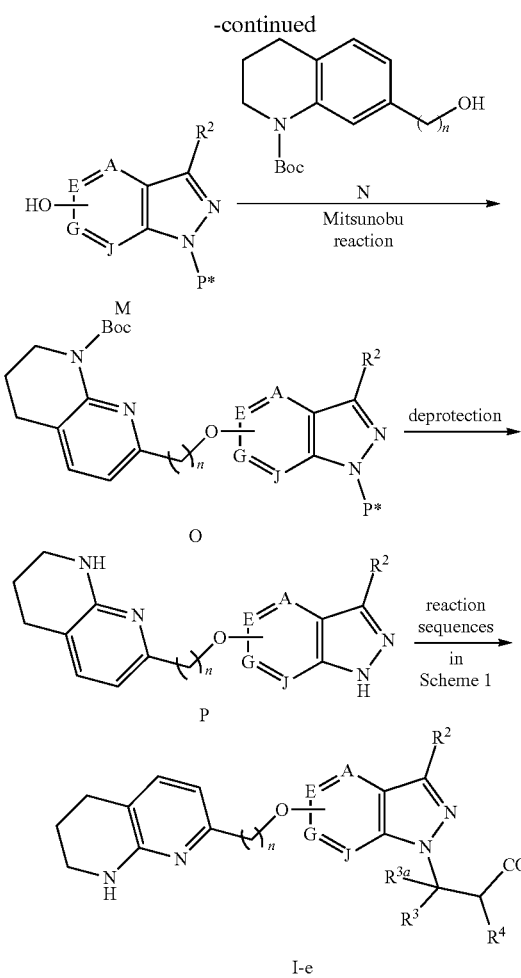

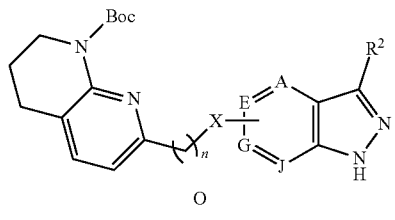

n = 1, 2, 3 L is leaving group such as Br—, I—, —OTf etc P* is protecting group X = NH or O Y = NH₂ or OH Scheme 4 describes an alternative route to synthesize intermediate O. The reaction between B and N can be catalyzed by Pd, Cu, Ni catalysts and suitable ligands under elevated temperature. For a review of O-arylation, see: Muci, A. R.; Buchwald, S. L. *Topics in Current Chemistry* 2002, 219 (Cross-Coupling Reactions), 131-209.

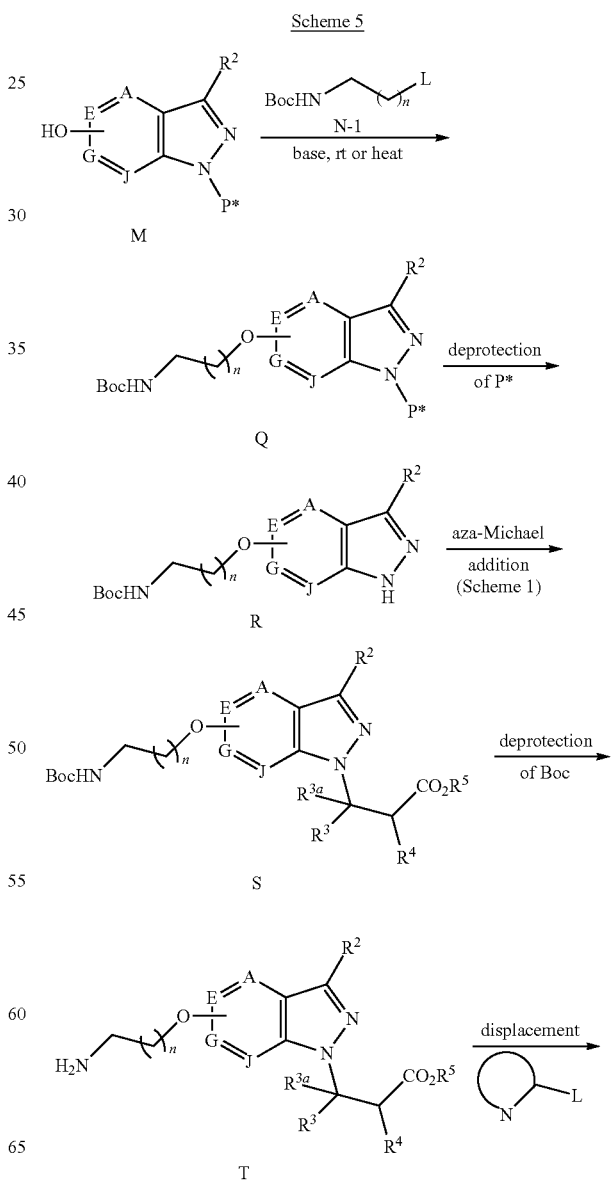

n = 1, 2, 3 P* is protecting group, preferable to be Boc or Ar—SO₂—

Scheme 3 describes the preparation of formula I-e, a subset of formula I. The starting hydroxy bearing indazoles L are either commercially available or can be obtained via indazole synthesis by following literature procedures. L can be converted to M via protecting group manipulation (to install a suitable protecting group such as Boc- or ArSO₂—). The 3,4-dihydro-1,8-naphthyridine alcohols N are commercially available or can be synthesized by following literature procedures. Mitsunobu reaction between M and N can afford O, which can be further converted to P via cleavage of protecting group. The key intermediate P can be then converted to formula I-e via the reaction sequence depicted in Scheme 1.

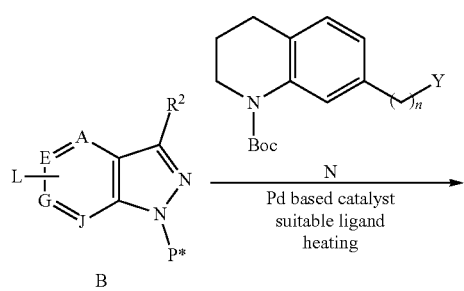

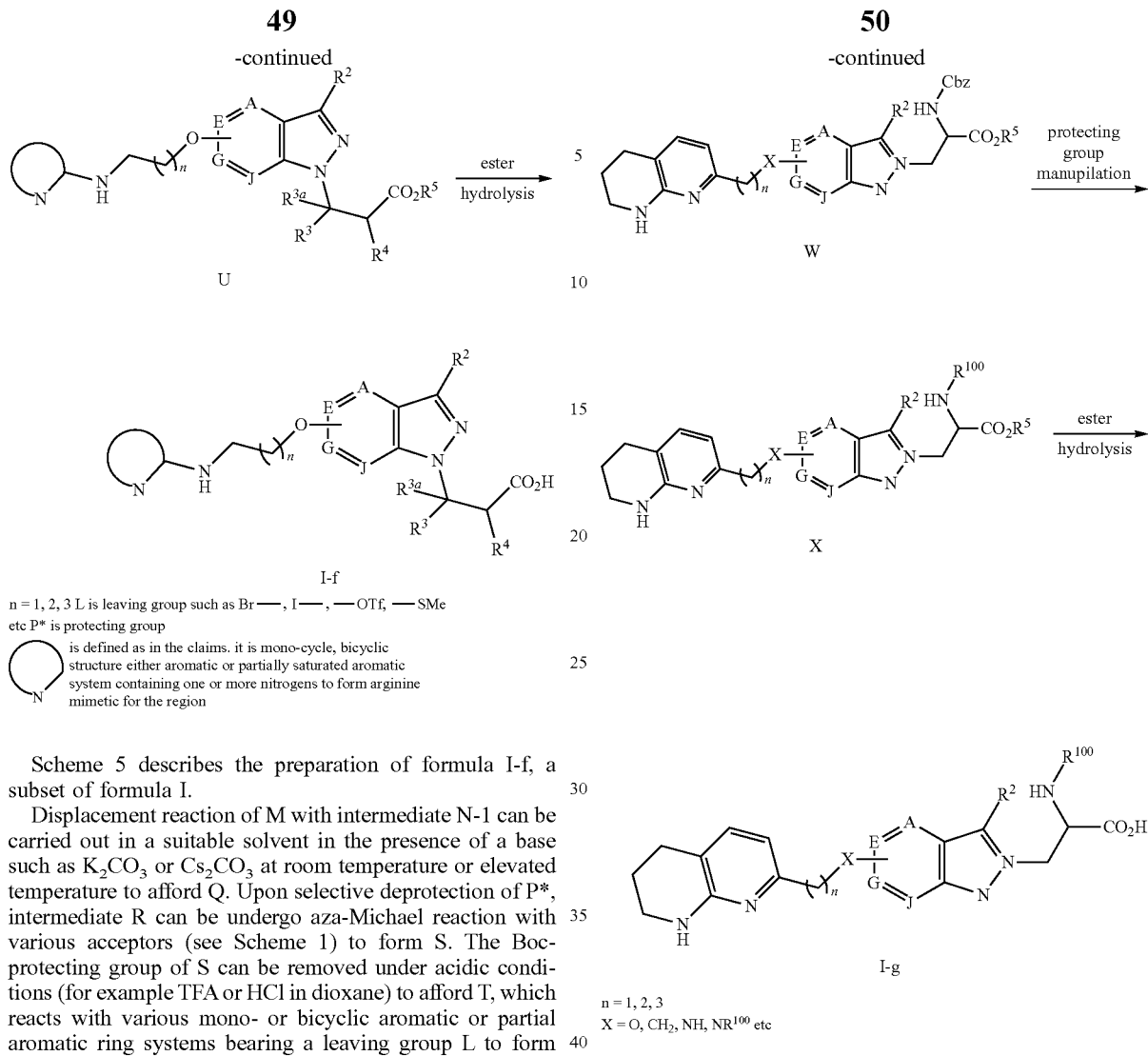

n = 1, 2, 3 L is leaving group such as Br—, I—, —OTf, —SMe etc P* is protecting group is defined as in the claims. it is mono-cycle, bicyclic structure either aromatic or partially saturated aromatic system containing one or more nitrogens to form arginine mimetic for the region Scheme 5 describes the preparation of formula I-f, a subset of formula I.

Displacement reaction of M with intermediate N-1 can be carried out in a suitable solvent in the presence of a base such as $K_2CO_3$ or $Cs_2CO_3$ at room temperature or elevated temperature to afford Q. Upon selective deprotection of P*, intermediate R can be undergo aza-Michael reaction with various acceptors (see Scheme 1) to form S. The Boc-protecting group of S can be removed under acidic conditions (for example TFA or HCl in dioxane) to afford T, which reacts with various mono- or bicyclic aromatic or partial aromatic ring systems bearing a leaving group L to form intermediate U. Upon ester hydrolysis under aqueous basic condition, formula I-f can be obtained.

n = 1, 2, 3
X = O, $CH_2$, NH, $NR^{100}$ etc

Scheme 6 describes the preparation of formula I-g, a subset of formula I. The key intermediate G-3 can be the intermediate G-1 (from Scheme 1) or any similar intermediate from Scheme 2 to Scheme 4. The aziridine ring opening reaction between G-3 and V can be performed selectively in the presence of Lewis acid such as TFA under elevated temperature to afford the 2H-indazole W as the major product. W can then be converted to intermediate X ($R^{100}$=H), which can be further converted to X bearing other $R^{100}$ groups (such as $R^{100}$=$R^{101}SO_2$—, $R^{101}C(O)$—, etc; wherein $R^{101}$ can be optionally substituted alkyl, aryl, or arylalkyl). Upon hydrolysis in the presence of a base, formula I-g can be obtained.

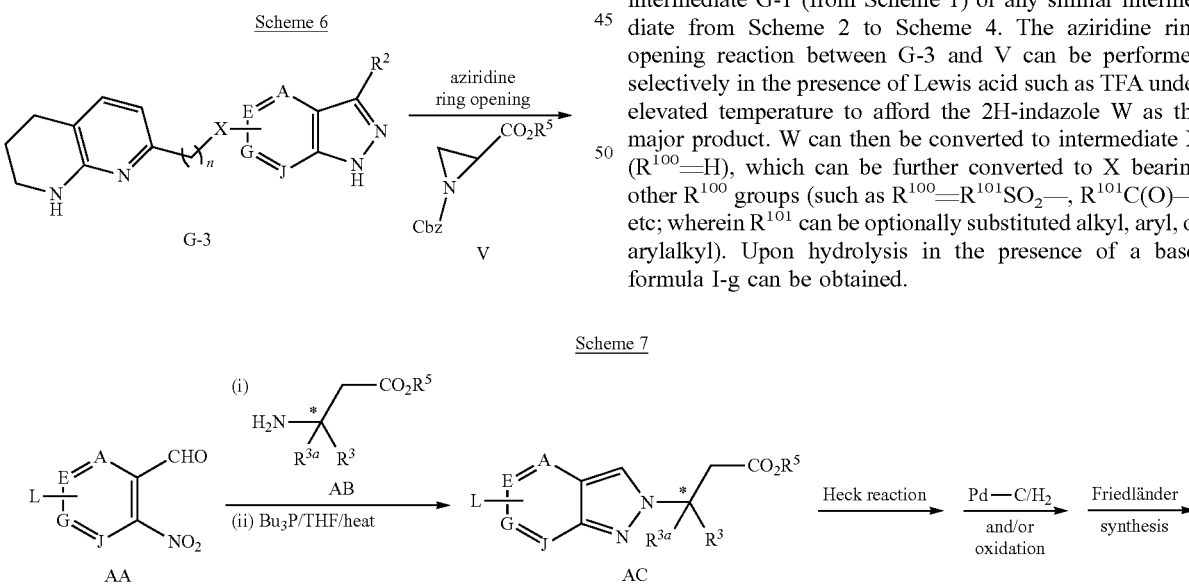

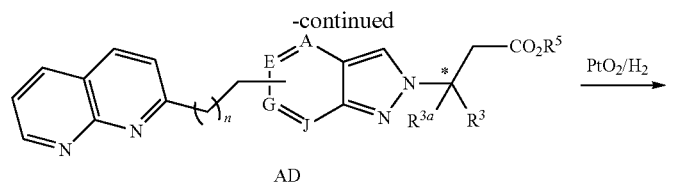

AD

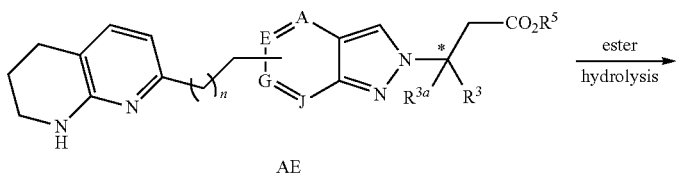

AE

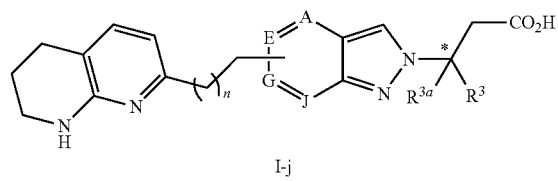

I-j n = 1, 2, 3

Scheme 7 describes the preparation of formula I-j, a subset of formula I. 2-Nitrobenzaldehyde analogs AA are commercially available or can be synthesized using literature procedures. Intermediate AB (either chiral or racemic) can be obtained from commercial sources or from synthesis following literature procedures. AA can react with AB under thermal conditions to form an imine, which can be reduced by Bu$_3$P in one pot to afford ring-closed product 2H-indazole AC. AC can be transformed to formal I-j following a sequence analogous to the one described in Scheme 1.

Scheme 8

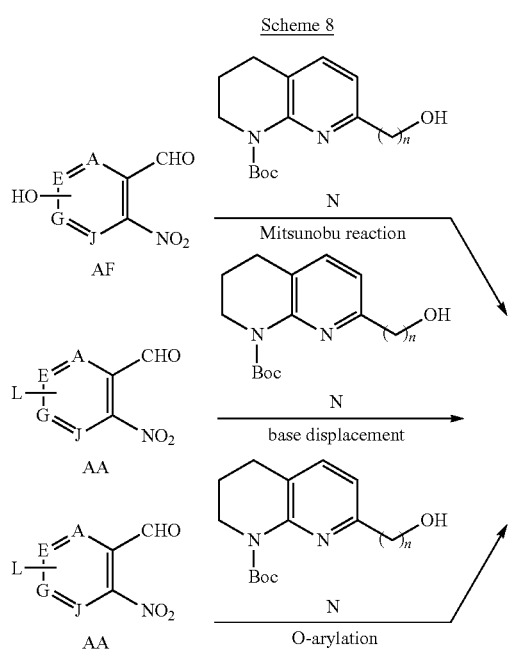

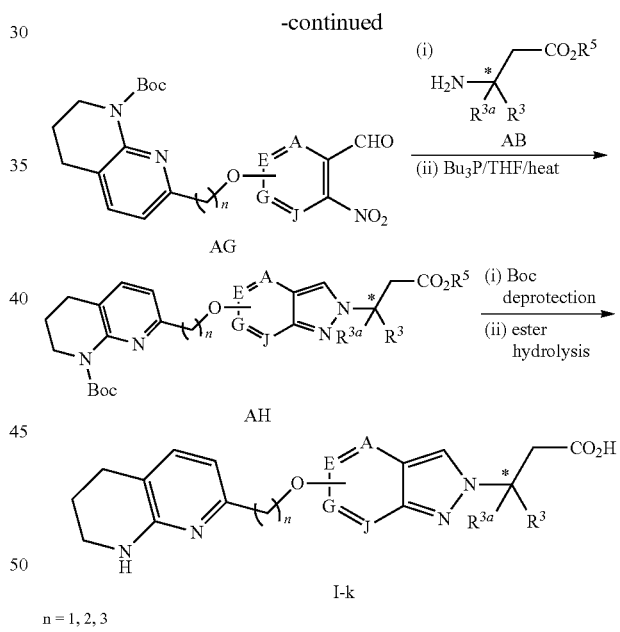

I-k n = 1, 2, 3

Scheme 8 describes the preparation of formula I-k, a subset of formula I. There are three different methods to access intermediate AG. Method 1 is the Mitsunobu reaction between AF and N; Method 2 involves in the base-mediated SNA2 displacement reaction between hydroxy group of N and leaving group L in AA; Method 3 is the typical O-arylation where hydroxy group of N reacts with AA in the presence of Pd-based catalyst and suitable ligand. The ring closure reaction between AB and AG can occur as described in Scheme 7 to afford AH. Upon Boc deprotection and ester hydrolysis, formula I-k can be obtained.

Scheme 9

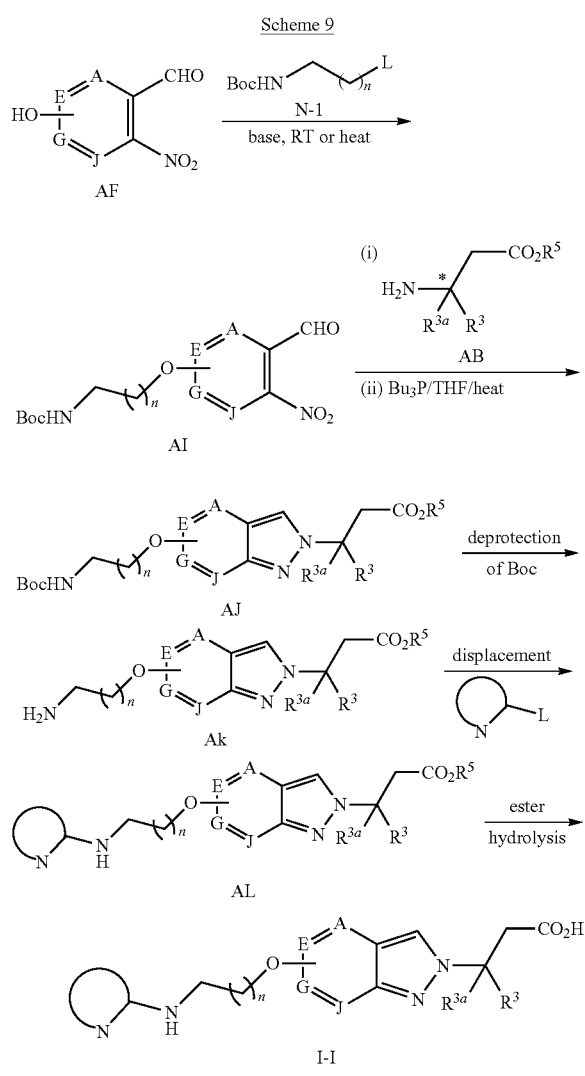

n = 1, 2, 3 L is leaving group such as Br—, I—, —OTf, —SMe etc

◯ is defined as in the claims. it is mono-cycle, bicyclic
N—H structure either aromatic or partially saturated aromatic
system containing one or more nitrogens to form arginine
mimetic for the region Scheme 9 describes the preparation of formula I-1, a subset of formula I. Intermediate AF can react with N-1 under basic condition to form AI, which can be subsequently cyclized with AB to form AJ as described in Scheme 7 The Boc protecting group can be removed under acidic conditions (TFA or HCl in dioxane) to afford AK. The transformation of AK to formula I-1 can occur following a sequence familiar to the one shown in Scheme 5.

Scheme 10

Method 1

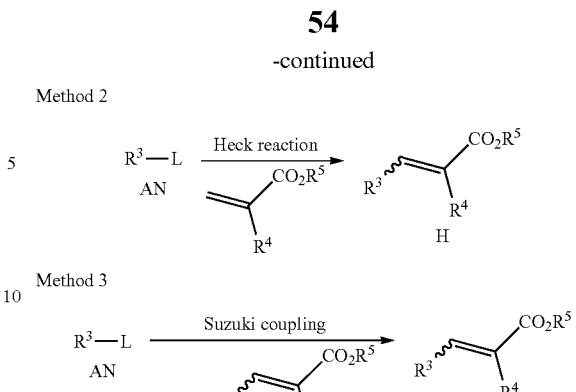

Method 2

Method 3

L is leaving group, such as Br, I, Cl, OTf, etc.
$R^{102}$ is H, alkyl, aryl, or arylalkyl.

Scheme 10 describes the synthesis of intermediate H, which is used in the above synthetic schemes. For example, appropriate aldehyde AM can react with a suitable Wittig reagent to form intermediate H (Method 1). Alternatively, AN can react with a suitable olefin under Heck reaction conditions (Method 2) or Suzuki coupling reaction conditions (Method 3) to provide intermediate H. For Method 2 and 3, $R^3$ is typically aryl or heteroaryl, rather than alkyl (less common). However, Method 1 can be used when $R^3$ or $R^{3a}$ is either alkyl or aryl or heteroaryl.

Scheme 11

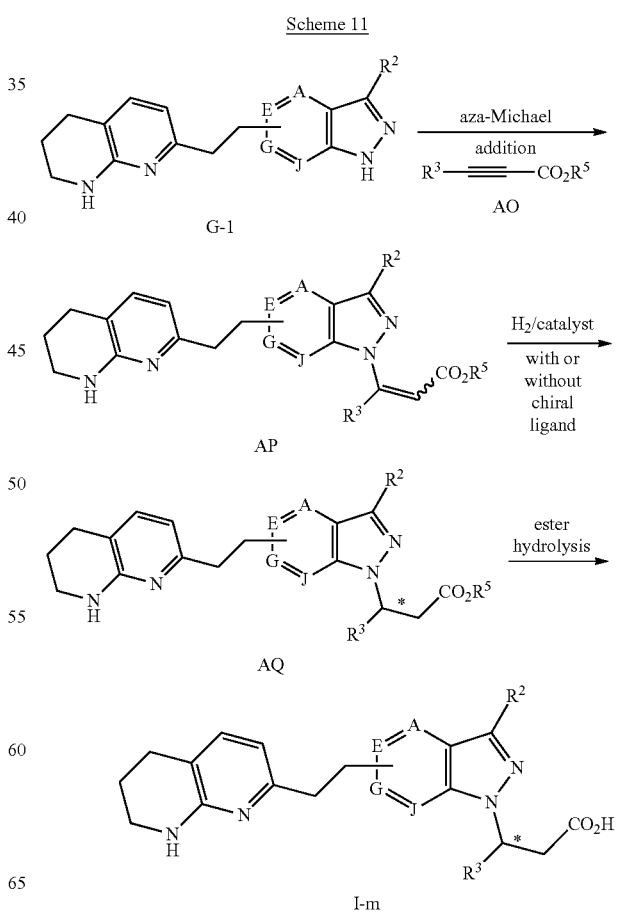

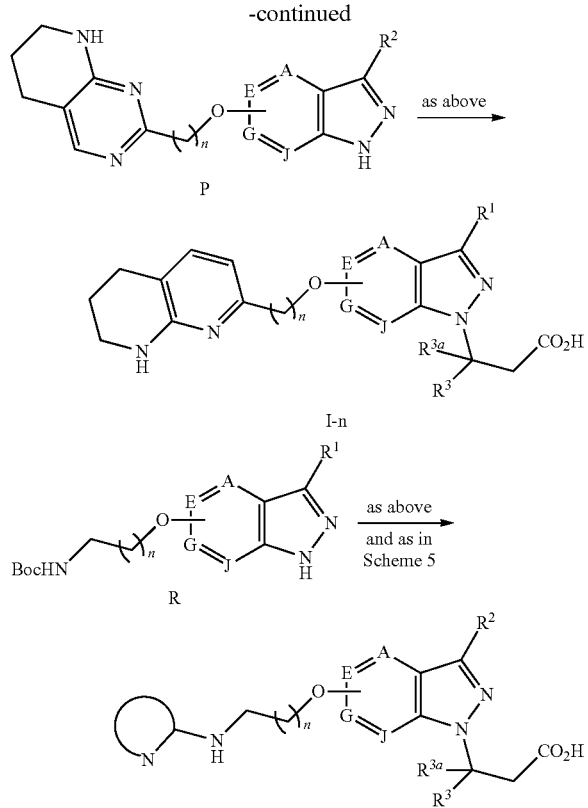

n = 1, 2, 3 L is leaving group such as Br—, I—, —OTf, —SMe etc
P* is protecting group

is defined as in the claims. it is mono-cycle, bicyclic structure either aromatic or partially saturated aromatic system containing one or more nitrogens to form arginine mimetic for the region

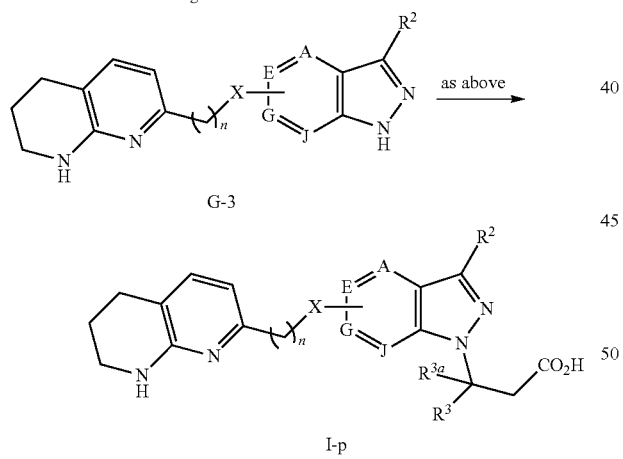

Scheme 11 describes the preparation of formula I-m, I-n, I-o, and I-p, subsets of formula I. Intermediate G-1 (from Scheme 5) can react with alkynyl ester AO (commercially available or can be synthesized by following literature procedures) to form Michael addition adduct AP. Upon the hydrogenation of AP under Pd catalysis (with or without chiral ligand), intermediate AQ can be obtained in chiral or racemic form. Ester hydrolysis of AQ can afford formula I-m. Similarly, intermediates P, R, G-3 can undergo the above sequence to afford formula I-n, I-o, and I-p respectively.

Scheme 12

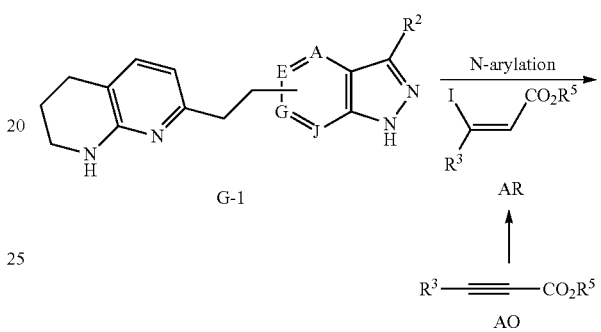

Alternatively, intermediate AP can be prepared using N-arylation method detailed in Scheme 12. Thus, alkynyl ester AO can be converted to AR via treatment with NaI in acetic acid. The reaction between G-1 and AR can be achieved using standard Buckwald N-arylation reaction conditions (see: *PNAS,* 2004, 101, 5821-5823).

Scheme 13

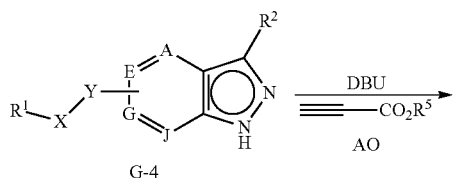

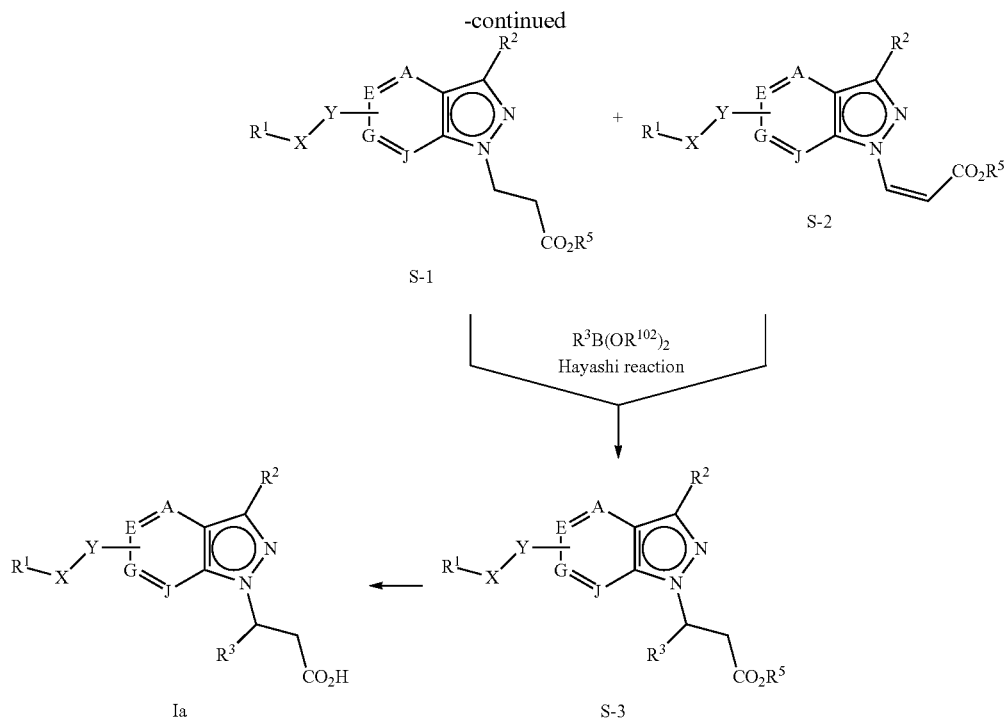

Scheme 13 describes the preparation of formula Ia using an alternative route. Intermediate G-4 (see above schemes for preparation) can undergo the aza-Michael addition with alkyl propiolate AO to form trans-adduct S-1 (major) and cis-adduct S-2. The Rh(I)-mediated Hayashi reaction of S-1 or S-2 or the mixture with $R^3B(OR^{102})_2$ can afford S-3, which can be further converted to formula Ia upon ester hydrolysis.

V. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/Ms and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

HPLC-1: Sunfire C18 column (4.6×150 mm) 3.5 μm, gradient from 10 to 100% B:A for 12 min, then 3 min hold at 100% B.

Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.

HPLC-2: XBridge Phenyl (4.6×150 mm) 3.5 μm, gradient from 10 to 100% B:A for 12 min, then 3 min hold at 100% B.

Mobile phase A: 0.05% TFA in water:CH$_3$CN (95:5)
Mobile phase B: 0.05% TFA in CH$_3$CN:water (95:5)
TFA Buffer pH=2.5; Flow rate: 1 mL/min; Wavelength: 254 nm, 220 nm.

HPLC-3: Chiralpak AD-H, 4.6×250 mm, 5 μm.
Mobile Phase: 30% EtOH-heptane (1:1)/70% CO$_2$
Flow rate=40 mL/min, 100 Bar, 35° C.; Wavelength: 220 nm HPLC-4: Waters Acquity UPLC BEH C18, 2.1×50 mm, 1.7-μm particles;
Mobile Phase A: 5:95 CH$_3$CN:water with 10 mM NH$_4$OAc;
Mobile Phase B: 95:5 CH$_3$CN:water with 10 mM NH$_4$OAc;
Temperature: 50° C.; Gradient: 0-100% B over 3 min, then a 0.75-min hold at 100% B;
Flow: 1.11 mL/min; Detection: UV at 220 nm.

HPLC-5: Waters Acquity UPLC BEH C18, 2.1×50 mm, 1.7-μm particles;
Mobile Phase A: 5:95 CH$_3$CN:water with 0.1% TFA;
Mobile Phase B: 95:5 CH$_3$CN:water with 0.1% TFA;
Temperature: 50° C.; Gradient: 0-100% B over 3 min, then a 0.75-min hold at 100% B; Flow: 1.11 mL/min; Detection: UV at 220 nm.

Intermediate 1A

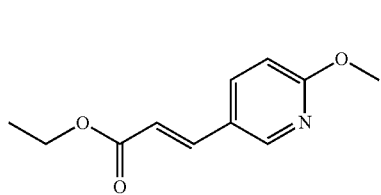

Intermediate 1A can be synthesized using three different methods: Heck reaction, Wittig reaction, or Suzuki coupling reaction. The following procedures serve as the examples for all acrylates synthesized and used in this application.

Method 1. To a solution of 6-methoxynicotinaldehyd (3 g, 21.88 mmol) in THF (45 mL) was added 15 g of Molecular sieves 4 Å followed by ethyl 2-(diethoxyphosphoryl)acetate (5.25 mL, 26.3 mmol) and LiOH (0.629 g, 26.3 mmol). The reaction was stirred at rt overnight. The reaction mixture was filtered through a pad of celite and the volatiles were removed under reduced pressure. The residue was dissolved in EtOAc (25 mL) and washed with 10% NaHCO$_3$ (aqueous, 12 mL) followed by brine (12 mL). The organic layer was dried (Na$_2$SO$_4$), filtered, and concentrated under reduced pressure. The residue was purified via flash column chromatography (220 g silica gel, 0 to 20% hexane/ethyl acetate) to afford Intermediate 1A (4.5 g, 21.72 mmol, 99% yield) as a yellow solid. $^1$H NMR (500 MHz, CDCl$_3$) δ 8.28 (d, J=2.5 Hz, 1H), 7.77 (dd, J=8.8, 2.5 Hz, 1H), 7.64 (d, J=16.2 Hz, 1H), 6.77 (d, J=8.8 Hz, 1H), 6.34 (d, J=16.0 Hz, 1H), 4.27 (q, J=7.2 Hz, 2H), 3.98 (s, 3H), 1.34 (t, J=7.2 Hz, 3H). LCMS (ES): m/z 208.1 [M+H]$^+$.

Method 2. A solution of 5-bromo-2-methoxypyridine (1.03 mL, 7.98 mmol), ethyl acrylate (3.0 mL, 27.9 mmol), Et$_3$N (3.0 mL, 21.54 mmol), Pd(OAc)$_2$ (0.202 g, 0.899 mmol) and tri-o-tolylphosphine (0.404 g, 1.327 mmol) in ACN (2.0 mL) was degassed with argon for 10 min. The mixture was heated at 90° C. for 12 h. The solvent was removed under reduced pressure. Toluene (1.5 mL) was added and the mixture was concentrated again under reduced pressure. Ether (10 mL) was added and the mixture was filtered through a pad of silica gel eluting with ether. The solvent was removed and the residue was purified via flash chromatography (80 g silica gel, 0 to 100% hexanes/ethyl acetate) to afford Intermediate 1A (1.59 g, 7.67 mmol, 96% yield) as a yellow solid.

Method 3. To a degassed solution of 5-bromo-2-methoxypyridine (2 g, 10.64 mmol), (E)-ethyl 3-(4,4,5,5-tetramethyl-1,3,2-dioxaborolan-2-yl)acrylate (2.405 g, 10.64 mmol) and K$_2$CO$_3$ (4.41 g, 31.9 mmol) in 1,4-dioxane (30 mL) and water (10 mL) was added Pd(PPh$_3$)$_4$ (0.492 g, 0.425 mmol). The reaction mixture was stirred in a seal vial at 100° C. overnight. After cooled to rt, the mixture was diluted with water (15 mL), and extracted with CH$_2$Cl$_2$ (3×10 mL), the combine organics were dried (Na$_2$SO$_4$), filtered, and concentrated. the residue was purified via flash chromatography (80 g silica gel, 0 to 100% hexane/ethyl acetate) to afford Intermediate 1A (662 mg, 3.19 mmol, 30% yield) as a yellow solid.

The following intermediates can be synthesized using one of the methods above or the procedures in the literature known to the one skilled of the art.

Intermediate 1B

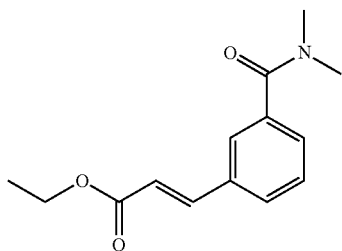

Intermediate 1B: $^1$H NMR (400 MHz, chloroform-d) δ 7.70 (dt, J=16.0, 0.5 Hz, 1H), 7.62-7.54 (m, 2H), 7.50-7.38 (m, 2H), 6.48 (d, J=16.0 Hz, 1H), 4.29 (q, J=7.1 Hz, 2H), 3.15 (s, 3H), 3.01 (s, 3H), 1.36 (t, J=7.1 Hz, 3H). LCMS (ES): m/z 248.2 [M+H]$^+$.

Intermediate 1C

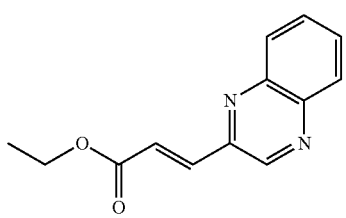

Intermediate 1C: $^1$H NMR (500 MHz, chloroform-d) δ 8.94 (s, 1H), 8.08-7.99 (m, 2H), 7.83 (d, J=15.9 Hz, 1H), 7.73 (td, J=6.3, 5.8, 3.3 Hz, 2H), 7.08 (d, J=15.9 Hz, 1H), 4.26 (q, J=7.1 Hz, 2H), 1.31 (t, J=7.1 Hz, 3H). LCMS (ES): m/z 229.1 [M+H]$^+$.

Intermediate 1D

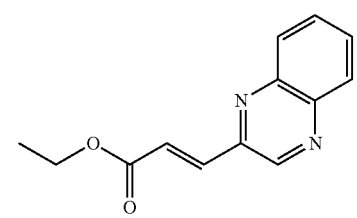

Intermediate 1D: $^1$H NMR (400 MHz, chloroform-d) δ 7.64-7.51 (d, J=16.0 Hz, 1H), 7.43-7.33 (m, 3H), 6.46 (d, J=16.0 Hz, 1H), 4.29 (q, J=7.2 Hz, 2H), 1.36 (t, J=7.1 Hz, 3H). LCMS (ES): m/z 245.1 [M+H]$^+$.

Intermediate 1E

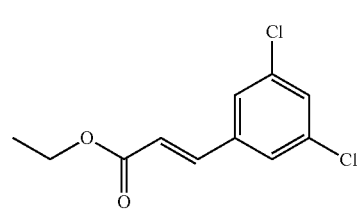

Intermediate 1E: $^1$H NMR (500 MHz, chloroform-d) δ 8.10 (d, J=1.7 Hz, 1H), 7.89-7.80 (m, 2H), 7.56 (dd, J=8.4, 1.6 Hz, 1H), 6.54 (d, J=16.0 Hz, 1H), 4.31 (q, J=7.1 Hz, 2H), 2.88 (s, 3H), 1.38 (t, J=7.1 Hz, 3H). LCMS (ES): m/z 248.0 [M+H]$^+$.

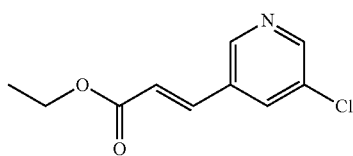

Intermediate 1F

Intermediate 1F: $^1$H NMR (400 MHz, chloroform-d) δ 8.61 (dd, J=19.0, 2.0 Hz, 2H), 7.84 (t, J=2.1 Hz, 1H), 7.64 (d, J=16.1 Hz, 1H), 6.54 (d, J=16.1 Hz, 1H), 4.31 (q, J=7.2 Hz, 2H), 1.37 (t, J=7.1 Hz, 3H). LCMS (ES): m/z 211.9 [M+H]$^+$.

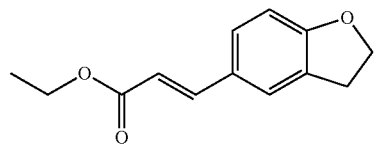

Intermediate 1G

Intermediate 1G: $^1$H NMR (400 MHz, chloroform-d) δ 7.66 (d, J=16.0 Hz, 1H), 7.43 (d, J=1.7 Hz, 1H), 7.33 (dd, J=8.6, 1.8 Hz, 1H), 6.81 (d, J=8.3 Hz, 1H), 6.30 (d, J=16.0 Hz, 1H), 4.65 (t, J=8.7 Hz, 2H), 4.28 (q, J=7.1 Hz, 2H), 3.25 (t, J=8.7 Hz, 2H), 1.36 (t, J=7.1 Hz, 3H). LCMS (ES): m/z 219.1 [M+H]$^+$.

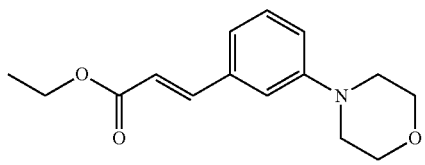

Intermediate 1H

Intermediate 1H: $^1$H NMR (500 MHz, chloroform-d) δ 7.68 (d, J=16.1 Hz, 1H), 7.31 (t, J=7.9 Hz, 1H), 7.08 (dt, J=7.6, 1.1 Hz, 1H), 7.06 (t, J=2.1 Hz, 1H), 6.97 (dd, J=8.1, 2.5 Hz, 1H), 6.44 (d, J=16.0 Hz, 1H), 4.29 (q, J=7.1 Hz, 2H), 3.93-3.82 (m, 4H), 3.25-3.13 (m, 4H), 1.36 (t, J=7.1 Hz, 3H). LCMS (ES): m/z 262.0 [M+H]$^+$.

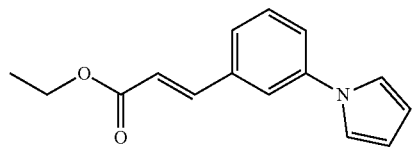

Intermediate 1I

Intermediate 1I: $^1$H NMR (500 MHz, chloroform-d) δ 7.73 (d, J=16.0 Hz, 1H), 7.56 (t, J=1.8 Hz, 1H), 7.51-7.39 (m, 3H), 7.13 (t, J=2.2 Hz, 2H), 6.51 (d, J=16.0 Hz, 1H), 6.40 (t, J=2.1 Hz, 2H), 4.31 (q, J=7.1 Hz, 2H), 1.38 (t, J=7.1 Hz, 3H). LCMS (ES): m/z 242.1 [M+H]$^+$.

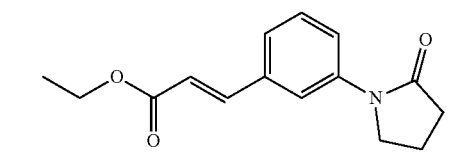

Intermediate 1J

Intermediate 1J: $^1$H NMR (500 MHz, chloroform-d) δ 7.82 (t, J=2.0 Hz, 1H), 7.74-7.66 (m, 2H), 7.41 (t, J=7.9 Hz, 1H), 7.34 (dt, J=7.7, 1.3 Hz, 1H), 6.48 (d, J=16.0 Hz, 1H), 4.29 (q, J=7.1 Hz, 2H), 3.91 (t, J=7.1 Hz, 2H), 2.66 (t, J=8.1 Hz, 2H), 2.28-2.14 (m, 2H), 1.37 (t, J=7.1 Hz, 3H). LCMS (ES): m/z 260.1 [M+H]$^+$.

Intermediate 1K

Intermediate 1K: $^1$H NMR (500 MHz, chloroform-d) δ 7.72 (s, 1H), 7.62-7.54 (m, 2H), 6.18 (d, J=16.0 Hz, 1H), 4.25 (q, J=7.1 Hz, 2H), 4.10 (t, J=7.0 Hz, 2H), 1.92 (h, J=7.3 Hz, 2H), 1.34 (t, J=7.1 Hz, 3H), 0.95 (t, J=7.4 Hz, 3H). LCMS (ES): m/z 209.2 [M+H]$^+$.

Intermediate 1L

Intermediate 1L: $^1$H NMR (500 MHz, chloroform-d) δ 7.61 (dd, J=9.6, 2.5 Hz, 1H), 7.47 (d, J=2.5 Hz, 1H), 7.42 (d, J=15.9 Hz, 1H), 6.64 (d, J=9.5 Hz, 1H), 6.17 (d, J=15.8 Hz, 1H), 4.27 (q, J=7.1 Hz, 2H), 3.60 (s, 3H), 1.35 (t, J=7.1 Hz, 3H). LCMS (ES): m/z 208.1 [M+H]$^+$.

Intermediate 1M

Intermediate 1M: $^1$H NMR (500 MHz, chloroform-d) δ 7.44 (d, J=15.9 Hz, 1H), 7.30 (d, J=9.1 Hz, 1H), 6.66 (d, J=1.8 Hz, 1H), 6.45 (d, J=15.9 Hz, 1H), 6.31 (dd, J=7.1, 2.0 Hz, 1H), 4.30 (q, J=7.1 Hz, 2H), 3.57 (s, 3H), 1.36 (t, J=7.1 Hz, 3H). LCMS (ES): m/z 208.1 [M+H]$^+$.

Intermediate 1N

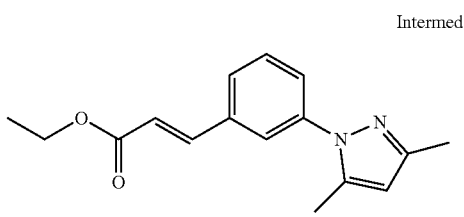

Intermediate 1N: $^1$H NMR (500 MHz, chloroform-d) δ 7.72 (d, J=16.0 Hz, 1H), 7.64 (d, J=2.2 Hz, 1H), 7.54-7.44 (m, 3H), 6.50 (d, J=16.0 Hz, 1H), 6.04 (s, 1H), 4.29 (q, J=7.1 Hz, 2H), 2.35 (s, 3H), 2.33 (s, 3H), 1.36 (t, J=7.1 Hz, 3H). LCMS (ES): m/z 271.1 [M+H]$^+$.

Intermediate 1O

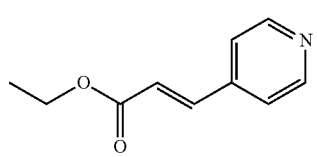

Intermediate 1O: $^1$H NMR (500 MHz, chloroform-d) δ 8.71-8.65 (m, 2H), 7.62 (d, J=16.0 Hz, 1H), 7.41-7.35 (m, 2H), 6.62 (d, J=16.0 Hz, 1H), 4.32 (q, J=7.1 Hz, 2H), 1.38 (t, J=7.1 Hz, 3H). LCMS (ES): m/z 178.2 [M+H]$^+$.

Intermediate 1P

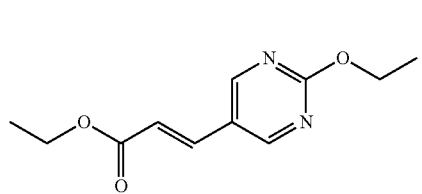

Intermediate 1P: $^1$H NMR (500 MHz, chloroform-d) δ 8.68 (s, 2H), 7.59 (d, J=16.1 Hz, 1H), 6.46 (d, J=16.2 Hz, 1H), 4.50 (q, J=7.1 Hz, 2H), 4.30 (q, J=7.1 Hz, 2H), 1.47 (t, J=7.0 Hz, 3H), 1.36 (t, J=7.1 Hz, 3H). LCMS (ES): m/z 223.2 [M+H]$^+$.

Intermediate 1Q

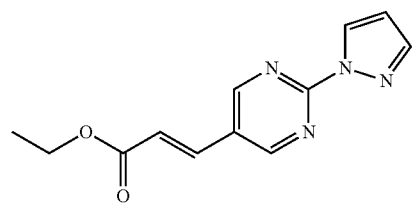

Intermediate 1Q: $^1$H NMR (500 MHz, chloroform-d) δ 8.90 (s, 2H), 8.63 (d, J=2.6 Hz, 1H), 7.89 (d, J=1.4 Hz, 1H), 7.66 (d, J=16.2 Hz, 1H), 6.60 (d, J=16.1 Hz, 1H), 6.56 (dd, J=2.7, 1.6 Hz, 1H), 4.33 (q, J=7.1 Hz, 2H), 1.38 (t, J=7.1 Hz, 3H).
LCMS (ES): m/z 245.1 [M+H]$^+$.

Intermediate 1R

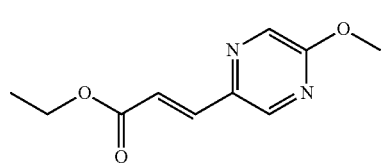

Intermediate 1R: $^1$H NMR (500 MHz, chloroform-d) δ 8.26 (d, J=1.3 Hz, 1H), 8.18 (d, J=1.3 Hz, 1H), 7.67 (d, J=15.7 Hz, 1H), 6.86 (d, J=15.6 Hz, 1H), 4.30 (q, J=7.1 Hz, 2H), 4.03 (s, 3H), 1.36 (t, J=7.1 Hz, 3H). LCMS (ES): m/z 209.1 [M+H]$^+$.

Intermediate 1S

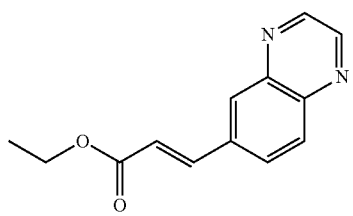

Intermediate 1S: $^1$H NMR (500 MHz, chloroform-d) δ 8.90 (d, J=1.9 Hz, 1H), 8.88 (d, J=1.8 Hz, 1H), 8.23 (d, J=2.0 Hz, 1H), 8.14 (d, J=8.7 Hz, 1H), 7.99 (dd, J=8.7, 2.0 Hz, 1H), 7.91 (d, J=16.0 Hz, 1H), 6.67 (d, J=16.0 Hz, 1H), 4.34 (q, J=7.1 Hz, 2H), 1.40 (t, J=7.1 Hz, 3H). LCMS (ES): m/z 229.2 [M+H]$^+$.

Intermediate 1T

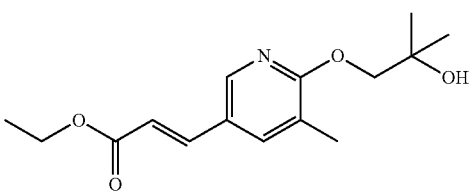

Intermediate 1T: $^1$H NMR (500 MHz, chloroform-d) δ 7.53 (dd, J=2.6, 1.3 Hz, 1H), 7.47-7.37 (m, 2H), 6.19 (d, J=15.9 Hz, 1H), 4.27 (q, J=7.1 Hz, 2H), 4.07 (s, 2H), 3.59 (s, 1H), 2.22 (d, J=1.2 Hz, 3H), 1.35 (t, J=7.1 Hz, 3H), 1.30 (s, 6H). LCMS (ES): m/z 280.2 [M+H]$^+$.

Intermediate 1U

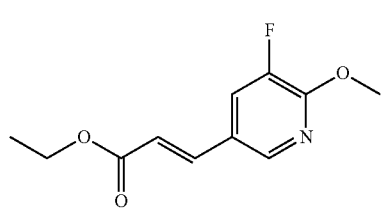

Intermediate 1U: $^1$H NMR (500 MHz, chloroform-d) δ 8.07 (d, J=2.1 Hz, 1H), 7.64 (dd, J=16.0, 1.6 Hz, 1H), 7.53 (dd, J=10.8, 2.1 Hz, 1H), 6.34 (d, J=16.0 Hz, 1H), 4.30 (q, J=7.1 Hz, 2H), 4.09 (s, 3H), 1.37 (t, J=7.1 Hz, 3H). LCMS (ES): m/z 226.2 [M+H]$^+$.

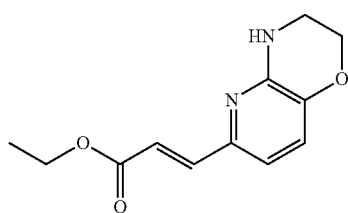

Intermediate 1V

Intermediate 1V: $^1$H NMR (500 MHz, chloroform-d) δ 7.49 (d, J=15.5 Hz, 1H), 6.96 (d, J=7.9 Hz, 1H), 6.74 (d, J=7.9 Hz, 1H), 6.68 (d, J=15.6 Hz, 1H), 4.33-4.20 (m, 5H), 3.59 (td, J=4.5, 2.3 Hz, 2H), 1.34 (t, J=7.1 Hz, 3H). LCMS (ES): m/z 235.2 [M+H]$^+$.

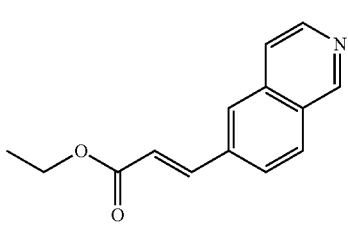

Intermediate 1W

Intermediate 1W: $^1$H NMR (500 MHz, chloroform-d) δ 9.28 (s, 1H), 8.60 (d, J=5.7 Hz, 1H), 8.01 (d, J=8.5 Hz, 1H), 7.93 (d, J=1.5 Hz, 1H), 7.86 (d, J=16.1 Hz, 1H), 7.81 (dd, J=8.6, 1.7 Hz, 1H), 7.69 (d, J=5.6 Hz, 1H), 6.64 (d, J=16.0 Hz, 1H), 4.33 (q, J=7.1 Hz, 2H), 1.39 (t, J=7.1 Hz, 3H). LCMS (ES): m/z 228.1 [M+H]$^+$.

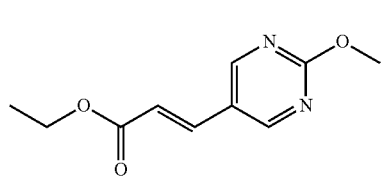

Intermediate 1X

Intermediate 1X: $^1$H NMR (500 MHz, chloroform-d) δ 8.69 (s, 2H), 7.60 (d, J=16.2 Hz, 1H), 6.47 (d, J=16.2 Hz, 1H), 4.30 (q, J=7.1 Hz, 2H), 4.08 (s, 3H), 1.37 (t, J=7.1 Hz, 3H). LCMS (ES): m/z 209.2 [M+H]$^+$.

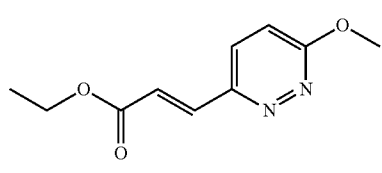

Intermediate 1Y

Intermediate 1Y: $^1$H NMR (500 MHz, chloroform-d) δ 7.86 (d, J=16.2 Hz, 1H), 7.58 (d, J=9.2 Hz, 1H), 7.02 (d, J=9.1 Hz, 1H), 6.78 (d, J=16.2 Hz, 1H), 4.32 (q, J=7.1 Hz, 2H), 4.21 (s, 3H), 1.38 (t, J=7.1 Hz, 3H). LCMS (ES): m/z 209.3 [M+H]$^+$.

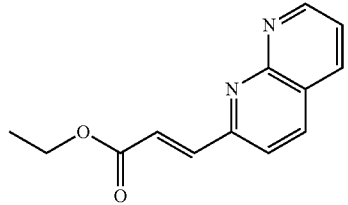

Intermediate 1Z

Intermediate 1Z: $^1$H NMR (500 MHz, chloroform-d) δ 9.19 (dd, J=4.2, 2.1 Hz, 1H), 8.26 (d, J=8.3 Hz, 1H), 8.22 (dd, J=8.1, 2.0 Hz, 1H), 7.93 (d, J=15.8 Hz, 1H), 7.71 (d, J=8.3 Hz, 1H), 7.53 (dd, J=8.1, 4.2 Hz, 1H), 7.22 (d, J=15.9 Hz, 1H), 4.33 (q, J=7.1 Hz, 2H), 1.31 (t, J=7.1 Hz, 3H). LCMS (ES): m/z 229.2 [M+H]$^+$.

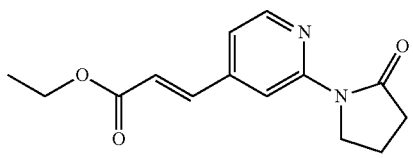

Intermediate 1AA

Intermediate 1AA: $^1$H NMR (500 MHz, chloroform-d) δ 8.60-8.56 (m, 1H), 8.39 (d, J=5.2 Hz, 1H), 7.65 (d, J=16.1 Hz, 1H), 7.14 (dd, J=5.3, 1.5 Hz, 1H), 6.64 (d, J=16.1 Hz, 1H), 4.30 (q, J=7.1 Hz, 2H), 4.18-4.08 (m, 2H), 2.71 (t, J=8.1 Hz, 2H), 2.23-2.10 (m, 2H), 1.37 (t, J=7.1 Hz, 3H). LCMS (ES): m/z 261.2 [M+H]$^+$.

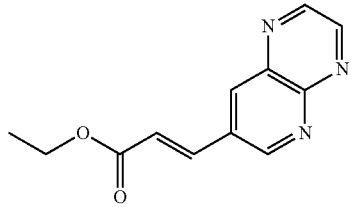

Intermediate 1AB

Intermediate 1AB: $^1$H NMR (500 MHz, chloroform-d) δ 9.38 (d, J=2.4 Hz, 1H), 9.10 (d, J=1.7 Hz, 1H), 9.01 (d, J=1.7 Hz, 1H), 8.57 (d, J=2.5 Hz, 1H), 7.92 (d, J=16.2 Hz, 1H), 6.80 (d, J=16.1 Hz, 1H), 4.36 (q, J=7.1 Hz, 2H), 1.41 (t, J=7.1 Hz, 3H).
LCMS (ES): m/z 230.2 [M+H]$^+$.

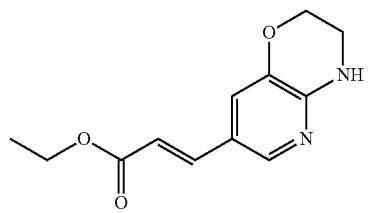

Intermediate 1AC

Intermediate 1AC: $^1$H NMR (500 MHz, chloroform-d) δ 7.82 (d, J=2.1 Hz, 1H), 7.58 (d, J=16.0 Hz, 1H), 7.19 (d, J=2.1 Hz, 1H), 6.22 (d, J=15.9 Hz, 1H), 5.34 (s, 1H), 4.31-4.20 (m, 4H), 3.63 (td, J=4.6, 2.2 Hz, 2H), 1.35 (t, J=7.1 Hz, 3H). LCMS (ES): m/z 235.2 [M+H]⁺.

Intermediate 1AD

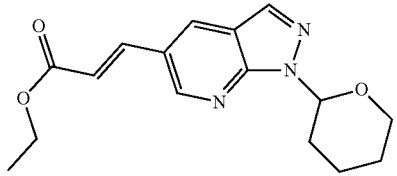

Intermediate 1AD: ¹H NMR (500 MHz, chloroform-d) δ 8.75 (d, J=2.0 Hz, 1H), 8.22 (d, J=2.2 Hz, 1H), 8.13 (s, 1H), 7.82 (d, J=16.0 Hz, 1H), 6.53 (d, J=16.0 Hz, 1H), 6.14 (dd, J=10.5, 2.6 Hz, 1H), 4.31 (q, J=7.1 Hz, 2H), 4.18-4.10 (m, 1H), 3.85 (tt, J=11.5, 2.5 Hz, 1H), 2.25-2.11 (m, 1H), 2.05-1.97 (m, 1H), 1.89-1.75 (m, 2H), 1.73-1.61 (m, 2H), 1.37 (t, J=7.1 Hz, 3H). LCMS (ES): m/z 302.1 [M+H]⁺.

Intermediate 1AE

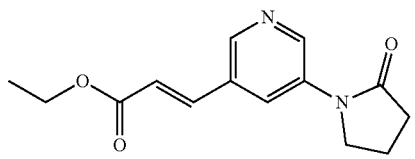

Intermediate 1AE: ¹H NMR (500 MHz, chloroform-d) δ 8.72 (d, J=2.5 Hz, 1H), 8.54 (d, J=1.9 Hz, 1H), 8.48 (t, J=2.3 Hz, 1H), 7.71 (d, J=16.2 Hz, 1H), 6.57 (d, J=16.1 Hz, 1H), 4.31 (q, J=7.1 Hz, 2H), 3.95 (t, J=7.1 Hz, 2H), 2.68 (t, J=8.1 Hz, 2H), 2.32-2.21 (m, 2H), 1.37 (t, J=7.1 Hz, 3H). LCMS (ES): m/z 261.2 [M+H]⁺.

Intermediate 1AF

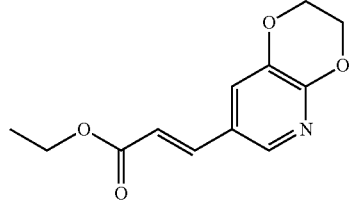

Intermediate 1AF: ¹H NMR (500 MHz, chloroform-d) δ 7.98 (d, J=2.2 Hz, 1H), 7.61 (d, J=16.0 Hz, 1H), 7.38 (d, J=2.1 Hz, 1H), 6.35 (d, J=16.0 Hz, 1H), 4.53-4.47 (m, 2H), 4.34-4.23 (m, 4H), 1.36 (t, J=7.1 Hz, 3H). LCMS (ES): m/z 236.0 [M+H]⁺.

Intermediate 1AG

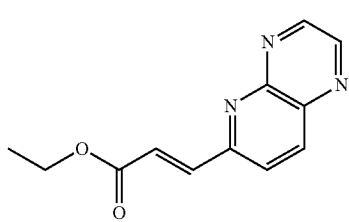

Intermediate 1AG: ¹H NMR (500 MHz, chloroform-d) δ 9.13 (d, J=1.7 Hz, 1H), 8.97 (d, J=1.8 Hz, 1H), 8.53 (d, J=8.6 Hz, 1H), 7.99-7.90 (m, 2H), 7.23 (d, J=15.9 Hz, 1H), 4.35 (q, J=7.1 Hz, 2H), 1.40 (t, J=7.1 Hz, 3H). LCMS (ES): m/z 230.2 [M+H]⁺.

Intermediate 1AH

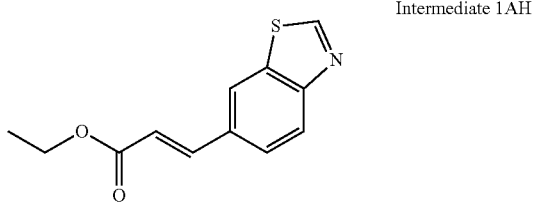 [SMILES: CCOC(=O)/C=C/c1ccc2ncsc2c1]

Intermediate 1AH: ¹H NMR (500 MHz, chloroform-d) δ 9.07 (s, 1H), 8.16 (d, J=8.5 Hz, 1H), 8.13 (d, J=1.7 Hz, 1H), 7.83 (d, J=16.0 Hz, 1H), 7.74 (dd, J=8.5, 1.8 Hz, 1H), 6.55 (d, J=16.1 Hz, 1H), 4.32 (q, J=7.1 Hz, 2H), 1.38 (td, J=7.2, 1.4 Hz, 3H). LCMS (ES): m/z 234.1 [M+H]⁺.

Intermediate 1AI

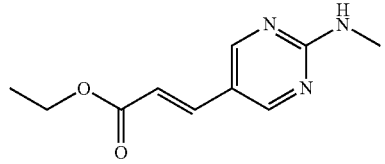

Intermediate 1AI: ¹H NMR (500 MHz, chloroform-d) δ 8.49 (s, 2H), 7.52 (d, J=16.2 Hz, 1H), 6.33 (d, J=16.1 Hz, 1H), 5.40 (s, 1H), 4.28 (q, J=7.1 Hz, 2H), 3.08 (d, J=5.1 Hz, 3H), 1.36 (t, J=7.1 Hz, 3H). LCMS (ES): m/z 208.3 [M+H]⁺.

Intermediate 1AJ

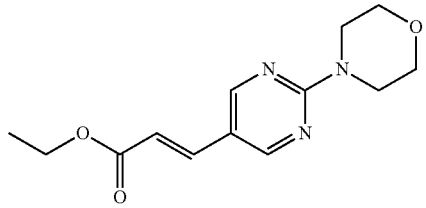

Intermediate 1AJ: ¹H NMR (500 MHz, chloroform-d) δ 8.50 (s, 2H), 7.52 (d, J=16.0 Hz, 1H), 6.33 (d, J=16.0 Hz, 1H), 4.28 (q, J=7.1 Hz, 2H), 3.90 (dd, J=5.7, 4.0 Hz, 4H), 3.79 (dd, J=5.7, 4.1 Hz, 4H), 1.36 (t, J=7.1 Hz, 3H). LCMS (ES): m/z 264.2 [M+H]⁺.

Intermediate 1AK

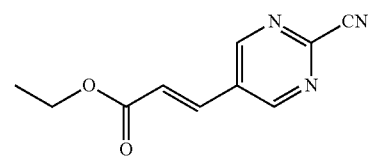

Intermediate 1AK: ¹H NMR (500 MHz, chloroform-d) δ 8.98 (s, 2H), 7.64 (d, J=16.2 Hz, 1H), 6.70 (d, J=16.2 Hz, 1H), 4.34 (q, J=7.1 Hz, 2H), 1.39 (t, J=7.1 Hz, 3H). LCMS (ES): m/z 204.4 [M+H]⁺.

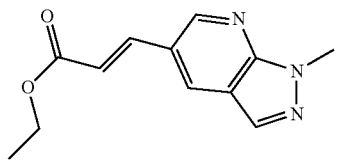

Intermediate 1AL

Intermediate 1AL: $^1$H NMR (500 MHz, chloroform-d) δ 8.75 (d, J=2.0 Hz, 1H), 8.22 (d, J=2.1 Hz, 1H), 8.07 (s, 1H), 7.84 (d, J=16.1 Hz, 1H), 6.54 (d, J=16.1 Hz, 1H), 4.32 (q, J=7.2 Hz, 2H), 4.20 (s, 3H), 1.39 (t, J=7.1 Hz, 3H). LCMS (ES): m/z 232.4 [M+H]$^+$.

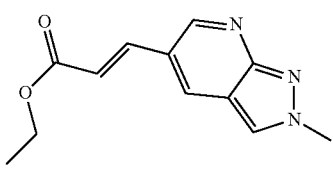

Intermediate 1AM

Intermediate 1AM: $^1$H NMR (500 MHz, chloroform-d) δ 8.93 (d, J=2.2 Hz, 1H), 8.15 (d, J=2.2 Hz, 1H), 7.99 (s, 1H), 7.79 (d, J=16.0 Hz, 1H), 6.55 (d, J=16.0 Hz, 1H), 4.35-4.30 (m, 2H), 4.30 (s, 3H), 1.38 (t, J=7.1 Hz, 3H). LCMS (ES): m/z 232.4 [M+H]$^+$.

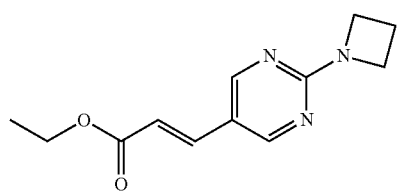

Intermediate 1AN

Intermediate 1AN: $^1$H NMR (500 MHz, chloroform-d) δ 8.48 (s, 2H), 7.51 (d, J=16.0 Hz, 1H), 6.31 (d, J=16.0 Hz, 1H), 4.27 (dt, J=15.1, 7.3 Hz, 6H), 2.45 (p, J=7.6 Hz, 2H), 1.35 (t, J=7.1 Hz, 3H). LCMS (ES): m/z 234.4 [M+H]$^+$.

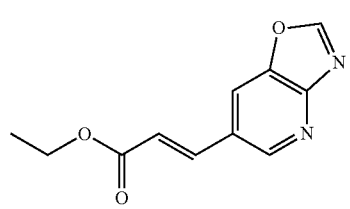

Intermediate 1AO

Intermediate 1AO: $^1$H NMR (500 MHz, chloroform-d) δ 8.81 (d, J=1.9 Hz, 1H), 8.41 (s, 1H), 8.08 (d, J=1.9 Hz, 1H), 7.84 (d, J=16.2 Hz, 1H), 6.59 (d, J=16.1 Hz, 1H), 4.33 (q, J=7.1 Hz, 2H), 1.39 (t, J=7.1 Hz, 3H). LCMS (ES): m/z 219.2 [M+H]$^+$.

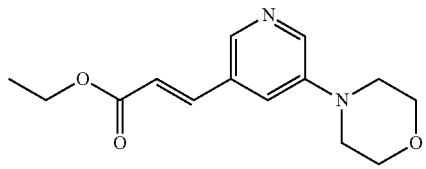

Intermediate 1AP

Intermediate 1AP: $^1$H NMR (500 MHz, chloroform-d) δ 8.32 (d, J=2.8 Hz, 1H), 8.28 (d, J=1.8 Hz, 1H), 7.66 (d, J=16.0 Hz, 1H), 7.27 (t, J=2.3 Hz, 1H), 6.50 (d, J=16.0 Hz, 1H), 4.30 (q, J=7.1 Hz, 2H), 3.98-3.84 (m, 4H), 3.28-3.20 (m, 4H), 1.37 (t, J=7.1 Hz, 3H). LCMS (ES): m/z 263.2 [M+H]$^+$.

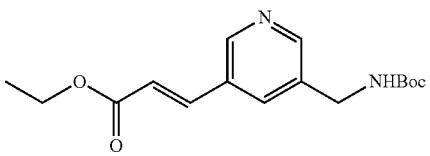

Intermediate 1AR

Intermediate 1AR: $^1$H NMR (500 MHz, chloroform-d) δ 8.67 (d, J=2.2 Hz, 1H), 8.55 (d, J=2.0 Hz, 1H), 7.78 (t, J=2.2 Hz, 1H), 7.69 (d, J=16.1 Hz, 1H), 6.53 (d, J=16.0 Hz, 1H), 4.96 (s, 1H), 4.39 (d, J=6.2 Hz, 2H), 4.31 (q, J=7.1 Hz, 2H), 1.49 (s, 9H), 1.37 (t, J=7.1 Hz, 3H). LCMS (ES): m/z 307.1 [M+H]$^+$.

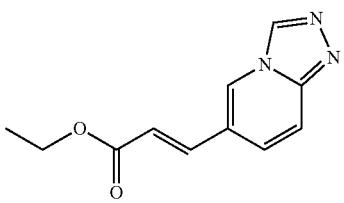

Intermediate 1AS

Intermediate 1AS: $^1$H NMR (500 MHz, chloroform-d) δ 8.87 (s, 1H), 8.26 (s, 1H), 7.84 (d, J=9.6 Hz, 1H), 7.63 (d, J=15.9 Hz, 1H), 7.52 (dd, J=9.6, 1.6 Hz, 1H), 6.51 (d, J=15.9 Hz, 1H), 4.32 (q, J=7.1 Hz, 2H), 1.38 (t, J=7.1 Hz, 3H). LCMS (ES): m/z 218.4 [M+H]$^+$.

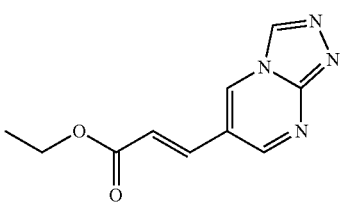

Intermediate 1AT

Intermediate 1AT: LCMS (ES): m/z 219.2 [M+H]$^+$.

Intermediate 1AU

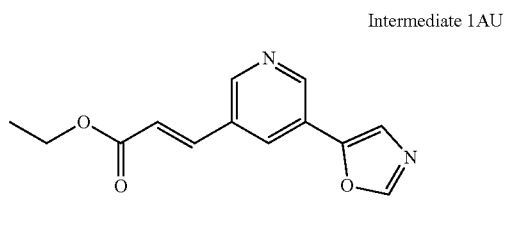 [SMILES: CCOC(=O)/C=C/c1cncc(-c2cnco2)c1]

Intermediate 1AU: ¹H NMR (500 MHz, chloroform-d) δ 8.94 (d, J=2.1 Hz, 1H), 8.73 (d, J=2.0 Hz, 1H), 8.09 (t, J=2.1 Hz, 1H), 8.03 (s, 1H), 7.73 (d, J=16.2 Hz, 1H), 7.54 (s, 1H), 6.62 (d, J=16.0 Hz, 1H), 4.33 (q, J=7.1 Hz, 2H), 1.39 (t, J=7.1 Hz, 3H). LCMS (ES): m/z 245.4 [M+H]$^+$.

Intermediate 1AV

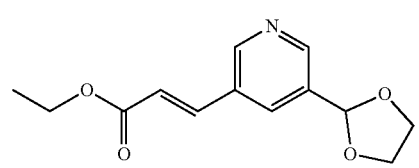

Intermediate 1AV: ¹H NMR (500 MHz, MeOH-d$_4$) δ 8.74 (d, J=2.1 Hz, 1H), 8.62 (d, J=2.0 Hz, 1H), 8.13 (d, J=2.2 Hz, 1H), 7.71 (d, J=16.1 Hz, 1H), 6.68 (d, J=16.4 Hz, 1H), 5.87 (s, 1H), 4.31-4.22 (m, 2H), 4.19-4.00 (m, 4H), 1.34 (t, J=7.2 Hz, 3H). LCMS (ES): m/z 250.2 [M+H]$^+$.

Intermediate 1AW

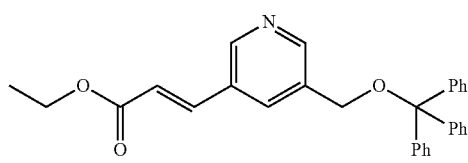

Intermediate 1AW: ¹H NMR (400 MHz, chloroform-d) δ 8.64 (d, J=2.1 Hz, 1H), 8.56 (d, J=2.0 Hz, 1H), 7.78-7.74 (m, 1H), 7.67 (d, J=16.1 Hz, 1H), 7.54-7.45 (m, 6H), 7.36-7.30 (m, 6H), 7.28 (t, J=1.4 Hz, 1H), 7.26 (m, 2H), 6.49 (d, J=16.2 Hz, 1H), 4.29 (m, 4H), 1.35 (t, J=7.1 Hz, 3H). LCMS (ES): m/z 450.4 [M+H]$^+$.

Intermediate 1AX

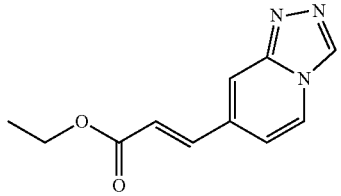

Intermediate 1AX: ¹H NMR (500 MHz, chloroform-d) δ 8.86 (s, 1H), 8.15 (d, J=7.2 Hz, 1H), 7.89 (s, 1H), 7.69 (d, J=16.0 Hz, 1H), 7.07 (dd, J=7.2, 1.4 Hz, 1H), 6.54 (d, J=16.0 Hz, 1H), 4.33 (q, J=7.1 Hz, 2H), 1.39 (t, J=7.1 Hz, 3H). LCMS (ES): m/z 218.4 [M+H]$^+$.

Intermediate 1AY

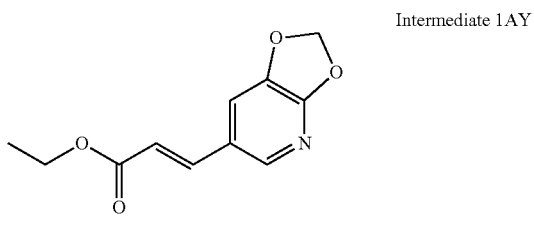 [SMILES: CCOC(=O)/C=C/c1cnc2c(c1)OCO2]

Intermediate 1AY: ¹H NMR (400 MHz, MeOH-d$_4$) δ 7.76 (d, J=1.9 Hz, 1H), 7.61 (d, J=16.0 Hz, 1H), 7.48 (d, J=1.8 Hz, 1H), 6.45 (d, J=16.0 Hz, 1H), 6.16 (s, 2H), 4.23 (q, J=7.1 Hz, 2H), 1.31 (t, J=7.1 Hz, 3H). LCMS (ES): m/z 222.2 [M+H]$^+$.

Intermediate 1AZ

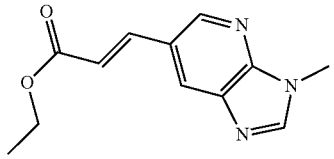

Intermediate 1AZ: ¹H NMR (500 MHz, chloroform-d) δ 8.57 (d, J=2.0 Hz, 1H), 8.24 (d, J=1.9 Hz, 1H), 8.07 (s, 1H), 7.84 (d, J=16.0 Hz, 1H), 6.53 (d, J=16.1 Hz, 1H), 4.29 (q, J=7.1 Hz, 2H), 3.93 (s, 3H), 1.36 (t, J=7.2 Hz, 3H). LCMS (ES): m/z 232.2 [M+H]$^+$.

Intermediate 1BA

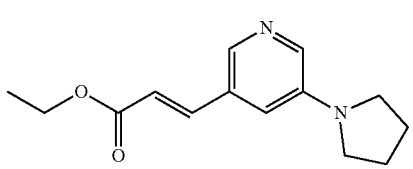

Intermediate 1BA: ¹H NMR (500 MHz, chloroform-d) δ 8.06 (d, J=1.7 Hz, 1H), 7.98 (d, J=2.7 Hz, 1H), 7.63 (d, J=16.0 Hz, 1H), 6.88 (t, J=2.3 Hz, 1H), 6.47 (d, J=16.0 Hz, 1H), 4.27 (q, J=7.1 Hz, 2H), 3.37-3.26 (m, 4H), 2.09-2.00 (m, 4H), 1.34 (t, J=7.1 Hz, 3H). LCMS (ES): m/z 247.2 [M+H]$^+$.

Intermediate 1BB

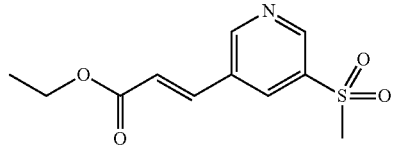

Intermediate 1BB: ¹H NMR (500 MHz, chloroform-d) δ 9.12 (d, J=2.1 Hz, 1H), 8.98 (d, J=2.1 Hz, 1H), 8.34 (t, J=2.2 Hz, 1H), 7.71 (d, J=16.1 Hz, 1H), 6.63 (d, J=16.2 Hz, 1H), 4.30 (q, J=7.1 Hz, 2H), 3.14 (s, 3H), 1.36 (t, J=7.1 Hz, 3H). LCMS (ES): m/z 256.1 [M+H]$^+$.

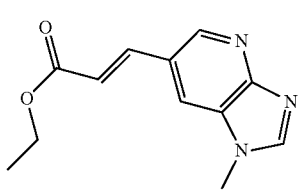

Intermediate 1BC

Intermediate 1BC: ¹H NMR (500 MHz, chloroform-d) δ 8.75 (d, J=2.2 Hz, 1H), 8.13 (s, 1H), 7.87 (d, J=2.0 Hz, 1H), 7.84 (d, J=16.0 Hz, 1H), 6.55 (d, J=16.0 Hz, 1H), 4.29 (q, J=7.1 Hz, 2H), 3.91 (s, 3H), 1.36 (t, J=7.1 Hz, 3H). LCMS (ES): m/z 232.2 [M+H]$^+$.

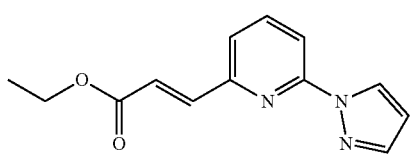

Intermediate 1BD

Intermediate 1BD: ¹H NMR (400 MHz, chloroform-d) δ 8.65 (dd, J=2.6, 0.7 Hz, 1H), 7.99 (dd, J=8.3, 0.9 Hz, 1H), 7.83 (dd, J=8.3, 7.5 Hz, 1H), 7.75 (dd, J=1.7, 0.8 Hz, 1H), 7.66 (d, J=15.5 Hz, 1H), 7.28 (dd, J=7.6, 0.9 Hz, 1H), 7.01 (d, J=15.6 Hz, 1H), 6.48 (dd, J=2.6, 1.7 Hz, 1H), 4.30 (q, J=7.1 Hz, 2H), 1.37 (t, J=7.1 Hz, 3H). LCMS (ES): m/z 244.1 [M+H]$^+$.

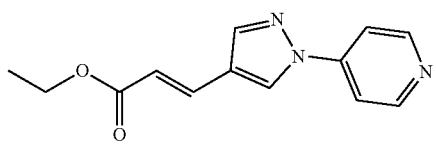

Intermediate 1BE

Intermediate 1BE: ¹H NMR (400 MHz, chloroform-d) δ 8.74-8.67 (m, 2H), 8.17 (s, 1H), 7.97 (s, 1H), 7.65-7.62 (m, 2H), 7.59 (d, J=16.0 Hz, 1H), 6.32 (d, J=16.0 Hz, 1H), 4.27 (q, J=7.1 Hz, 2H), 1.34 (t, J=7.1 Hz, 3H). LCMS (ES): m/z 244.1 [M+H]$^+$.

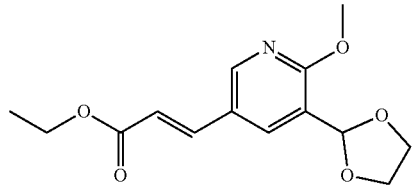

Intermediate 1BF

Intermediate 1BF: LCMS (ES): m/z 232.1 [M+H]$^+$.

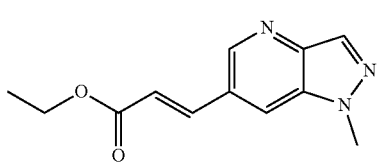

Intermediate 1BG

Intermediate 1BG: ¹H NMR (500 MHz, chloroform-d) δ 8.79 (d, J=1.9 Hz, 1H), 8.25 (d, J=1.0 Hz, 1H), 7.91-7.81 (m, 2H), 6.66 (d, J=16.2 Hz, 1H), 4.33 (q, J=7.1 Hz, 2H), 4.15 (s, 3H), 1.39 (t, J=7.1 Hz, 3H). LCMS (ES): m/z 232.1 [M+H]$^+$.

Intermediate 1BH

Intermediate 1BH: ¹H NMR (500 MHz, chloroform-d) δ 8.79 (d, J=1.9 Hz, 1H), 8.21 (s, 1H), 8.14 (d, J=1.8 Hz, 1H), 7.83 (d, J=16.0 Hz, 1H), 6.62 (d, J=16.1 Hz, 1H), 4.33 (q, J=7.1 Hz, 2H), 4.31 (s, 3H), 1.39 (t, J=7.1 Hz, 3H). LCMS (ES): m/z 232.1 [M+H]$^+$.

Intermediate 1BI

Intermediate 1BI: ¹H NMR (500 MHz, chloroform-d) δ 8.80-8.74 (m, 1H), 8.19-8.14 (m, 1H), 7.93-7.82 (m, 2H), 6.61-6.52 (m, 1H), 4.32 (q, J=7.2 Hz, 2H), 3.93 (s, 3H), 1.38 (t, J=7.0 Hz, 3H). LCMS (ES): m/z 232.2 [M+H]$^+$.

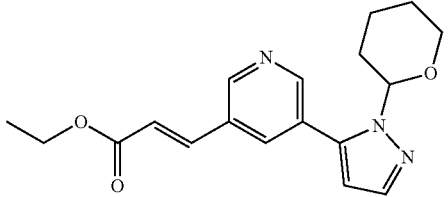

Intermediate 1BJ

Intermediate 1BJ: LCMS (ES): m/z 328.1 [M+H]$^+$.

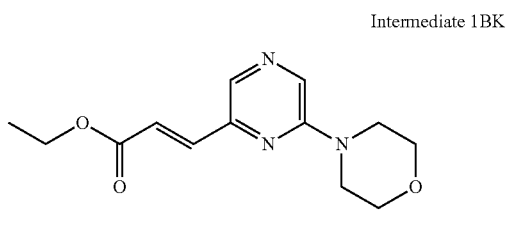 [SMILES: CCOC(=O)/C=C/c1cncc(N2CCOCC2)n1]

Intermediate 1BK

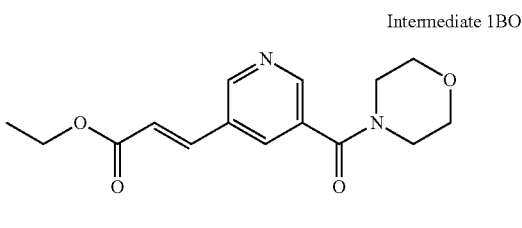 [SMILES: CCOC(=O)/C=C/c1cncc(C(=O)N2CCOCC2)c1]

Intermediate 1BO

Intermediate 1BK: $^1$H NMR (500 MHz, chloroform-d) δ 8.16-8.11 (m, 1H), 8.00-7.92 (m, 1H), 7.60-7.50 (m, 1H), 7.00-6.87 (m, 1H), 4.28 (q, J=7.3 Hz, 2H), 3.89-3.80 (m, 4H), 3.70-3.59 (m, 4H), 1.35 (t, J=7.2 Hz, 3H). LCMS (ES): m/z 264.1 [M+H]$^+$.

Intermediate 1BO: $^1$H NMR (500 MHz, chloroform-d) δ 8.86-8.74 (m, 1H), 8.70-8.58 (m, 1H), 7.96-7.84 (m, 1H), 7.75-7.62 (m, 1H), 6.62-6.49 (m, 1H), 4.36-4.24 (m, 2H), 3.97-3.40 (m, 8H), 1.42-1.31 (m, 3H). LCMS (ES): m/z 291.1 [M+H]$^+$.

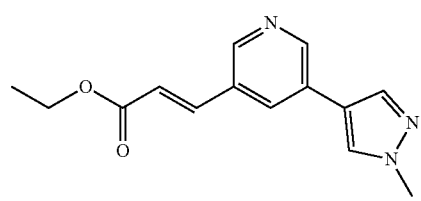

Intermediate 1BL

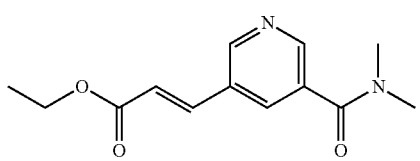

Intermediate 1BP

Intermediate 1BL: $^1$H NMR (400 MHz, chloroform-d) δ 8.72 (d, J=2.1 Hz, 1H), 8.58 (d, J=2.0 Hz, 1H), 7.86 (t, J=2.2 Hz, 1H), 7.81 (d, J=0.9 Hz, 1H), 7.69 (m, 1H), 7.69 (d, J=16.2 Hz, 1H), 6.55 (d, J=16.1 Hz, 1H), 4.29 (q, J=7.1 Hz, 2H), 3.98 (s, 3H), 1.36 (t, J=7.1 Hz, 3H). LCMS (ES): m/z 258.1 [M+H]$^+$.

Intermediate 1BP: $^1$H NMR (500 MHz, chloroform-d) δ 8.79 (d, J=1.9 Hz, 1H), 8.67 (d, J=1.9 Hz, 1H), 7.93 (t, J=1.9 Hz, 1H), 7.69 (d, J=16.2 Hz, 1H), 6.56 (d, J=16.2 Hz, 1H), 4.35-4.25 (m, 2H), 3.25-3.10 (m, 3H), 3.10-3.00 (m, 3H), 2.99-2.87 (m, 2H), 1.37 (t, J=7.2 Hz, 3H). LCMS (ES): m/z 249.1 [M+H]$^+$.

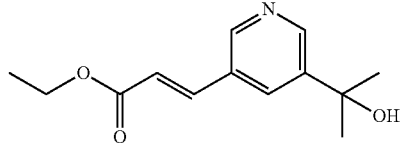

Intermediate 1BM

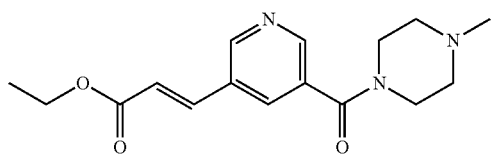

Intermediate 1BQ

Intermediate 1BM: $^1$H NMR (400 MHz, chloroform-d) δ 8.73-8.66 (m, 1H), 8.62-8.55 (m, 1H), 8.05-7.98 (m, 1H), 7.67 (d, J=16.1 Hz, 1H), 6.60-6.45 (m, 1H), 4.33-4.20 (m, 2H), 1.63 (s, 6H), 1.34 (t, J=7.2 Hz, 3H). LCMS (ES): m/z 236.1 [M+H]$^+$.

Intermediate 1BQ: $^1$H NMR (500 MHz, chloroform-d) δ 8.84-8.76 (m, 1H), 8.68-8.62 (m, 1H), 7.91 (t, J=2.1 Hz, 1H), 7.75-7.65 (m, 1H), 6.61-6.51 (m, 1H), 4.35-4.27 (m, 2H), 3.95-3.78 (m, 2H), 3.55-3.38 (m, 2H), 2.61-2.38 (m, 4H), 2.36 (s, 3H), 1.37 (t, J=7.2 Hz, 3H). LCMS (ES): m/z 304.1 [M+H]$^+$.

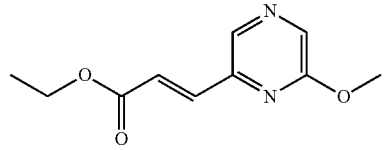

Intermediate 1BN

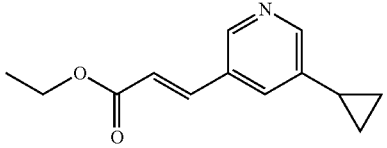

Intermediate 1BR

Intermediate 1BN: $^1$H NMR (400 MHz, chloroform-d) δ 8.25-8.17 (m, 2H), 7.67-7.60 (m, 1H), 7.04 (d, J=15.4 Hz, 1H), 4.37-4.27 (m, 2H), 4.07-3.98 (m, 3H), 1.38 (t, J=7.2 Hz, 3H). LCMS (ES): m/z 209.0 [M+H]$^+$.

Intermediate 1BR: $^1$H NMR (500 MHz, chloroform-d) δ 8.59-8.47 (m, 1H), 8.47-8.37 (m, 1H), 7.70-7.61 (m, 1H), 7.49-7.42 (m, 1H), 6.57-6.43 (m, 1H), 4.30 (q, J=7.2 Hz, 2H), 2.01-1.89 (m, 1H), 1.42-1.32 (m, 3H), 1.13-1.07 (m, 2H), 0.81-0.75 (m, 2H). LCMS (ES): m/z 218.2 [M+H]$^+$.

Intermediate 1BS

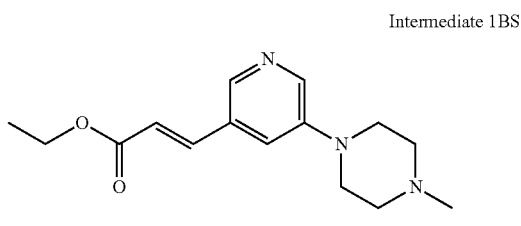 [SMILES: CCOC(=O)/C=C/c1cncc(N2CCN(C)CC2)c1]

Intermediate 1BS: $^1$H NMR (500 MHz, chloroform-d) δ 8.39-8.30 (m, 1H), 8.30-8.21 (m, 1H), 7.72-7.61 (m, 1H), 7.35-7.24 (m, 1H), 6.49 (d, J=16.0 Hz, 1H), 4.30 (q, J=7.2 Hz, 2H), 3.35-3.23 (m, 4H), 2.70-2.55 (m, 4H), 2.39 (s, 3H), 1.36 (t, J=7.2 Hz, 3H). LCMS (ES): m/z 276.1 [M+H]$^+$.

Intermediate 1BT

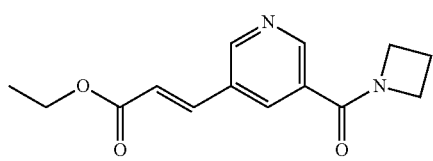

Intermediate 1BT: $^1$H NMR (500 MHz, chloroform-d) δ 8.88-8.74 (m, 2H), 8.23-8.10 (m, 1H), 7.77-7.61 (m, 1H), 6.73-6.49 (m, 1H), 4.50-4.21 (m, 6H), 2.41 (quin, J=7.8 Hz, 2H), 1.35 (t, J=7.2 Hz, 3H). LCMS (ES): m/z 261.1 [M+H]$^+$.

Intermediate 1BU

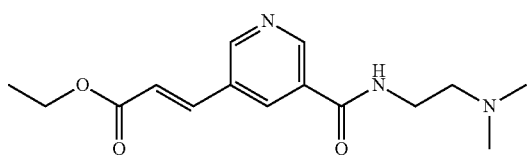

Intermediate 1BU: $^1$H NMR (500 MHz, chloroform-d) δ 9.04-8.95 (m, 1H), 8.90-8.82 (m, 1H), 8.36-8.25 (m, 1H), 7.78-7.67 (m, 1H), 7.09-6.97 (m, 1H), 6.69-6.54 (m, 1H), 4.32 (q, J=7.2 Hz, 2H), 3.57 (q, J=5.4 Hz, 2H), 2.58 (t, J=5.9 Hz, 2H), 2.37-2.29 (m, 6H), 1.38 (t, J=7.0 Hz, 3H). LCMS (ES): m/z 292.1 [M+H]$^+$.

Intermediate 1BV

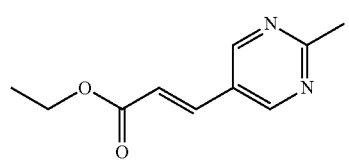

Intermediate 1BV: $^1$H NMR (400 MHz, DMSO-d$_6$) δ 9.04 (s, 2H), 7.63 (d, J=16.1 Hz, 1H), 6.87 (d, J=16.3 Hz, 1H), 4.21 (q, J=7.2 Hz, 2H), 2.64 (s, 3H), 1.26 (t, J=7.2 Hz, 3H). LCMS (ES): m/z 193.1 [M+H]$^+$.

Intermediate 1BW

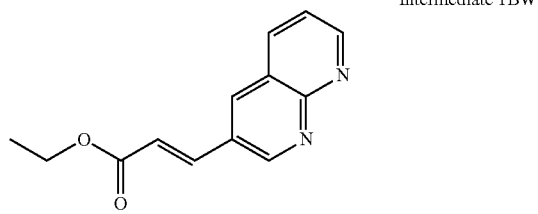

Intermediate 1BW: $^1$H NMR (500 MHz, chloroform-d) δ 9.40-9.31 (m, 1H), 9.24-9.15 (m, 1H), 8.32-8.28 (m, 1H), 8.28-8.23 (m, 1H), 7.88 (d, J=16.2 Hz, 1H), 7.57 (dd, J=8.1, 4.3 Hz, 1H), 6.73 (d, J=16.0 Hz, 1H), 4.34 (q, J=7.2 Hz, 2H), 1.40 (t, J=7.2 Hz, 3H). LCMS (ES): m/z 229.2 [M+H]$^+$.

Intermediate 1BX

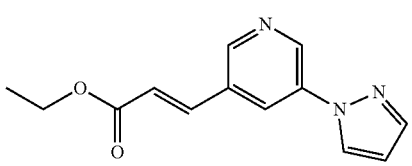

Intermediate 1BX: LCMS (ES): m/z 244.0 [M+H]$^+$.

Intermediate 1BY

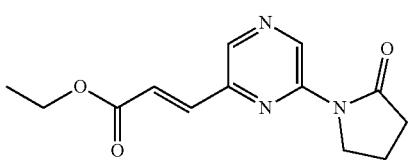

Intermediate 1BY: LCMS (ES): m/z 262.1 [M+H]$^+$.

Intermediate 1BZ

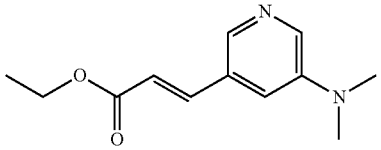

Intermediate 1BZ: LCMS (ES): m/z 249.1 [M+H]$^+$.

Intermediate 1CA

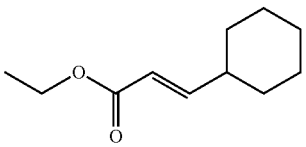

Intermediate 1CA: $^1$H NMR (500 MHz, chloroform-d) δ 6.96-6.72 (m, 1H), 5.84-5.71 (m, 1H), 4.19-3.99 (m, 2H), 2.24-2.05 (m, 1H), 1.82-1.54 (m, 5H), 1.35-1.00 (m, 8H).

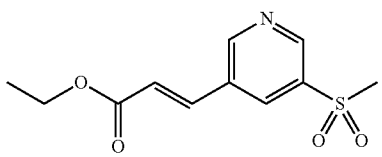

Intermediate 1CB

Intermediate 1CB: $^1$H NMR (500 MHz, chloroform-d) δ 9.18-9.12 (m, 1H), 9.04-8.97 (m, 1H), 8.41-8.33 (m, 1H), 7.79-7.69 (m, 1H), 6.71-6.61 (m, 1H), 4.33 (q, J=7.2 Hz, 2H), 3.17 (s, 3H), 1.38 (t, J=7.2 Hz, 3H). LCMS (ES): m/z 256.1 [M+H]$^+$.

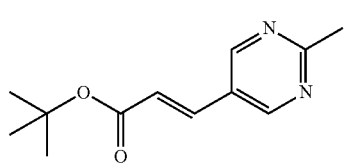

Intermediate 1CC

Intermediate 1CC: $^1$H NMR (500 MHz, chloroform-d) δ 8.77 (s, 2H), 7.55-7.44 (m, 1H), 6.57-6.39 (m, 1H), 2.85-2.72 (m, 3H), 1.61-1.47 (m, 9H)).

Intermediate 2A. Ethyl (S)-3-amino-3-(3-fluoro-4-methoxyphenyl)propanoate

Intermediate 2A was prepared according to the procedure described in: Hutchinson, J. H. et. al., J. Med. Chem. 2003, 46, 4790. $^1$H NMR (500 MHz, chloroform-d) δ 8.16 (d, J=2.2 Hz, 1H), 7.67 (dd, J=8.5, 2.5 Hz, 1H), 6.76 (d, J=8.5 Hz, 1H), 4.47 (dd, J=8.8, 5.0 Hz, 1H), 4.00-3.92 (m, 3H), 2.92-2.64 (m, 2H). LCMS (ES): m/z 225.0 [M+H]$^+$. $^1$H NMR (500 MHz, CDCl$_3$) δ 8.28 (d, J=2.5 Hz, 1H), 7.77 (dd, J=8.8, 2.5 Hz, 1H), 7.64 (d, J=16.2 Hz, 1H), 6.77 (d, J=8.8 Hz, 1H), 6.34 (d, J=16.0 Hz, 1H), 4.27 (q, J=7.2 Hz, 2H), 3.98 (s, 3H), 1.34 (t, J=7.2 Hz, 3H).

Intermediate 2B. Ethyl (S)-3-amino-3-(2-methoxy-pyrimidin-5-yl)propanoate

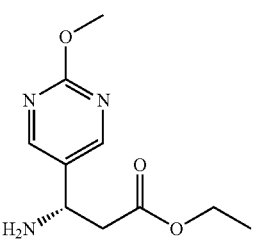

Intermediate 2B

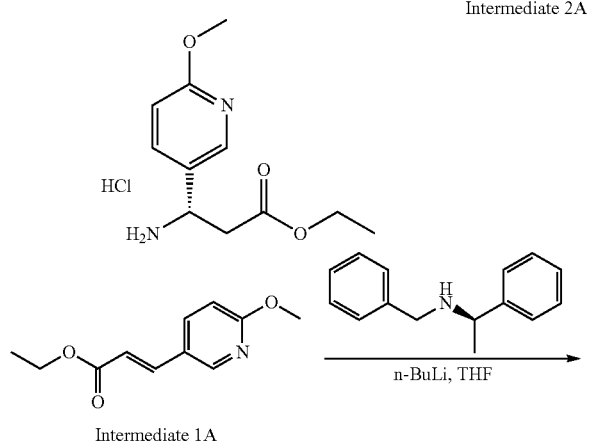

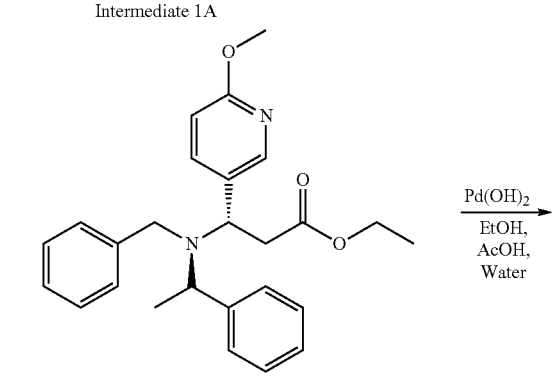

NH$_3$ gas was bubbled into a cooled t-BuOH (300 mL) for 1 hr. It was then added together with (E)-ethyl 3-(2-methoxypyrimidin-5-yl)acrylate (20 g, 96 mmol) into an 1 L auto clave. The mixture was heated at 80° C. for 30 hrs. The mixture was concentrated under reduced pressure. The residue was purified via flash column chromatography (5% methanol in chloroform) to afford racemic ethyl-3-amino-3-(2-methoxypyrimidin-5-yl)propanoate. It was further purified in chiral SFC (Chiralpak IA, 0.4% DEA in EtOH) to afford Intermediate 2B (2.3 g, 9.80 mmol, 10.2% yield). LCMS (ES): m/z 226.8 [M+H]$^+$.

Other β-aminoacids were prepared analogously using the procedure described for Intermediates 2A and 2B above.

Example 1

3-(6-Methoxypyridin-3-yl)-3-(4-(3-(5,6,7,8-tetrahydro-1,8-naphthyridin-2-yl)propyl)-1H-indazol-1-yl)propanoic acid

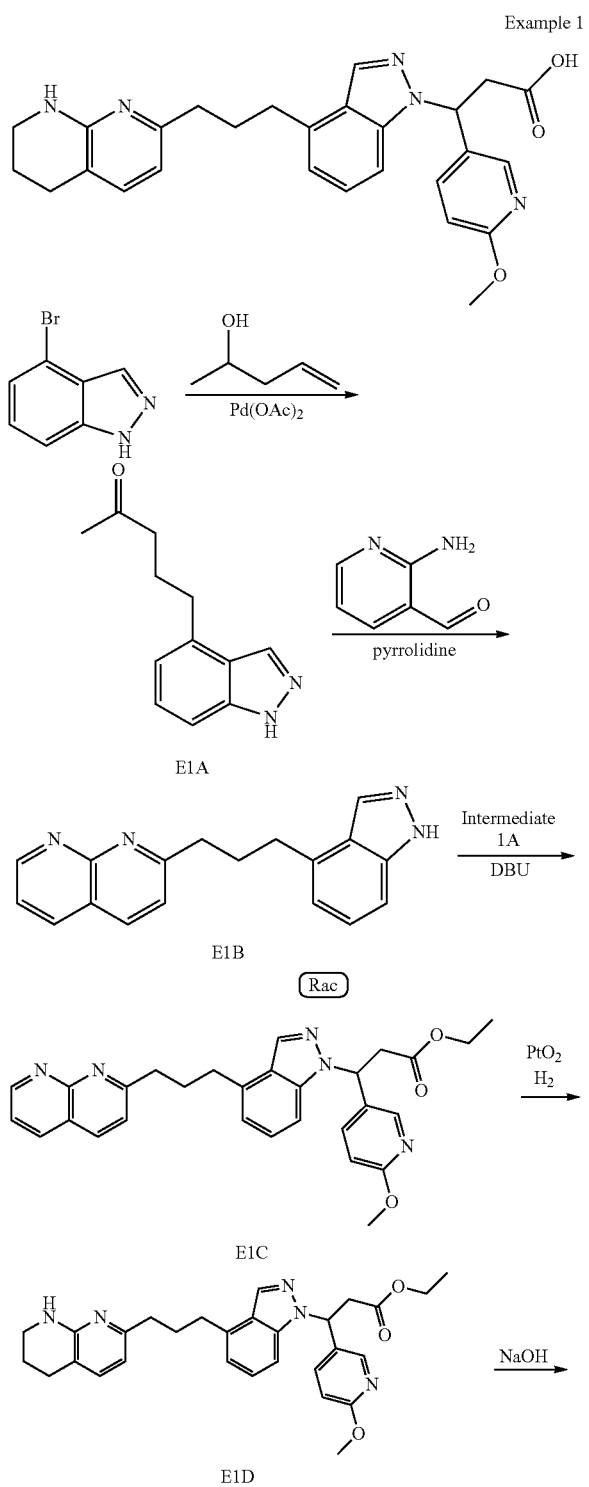

Intermediate E1A: To a solution of 4-bromoindazole (0.35 g, 1.776 mmol) in DMF (5.59 mL) was added pent-4-en-2-ol (0.28 ml, 2.66 mmol), Pd(OAc)$_2$ (0.199 g, 0.888 mmol), LiCl (75 mg, 1.776 mmol), tetra-n-butylammonium chloride (0.99 g, 3.55 mmol), and LiOAc (0.294 g, 4.46 mmol). The mixture was heated at 100° C. for 72 hrs. The mixture was diluted with H$_2$O (10 mL) and extracted with EtOAc (3×5 mL). The combined organic layers were washed with H$_2$O (3 mL) and brine (5 mE). It was concentrated and purified via flash chromatography (SiO$_2$) to give Intermediate E1A (82 mg, 23%). $^1$H NMR (500 MHz, chloroform-d) δ 8.17 (s, 1H), 7.40-7.25 (i, 2H), 6.94 (d, J=6.9 Hz, 1H), 2.96 (t, J=7.6 Hz, 2H), 2.48 (t, J=7.3 Hz, 2H), 2.12 (s, 3H), 2.11-2.01 (m, 2H).

Intermediate E1B: To a solution of Intermediate E1A (82 mg, 0.406 mmol) in CH$_2$Cl$_2$ (203 μL) and MeOH (610 μL) was added pyrrolidine (8.4 μL, 0.102 mmol), followed by 2-aminonicotinaldehyde (49.6 mg, 0.406 mmol). The mixture was stirred at room temperature overnight. The reaction was evaporated under the reduced pressure. The residue was purified via flash chromatography (SiO$_2$) to give Intermediate E1B (93 mg, 80%). $^1$H NMR (500 MHz, chloroform-d) δ 9.09 (dd, J=4.3, 2.1 Hz, 1H), 8.15 (dd, J=8.1, 2.0 Hz, 1H), 8.12-8.06 (m, 2H), 7.44 (dd, J=8.1, 4.2 Hz, 1H), 7.36 (dd, J=8.3, 6.6 Hz, 2H), 7.30-7.23 (m, 1H), 6.98 (d, J=6.9 Hz, 1H), 3.18-3.11 (m, 2H), 3.08 (t, J=7.6 Hz, 2H), 2.48-2.33 (m, 2H).

Intermediate E1C: A mixture of E1B (31 mg, 0.108 mmol), Intermediate 1A (44.6 mg, 0.215 mmol), and DBU (16.20 μL, 0.108 mmol) in acetonitrile (717 μL) was heated at 100° C. overnight. The solvent was removed under reduced pressure. The residue was purified via preparative HPLC (Phenomenex Luna Axia 5μ C18 30×100 mm; 10 min gradient from 30% A: 70% B to 0% A:100% B (A=90% H$_2$O/10% MeOH+0.1% TFA); (B=90% MeOH/10% H$_2$O+0.1% TFA); detection at 220 nm) to yield Intermediate E1C (17 mg, 32%). LCMS (ES): m/z 492.2 [M+H]$^+$.

Intermediate E1D: To a solution of E1C (19 mg, 0.038 mmol) in ethanol (1.0 mL) was added PtO$_2$ (1.74 mg, 7.67 μmol). It was purged with N2, and then charged with H$_2$ balloon. The mixture was stirred at rt overnight. It was filtered through a pad of celite.

Solvent was removed and the residue was used in the next step without further purification. LCMS (ES): m/z 500.5 [M+H]$^+$.

Example 1

To a solution of Intermediate E1D (16 mg, 0.032 mmol) in ethanol (582 μL) was added NaOH (aq, 1 N, 96 μL, 0.096 mmol) and the mixture was stirred at room temperature for two hours. It was neutralized with AcOH (0.1 mL). The solvent was removed under reduced pressure and the residue was purified via preparative LC/MS (Column: XBridge C18, 19×200 mm, 5-μm particles; Mobile Phase A: 5:95 acetonitrile: water with 0.1% TFA; Mobile Phase B: 95:5 acetonitrile: water with 0.1% TFA; Gradient: 10-50% B over 20 minutes, then a 5-minute hold at 100% B; Flow: 20 mL/min) to give Example 1 (4.8 mg, 30%). $^1$H NMR (500 MHz, DMSO-d$_6$) δ 8.20 (d, J=2.5 Hz, 1H), 8.12 (s, 1H), 7.67 (dd, J=8.8, 2.5 Hz, 1H), 7.56 (d, J=8.6 Hz, 1H), 7.25 (t, J=7.7 Hz, 1H), 7.03 (d, J=7.3 Hz, 1H), 6.89 (d, J=7.0 Hz, 1H), 6.71 (d, J=8.6 Hz, 1H), 6.26 (d, J=7.3 Hz, 1H), 6.15 (dd, J=9.4, 5.3 Hz, 1H), 3.74 (dt, J=14.7, 7.1 Hz, 2H), 3.54 (dd, J=16.5, 9.4 Hz, 1H), 3.27-3.07 (m, 3H), 2.84 (t, J=7.7 Hz, 2H), 2.56 (q, J=7.8, 7.0 Hz, 2H), 2.45 (t, J=7.7 Hz, 2H), 1.91 (dd, J=14.3, 6.5 Hz, 2H), 1.77-1.62 (m, 2H). LC/MS (m/z)=472.0 (M+H)+. Human αVβ6 IC$_{50}$ (nM)=1600.

Example 2

3-(6-Methoxypyridin-3-yl)-3-(5-(2-(5,6,7,8-tetrahydro-1,8-naphthyridin-2-yl)ethyl)-1H-indazol-1-yl)propanoic acid

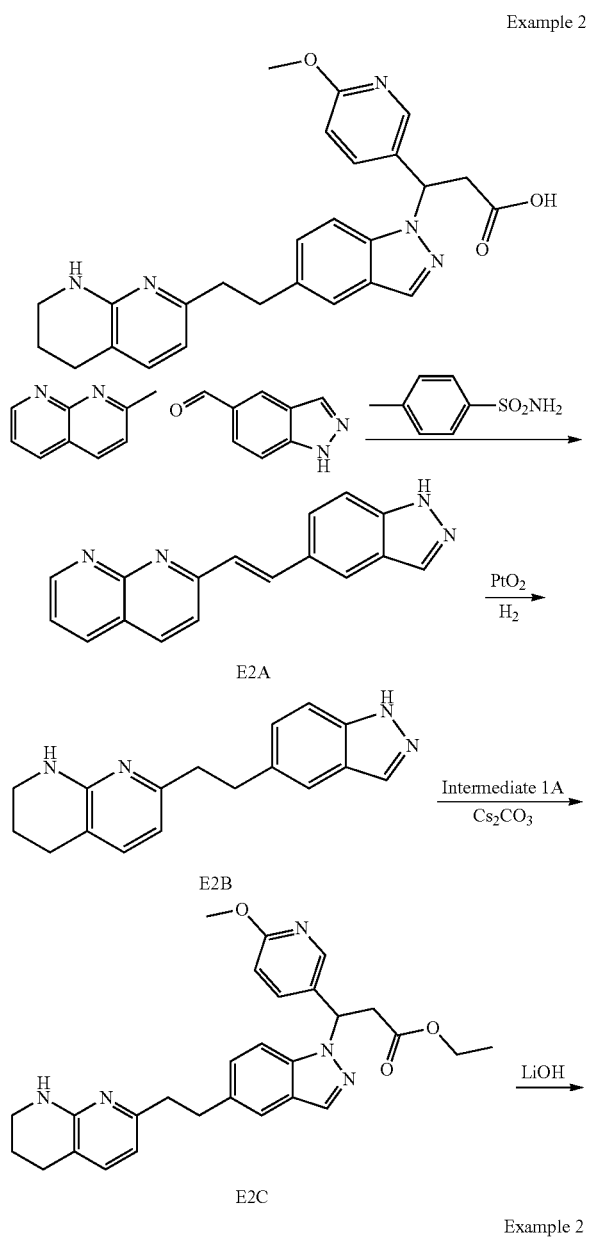

Intermediate E2A: A mixture of 2-methyl-1,8-naphthyridine (250 mg, 1.734 mmol), 1H-indazole-5-carbaldehyde (253 mg, 1.734 mmol) and 4-methylbenzenesulfonamide (297 mg, 1.734 mmol) in toluene (4 mL) was heated at 110° C. overnight. The reaction was cooled to rt and diluted with EtOAc (15 mL). The solid was collected via filtering and rinsed with EtOAc (2×2 mL) and dried in vacuum to afford Intermediate E2A (415 mg, 1.524 mmol, 88% yield). The crude product was used in the next reaction without further purification. LCMS (ES): m/z 273.2 [M+H]+.

Intermediate E2B: To a degassed solution of Intermediate E2A (200 mg, 0.734 mmol) in EtOH (5 mL) was added PtO$_2$ (33.4 mg, 0.147 mmol). The mixture was charged with a H$_2$ balloon and stirred at rt overnight. The reaction was filtered and concentrated to obtain Intermediate E2B (203 mg, 0.729 mmol, 99% yield), and the product was used in the next reaction. LCMS (ES): m/z 279.2 [M+H]+.

Intermediate E2C: To a solution of Intermediate E2B (25 mg, 0.09 mmol) in acetonitrile (0.5 mL) was added cesium carbonate (29.3 mg, 0.09 mmol). After stirring at rt for 5 min, Intermediate 1A (18.61 mg, 0.09 mmol) was added. The resulting mixture was stirred at 80° C. overnight. The mixture was cooled to rt, filtered, and concentrated. The residue was purified via preparative HPLC (Phenomenex Luna Axia 5μ C18 30×100 mm; 10 min gradient from 75% A: 25% B to 0% A:100% B (A=90% H$_2$O/10% MeOH+ 0.1% TFA); (B=90% MeOH/10% H$_2$O+0.1% TFA); detection at 220 nm) to give Intermediate E2C (19 mg, 0.039 mmol, 43.6% yield). LCMS (ES): m/z 486.4 [M+H]+.

Example 2

To a solution of Intermediate E2C (19 mg, 0.039 mmol) in THF (0.5 mL) was added a solution of LiOH (aqueous, 1 N, 0.12 mL, 0.12 mmol). After stirring at rt for 5 hrs, the mixture was neutralized with TFA (50 μL), filtered, and concentrated. The residue was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min to yield Example 2 (5.5 mg, 30% yield). LCMS (ES): m/z 458.2 [M+H]+. $^1$H NMR (500 MHz, DMSO-d$_6$) δ 8.23 (br. s., 1H), 8.00 (s, 1H), 7.67 (t, J=8.5 Hz, 2H), 7.51 (s, 1H), 7.24 (d, J=8.6 Hz, 1H), 7.01 (d, J=7.3 Hz, 1H), 6.72 (d, J=8.6 Hz, 1H), 6.28 (d, J=7.2 Hz, 1H), 6.17 (br. s., 1H), 3.76 (s, 3H), 3.23 (br. s., 2H), 3.16 (br. s., 2H), 2.98-2.88 (m, 2H), 2.72 (t, J=7.8 Hz, 2H), 2.58 (t, J=5.8 Hz, 2H), 1.73 (br. s., 2H). Human α$_V$β6 IC$_{50}$ (nM)=110.

Example 3

3-(6-Methoxypyridin-3-yl)-3-(4-(2-(5,6,7,8-tetrahydro-1,8-naphthyridin-2-yl)ethoxy)-1H-indazol-1-yl)propanoic acid

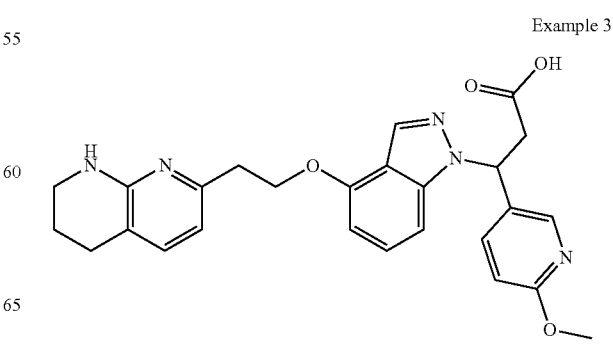

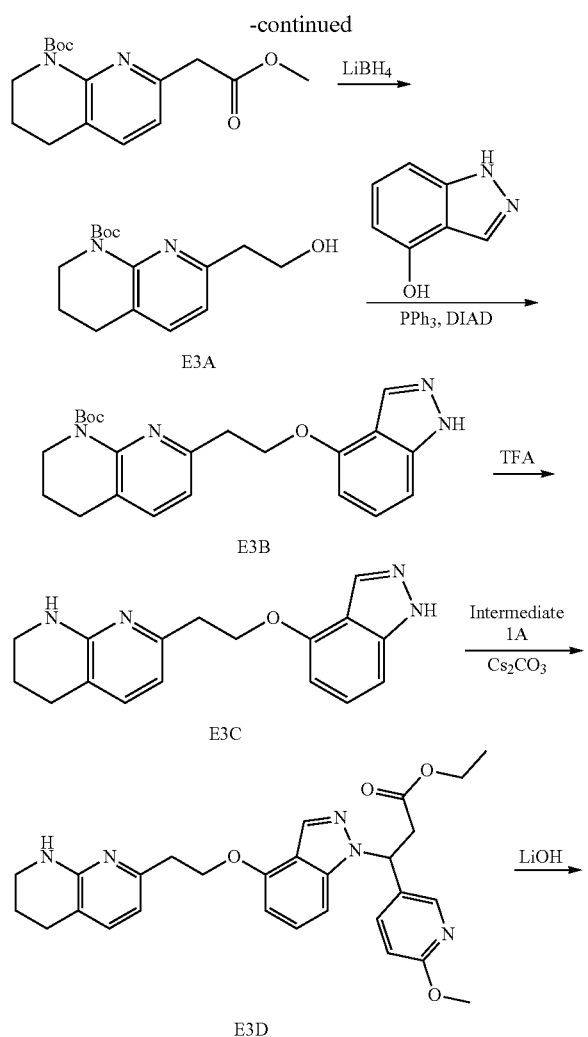

E3A

E3B

E3C

E3D

Example 3

Intermediate E3A: To a solution of tert-butyl 7-(2-methoxy-2-oxoethyl)-3,4-dihydro-1,8-naphthyridine-1(2H)-carboxylate (1 g, 3.26 mmol) in THF (20 mL) was added a solution of lithium borohydride (2 M, 2.12 mL, 4.24 mmol) in THF. The reaction was stirred at rt overnight. Water (15 mL) was added slowly to the reaction. After stirring at rt for 10 min, the mixture was diluted with EtOAc (12 mL), and extracted with EtOAc (3×8 mL). The combine organic layers were dried ($Na_2SO_4$), filtered, and concentrated. The residue was purified via flash chromatography ($SiO_2$) to give Intermediate E3A (782 mg, 86%). LCMS (ES): m/z 279.1 $[M+H]^+$.

Intermediate E3B: To a solution of Intermediate E3A (340 mg, 1.221 mmol), 1H-indazol-4-ol (164 mg, 1.22 mmol), and $Ph_3P$ (336 mg, 1.283 mmol) in THF (10 mL) was added DIAD (0.249 mL, 1.283 mmol) slowly. The reaction was stirred at rt for 3 hrs. The mixture was washed with $NaHCO_3$ solution (aqueous, saturated, 10 mL), the aqueous layer was back extracted with EtOAc (3×5 mL). The combine organic layers were washed with brine (10 mL), and then dried over $Na_2SO_4$. The mixture was filtered and concentrated under reduced pressure. The residue was purified via flash chromatography to give Intermediate E3B (178 mg, 37%). LCMS (ES): m/z 395.3 $[M+H]^+$.

Intermediate E3C: To a solution of Intermediate E3B (178 mg, 0.451 mmol) in DCM (3 mL) was added TFA (0.174 mL, 2.256 mmol) and the mixture was stirred at rt for 5 hrs. It was concentrated and the crude product was used in the next step without further purification. LCMS (ES): m/z 295.2 $[M+H]^+$.

Intermediate E3D: To a solution of Intermediate E3C (20 mg, 0.038 mmol) in acetonitrile (0.5 mL) was added cesium carbonate (37.4 mg, 0.115 mmol). After stirring at rt for 5 min, Intermediate 1A (7.93 mg, 0.038 mmol) was added and the resulting mixture was stirred at 80° C. for 4 hrs. The mixture was cooled to rt, filtered, and concentrated. The residue purified via preparative HPLC (Phenomenex Luna Axia 5µ C18 30×100 mm; 10 min gradient from 75% A: 25% B to 0% A:100% B (A=90% $H_2O$/10% MeOH+0.1% TFA); (B=90% MeOH/10% $H_2O$+0.1% TFA); detection at 220 nm) to give Intermediate E3D (6 mg, 0.012 mmol, 31.2% yield). LCMS (ES): m/z 502.1 $[M+H]^+$.

Example 3

To a solution of Intermediate E3D (6 mg, 0.012 mmol) in THF (0.5 mL) was added a solution of LiOH (aqueous, 1 M, 0.036 mL, 0.036 mmol). The reaction mixture was stirred at rt for 6 hrs. The reaction mixture was neutralized with TFA (25 µL), filtered, and concentrated under reduced pressure. The residue was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 30 minutes, then a 5-minute hold at 100% B; Flow: 20 mL/min to yield Example 3 (5.8 mg, 102% yield). $^1H$ NMR (500 MHz, DMSO-$d_6$) δ 8.22 (br. s., 1H), 8.04 (s, 1H), 7.68-7.62 (m, 1H), 7.59 (d, J=7.3 Hz, 1H), 7.35 (d, J=8.5 Hz, 1H), 7.29-7.23 (m, 1H), 6.74 (dd, J=13.7, 8.0 Hz, 2H), 6.58 (d, J=7.7 Hz, 1H), 6.15 (dd, J=9.8, 5.1 Hz, 1H), 4.42-4.32 (m, 2H), 3.76 (s, 2H), 3.39 (br. s., 1H), 3.16 (s, 5H), 2.71 (br. s., 2H), 1.80 (br. s., 2H). LCMS (ES): m/z 473.9 $[M+H]^+$. Human αVβ6 $IC_{50}$ (nM)=2300.

Example 4

(S)-2-(((Benzyloxy)carbonyl)amino)-3-(5-(2-(5,6,7,8-tetrahydro-1,8-naphthyridin-2-yl)ethoxy)-2H-indazol-2-yl)propanoic acid Example 4

E4A

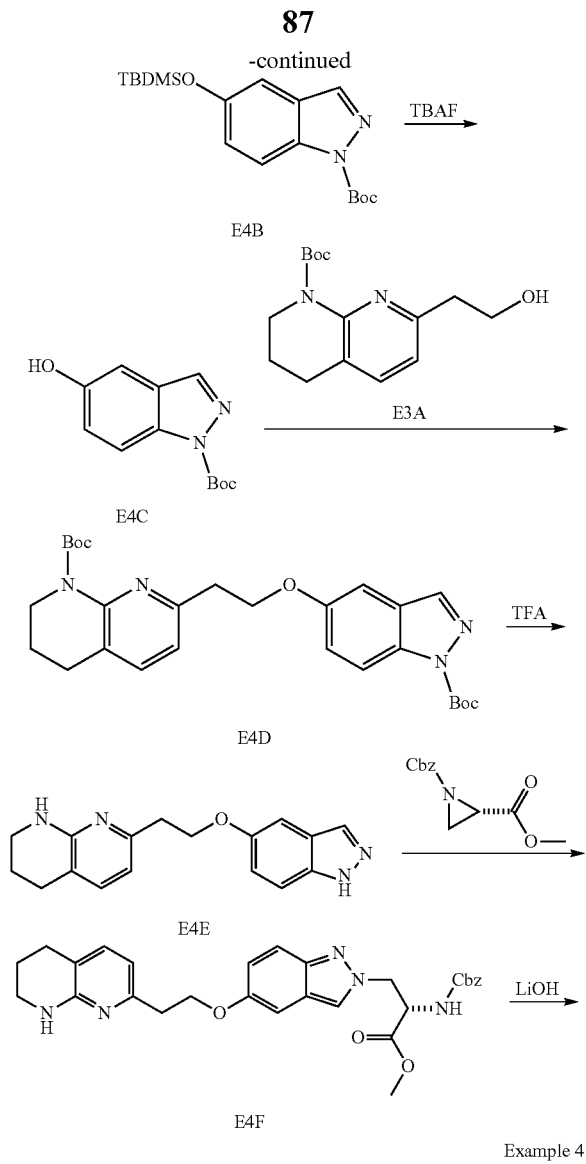

E4B

E4C

E4D

E4E

E4F

Example 4

Intermediate E4A: A solution of 1H-indazol-5-ol (5.1 g, 38.0 mmol), tert-butylchlorodimethylsilane (16.8 g, 111 mmol) and imidazole (12.7 g, 187 mmol) in DCM (200 ml) was stirred at rt overnight. The mixture was diluted with brine (60 mL) and extracted with DCM (3×50 mL). The combined organic layers were washed with water (50 mL), then brine (50 mL). It was dried (Na$_2$SO$_4$), filtered, and concentrated. The residue was purified via flash column (SiO$_2$) chromatography to afford E4A as a light yellow solid (7.48 g, 30.1 mmol, yield 79%). $^1$H NMR (400 MHz, chloroform-d) δ 10.27 (s, 1H), 7.99 (d, J=1.1 Hz, 1H), 7.38 (dt, J=8.9, 0.9 Hz, 1H), 7.17-7.14 (m, 1H), 7.01 (dd, J=8.9, 2.2 Hz, 1H), 1.04 (s, 9H), 0.24 (s, 6H).

Intermediate E4B: To a solution of E4A (5-((tert-butyldimethylsilyl)oxy)indazole) (5.56 g, 22.38 mmol) in DCM (100 mL) was added Boc$_2$O (5.72 mL, 24.62 mmol) followed by DMAP (0.547 g, 4.48 mmol) and Et$_3$N (3.43 mL, 24.62 mmol). The mixture was stirred at rt overnight. The mixture was concentrated and residue was purified via flash column chromatography (silica gel, hexanes/EtOAc gradient 0 to 25% EtOAc) to give E4B (7.74 g, 22.21 mmol, 99% yield) as a mixture of isomers: tert-butyl 5-((tert-butyldimethylsilyl)oxy)indazole-1-carboxylate and tert-butyl 5-((tert-butyldimethylsilyl)oxy)-2H-indazole-2-carboxylate.

Intermediate E4C: To a solution of Intermediate E4B (tert-butyl 5-((tert-butyldimethylsilyl)oxy)indazole-1-carboxylate) (7.74 g, 22.21 mmol) in THF (100 mL) was added a solution of TBAF (44.4 mL, 44.4 mmol). The mixture was stirred at rt for 2 hrs. The mixture was diluted with NH$_4$Cl (aqueous, saturated, 30 mL) and extracted with EtOAc (3×25 mL). The combine organic layers were washed with brine (30 mL) and dried (Na$_2$SO$_4$), filtered, and concentrated. The residue was purified via flash column chromatography to afford Intermediate E4C (3.42 g, 14.60 mmol, 65.7% yield) as a mixture of two regioisomers: tert-butyl 5-hydroxyindazole-1-carboxylate and tert-butyl 5-hydroxy-2H-indazole-2-carboxylate.

Intermediate E4D: To a solution of E4C (3.53 g, 12.68 mmol) and Ph$_3$P (3.78 g, 14.41 mmol) in THF (70 mL) at 0° C. was added E3A (tert-butyl 5-hydroxyindazole-1-carboxylate) (2.7 g, 11.53 mmol) followed by (E)-diazene-1,2-diylbis(piperidin-1-ylmethanone) (3.64 g, 14.41 mmol). The reaction was stirred and gradually warmed to rt overnight. A solution of NaHCO$_3$ (aqueous, saturated, 25 mL) was added, and the mixture was extracted with EtOAc (3×20 mL). The combined organic layers were washed with water (20 mL) then with brine (20 mL). It was dried (Na$_2$SO$_4$), filtered, and concentrated under reduced pressure. The residue was purified via flash column chromatography to afford Intermediate E4D as a light yellow solid (3.94 g, 7.97 mmol, 69.1% yield). LCMS (ES): m/z 495.1 [M+H]$^+$.

Intermediate E4E: To a solution of E4D (3.94 g, 7.97 mmol) in DCM (40 mL) at 0° C. was added TFA (8 mL, 104 mmol). The mixture was gradually warmed to rt and stirred at rt overnight. The reaction was monitored by LCMS. When necessary, additional TFA was added. After completion, the mixture was concentrated under reduced pressure and the residue was purified via flash column chromatography (C18 column, 10% ACN in water with 0.1% TFA to 80% ACN in water, 12 min gradient) to give E4E (7-(2-((1H-indazol-5-yl)oxy)ethyl)-1,2,3,4-tetrahydro-1,8-naphthyridine TFA salt) (2.63 g, 6.44 mmol, 81% yield) as light yellow solid. $^1$H NMR (500 MHz, chloroform-d) δ 15.60 (s, 1H), 10.31 (s, 1H), 8.01 (s, 1H), 7.40 (d, J=8.9 Hz, 1H), 7.34 (d, J=7.3 Hz, 1H), 7.15 (d, J=2.3 Hz, 1H), 7.11-6.99 (m, 1H), 6.53 (d, J=7.2 Hz, 1H), 4.34 (t, J=5.8 Hz, 2H), 3.51 (d, J=6.0 Hz, 2H), 3.22 (t, J=5.9 Hz, 2H), 2.77 (t, J=6.3 Hz, 2H), 1.94 (q, J=5.9 Hz, 2H). LCMS (ES): m/z 295.2 [M+H]$^+$.

Intermediate E4F: A mixture of Intermediate E4E (37 mg, 0.091 mmol) and (S)-1-benzyl 2-methyl aziridine-1,2-dicarboxylate (27.7 mg, 0.118 mmol) in toluene (1 mL) was heated at 110° C. overnight. The solution was concentrated and the crude product was purified via preparative HPLC (Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-42% B over 25 minutes, then a 2-minute hold at 42% B; Flow: 20 mL/min.) to give Intermediate E4F (16 mg, 0.030 mmol, 33.3% yield). LCMS (ES): m/z 530.0 [M+H]$^+$.

Example 4

To a solution of Intermediate E4F (16 mg, 0.030 mmol) in THF (0.5 mL) was added a solution of LiOH (aqueous, 1 M, 0.091 mL, 0.091 mmol). The mixture was stirred at rt for 2 hrs. The mixture was neutralized with TFA (20 μL) and concentrated under reduced pressure. The residue was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-60% B over 20 minutes, then a 5-minute hold at 100% B; Flow: 20 mL/min to give Example 4 (11.3 mg, 73%). $^1$H NMR (400 MHz, MeOH-$d_4$) δ 7.87 (s, 1H), 7.44-7.33 (m, 2H), 7.22 (d, J=9.2 Hz, 5H), 6.85 (d, J=8.9 Hz, 2H), 6.58 (d, J=7.3 Hz, 1H), 5.07-4.89 (m, 2H), 4.88-4.65 (m, 2H), 4.58 (s, 1H), 4.16 (t, J=6.3 Hz, 2H), 3.41 (t, J=5.7 Hz, 2H), 3.02 (t, J=6.3 Hz, 2H), 2.73 (t, J=6.3 Hz, 2H), 1.92-1.82 (m, 2H). LCMS (ES): m/z 516.3 [M+H]$^+$. Human $α_vβ6$ IC$_{50}$ (nM)=21.

Example 5

3-Phenyl-3-(5-(3-(5,6,7,8-tetrahydro-1,8-naphthyridin-2-yl)propoxy)-1H-indazol-1-yl)propanoic acid

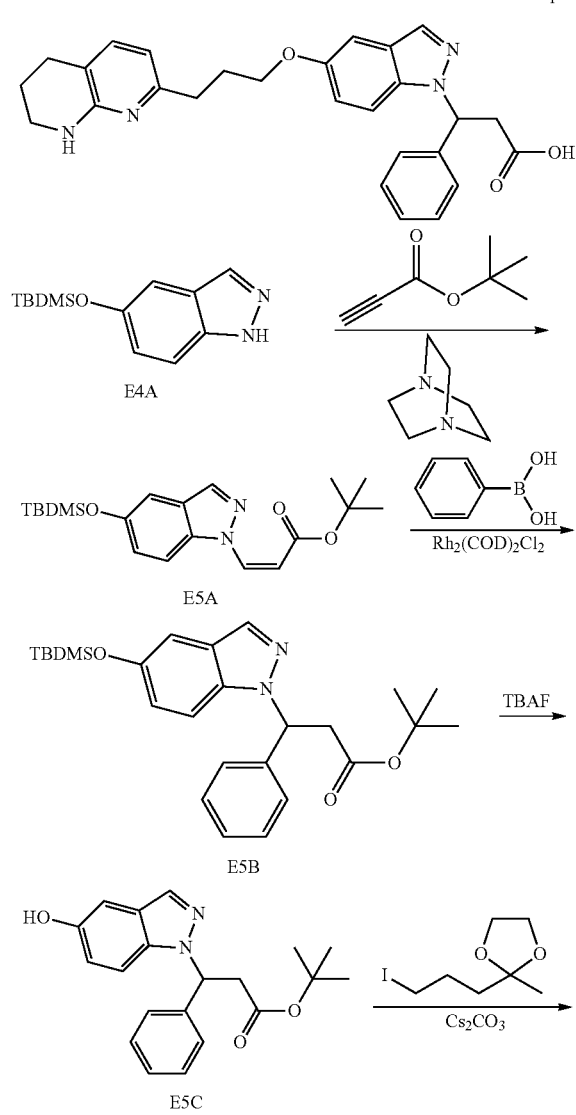

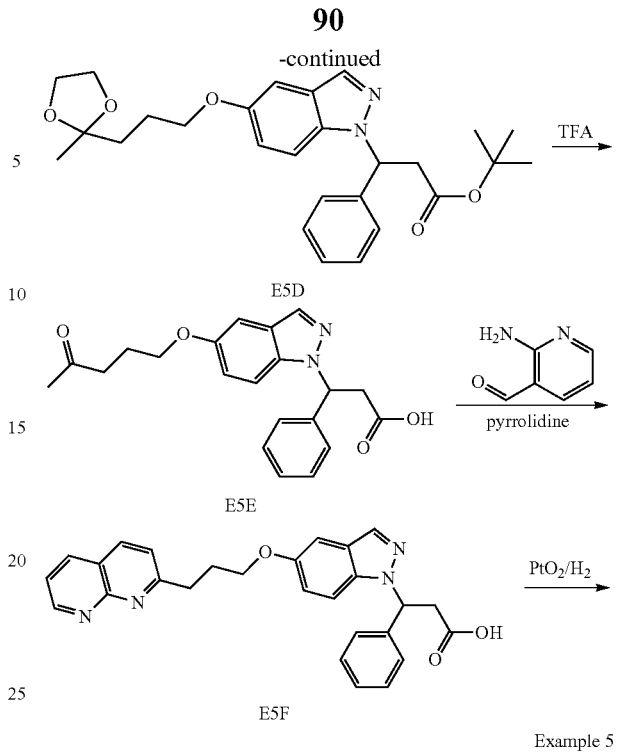

Example 5

Intermediate E5A: To a solution of E4A (0.745 g, 3.00 mmol) in DCM (6 mL) at 0 HC under argon was added DABCO (0.034 g, 0.300 mmol), followed by slow addition of tert-butyl propiolate (0.51 mL, 3.6 mmol). The mixture was stirred at this temperature for additional 20 min, then gradually warmed to rt overnight. The mixture was acidified with HOAc (34 μL). The solvent was removed under reduced pressure and the residue was purified via flash column chromatography (SiO$_2$, hexanes/EtOAc gradient 0 to 40% EtOAc) to give E5B (0.19 g, 17% yield). $^1$H NMR (500 MHz, chloroform-d) δ 8.03 (d, J=0.9 Hz, 1H), 7.27 (d, J=8.8 Hz, 1H), 7.21 (d, J=9.6 Hz, 1H), 7.12 (d, J=2.2 Hz, 1H), 7.03 (dd, J=8.9, 2.2 Hz, 1H), 5.62 (d, J=9.5 Hz, 1H), 1.47 (s, 9H), 1.03 (s, 9H), 0.23 (s, 6H).

Intermediate E5B: To a solution of E5A (46.2 mg, 0.123 mmol), Et$_3$N (103 μL, 0.740 mmol), and phenylboronic acid (30.1 mg, 0.247 mmol) in MeOH (617 μL) was added chloro(1,5-cyclooctadiene)rhodium(I) dimer (3.04 mg, 6.17 μmol). The mixture was degassed for 10 min, and heated at 60° C. overnight. The solvent was removed and the residue was purified via flash column chromatography (SiO$_2$) to give E5B (39 mg, 70% yield). $^1$H NMR (500 MHz, chloroform-d) δ 7.93 (d, J=0.9 Hz, 1H), 7.40-7.22 (m, 6H), 7.08 (d, J=2.2 Hz, 1H), 6.92 (dd, J=8.9, 2.3 Hz, 1H), 6.40 (d, J=13.7 Hz, 0H), 6.03 (dd, J=9.6, 5.6 Hz, 1H), 3.65 (dd, J=15.9, 9.6 Hz, 1H), 3.18 (dd, J=15.9, 5.7 Hz, 1H), 1.26 (s, 9H), 1.01 (s, 9H), 0.20 (d, J=1.7 Hz, 6H).

Intermediate E5C: To a solution of Intermediate E5B (80 mg, 0.177 mmol) in CH$_2$Cl$_2$ (353 μL) was added TBAF (265 μL, 0.265 mmol). The mixture was stirred at rt for 3 hrs. It was neutralized with HOAc (150 μL). Solvent was removed and the residue was purified via flash column chromatography (SiO$_2$) to give Intermediate E5C (51 mg, 92% yield). $^1$H NMR (400 MHz, chloroform-d) δ 7.88 (d, J=0.9 Hz, 1H), 7.36-7.18 (m, 7H), 7.10-6.94 (m, 1H), 6.89 (dd, J=9.0, 2.3 Hz, 1H), 6.02 (dd, J=9.7, 5.6 Hz, 1H), 3.65 (dd, J=15.9, 9.8 Hz, 1H), 3.16 (dd, J=16.0, 5.6 Hz, 1H), 1.26 (s, 9H).

Intermediate E5D: To a solution of Intermediate E5C (32 mg, 0.095 mmol) and 2-(3-iodopropyl)-2-methyl-1,3-dioxolane (36.3 mg, 0.142 mmol) in acetonitrile (946 µL) was added Cs$_2$CO$_3$ (92 mg, 0.284 mmol). The mixture was stirred at rt overnight. The solvent was removed and the residue was purified via flash column chromatography (SiO$_{O2}$) to give E5D (37 mg, 84% yield). LCMS (ES): m/z 467.3 [M+H]$^+$.

Intermediate E5E: To a solution of Intermediate E5D (37 mg, 0.079 mmol) in DCM (227 µL) was added TFA (566 µL). The mixture was stirred at rt for 4 hrs. The solvent was removed under reduced pressure and the residue was used in the next reaction without further purification. LCMS (ES): m/z 367.1 [M+H]$^+$.

Intermediate E5F: To a solution of Intermediate E5E (29 mg, 0.079 mmol) in DCM (198 µL) and MeOH (594 µL) was added pyrrolidine (13.1 µL, 0.158 mmol). The mixture was stirred at rt for 15 min. Then 2-aminonicotinaldehyde (11.60 mg, 0.095 mmol) was added. The mixture was stirred at rt overnight. The solvent was removed and the residue was purified via preparative HPLC (Phenomenex Luna Axia 5µ C18 30×100 mm; 10 min gradient from 85% A: 15% B to 0% A:100% B (A=90% H$_2$O/10% ACN+0.1% TFA); (B=90% ACN/10% H$_2$O+0.1% TFA); detection at 220 nm) to yield Intermediate E5F (11.3 mg, 36% yield). $^1$H NMR (500 MHz, MeOH-d$_4$) δ 9.11 (s, 1H), 8.90 (dd, J=8.2, 1.7 Hz, 1H), 8.80 (d, J=8.5 Hz, 1H), 8.00 (d, J=8.5 Hz, 1H), 7.95 (dd, J=8.2, 4.8 Hz, 1H), 7.91 (d, J=0.7 Hz, 1H), 7.36-7.22 (m, 6H), 7.06 (d, J=2.2 Hz, 1H), 6.67 (dd, J=9.1, 2.3 Hz, 1H), 6.12 (dd, J=9.9, 5.1 Hz, 1H), 4.18 (t, J=5.7 Hz, 2H), 3.71 (dd, J=16.7, 9.9 Hz, 1H), 3.44 (t, J=7.2 Hz, 2H), 3.24 (dd, J=16.6, 5.1 Hz, 1H), 2.54-2.43 (m, 2H).

Example 5

To a solution of Intermediate E5F (11.3 mg, 0.025 mmol) in MeOH (675 µL) was added sodium bicarbonate (4.20 mg, 0.050 mmol), followed by PtO$_2$ (1.134 mg, 4.99 µmol). The mixture was charged with H$_2$ balloon. It was stirred at room temperature overnight. The mixture was filtered through a pad of celite. The filtrate was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-55% B over 15 minutes, then a 3-minute hold at 100% B; Flow: 20 mL/min to give Example 5 (3.9 mg, 33%). LCMS (ES): m/z 457.1 [M+H]$^+$. $^1$H NMR (500 MHz, MeOH-d$_4$) δ 7.95 (d, J=0.8 Hz, 1H), 7.55 (d, J=7.4 Hz, 1H), 7.46 (d, J=9.1 Hz, 1H), 7.30 (d, J=4.3 Hz, 4H), 7.28-7.23 (m, 1H), 7.13 (d, J=2.3 Hz, 1H), 6.94 (dd, J=9.1, 2.3 Hz, 1H), 6.64 (d, J=7.3 Hz, 1H), 6.18 (dd, J=9.9, 5.1 Hz, 1H), 4.07 (t, J=5.7 Hz, 2H), 3.72 (dd, J=16.6, 9.9 Hz, 1H), 3.46 (td, J=5.3, 2.3 Hz, 2H), 3.25 (dd, J=16.6, 5.0 Hz, 1H), 2.92 (t, J=7.5 Hz, 2H), 2.80 (t, J=6.3 Hz, 2H), 2.20 (dq, J=13.2, 6.2 Hz, 2H), 1.94 (p, J=6.1 Hz, 2H). Human α$_v$β6 IC$_{50}$ (nM)=440.

Example 6

(S)-3-(6-Methoxypyridin-3-yl)-3-(5-(2-(5,6,7,8-tetrahydro-1,8-naphthyridin-2-yl)ethoxy)-2H-indazol-2-yl)propanoic acid

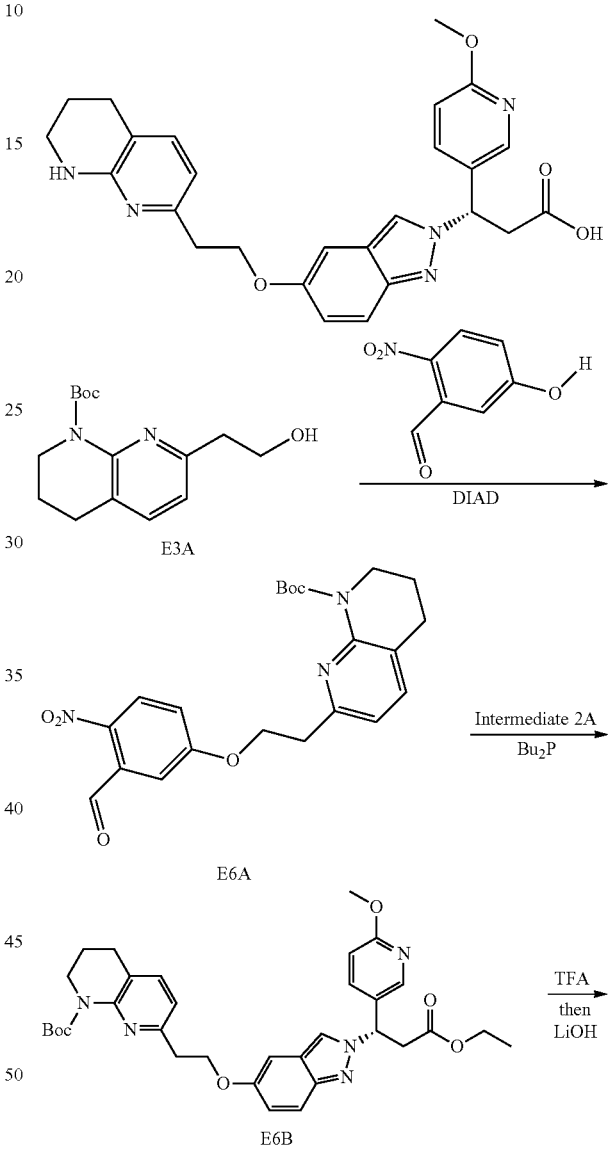

Example 6

Intermediate E6A: To a solution of Ph$_3$P (104 mg, 0.396 mmol) and Intermediate E3A (97 mg, 0.349 mmol) in THF (1.86 mL) at 0° C. was added 5-hydroxy-2-nitrobenzaldehyde (53 mg, 0.317 mmol), followed by DIAD (77 µL, 0.396 mmol). The mixture was stirred under argon and gradually warmed to rt overnight. The reaction was diluted with EtOAc (10 mL), washed with NaHCO$_3$ (aqueous, saturated, 8 mL). The aqueous layer was extracted with EtOAc (3×6 mL). The combined organic layers were washed with water (8 mL), then with brine (8 mL). It was dried (Na$_2$SO$_4$), filtered, and concentrated under reduced pressure. The residue was purified via flash column chromatography (SiO$_2$, hexanes/EtOAc gradient 0 to 100% EtOAc) to give Intermediate E6A (73.8 mg, 0.173 mmol, 54.4% yield). $^1$H NMR (500 MHz, chloroform-d) δ 10.49 (s, 1H), 8.16 (d, J=9.1 Hz, 1H), 7.38-7.33 (m, 2H), 7.19 (dd, J=9.1, 2.9 Hz, 1H), 6.92 (d, J=7.5 Hz, 1H), 4.55 (t, J=6.7 Hz, 2H), 3.84-3.73 (m, 2H), 3.25 (t, J=6.7 Hz, 2H), 2.77 (t, J=6.7 Hz, 2H), 1.95 (p, J=6.5 Hz, 2H), 1.53 (s, 9H).

Intermediate E6B: To a solution of Intermediate 2A (24.82 mg, 0.111 mmol) in 2-propanol (234 µL) was added E6A (43 mg, 0.101 mmol). The mixture was heated at 80° C. for 4 hours. It was cooled to rt. PBu$_3$ (74.5 µl, 0.302 mmol) was added in one portion. The mixture was heated at 80° C. for 16 hrs. The mixture was cooled to rt, diluted with EtOAc (5 mL), then washed with ammonium chloride (5 mL), followed by brine (5 ml). The organic layer was dried (MgSO$_4$), filtered, and concentrated under reduced pressure. The residue was purified via flash column chromatography (SiO$_2$, 0-100% EtOAc/heptane) to afford Intermediate E6B (16 mg, 27%). LCMS (ES): m/z 602.8 [M+H]$^+$.

Example 6

To a solution of Intermediate E6B (16.3 mg, 0.027 mmol) in CH$_2$Cl$_2$ (342 µL) was added TFA (68.4 µL). The mixture was stirred at rt overnight. The solvent was removed under reduced pressure. The above residue was dissolved in THF (342 µL), LiOH (aqueous, 1 N, 81 µL, 0.081 mmol) was added. The mixture was stirred at rt overnight. It was neutralized with HCl (aqueous, 1 N, 100 µL) and purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 3-40% B over 25 minutes, then a 5-minute hold at 100% B; Flow: 20 mL/min to give Example 6 (5 mg, 37%). $^1$H NMR (500 MHz, MeOH-d$_4$) δ 8.18 (d, J=0.9 Hz, 1H), 8.15 (d, J=2.6 Hz, 1H), 7.71 (dd, J=8.7, 2.6 Hz, 1H), 7.44 (dt, J=9.0, 1.0 Hz, 1H), 7.30 (dt, J=7.4, 1.1 Hz, 1H), 6.89-6.85 (m, 2H), 6.73 (dd, J=8.7, 0.7 Hz, 1H), 6.53 (d, J=7.3 Hz, 1H), 6.10 (dd, J=9.1, 6.1 Hz, 1H), 4.13 (td, J=6.5, 4.2 Hz, 2H), 3.86 (s, 3H), 3.49 (dd, J=16.0, 9.2 Hz, 1H), 3.38 (dd, J=6.5, 4.7 Hz, 2H), 3.18 (dd, J=16.0, 6.1 Hz, 1H), 2.98 (t, J=6.3 Hz, 2H), 2.71 (t, J=6.3 Hz, 2H), 1.91-1.81 (m, 2H). LCMS (ES): m/z 474.0 [M+H]$^+$. Human α$_v$β6 IC$_{50}$ (nM)=600.

Example 7

(S)-3-(6-Methoxypyridin-3-yl)-3-(6-(2-(5,6,7,8-tetrahydro-1,8-naphthyridin-2-yl)ethyl)-2H-indazol-2-yl)propanoic acid and Example 8

(S)-3-(6-Methoxypyridin-3-yl)-3-(6-((2-methyl-5,6,7,8-tetrahydro-1,8-naphthyridin-3-yl)methyl)-2H-indazol-2-yl)propanoic acid

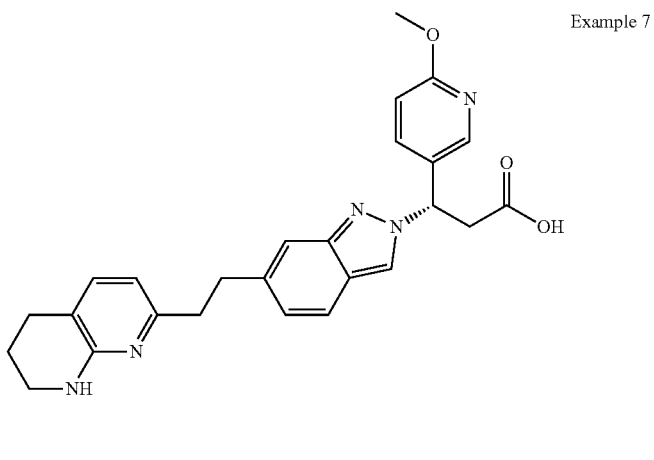

Example 7

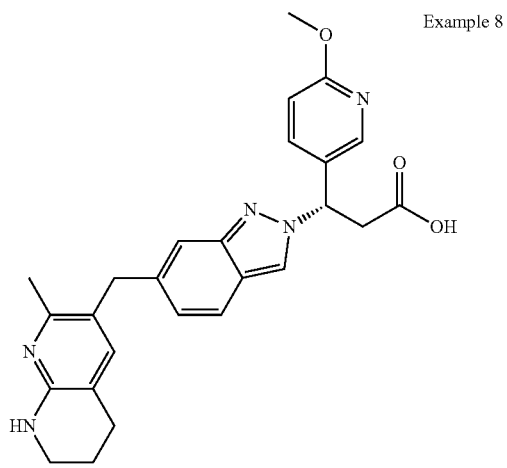

Example 8

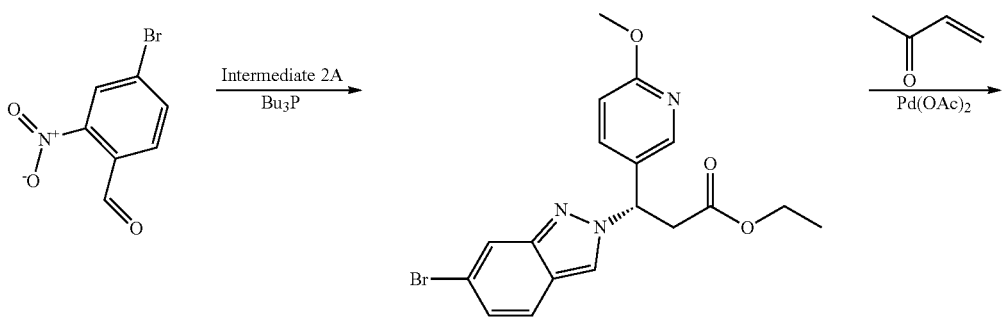

E7A

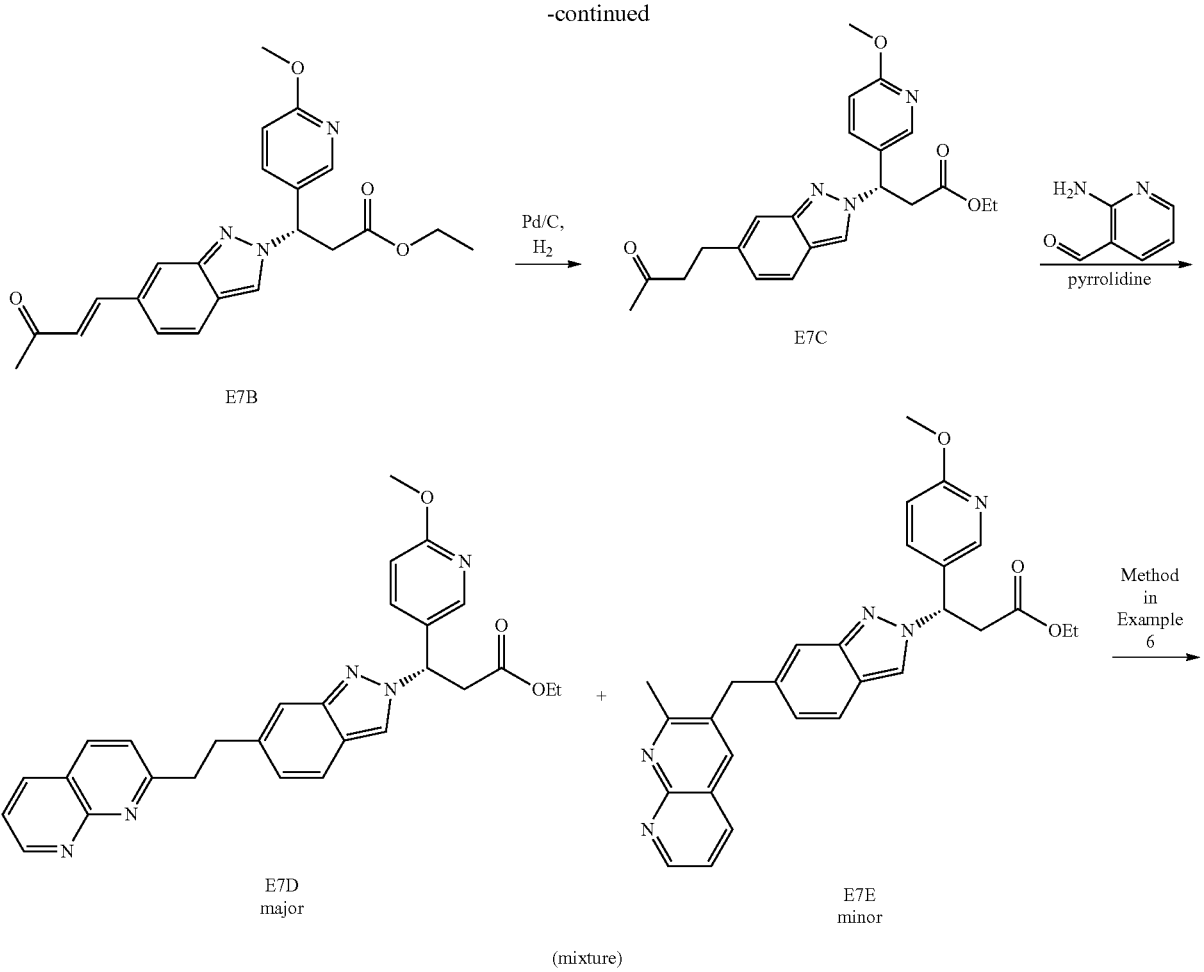

Example 7 and Example 8

Intermediate E7A: To a solution of Intermediate 2A (350 mg, 1.559 mmol) in 2-propanol (3.3 mL) was added 4-bromo-2-nitrobenzaldehyde (326 mg, 1.417 mmol). The mixture was heated at 80° C. for 4 hrs under argon. It was cooled to rt. $PBu_3$ (1.1 mL, 4.25 mmol) was added. The mixture was heated at 80° C. for 16 hrs. The mixture was cooled to rt and diluted with EtOAc (5 mL) and washed with ammonium chloride (5 mL), followed by brine (5 mL). The organic layer was dried ($MgSO_4$), filtered, and concentrated under reduced pressure. The residue was purified via flash column chromatography ($SiO_2$, 0-100% EtOAc/heptane) to afford Intermediate E7A (501 mg, 70%). $^1$H NMR (400 MHz, chloroform-d) δ 8.21 (d, J=2.5 Hz, 1H), 7.95 (d, J=1.0 Hz, 1H), 7.88 (dt, J=1.7, 0.9 Hz, 1H), 7.67 (dd, J=8.7, 2.5 Hz, 1H), 7.47 (dd, J=9.0, 0.8 Hz, 1H), 7.13 (dd, J=8.8, 1.6 Hz, 1H), 6.71 (dd, J=8.6, 0.7 Hz, 1H), 6.01 (dd, J=8.8, 6.0 Hz, 1H), 4.07 (qd, J=7.2, 1.0 Hz, 2H), 3.91 (s, 3H), 3.75 (dd, J=16.6, 8.8 Hz, 1H), 3.19 (dd, J=16.5, 6.0 Hz, 1H), 1.15 (t, J=7.1 Hz, 3H).

Intermediate E7B: A solution of Intermediate E7A (0.199 g, 0.492 mmol), but-3-en-2-one (0.142 mL, 1.723 mmol), $Et_3N$ (0.185 mL, 1.329 mmol), $Pd(OAc)_2$ (12 mg, 0.055 mmol) and tri-o-tolylphosphine (0.025 g, 0.082 mmol) in ACN (4 mL) was degassed with argon for 10 min. The mixture was then sealed and heated at 120° C. for 12 hrs. The solvent was removed under reduced pressure, and the residue was purified via flash column chromatography ($SiO_2$) to afford Intermediate E7B (0.156 g, 0.397 mmol, 81% yield). $^1$H NMR (400 MHz, chloroform-d) δ 8.23 (d, J=2.4 Hz, 1H), 7.96 (d, J=1.0 Hz, 1H), 7.84 (s, 1H), 7.68 (dd, J=8.7, 2.6 Hz, 1H), 7.62 (d, J=5.2 Hz, 1H), 7.59 (d, J=2.2 Hz, 1H), 7.29 (dd, J=8.8, 1.4 Hz, 1H), 6.79-6.70 (m, 2H), 6.04 (dd, J=8.7, 6.1 Hz, 1H), 4.08 (qd, J=7.2, 0.8 Hz, 2H), 3.91 (s, 3H), 3.77 (dd, J=16.6, 8.8 Hz, 1H), 3.22 (dd, J=16.5, 6.1 Hz, 1H), 2.40 (s, 3H), 1.15 (t, J=7.1 Hz, 3H).

Intermediate E7C: To a solution of Intermediate E7B (0.156 g, 0.397 mmol) in EtOAc (3.97 ml) was added Pd/C (10%, 0.021 g, 0.020 mmol). The mixture was purged with $H_2$ gas, then charged with $H_2$ balloon. It was stirred at rt overnight. It was filtered through a pad of celite and rinsed with MeOH. The filtrate was concentrated under reduced pressure to afford E7C, which was used in the next reaction without further purification. LCMS (ES): m/z 396.1 $[M+H]^+$.

Intermediate E7D and Intermediate E7E: To a solution of Intermediate E7C (38.7 mg, 0.098 mmol) in $CH_2Cl_2$ (245 μL) and MeOH (734 μL) was added pyrrolidine (16.19 μL, 0.196 mmol). After stirring at rt for 15 min, 2-aminonicotinaldehyde (14.34 mg, 0.117 mmol) was added. The mixture was stirred at rt overnight. The solvent was removed and the residue was purified via chromatography to afford Intermediates E7D and E7E as a mixture. Intermediate E7D: LCMS (ES): m/z 482.0 [M+H]⁺. Intermediate E7E: LCMS (ES): m/z 482.0 [M+H]⁺.

Example 7 and Example 8 were prepared from the mixture of Intermediates E7D and E7E according to the method described in Example 6.

Example 7: $^1$H NMR (500 MHz, MeOH-$d_4$) δ 8.28 (s, 1H), 8.15 (d, J=2.5 Hz, 1H), 7.72 (dd, J=8.7, 2.6 Hz, 1H), 7.53 (d, J=8.6 Hz, 1H), 7.30 (d, J=7.3 Hz, 1H), 7.17 (s, 1H), 6.87 (dd, J=8.7, 1.4 Hz, 1H), 6.73 (d, J=8.6 Hz, 1H), 6.37 (d, J=7.3 Hz, 1H), 6.13 (dd, J=9.4, 5.9 Hz, 1H), 3.86 (s, 3H), 3.49 (dd, J=15.8, 9.4 Hz, 1H), 3.39 (t, J=5.7 Hz, 2H), 3.18 (dd, J=15.8, 5.9 Hz, 1H), 2.88 (h, J=6.1, 5.0 Hz, 4H), 2.70 (t, J=6.3 Hz, 2H), 1.86 (p, J=6.1 Hz, 2H). LCMS (ES): m/z 458.3 [M+H]⁺. Human αVβ6 IC$_{50}$ (nM)=6.6. Example 8: $^1$H NMR (500 MHz, MeOH-$d_4$) δ 8.32 (s, 1H), 8.16 (d, J=2.5 Hz, 1H), 7.73 (dd, J=8.7, 2.6 Hz, 1H), 7.59 (d, J=8.6 Hz, 1H), 7.29 (s, 1H), 7.22 (s, 1H), 6.87 (dd, J=8.6, 1.4 Hz, 1H), 6.73 (d, J=8.7 Hz, 1H), 6.12 (dd, J=8.9, 6.4 Hz, 1H), 3.90 (s, 2H), 3.85 (s, 3H), 3.48-3.35 (m, 3H), 3.16 (dd, J=15.6, 6.4 Hz, 1H), 2.70 (t, J=6.3 Hz, 2H), 2.28 (s, 3H), 1.92-1.82 (n, 2H). LCMS (ES): m/z 458.3 [M+H]⁺.

Human αVβ6 IC$_{50}$ (nM)=390.

Example 9

(S)-3-(6-Methoxypyridin-3-yl)-3-(6-(3-(5,6,7,8-tetrahydro-1,8-naphthyridin-2-yl)propyl)-2H-indazol-2-yl)propanoic acid and Example 10

(S)-3-(6-Methoxypyridin-3-yl)-3-(6-(2-(2-methyl-5,6,7,8-tetrahydro-1,8-naphthyridin-3-yl)ethyl)-2H-indazol-2-yl)propanoic acid

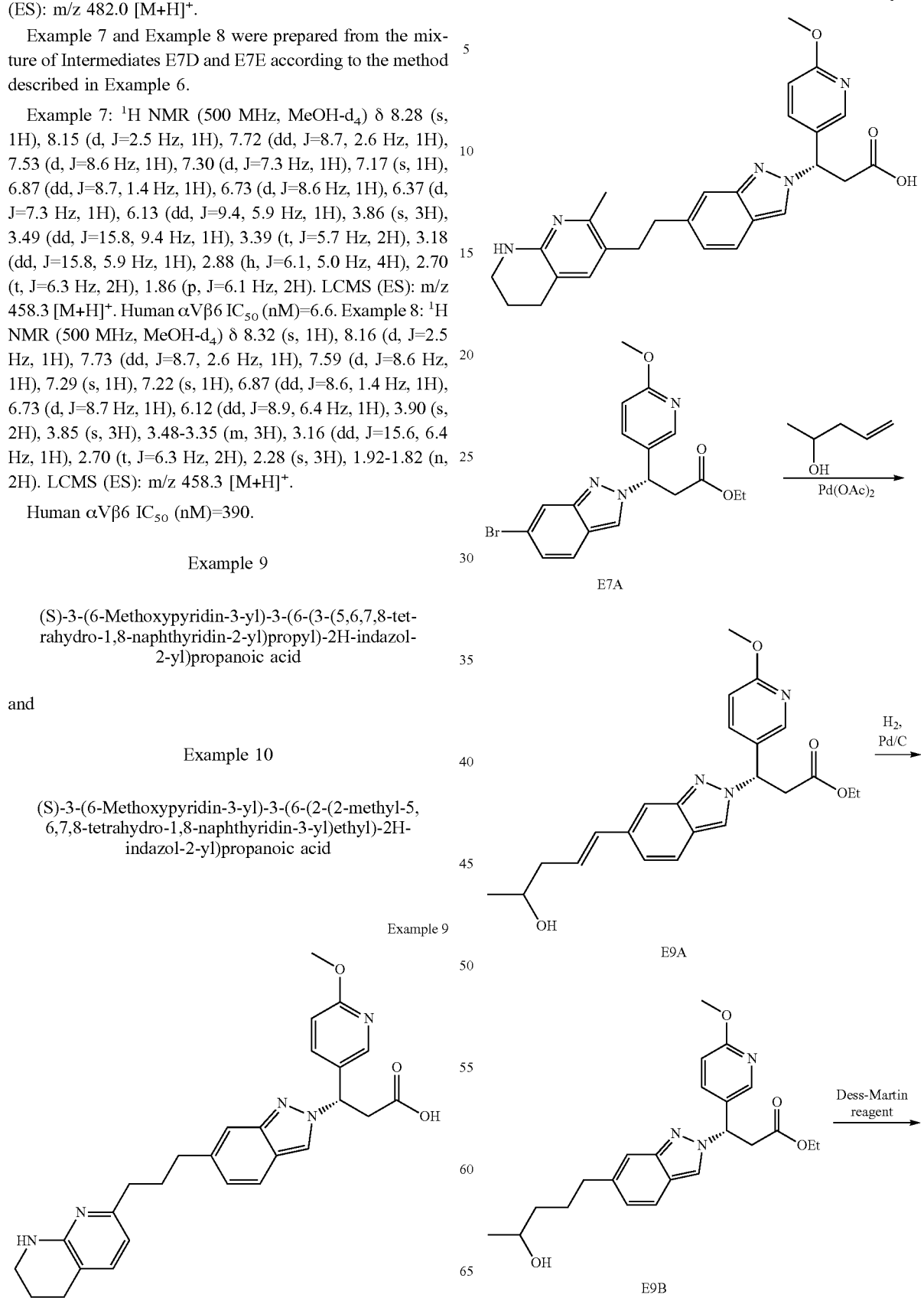

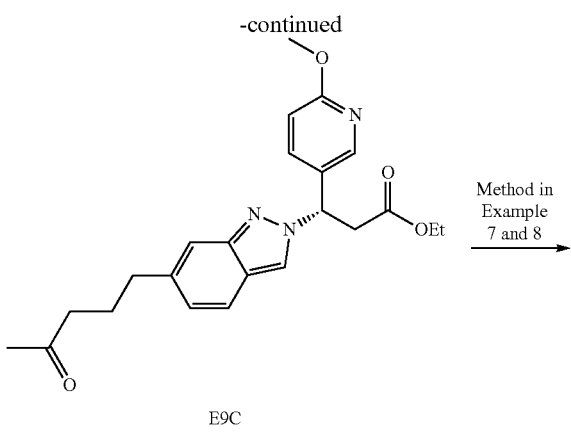

E9C

Example 9 + Example 10

Intermediate E9A: A solution of Intermediate E7A (0.1295 g, 0.320 mmol), pent-4-en-2-ol (0.117 mL, 1.121 mmol), Et$_3$N (0.12 mL, 0.865 mmol), Pd(OAc)$_2$ (8.11 mg, 0.036 mmol) and tri-o-tolylphosphine (0.016 g, 0.053 mmol) in ACN (4 mL) was degassed with argon for 10 min. The mixture was sealed and heated at 120° C. for 12 hrs. After cooled to rt, the solvent was removed under reduced pressure, and the residue was purified via chromatography to afford Intermediate E9A (85 mg, 65%). $^1$H NMR (400 MHz, chloroform-d) δ 8.21 (d, J=2.5 Hz, 1H), 7.89 (d, J=0.9 Hz, 1H), 7.67 (dd, J 8.7, 2.7 Hz, 1H), 7.59-7.48 (m, 2H), 7.21 (dd, J=8.8, 1.5 Hz, 1H), 6.70 (d, J=8.6 Hz, 1H), 6.57 (d, J=15.8 Hz, 1H), 6.25 (ddd, J=15.8, 7.8, 6.9 Hz, 1H), 6.01 (dd, J=8.6, 6.3 Hz, 1H), 4.18-4.01 (m, 3H), 3.99-3.92 (m, 1H), 3.90 (s, 3H), 3.75 (dd, J=16.4, 8.6 Hz, 1H), 3.21 (dd, J=16.5, 6.4 Hz, 1H), 2.53-2.28 (m, 2H), 1.32-1.20 (m, 3H), 1.20-1.08 (m, 3H).

Intermediate E9B: To a solution of Intermediate E9A (85.3 mg, 0.208 mmol) in EtOAc (2.1 mL) was added Pd/C (10%, 11.08 mg, 10.42 μmol). The mixture was purged with H$_2$ gas and then charged with H$_2$ balloon. The mixture was stirred at rt overnight. It was filtered through a pad of celite and rinsed with MeOH. The filtrate was concentrated and the residue was used in the next reaction without further purification. LCMS (ES): m/z 412.1 [M+H]$^+$.

Intermediate E9C: To a solution of Intermediate E9B (83 mg, 0.202 mmol) in CH$_2$Cl$_2$ (2.1 mL) was added Dess-Martin periodinane (103 mg, 0.242 mmol). After stirred at rt for 1 hr, the mixture was diluted with Et$_2$O (10 mL), the precipitate was filtered off, and rinsed with Et$_2$O (10 mL). The filtrate was concentrated under reduced pressure, and the residue was purified via flash column chromatography to give Intermediate E9C (74 mg, 90%). $^1$H NMR (500 MHz, chloroform-d) δ 8.23 (d, J=2.5 Hz, 1H), 7.93 (s, 1H), 7.70 (dd, J=8.7, 2.5 Hz, 1H), 7.58-7.50 (m, 1H), 7.47 (s, 1H), 6.93 (dd, J=8.5, 1.4 Hz, 1H), 6.72 (d, J=8.6 Hz, 1H), 6.04 (dd, J=8.5, 6.3 Hz, 1H), 4.10 (qd, J=7.1, 1.5 Hz, 2H), 3.92 (d, J=2.2 Hz, 3H), 3.76 (dd, J=16.5, 8.5 Hz, 1H), 3.25 (dd, J=16.5, 6.4 Hz, 1H), 2.72 (t, J=7.4 Hz, 2H), 2.47 (t, J=7.4 Hz, 2H), 2.13 (d, J=1.9 Hz, 3H), 1.97 (p, J=7.4 Hz, 2H), 1.17 (td, J=7.2, 1.8 Hz, 3H).

Example 9 and Example 10 were prepared from Intermediate E9C according to the method described in Example 7. Example 9: $^1$H NMR (500 MHz, DMSO-d$_6$) δ 8.45 (s, 1H), 8.27 (s, 1H), 7.94 (s, 1H), 7.79 (dd, J=8.6, 2.4 Hz, 1H), 7.56 (d, J=8.5 Hz, 1H), 7.33 (s, 1H), 7.02 (d, J=7.3 Hz, 1H), 6.87 (d, J=8.6 Hz, 1H), 6.76 (d, J=8.7 Hz, 1H), 6.25 (d, J=7.3 Hz, 1H), 6.09 (s, 1H), 3.79 (s, 2H), 3.23 (d, J=23.7 Hz, 3H), 2.88 (m, 1H), 2.72 (m, 1H), 2.62 (t, J=7.4 Hz, 2H), 2.57 (d, J=6.3 Hz, 1H), 2.43 (t, J=7.7 Hz, 2H), 1.78-1.67 (m, 3H), 1.22 (m, 2H). LC/MS (m/z)=472.0 (M+H)$^+$. Human αVβ6 IC$_{50}$ (nM)=2.6. Example 10: $^1$H NMR (500 MHz, DMSO-d$_6$) δ 8.45 (s, 1H), 8.25 (d, J=2.5 Hz, 1H), 7.94 (s, 1H), 7.77 (dd, J=8.6, 2.5 Hz, 1H), 7.58 (d, J=8.5 Hz, 1H), 7.36 (s, 1H), 6.99-6.88 (m, 1H), 6.76 (d, J=8.7 Hz, 1H), 6.09 (t, J=7.8 Hz, 1H), 3.80 (s, 2H), 3.60 (s, 3H), 3.25-3.12 (m, 2H), 2.89 (s, 1H), 2.82-2.70 (m, 2H), 2.65 (dd, J=10.2, 6.0 Hz, 1H), 2.55 (d, J=5.8 Hz, 2H), 1.90 (s, 3H), 1.76 (s, 1H), 1.73 (d, J=6.3 Hz, 2H). LC/MS (m/z)=472.0 (M+H)$^+$. Human αVβ6 IC$_{50}$ (nM)=160.

Example 11

3-(6-Methoxypyridin-3-yl)-3-(5-(2-(5,6,7,8-tetra-hydro-1,8-naphthyridin-2-yl)ethoxy)pyrazolo[4,3-b]pyridin-1-yl)propanoic acid

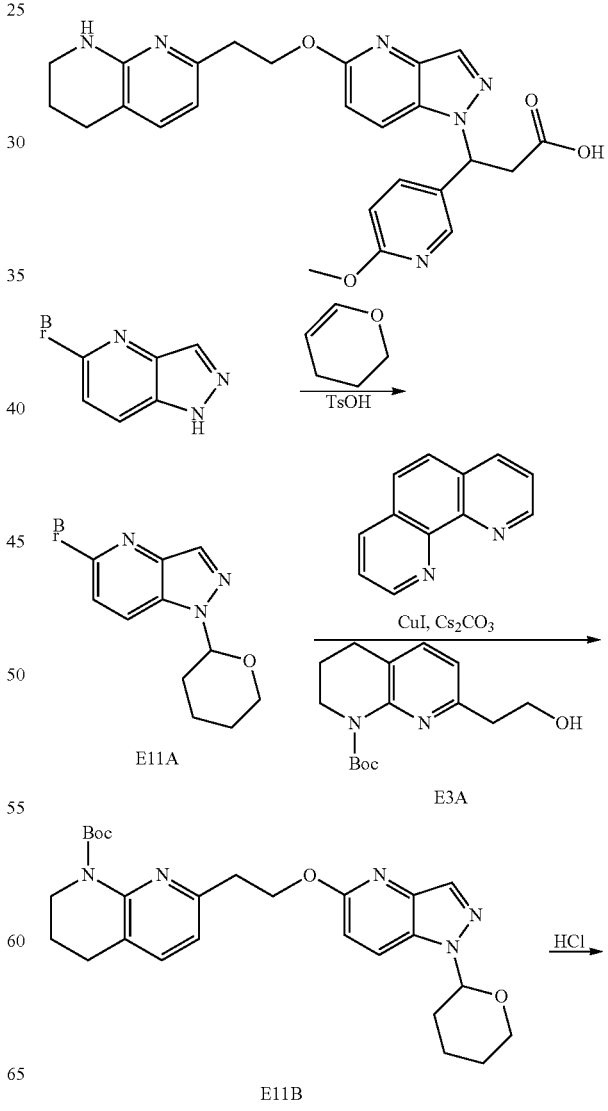

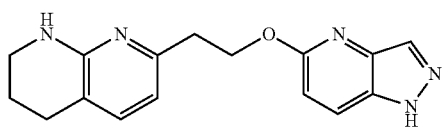

E11C

Example 11

Intermediate E11A: To a solution of 5-bromopyrazolo[4,3-b]pyridine (0.4395 g, 2.22 mmol) and 3,4-dihydro-2H-pyran (0.25 mL, 2.66 mmol) in $CH_2Cl_2$ (4.1 mL) was added 4-methylbenzenesulfonic acid (38 mg, 0.222 mmol). The mixture was stirred at rt overnight. The mixture was diluted with DCM (20 mL) and washed with water (3×8 mL). The organic layer was dried ($Na_2SO_4$), filtered, and concentrated under reduced pressure. The residue was purified via flash column chromatography to give E11A (527 mg, 84%). $^1$H NMR (500 MHz, chloroform-d) δ 8.19 (d, J=1.0 Hz, 1H), 7.89 (dd, J 8.8, 0.9 Hz, 1H), 7.45 (d, J=8.7 Hz, 1H), 5.75 (dd, J=8.7, 2.6 Hz, 1H), 3.99 (dtd, J 11.7, 4.0, 1.4 Hz, 1H), 3.81-3.71 (m, 1H), 2.56-2.42 (m, 1H), 2.20-2.10 (m, 2H), 1.87-1.67 (m, 3H).

Intermediate E11B: A mixture of Intermediate E11A (284 mg, 1.021 mmol), 1,10-phenanthroline (30.7 mg, 0.170 mmol), copper(I) iodide (16.2 mg, 0.085 mmol), and $Cs_2CO_3$ (416 mg, 1.276 mmol) in toluene (1.1 mL) was degassed with argon for 10 min. The mixture was then sealed and heated at 120° C. overnight. The mixture was concentrated under reduced pressure, and the residue was purified via flash column chromatography (using 10% EtOAc in hexanes) to give E11B (90 mg, 22%). LCMS (ES): m/z 480.5 $[M+H]^+$.

Intermediate E11C: To a solution of E11B (90 mg, 0.19 mmol) in MeOH (164 μL) was added a solution of HCl in dioxane (4 M, 1 mL, 4 mmol). After stirred at rt for 48 hrs, the mixture was concentrated under reduced pressure, and the residue was purified via preparative HPLC (Phenomenex Luna Axia 5μ C18 30×100 mm; 10 min gradient from 85% A: 15% B to 0% A:100% B (A=90% $H_2O$/10% ACN+0.1% TFA); (B=90% ACN/10% $H_2O$+0.1% TFA); detection at 220 nm) to give E11C (10 mg, 18%). LCMS (ES): m/z 296.3 $[M+H]^+$.

Example 11 was prepared from Intermediate E11C according to the method described in Example 3. $^1$H NMR (500 MHz, MeOH-$d_4$) δ 8.23-8.19 (m, OH), 8.15 (d, J=2.5 Hz, 1H), 8.04 (d, J=9.1 Hz, 1H), 7.92 (s, 1H), 7.72 (dd, J=8.7, 2.6 Hz, 1H), 7.44 (d, J=7.4 Hz, 1H), 6.79 (d, J=9.1 Hz, 1H), 6.73 (d, J=8.8 Hz, 1H), 6.62 (d, J 7.4 Hz, 1H), 6.17 (dd, J=9.8, 5.1 Hz, 1H), 4.65 (ddt, J=14.6, 11.5, 5.7 Hz, 2H), 3.85 (s, 3H), 3.67 (dd, J=16.5, 9.8 Hz, 1H), 3.47-3.40 (m, 2H), 3.20 (dd, J=16.6, 5.1 Hz, 1H), 3.13 (t, J=6.1 Hz, 2H), 2.67 (d, J=11.3 Hz, 2H), 1.85 (p, J=6.0 Hz, 2H). LC/MS (m/z)=475.2 $(M+H)^+$. Human $α_vβ6$ $IC_{50}$ (nM)=120.

Example 12

3-(5-(2-((4,5-Dihydroimidazol-2-yl)amino)ethoxy)-1H-indazol-1-yl)-3-(6-methoxypyridin-3-yl)propanoic acid

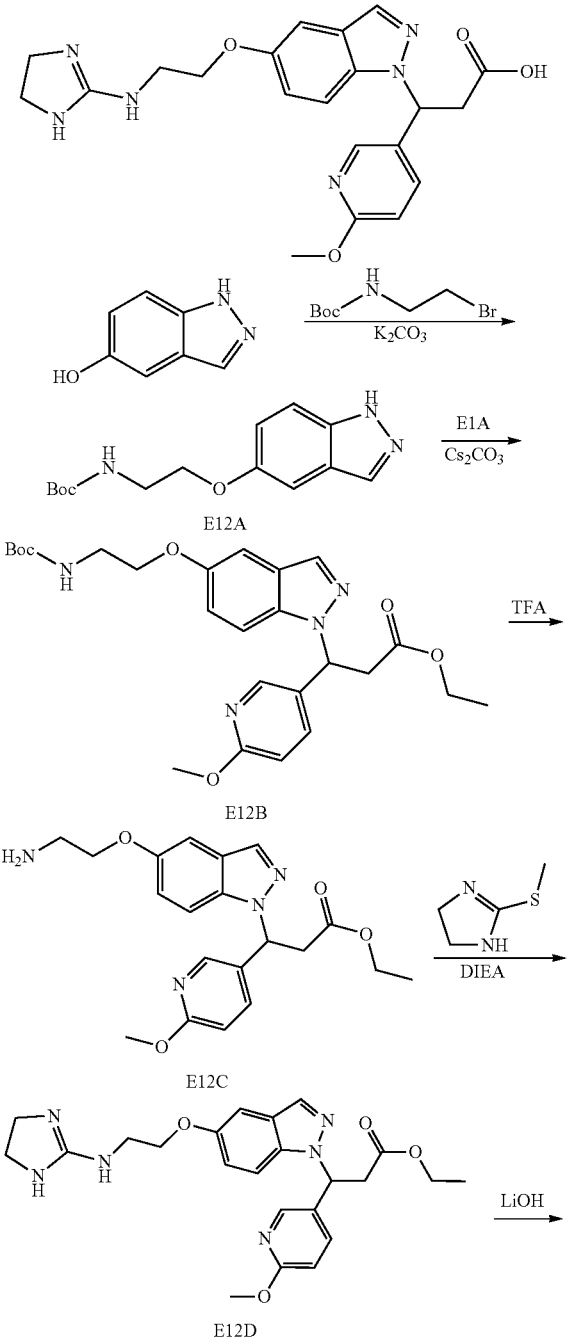

Example 12

Intermediate E12A: To a solution of 1H-indazol-5-ol (1 g, 7.46 mmol) in DMF (5 mL) was added $K_2CO_3$ (2.06 g, 14.91 mmol) followed by tert-butyl (2-bromoethyl)carbamate (2.01 g, 8.95 mmol). The reaction mixture was stirred at rt for 1 day. The mixture was diluted with water (10 mL) and extracted with EtOAc (3×5 mL). The combined organic layers were washed with water (10 mL), followed by brine (10 mL). It was dried (Na$_2$SO$_4$), filtered, and concentrated under reduced pressure. The residue was purified via preparative HPLC (Phenomenex Luna Axia 5μ C18 30×100 mm; 10 min gradient from 85% A: 15% B to 0% A:100% B (A=90% H$_2$O/10% ACN+0.1% TFA); (B=90% ACN/10% H$_2$O+0.1% TFA); detection at 220 nm) to give E12A (526 mg, 1.897 mmol, 25.4% yield). LCMS (ES): m/z 278.2 [M+H]$^+$.

Intermediate E12B: To a solution of E12A (75 mg, 0.270 mmol) in acetonitrile (1.5 mL) was added cesium carbonate (264 mg, 0.811 mmol) and stirred for 5 min at rt then Intermediate E1A (56.0 mg, 0.270 mmol) was added and stirred at 80° C. for 5 hrs. The reaction was cooled to room temperature, filtered and concentrated. The crude product was diluted with MeCN filtered and purified by preparative HPLC (Phenomenex Luna Axia 5μ C18 30×100 mm; 10 min gradient from 85% A: 15% B to 0% A:100% B (A=90% H$_2$O/10% ACN+0.1% TFA); (B=90% ACN/10% H$_2$O+ 0.1% TFA); detection at 220 nm) to give E12B (53 mg, 0.089 mmol, 32.7% yield). LCMS (ES): m/z 485.1 [M+H]$^+$.

Intermediate E12C: To a solution of Intermediate E12B (53 mg, 0.089 mmol) in DCM (0.7 mL) was added TFA (0.05 mL, 0.649 mmol) and stirred at rt for 5 hrs. The reaction was concentrated. The crude product was diluted with MeCN filtered and purified by preparative HPLC (Phenomenex Luna Axia 5μ C18 30×100 mm; 10 min gradient from 85% A: 15% B to 0% A:100% B (A=90% H$_2$O/10% ACN+0.1% TFA); (B=90% ACN/10% H$_2$O+ 0.1% TFA); detection at 220 nm) to give Intermediate E12C (57 mg, 0.093 mmol, 105% yield). LCMS (ES): m/z 385.1 [M+H]$^+$.

Intermediate E12D: A solution of E12C (57 mg, 0.093 mmol), 2-(methylthio)-4,5-dihydroimidazole HCl salt (21.31 mg, 0.140 mmol) and DIPEA (0.081 mL, 0.465 mmol) in EtOH (2 mL) was heated to 150° C. in a microwave reactor for 15 min. The crude product was purified via preparative HPLC (Phenomenex Luna Axia 5μ C18 30×100 mm; 10 min gradient from 85% A: 15% B to 0% A:100% B (A=90% H$_2$O/10% ACN+0.1% TFA); (B=90% ACN/10% H$_2$O+0.1% TFA); detection at 220 nm) to E12D (46 mg, 0.081 mmol, 87% yield). LCMS (ES): m/z 453.4 [M+H]$^+$.

Example 12

To a solution of Intermediate E12D (46 mg, 0.081 mmol) in THF (1 mL) was added a solution of LiOH (aqueous, 1 N, 0.244 mL, 0.244 mmol). The reaction mixture was stirred at rt overnight. The mixture was concentrated and purified by preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 12-52% B over 25 minutes, then a 3-minute hold at 100% B; Flow: 20 mL/min to give Example 12 (2.5 mg, 7.4%). $^1$H NMR (500 MHz, chloroform-d) δ 7.94 (s, 1H), 7.66 (d, J=9.1 Hz, 1H), 7.34 (d, J=7.2 Hz, 1H), 7.12-7.03 (m, 2H), 6.99 (d, J=9.1 Hz, 1H), 6.57 (d, J=8.0 Hz, 1H), 6.50 (d, J=7.2 Hz, 1H), 6.21 (t, J=6.7 Hz, 1H), 4.28 (t, J=5.6 Hz, 2H), 4.19 (dt, J=8.5, 4.4 Hz, 2H), 3.69-3.52 (m, 3H), 3.51-3.39 (m, 3H), 3.16 (t, J=5.6 Hz, 2H), 2.74 (t, J=6.1 Hz, 2H), 1.97-1.85 (m, 2H). LC/MS (m/z)=501.4 (M+H)$^+$. Human α$_v$β6 IC$_{50}$ (nM)=2,000.

Example 13

3-(5-(2-(5,6,7,8-Tetrahydro-1,8-naphthyridin-2-yl)ethoxy)-1H-indazol-1-yl)-2-((2,4,6-trimethylphenyl)sulfonamido)propanoic acid Example 13

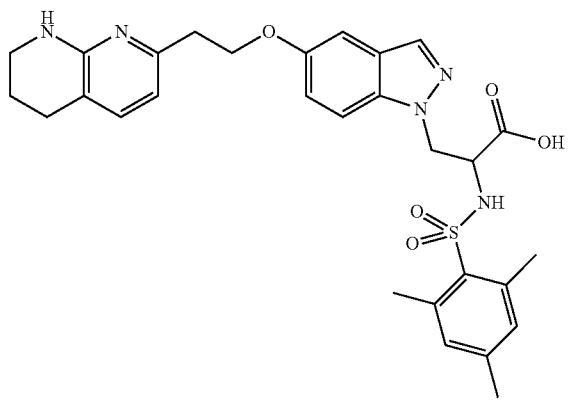

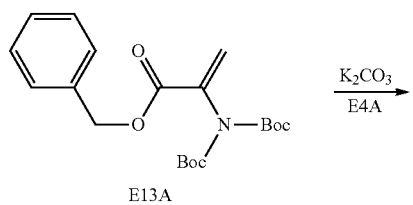

E13A

-continued

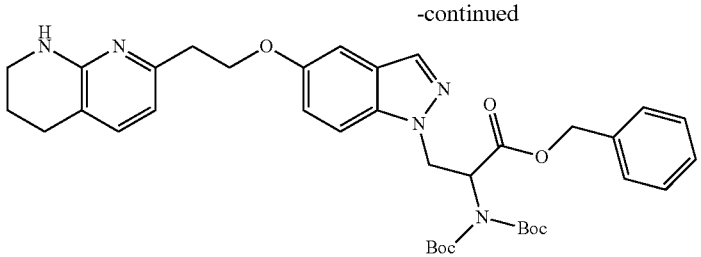

E12B

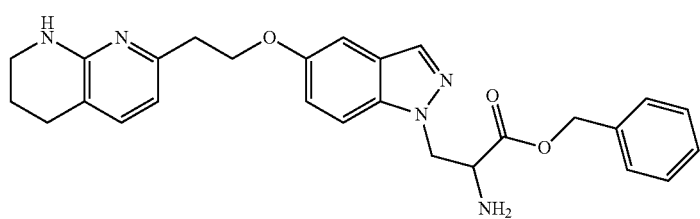

E12C

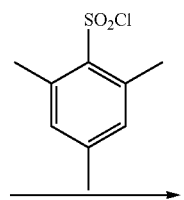

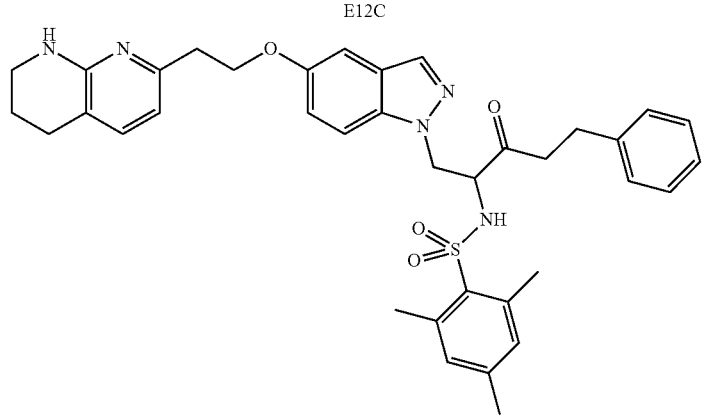

E13D

Intermediate E13B: To a solution of E4A (55.2 mg, 0.135 mmol) and E13A (51.0 mg, 0.135 mmol) in acetonitrile (1.35 mL) was added $K_2CO_3$ (112 mg, 0.811 mmol). The mixture was stirred at rt for overnight. The mixture was filtered, and rinsed with acetonitrile. The filtrate was concentrated and the residue was purified via flash column chromatography to afford E13B (55 mg, 60%). LCMS (ES): m/z 672.8 $[M+H]^+$.

Intermediate E13C: To a solution of E13B (54.9 mg, 0.082 mmol) in $CH_2Cl_2$ (545 μl) was added TFA (82 μL, 1.062 mmol). The mixture was stirred at rt overnight. The solvent was removed and the residue was used in the next reaction without further purification. LCMS (ES): m/z 472.5 $[M+H]^+$.

Intermediate E13D: To a solution of Intermediate E13C (19 mg, 0.040 mmol) in THF (403 μL) was added $Et_3N$ (22.46 μL, 0.161 mmol), followed by 2,4,6-trimethylbenzene-1-sulfonyl chloride (9.1 mg, 0.04 mmol). The mixture was stirred at rt overnight. The mixture was concentrated and purified via preparative HPLC (Sunfire 5μ C18 30×100 mm; 10 min gradient from 95% A: 5% B to 0% A:100% B (A=90% $H_2O$/10% ACN+0.1% TFA); (B=90% ACN/10% $H_2O$+0.1% TFA); detection at 220 nm) to E13D (4.4 mg, 17% yield). LCMS (ES): m/z 654.6 $[M+H]^+$.

Example 13

To a solution of Intermediate E13D (4.4 mg, 6.73 μmol) in MeOH (122 μL) was added NaOH (aqueous, 1 N, 20.2 μL, 0.020 mmol). The mixture was stirred at rt overnight. The mixture was neutralized with 1N HCl and concentrated. The crude was dissolved in 2 mL MeOH, filtered and purified by preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 19 minutes, then a 5-minute hold at 100% B; Flow: 20 mL/min to give Example 13 (1.5 mg, 32%). $^1H$ NMR (500 MHz, MeOH-$d_4$) δ 7.63 (s, 1H), 7.57 (d, J=7.3 Hz, 1H), 7.33 (d, J=9.0 Hz, 1H), 6.99 (d, J=2.2 Hz, 1H), 6.92 (d, J=9.2 Hz, 1H), 6.72 (d, J=7.4 Hz, 1H), 6.68 (s, 2H), 4.61 (dd, J=14.3, 4.4 Hz, 1H), 4.47 (dd, J=14.3, 8.1 Hz, 1H), 4.27 (t, J=6.0 Hz, 2H), 4.15 (s, 1H), 3.49 (t, J=5.6 Hz, 1H), 3.15 (t, J=6.1 Hz, 2H), 2.81 (t, J=6.3 Hz, 2H), 2.66 (s, 2H), 2.36 (s, 5H), 2.16 (s, 3H), 1.93 (t, J=6.0 Hz, 2H). LC/MS (m/z)=564.4 $(M+H)^+$. Human $α_vβ6$ $IC_{50}$ (nM)=320.

Example 14

2-(((Benzyloxy)carbonyl)amino)-3-(5-(2-(5,6,7,8-tetrahydro-1,8-naphthyridin-2-yl)ethoxy)-1H-indazol-1-yl)propanoic acid

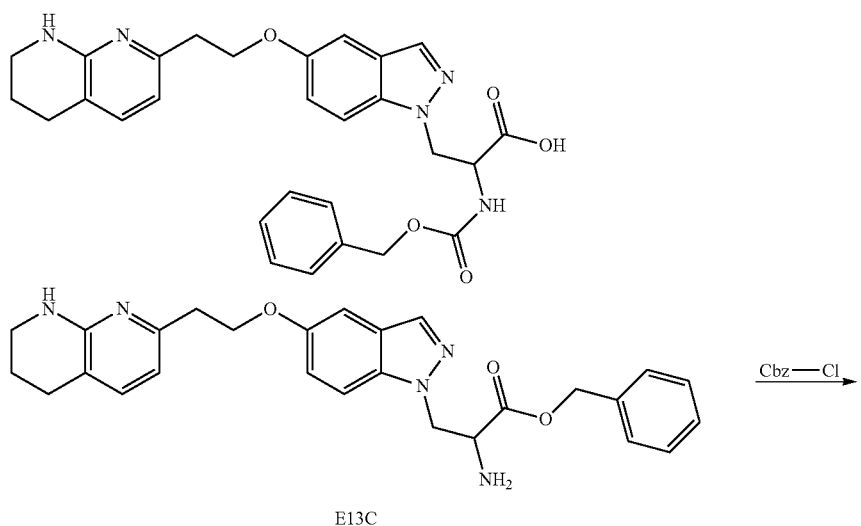

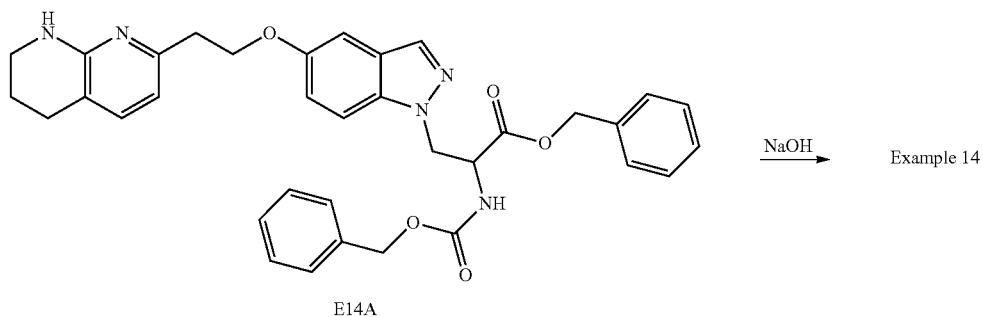

Intermediate E14A: To a solution of benzyl 2-amino-3-(5-(2-(5,6,7,8-tetrahydro-1,8-naphthyridin-2-yl)ethoxy)-1H-indazol-1-yl)propanoate (19 mg, 0.04 mmol) in THF (403 µL) was added sodium bicarbonate (aqueous, 1 N, 201 µL, 0.201 mmol), followed by benzyl carbonochloridate (6.87 µL, 0.048 mmol). The mixture was stirred at rt for 3 hrs. Solvent was removed under reduced pressure. The crude was dissolved in 2 mL MeOH, filtered and purified by preparative HPLC with the following conditions: Column: Phenomenex Luna AXIA 5u C18 21.2×100 mm; Mobile Phase A: 10:90 MeOH: water with 0.1% TFA; Mobile Phase B: 90:10 MeOH: water with 0.1% TFA; Gradient: 20-100% B over 10 minutes, then a 2-minute hold at 100% B; Flow: 20 mL/min to give Intermediate E14A (17.6 mg, 72%). $^1$H NMR (400 MHz, MeOH-$d_4$) δ 7.88 (s, 1H), 7.59 (dt, J=7.3, 1.3 Hz, 1H), 7.36 (d, J=9.1 Hz, 1H), 7.31-7.12 (m, 11H), 6.98 (dd, J=9.1, 2.3 Hz, 1H), 6.74 (d, J=7.3 Hz, 1H), 5.16-5.00 (m, 2H), 4.96 (s, 2H), 4.81-4.66 (m, 3H), 4.31 (t, J=5.9 Hz, 2H), 3.48 (dd, J=6.5, 4.8 Hz, 2H), 3.19 (t, J=5.9 Hz, 2H), 2.80 (t, J=6.3 Hz, 2H), 1.98-1.87 (m, 2H). LC/MS (m/z)=606.7 (M+H)$^+$.

Example 14

To a solution of E14A (benzyl 2-(((benzyloxy)carbonyl)amino)-3-(5-(2-(5,6,7,8-tetrahydro-1,8-naphthyridin-2-yl)ethoxy)-1H-indazol-1-yl)propanoate) (17.6 mg, 0.029 mmol) in MeOH (528 µL) was added NaOH (aqueous, 87 µL, 1 N, 0.087 mmol). The mixture was stirred at rt overnight. The mixture was neutralized with HCl (aqueous, 1 N, 87 µL) and concentrated under reduced pressure. The crude was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 4-minute hold at 100% B; Flow: 20 mL/min to give Example 14 (9.3 mg, 62%). $^1$H NMR (500 MHz, DMSO-$d_6$) δ 7.91 (s, 1H), 7.48 (s, 2H), 7.28 (d, J=7.0 Hz, 4H), 7.17 (d, J=6.7 Hz, 2H), 7.07 (d, J=7.2 Hz, 1H), 6.95 (d, J=9.0 Hz, 1H), 6.38 (d, J=7.3 Hz, 1H), 6.30 (s, 1H), 4.92 (s, 2H), 4.68 (s, 3H), 4.23 (s, 2H), 3.24 (s, 2H), 3.17 (s, 1H), 2.90 (s, 2H), 2.61 (t, J=6.3 Hz, 2H), 1.75 (t, J=6.1 Hz, 2H). LC/MS (m/z)=516.3 (M+H)$^+$. Human $\alpha_v\beta_6$ IC$_{50}$ (nM)=300.

Example 15

(±)-3-(Quinoxalin-2-yl)-3-(5-(2-(5,6,7,8-tetrahydro-1,8-naphthyridin-2-yl)ethoxy)-1H-indazol-1-yl)propanoic acid

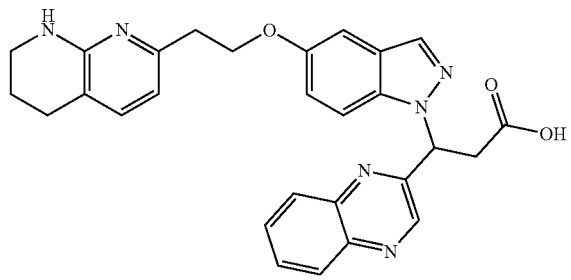 [SMILES: O=C(O)CC(c1cnc2ccccc2n1)n1ncc2cc(OCCc3ccc4c(n3)NCCC4)ccc21]

(±)-3-(Quinoxalin-2-yl)-3-(5-(2-(5,6,7,8-tetrahydro-1,8-naphthyridin-2-yl)ethoxy)-1H-indazol-1-yl)propanoic acid was synthesized according to the procedure described in Example 3 using Intermediate E4A and ethyl (E)-3-(quinoxalin-2-yl)acrylate. $^1$H NMR (500 MHz, MeOH-d$_4$) δ 8.39 (s, 1H), 8.14 (d, J=8.2 Hz, 1H), 8.02 (dd, J=9.5, 7.9 Hz, 2H), 7.91-7.78 (m, 2H), 7.67 (d, J=9.2 Hz, 1H), 7.57 (d, J=7.5 Hz, 1H), 7.22 (d, J=2.0 Hz, 1H), 7.10 (dd, J=9.2, 2.1 Hz, 1H), 6.73 (d, J=7.3 Hz, 1H), 6.62 (d, J=5.5 Hz, 1H), 4.33 (t, J=6.0 Hz, 2H), 3.85 (d, J=17.5 Hz, 1H), 3.52-3.44 (m, 2H), 3.17 (t, J=6.0 Hz, 2H), 2.79 (t, J=6.3 Hz, 2H), 1.97-1.85 (m, 2H). LC/MS (m/z)=495.1 (M+H)+. Human αVβ6 IC$_{50}$ (nM)=6.0; Human αVβ1 IC$_{50}$ (nM)=270; Human αVβ3 IC$_{50}$ (nM)=2.7; Human αVβ5 IC$_{50}$ (nM)=0.31; and Human αVβ8 IC$_{50}$ (nM)=1,500.

Example 16 and Example 17

(R)-3-(Quinoxalin-2-yl)-3-(5-(2-(5,6,7,8-tetrahydro-1,8-naphthyridin-2-yl)ethoxy)-1H-indazol-1-yl)propanoic acid and (S)-3-(quinoxalin-2-yl)-3-(5-(2-(5,6,7,8-tetrahydro-1,8-naphthyridin-2-yl)ethoxy)-1H-indazol-1-yl)propanoic acid

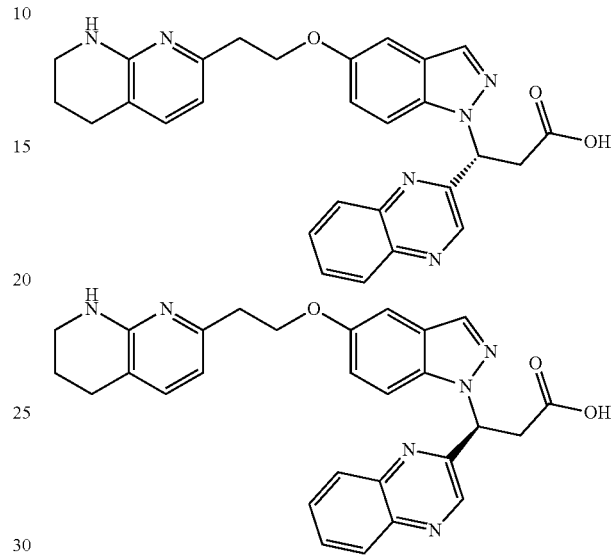

Example 15 (60 mg) was subjected to preparative chiral SFC purification (Column: Chiralpak IA, 21×250 mm, 5 micron, BPR Pressure: 120 bars, Temperature: 40° C., Flow rate: 45 mL/min, Mobile Phase: C02/MeOH (60/40), Detector Wavelength: 220 nm) to afford Example 16 (15 mg) and Example 17 (19 mg) as a yellow solid. The enantiomeric excess for both Example 16 and Example 17 is >99.0%. Example 16: Human αVβ6 IC$_{50}$ (nM)=136.76. Example 17: Human αVβ6 IC$_{50}$ (nM)=4.2; Human α$_V$β1 IC$_{50}$ (nM)=190; Human αVβ3 IC$_{50}$ (nM)=2.1; Human α$_V$β5 IC$_{50}$ (nM)=0.25; and Human αVβ8 IC$_{50}$ (nM)=1,900.

The following examples were prepared using methods analogous to the ones indicated in the table below.

| Example No. | Structure & Name | Analytical Data | Method |
|---|---|---|---|
| 18 | ![structure] 3-(3,5-Dichlorophenyl)-3-(4-(3-(5,6,7,8-tetrahydro-1,8-naphthyridin-2-yl)propyl)-1H-indazol-1-yl)propanoic acid | $^1$H NMR (500 MHz, DMSO-d$_6$) δ 8.22 (s, 1H), 7.60 (d, J = 8.5 Hz, 1H), 7.47 (d, J = 2.0 Hz, 1H), 7.40 (dd, J = 12.5, 4.6 Hz, 3H), 7.28 (t, J = 7.7 Hz, 1H), 6.94 (d, J = 7.0 Hz, 1H), 6.50 (d, J = 7.3 Hz, 1H), 6.22 (dd, J = 10.1, 4.9 Hz, 1H), 3.68 (s, 1H), 3.23 (dd, J = 16.8, 4.8 Hz, 1H), 2.96-2.82 (m, 2H), 2.64 (t, J = 7.2 Hz, 4H), 2.54 (s, 3H), 2.06-1.93 (m, 2H), 1.82-1.70 (m, 2H). LC/MS (m/z) = 509.1 (M + H)+. Human αVβ6 IC$_{50}$ (nM) = 2,700. | Example 1 |

| Example No. | Structure & Name | Analytical Data | Method |
|---|---|---|---|
| 19 | 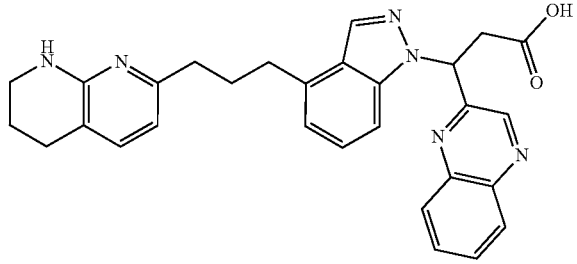 [SMILES: O=C(O)CC(c1cnc2ccccc2n1)n1ncc2c(CCCc3ccc4c(n3)NCCC4)cccc21]<br>3-(Quinoxalin-2-yl)-3-(4-(3-(5,6,7,8-tetrahydro-1,8-naphthyridin-2-yl)propyl)-1H-indazol-1-yl)propanoic acid | $^1$H NMR (500 MHz, DMSO-$d_6$) δ 8.66 (s, 1H), 8.17 (s, 1H), 8.07 (dd, J = 16.5, 7.9 Hz, 2H), 7.86 (dt, J = 13.2, 6.9 Hz, 2H), 7.68 (d, J = 8.5 Hz, 1H), 7.32 (t, J = 7.7 Hz, 1H), 7.02 (d, J = 7.3 Hz, 1H), 6.96 (d, J = 7.1 Hz, 1H), 6.62 (t, J = 7.2 Hz, 1H), 3.21 (s, 2H), 2.88 (t, J = 7.6 Hz, 2H), 2.58 (t, J = 6.3 Hz, 2H), 2.55 (m, 2H), 2.47 (d, J = 7.6 Hz, 2H), 1.96 (t, J = 7.8 Hz, 2H), 1.90 (s, 1H), 1.78-1.66 (m, 2H). LC/MS (m/z) = 493.1 (M + H)$^+$. Human αVβ6 IC$_{50}$ (nM) = 220. | Example 1 |
| 20 | 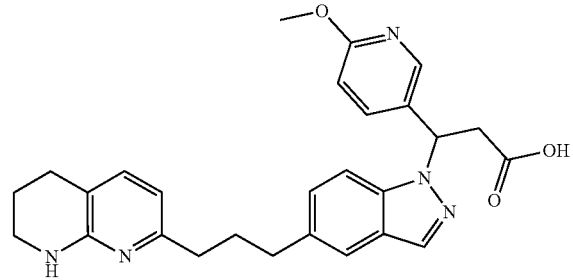 [SMILES: COc1ccc(C(CC(=O)O)n2ncc3cc(CCCc4ccc5c(n4)NCCC5)ccc32)cn1]<br>3-(6-Methoxypyridin-3-yl)-3-(5-(3-(5,6,7,8-tetrahydro-1,8-naphthyridin-2-yl)propyl)-1H-indazol-1-yl)propanoic acid | $^1$H NMR (500 MHz, DMSO-$d_6$) δ 8.21 (s, 1H), 8.00 (s, 1H), 7.66 (d, J = 8.5 Hz, 2H), 7.48 (s, 1H), 7.21 (d, J = 8.5 Hz, 1H), 7.02 (d, J = 7.3 Hz, 1H), 6.71 (d, J = 8.9 Hz, 1H), 6.25 (d, J = 7.3 Hz, 1H), 6.17-6.08 (m, 1H), 3.75 (s, 3H), 3.60 (br. s., 2H), 3.21 (br. s., 2H), 2.63 (t, J = 7.2 Hz, 2H), 2.59-2.55 (m, 2H), 2.41 (t, J = 7.6 Hz, 2H), 1.87-1.80 (m, 2H), 1.74-1.65 (m, 2H). LC/MS (m/z) = 472.4 (M + H)$^+$. Human αVβ6 IC$_{50}$ (nM) = 70. | Example 1 |
| 21 | 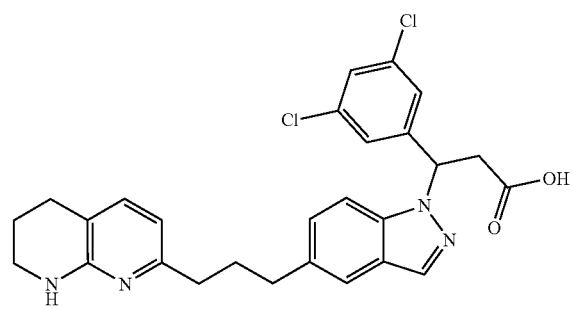 [SMILES: O=C(O)CC(c1cc(Cl)cc(Cl)c1)n1ncc2cc(CCCc3ccc4c(n3)NCCC4)ccc21]<br>3-(3,5-Dichlorophenyl)-3-(5-(3-(5,6,7,8-tetrahydro-1,8-naphthyridin-2-yl)propyl)-1H-indazol-1-yl)propanoic acid | $^1$H NMR (500 MHz, DMSO-$d_6$) δ 8.07 (s, 1H), 7.68 (d, J = 8.5 Hz, 1H), 7.51 (s, 1H), 7.46 (s, 1H), 7.39 (s, 2H), 7.23 (d, J = 8.5 Hz, 1H), 7.02 (d, J = 7.3 Hz, 1H), 6.25 (d, J = 7.3 Hz, 1H), 6.23-6.17 (m, 1H), 3.59 (br. s., 2H), 3.21 (br. s., 2H), 2.64 (t, J = 7.0 Hz, 2H), 2.57 (t, J = 6.1 Hz, 2H), 2.42 (t, J = 7.6 Hz, 2H), 1.89-1.82 (m, 2H), 1.71 (d, J = 5.5 Hz, 2H). LC/MS (m/z) = 509.4 (M + H)$^+$. Human αVβ6 IC$_{50}$ (nM) = 44. | Example 1 |
| 22 | 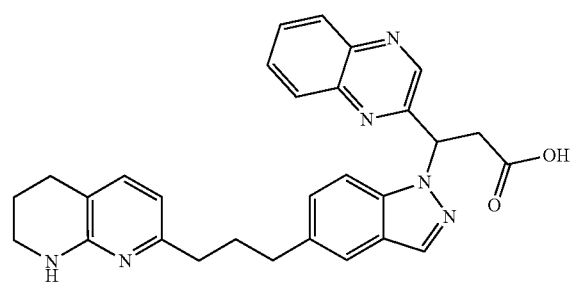 [SMILES: O=C(O)CC(c1cnc2ccccc2n1)n1ncc2cc(CCCc3ccc4c(n3)NCCC4)ccc21]<br>3-(Quinoxalin-2-yl)-3-(5-(3-(5,6,7,8-tetrahydro-1,8-naphthyridin-2-yl)propyl)-1H-indazol-1-yl)propanoic acid | $^1$H NMR (500 MHz, DMSO-$d_6$) δ 8.73 (s, 1H), 8.04 (t, J = 7.8 Hz, 2H), 8.00 (s, 1H), 7.83 (t, J = 7.2 Hz, 2H), 7.74 (d, J = 8.5 Hz, 1H), 7.24 (d, J = 8.2 Hz, 1H), 7.00 (d, J = 6.7 Hz, 1H), 6.56 (br. s., 1H), 6.29-6.15 (m, 2H), 3.21 (br. s., 2H), 2.72-2.62 (m, 2H), 2.58 (d, J = 5.2 Hz, 2H), 2.43 (t, J = 7.3 Hz, 2H), 1.93-1.82 (m, 4H), 1.73 (br. s., 2H). LC/MS (m/z) = 509.4 (M + H)$^+$. Human αVβ6 IC$_{50}$ (nM) = 190. | Example 1 |

-continued

| Example No. | Structure & Name | Analytical Data | Method |
|---|---|---|---|
| 23 | 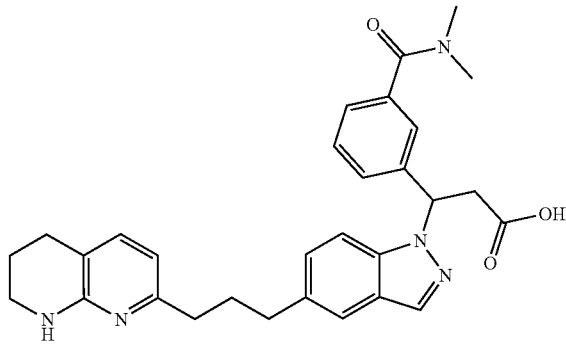 [SMILES: CN(C)C(=O)c1cccc(C(CC(=O)O)n2ncc3cc(CCCc4ccc5c(n4)NCCC5)ccc32)c1]<br>3-(3-(Dimethylcarbamoyl)phenyl)-3-(5-(3-(5,6,7,8-tetrahydro-1,8-naphthyridin-2-yl)propyl)-1H-indazol-1-yl)propanoic acid | $^1$H NMR (500 MHz, DMSO-$d_6$) δ 8.02 (br. s., 1H), 7.63 (d, J = 8.6 Hz, 1H), 7.55-7.46 (m, 1H), 7.40 (br. s., 1H), 7.37-7.29 (m, 2H), 7.24 (d, J = 7.4 Hz, 1H), 7.19 (d, J = 8.6 Hz, 1H), 7.01 (d, J = 7.1 Hz, 1H), 6.24 (d, J = 6.6 Hz, 2H), 3.21 (br. s., 2H), 2.93 (br. s., 3H), 2.78 (br. s., 3H), 2.64 (t, J = 7.1 Hz, 2H), 2.58 (t, J = 6.1 Hz, 2H), 2.42 (t, J = 7.4 Hz, 2H), 1.96-1.83 (m, 4H), 1.77-1.68 (m, 2H). LC/MS (m/z) = 512.2 (M + H)$^+$. Human αVβ6 IC$_{50}$ (nM) = 61. | Example 1 |
| 24 | 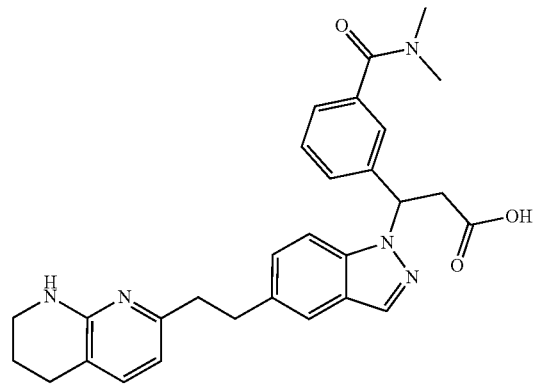<br>3-(3-(Dimethylcarbamoyl)phenyl)-3-(5-(2-(5,6,7,8-tetrahydro-1,8-naphthyridin-2-yl)ethyl)-1H-indazol-1-yl)propanoic acid | $^1$H NMR (500 MHz, DMSO-$d_6$) δ 8.05 (s, 1H), 7.67 (d, J = 8.9 Hz, 1H), 7.54 (s, 1H), 7.43 (d, J = 7.7 Hz, 1H), 7.39-7.33 (m, 2H), 7.25 (t, J = 8.2 Hz, 2H), 6.27-6.17 (m, 1H), 3.38 (m, 2H), 2.96 (m, 4H), 2.79 (m, 2H), 2.64 (m, 2H), 2.55 (s, 6H), 1.77 (s, 2H), 1.24 (s, 2H). LC/MS (m/z) = 458.2 (M + H)$^+$. Human αVβ6 IC$_{50}$ (nM) = 130. | Example 2 |
| 25 | 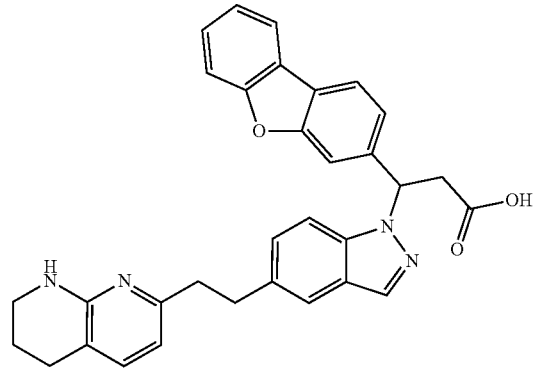 [SMILES: O=C(O)CC(c1ccc2c(c1)oc1ccccc12)n1ncc2cc(CCc3ccc4c(n3)NCCC4)ccc21]<br>3-(Dibenzo[b,d]furan-3-yl)-3-(5-(2-(5,6,7,8-tetrahydro-1,8-naphthyridin-2-yl)ethyl)-1H-indazol-1-yl)propanoic acid | $^1$H NMR (500 MHz, DMSO-$d_6$) δ 8.10-7.99 (m, 3H), 7.77-7.62 (m, 3H), 7.54-7.44 (m, 2H), 7.41-7.33 (m, 2H), 7.22 (d, J = 8.6 Hz, 1H), 6.99 (d, J = 7.2 Hz, 1H), 6.36 (br. s., 1H), 6.26 (d, J = 7.2 Hz, 1H), 3.68 (br. s., 1H), 3.22 (br. s., 2H), 2.98-2.87 (m, 2H), 2.71 (t, J = 7.8 Hz, 2H), 2.58 (t, J = 5.8 Hz, 2H), 1.73 (br. s., 2H). LC/MS (m/z) = 517.2 (M + H)$^+$. Human αVβ6 IC$_{50}$ (nM) = 530. | Example 2 |

| Example No. | Structure & Name | Analytical Data | Method |
|---|---|---|---|
| 26 | 3-(3-((Dimethylamino)methyl)phenyl)-3-(5-(2-(5,6,7,8-tetrahydro-1,8-naphthyridin-2-yl)ethyl)-1H-indazol-1-yl)propanoic acid | $^1$H NMR (500 MHz, DMSO-$d_6$) δ 8.01 (s, 1H), 7.58 (d, J = 8.8 Hz, 1H), 7.51 (s, 1H), 7.28 (s, 1H), 7.21 (d, J = 4.0 Hz, 3H), 7.12 (br. s., 1H), 7.01 (d, J = 7.2 Hz, 1H), 6.27 (d, J = 7.2 Hz, 1H), 6.14 (dd, J = 9.5, 4.9 Hz, 1H), 3.30 (s, 1H), 3.23 (br. s., 2H), 3.18-3.11 (m, 1H), 2.98-2.90 (m, 2H), 2.78-2.68 (m, 2H), 2.59 (t, J = 5.9 Hz, 2H), 2.07 (s, 5H), 1.90 (s, 3H), 1.74 (d, J = 8.3 Hz, 2H). LC/MS (m/z) = 484.3 (M + H)$^+$. Human αVβ6 IC$_{50}$ (nM) = 120. | Example 2 |
| 27 | 3-(Quinoxalin-2-yl)-3-(5-(2-(5,6,7,8-tetrahydro-1,8-naphthyridin-2-yl)ethyl)-1H-indazol-1-yl)propanoic acid | $^1$H NMR (500 MHz, DMSO-$d_6$) δ 8.65 (s, 1H), 8.12-7.98 (m, 3H), 7.85 (t, J = 7.5 Hz, 2H), 7.75 (d, J = 8.7 Hz, 1H), 7.54 (s, 1H), 7.30 (d, J = 8.5 Hz, 1H), 7.01 (d, J = 7.3 Hz, 1H), 6.59 (br. s., 1H), 6.29 (d, J = 7.2 Hz, 1H), 3.50 (br. s., 2H), 3.23 (br. s., 2H), 2.95 (t, J = 8.0 Hz, 2H), 2.79-2.70 (m, 2H), 2.59 (t, J = 6.0 Hz, 2H), 1.73 (br. s., 2H). LC/MS (m/z) = 479.1 (M + H)$^+$. Human αVβ6 IC$_{50}$ (nM) = 240. | Example 2 |
| 28 | 3-(3,5-Dichlorophenyl)-3-(5-(2-(5,6,7,8-tetrahydro-1,8-naphthyridin-2-yl)ethyl)-1H-indazol-1-yl)propanoic acid | $^1$H NMR (500 MHz, DMSO-$d_6$) δ 8.10-8.02 (m, 1H), 7.71 (br d, J = 8.5 Hz, 1H), 7.56-7.50 (m, 1H), 7.50-7.44 (m, 1H), 7.42 (s, 2H), 7.26 (br d, J = 8.5 Hz, 1H), 7.07-6.99 (m, 1H), 6.29 (br d, J = 7.3 Hz, 1H), 6.24 (br dd, J = 9.0, 5.3 Hz, 1H), 3.22-3.14 (m, 2H), 3.04 (br d, J = 7.6 Hz, 1H), 2.99-2.92 (m, 2H), 2.86 (br d, J = 7.9 Hz, 1H), 2.81-2.69 (m, 2H), 2.60 (br t, J = 6.0 Hz, 2H), 1.80-1.71 (m, 1H). LC/MS (m/z) = 495.1 (M + H)+. Human αVβ6 IC$_{50}$ (nM) = 210. | Example 2 |
| 29 | 3-(3-(Dimethylcarbamoyl)phenyl)-3-(4-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.06 (s, 1H), 7.62 (d, J = 7.2 Hz, 1H), 7.43-7.23 (m, 6H), 6.77 (d, J = 7.3 Hz, 1H), 6.57 (d, J = 7.5 Hz, 1H), 6.18 (dd, J = 9.8, 4.7 Hz, 1H), 4.37 (t, J = 5.7 Hz, 2H), 3.22-3.11 (m, 6H), 2.93 (br. s., 3H), 2.79 (br. s., 3H), 2.75-2.68 (m, 2H), 1.80 (br. s., 2H). LC/MS (m/z) = 514.0 (M + H)$^+$. Human αVβ6 IC$_{50}$ (nM)= 1,500. | Example 2 |

| Example No. | Structure & Name | Analytical Data | Method |
|---|---|---|---|
| 30 | 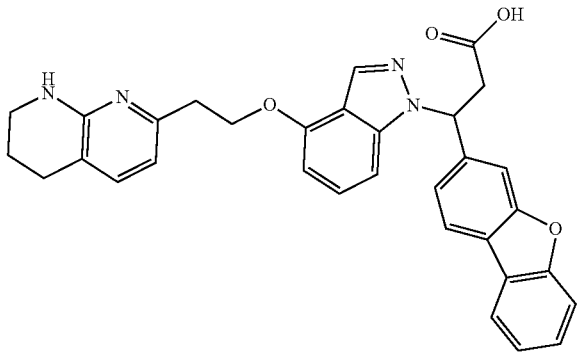 [SMILES: O=C(O)CC(c1ccc2c(c1)oc1ccccc12)n1ncc2c(OCCc3ccc4c(n3)NCCC4)cccc21]<br>3-(Dibenzo[b,d]furan-3-yl)-3-(4-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.10-7.98 (m, 3H), 7.70 (s, 1H), 7.65 (d, J = 8.2 Hz, 1H), 7.49 (t, J = 7.8 Hz, 1H), 7.41-7.33 (m, 2H), 7.30 (d, J = 8.2 Hz, 1H), 7.25-7.18 (m, 1H), 7.06 (d, J = 7.3 Hz, 1H), 6.56 (d, J = 7.6 Hz, 1H), 6.41 (d, J = 7.3 Hz, 1H), 6.32 (dd, J = 9.8, 4.6 Hz, 1H), 4.35 (t, J = 6.1 Hz, 2H), 3.69 (dd, J = 16.5, 10.1 Hz, 1H), 3.22 (br. s., 2H), 2.95 (t, J = 6.6 Hz, 2H), 2.59 (t, J = 6.0 Hz, 2H), 1.80-1.65 (m, 2H). LC/MS (m/z) = 532.9 (M + H)$^+$. Human αVβ6 IC$_{50}$ (nM) = 1,200. | Example 3 |
| 31 | 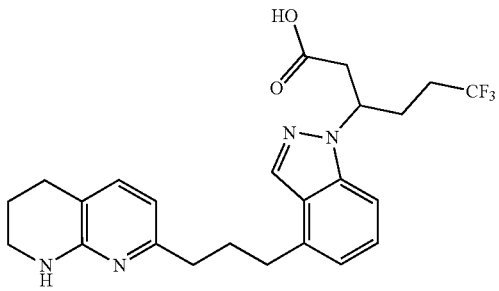 [SMILES: O=C(O)CC(CCC(F)(F)F)n1ncc2c(CCCc3ccc4c(n3)NCCC4)cccc21]<br>6,6,6-Trifluoro-3-(4-(3-(5,6,7,8-tetrahydro-1,8-naphthyridin-2-yl)propyl)-1H-indazol-1-yl)hexanoic acid | $^1$H NMR (500 MHz, DMSO-$d_6$) δ 8.20 (s, 1H), 7.58-7.48 (m, 2H), 7.30 (t, J = 7.6 Hz, 1H), 6.94 (d, J = 7.0 Hz, 1H), 6.60 (d, J = 7.3 Hz, 1H), 5.13 (br. s., 1H), 3.02-2.86 (m, 5H), 2.78-2.66 (m, 4H), 2.30-1.96 (m, 6H), 1.80 (br. s., 2H). LC/MS (m/z) = 460.9 (M + H)$^+$. Human αVβ6 IC$_{50}$ (nM) = 3,300. | Example 1 |
| 32 | 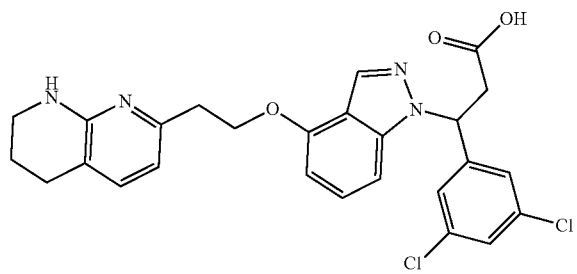 [SMILES: O=C(O)CC(c1cc(Cl)cc(Cl)c1)n1ncc2c(OCCc3ccc4c(n3)NCCC4)cccc21]<br>3-(3,5-Dichlorophenyl)-3-(4-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.10 (s, 1H), 7.57 (d, J = 7.3 Hz, 1H), 7.49 (s, 1H), 7.40 (d, J = 1.5 Hz, 2H), 7.36 (d, J = 8.5 Hz, 1H), 7.31-7.25 (m, 1H), 6.75 (d, J = 7.3 Hz, 1H), 6.60 (d, J = 7.6 Hz, 1H), 6.21 (dd, J = 10.1, 4.6 Hz, 1H), 4.38 (t, J = 6.1 Hz, 2H), 3.56 (dd, J = 16.8, 10.1 Hz, 1H), 3.17 (t, J = 5.6 Hz, 3H), 2.71 (t, J = 5.8 Hz, 2H), 1.80 (d, J = 5.5 Hz, 2H). LC/MS (m/z) = 511.2 (M + H)$^+$. Human αVβ6 IC$_{50}$. (nM) = 1,300. | Example 3 |
| 33 | 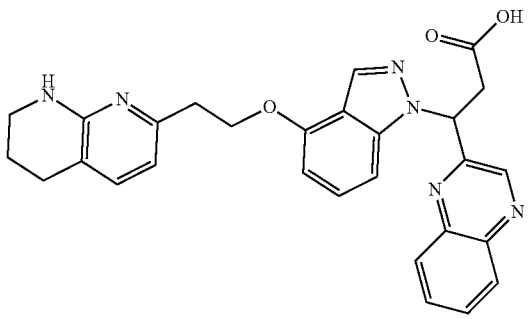 [SMILES: O=C(O)CC(c1cnc2ccccc2n1)n1ncc2c(OCCc3ccc4c(n3)NCCC4)cccc21]<br>3-(Quinoxalin-2-yl)-3-(4-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.64 (s, 1H), 8.10-8.04 (m, 3H), 7.87 (quin, J = 6.8 Hz, 2H), 7.45 (br s, 1H), 7.43 (br d, J = 8.5 Hz, 1H), 7.33 (t, J = 8.0 Hz, 1H), 6.68 (br d, J = 7.0 Hz, 1H), 6.66-6.58 (m, 2H), 4.40 (br t, J = 6.0 Hz, 2H), 3.72 (dd, J = 16.8, 5.7 Hz, 1H), 3.61-3.52 (m, 1H), 3.13 (br s, 2H), 2.71-2.65 (m, 2H), 1.81-1.75 (m, 2H). LC/MS (m/z) = 495.3 (M + H)+. Human αVβ6 IC$_{50}$ (nM) = 1,600. | Example 3 |

| Example No. | Structure & Name | Analytical Data | Method |
|---|---|---|---|
| 34 | 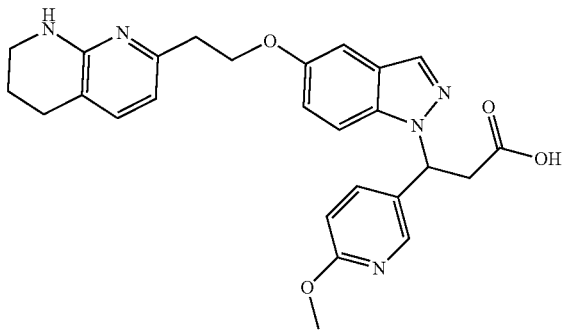<br>3-(6-Methoxypyridin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.26 (d, J = 2.2 Hz, 1H), 7.95 (s, 1H), 7.64 (dd, J = 8,8, 2.5 Hz, 1H), 7.35-7.28 (m, 2H), 7.06 (d, J = 1.9 Hz, 1H), 6.97 (dd, J = 9.1, 2.2 Hz, 1H), 6.73 (d, J = 8.8 Hz, 1H), 6.50 (d, J = 7,2 Hz, 1H), 6.06 (dd, J = 8.5, 5.8 Hz, 1H), 4.27 (t, J = 5.8 Hz, 2H), 3.92 (s, 3H), 3.73 (dd, J = 16.6, 8.7 Hz, 1H), 3.48 (t, J = 5.6 Hz, 2H), 3.29 (dd, J = 16.6, 5.6 Hz, 1H), 3.16 (t, J = 5.8 Hz, 2H), 2.74 (t, J = 6.1 Hz, 2H), 1.92 (quin, J = 5.9 Hz, 2H). LC/MS (m/z) = 474.1 (M + H)+. Human αVβ6 IC$_{50}$ (nM) = 12; Human αVβ1 IC$_{50}$ (nM) = 95; Human αVβ3 IC$_{50}$ (nM) = 2.5; Human αVβ5 IC$_{50}$ (nM) = 0.38; and Human αVβ8 IC$_{50}$ (nM) = 1,300. | Example 3 |
| 35 | 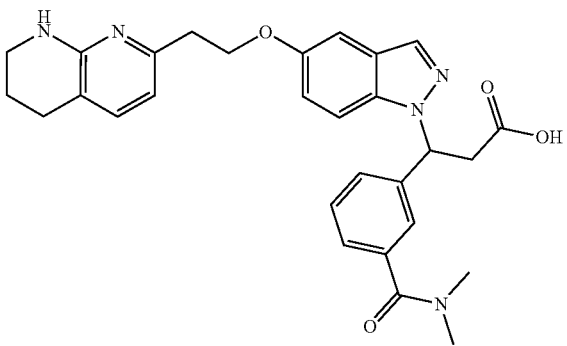 [SMILES: CN(C)C(=O)c1cccc(C(CC(=O)O)n2ncc3cc(OCCc4ccc5c(n4)NCCC5)ccc32)c1]<br>3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid | $^1$H NMR (500 MHz, MeOH-d$_4$) δ 7.93 (s, 1H), 7.46-7.44 (m, 1H), 7.44-7.42 (m, 1H), 7.37 (t, J = 7.7 Hz, 1H), 7.33 (t, J = 1.7 Hz, 1H), 7.30-7.26 (m, 2H), 7.02 (d, J = 2.1 Hz, 1H), 6.92 (dd, J = 9.0, 2.3 Hz, 1H), 6.51 (d, J = 7.3 Hz, 1H), 6.24 (dd, J = 9.5, 5.5 Hz, 1H), 4.16-4.03 (m, 2H), 3.62 (dd, J = 15.9, 9.5 Hz, 1H), 3.41-3.36 (m, 2H), 3.19 (dd, J = 15.9, 5.4 Hz, 1H), 3.05 (s, 3H), 2.95 (t, J = 6.3 Hz, 2H), 2.86 (s, 3H), 2.70 (t, J = 6.2 Hz, 2H), 1.89-1.81 (m, 2H). LC/MS (m/z) = 514.0 (M + H)+. Human αVβ6 IC$_{50}$ (nM) = 17. | Example 3 |
| 36 | 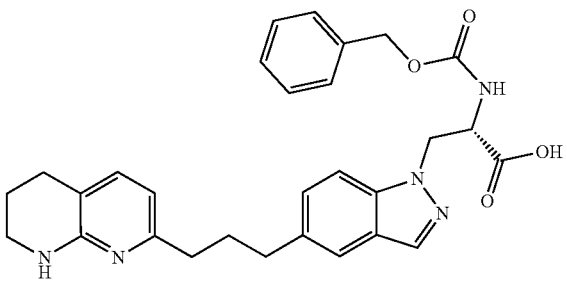 [SMILES: O=C(N[C@@H](Cn1ncc2cc(CCCc3ccc4c(n3)NCCC4)ccc21)C(=O)O)OCc1ccccc1]<br>(S)-2-(((Benzyloxy)carbonyl)amino)-3-(5-(3-(5,6,7,8-tetrahydro-1,8-naphthyridin-2-yl)propyl)-1H-indazol-1-yl)propanoic acid | $^1$H NMR (500 MHz, DMSO-d$_6$) δ 8.12 (s, 1H), 7.51 (s, 1H), 7.40 (s, 1H), 7.34-7.14 (m, 7H), 7.14-7.03 (m, 2H), 6.28 (d, J = 7.3 Hz, 1H), 4.95 (s, 2H), 3.62 (m, 4H), 3.23 (s, 3H), 2.60 (t, J = 6.5 Hz, 3H), 2.45 (t, J = 7.7 Hz, 1H), 1.89 (d, J = 14.9 Hz, 5H). LC/MS (m/z) = 514.2 (M + H)$^+$. Human αVβ6 IC$_{50}$ (nM) = 77. | Example 4 |

| Example No. | Structure & Name | Analytical Data | Method |
|---|---|---|---|
| 37 | 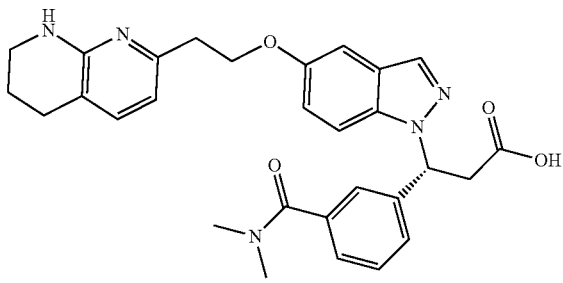 [SMILES: CN(C)C(=O)c1cccc([C@@H](CC(=O)O)n2ncc3cc(OCCc4ccc5c(n4)NCCC5)ccc32)c1]<br>(R)-3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 7.95 (d, J = 0.8 Hz, 1H), 7.50-7.43 (m, 2H), 7.39 (t, J = 7.7 Hz, 1H), 7.35 (t, J = 1.8 Hz, 1H), 7.33-7.27 (m, 2H), 7.04 (d, J = 2.2 Hz, 1H), 6.94 (dd, J = 9.1, 2.3 Hz, 1H), 6.53 (d, J = 7.3 Hz, 1H), 6.26 (dd, J = 9.5, 5.4 Hz, 1H), 4.11 (ddt, J = 25.1, 9.7, 6.4 Hz, 2H), 3.64 (dd, J = 16.0, 9.4 Hz, 1H), 3.43-3.38 (m, 2H), 3.21 (dd, J = 16.0, 5.5 Hz, 1H), 3.07 (s, 3H), 2.96 (t, J = 6.3 Hz, 2H), 2.88 (s, 3H), 2.72 (t, J = 6.3 Hz, 2H), 1.88 (dq, J = 6.9, 5.7 Hz, 2H). LC/MS (m/z) = 514.0 (M + H)$^+$. Human αVβ6 IC$_{50}$ (nM) = 1,100. | Example 16 and 17 |
| 38 | 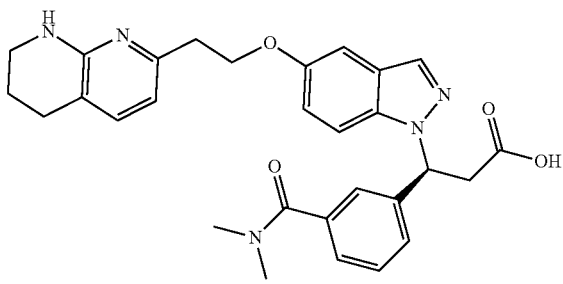 [SMILES: CN(C)C(=O)c1cccc([C@H](CC(=O)O)n2ncc3cc(OCCc4ccc5c(n4)NCCC5)ccc32)c1]<br>(S)-3-(3-(Dimethylcarbamoyl)phenyl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 7.95 (d, J = 0.8 Hz, 1H), 7.50-7.43 (m, 2H), 7.39 (t, J = 7.7 Hz, 1H), 7.35 (t, J = 1.8 Hz, 1H), 7.33-7.27 (m, 2H), 7.04 (d, J = 2.2 Hz, 1H), 6.94 (dd, J = 9.1, 2.3 Hz, 1H), 6.53 (d, J = 7.3 Hz, 1H), 6.26 (dd, J = 9.5, 5.4 Hz, 1H), 4.11 (ddt, J = 25.1, 9.7, 6.4 Hz, 2H), 3.64 (dd, J = 16.0, 9.4 Hz, 1H), 3.43-3.38 (m, 2H), 3.21 (dd, J = 16.0, 5.5 Hz, 1H), 3.07 (s, 3H), 2.96 (t, J = 6.3 Hz, 2H), 2.88 (s, 3H), 2.72 (t, J = 6.3 Hz, 2H), 1.88 (dq, J = 6.9, 5.7 Hz, 2H). LC/MS (m/z) = 514.0 (M + H)$^+$. Human αVβ6 IC$_{50}$ (nM) = 4.2. | Example 16 and 17 |
| 39 | 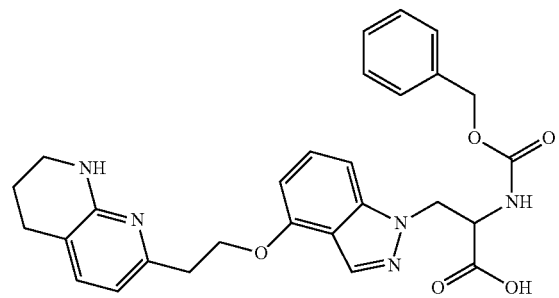 [SMILES: O=C(NC(Cn1ncc2c(OCCc3ccc4c(n3)NCCC4)cccc21)C(=O)O)OCc1ccccc1]<br>2-(((Benzyloxy)carbonyl)amino)-3-(4-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.22 (s, 1H), 7.41 (d, J = 7.1 Hz, 1H), 7.33-7.05 (m, 6H), 6.63 (d, J = 7.3 Hz, 1H), 6.41-6.33 (m, 1H), 5.12-4.94 (m, 2H), 4.85 (m, 2H), 4.60 (s, 1H), 4.36 (q, J = 6.0 Hz, 2H), 3.44-3.36 (m, 2H), 3.10 (t, J = 6.2 Hz, 2H), 2.69 (d, J = 18.0 Hz, 3H), 1.86 (d, J = 6.4 Hz, 2H). LC/MS (m/z) = 516.3 (M + H)$^+$. Human αVβ6 IC$_{50}$ (nM) = 340. | Example 4 |

| Example No. | Structure & Name | Analytical Data | Method |
|---|---|---|---|
| 40 | 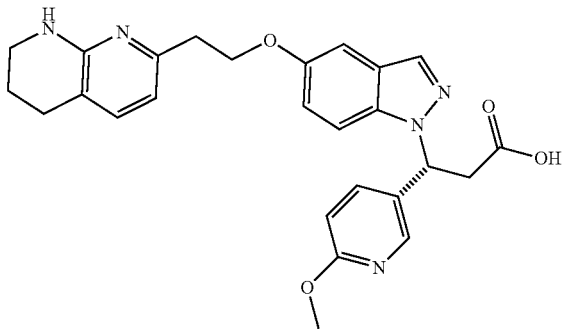<br>(R)-3-(6-Methoxypyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.12 (d, J = 2.1 Hz, 1H), 7.91 (s, 1H), 7.68 (dd, J = 8.7, 2.4 Hz, 1H), 7.50 (d, J = 9.0 Hz, 1H), 7.28 (d, J = 7.3 Hz, 1H), 7.00 (d, J = 1.8 Hz, 1H), 6.94 (dd, J = 9.0, 2.3 Hz, 1H), 6.69 (d, J = 8.7 Hz, 1H), 6.51 (d, J = 7.3 Hz, 1H), 6.18 (dd, J = 9.1, 5.7 Hz, 1H), 4.19-4.01 (m, 2H), 3.84 (s, 3H), 3.56 (dd, J = 15.7, 9.0 Hz, 1H), 3.41-3.34 (m, 2H), 3.15 (dd, J = 15.7, 5.6 Hz, 1H), 2.94 (t, J = 6.3 Hz, 2H), 2.68 (t, J = 6.3 Hz, 2H), 1.89-1.79 (m, 2H). LC/MS (m/z) = 474.2 (M + H)$^+$. Human αVβ6 IC$_{50}$ (nM) = 210. | Example 16 and 17 |
| 41 | 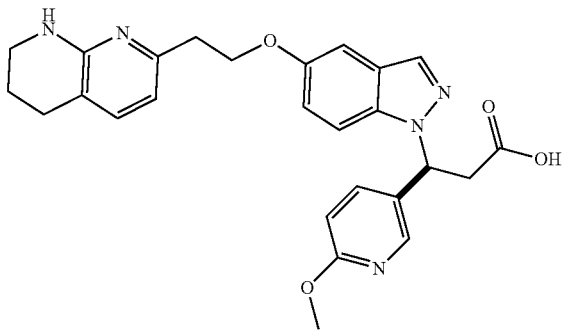<br>(S)-3-(6-Methoxypyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.11 (d, J = 2.4 Hz, 1H), 7.91 (s, 1H), 7.68 (dd, J = 8.7, 2.4 Hz, 1H), 7.50 (d, J = 9.2 Hz, 1H), 7.27 (d, J = 7.3 Hz, 1H), 7.01 (d, J = 2.0 Hz, 1H), 6.95 (dd, J = 9.2, 2.3 Hz, 1H), 6.69 (d, J = 8.7 Hz, 1H), 6.51 (d, J = 7.3 Hz, 1H), 6.18 (dd, J = 9.2, 5.8 Hz, 1H), 4.19-4.04 (m, 2H), 3.84 (s, 3H), 3.55 (dd, J = 15.8, 9.2 Hz, 1H), 3.41-3.34 (m, 2H), 3.15 (dd, J = 15.9, 5.8 Hz, 1H), 2.94 (t, J = 6.3 Hz, 2H), 2.69 (t, J = 6.3 Hz, 2H), 1.85 (dt, J = 11.7, 6.0 Hz, 2H). LC/MS (m/z) = 474.3 (M + H)$^+$. Human αVβ6 IC$_{50}$ (nM) = 6.2; Human αVβ1 IC$_{50}$ (nM) = 83; Human αVβ3 IC$_{50}$ (nM) = 2.3; Human αVβ5 IC$_{50}$ (nM) = 0.22; and Human αVβ8 IC$_{50}$ (nM) = 510. | Example 16 and 17 |
| 42 | 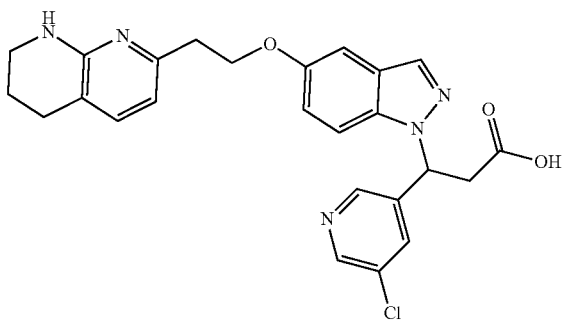 [SMILES: O=C(O)CC(c1cncc(Cl)c1)n1ncc2cc(OCCc3ccc4c(n3)NCCC4)ccc21]<br>3-(5-Chloropyridin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 8.46 (d, J = 7.5 Hz, 1H), 8.00 (s, 1H), 7.86 (s, 1H), 7.62-7.55 (m, 2H), 7.19 (d, J = 2.1 Hz, 1H), 7.06 (dd, J = 9.2, 2.3 Hz, 1H), 6.74 (d, J = 7.3 Hz, 1H), 6.29 (dd, J = 9.5, 5.5 Hz, 1H), 4.30 (t, J = 6.0 Hz, 2H), 3.69 (dd, J = 16.7, 9.7 Hz, 1H), 3.52-3.45 (m, 2H), 3.16 (t, J = 5.9 Hz, 2H), 2.80 (t, J = 6.2 Hz, 2H), 1.97-1.87 (m, 2H). LC/MS (m/z) = 477.9 (M + H)$^+$. Human αVβ6 IC$_{50}$ (nM) = 4.4. | Example 3 |

| Example No. | Structure & Name | Analytical Data | Method |
|---|---|---|---|
| 43 | 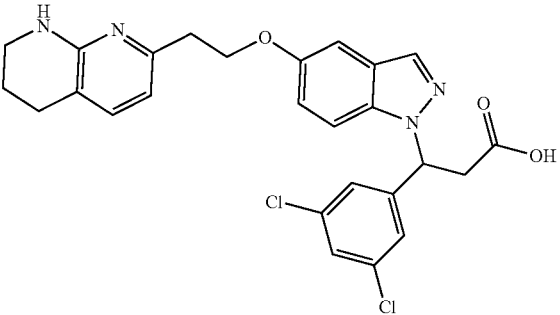 [SMILES: O=C(O)CC(c1cc(Cl)cc(Cl)c1)n1ncc2cc(OCCc3ccc4c(n3)NCCC4)ccc21]<br>3-(3,5-Dichlorophenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 8.02 (s, 1H), 7.71 (d, J = 9.2 Hz, 1H), 7.49 (t, J = 1.9 Hz, 1H), 7.41 (d, J = 2.0 Hz, 2H), 7.18 (d, J = 2.1 Hz, 1H), 7.05 (d, J = 7.3 Hz, 1H), 7.00 (dd, J = 9.1, 2.4 Hz, 1H), 6.37 (d, J = 7.2 Hz, 1H), 6.31 (br. s., 1H), 6.23 (dd, J = 10.0, 5.0 Hz, 1H), 4.24 (td, J = 6.9, 1.3 Hz, 2H), 3.56 (dd, J = 16.7, 10.0 Hz, 1H), 3.25-3.18 (m, 3H), 2.89 (t, J = 6.8 Hz, 2H), 2.61 (t, J = 6.2 Hz, 2H), 1.80-1.68 (m, 2H). LC/MS (m/z) = 511.1 (M + H)$^+$. Human αVβ6 IC$_{50}$ (nM) = 3.2. | Example 5 |
| 44 | 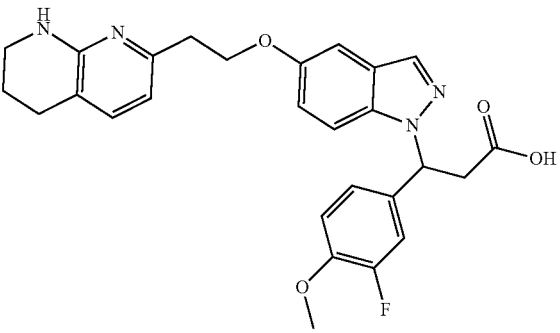 [SMILES: COc1ccc(C(CC(=O)O)n2ncc3cc(OCCc4ccc5c(n4)NCCC5)ccc32)cc1F]<br>3-(3-Fluoro-4-methoxyphenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.97 (s, 1H), 7.64 (d, J = 9.2 Hz, 1H), 7.27-7.15 (m, 3H), 7.11-7.02 (m, 2H), 6.97 (dd, J = 9.1, 2.4 Hz, 1H), 6.48 (d, J = 6.3 Hz, 1H), 6.11 (dd, J = 10.0, 5.0 Hz, 1H), 4.24 (td, J = 6.6, 1.8 Hz, 2H), 3.80-3.71 (m, 3H), 3.56 (dd, J = 16.6, 10.0 Hz, 1H), 3.15 (dd, J = 16.6, 5.0 Hz, 1H), 2.96 (t, J = 6.1 Hz, 2H), 2.64 (t, J = 6.0 Hz, 2H), 1.82-1.71 (m, 2H). LC/MS (m/z) = 490.9 (M + H)$^+$. Human αVβ6 IC$_{50}$ (nM) = 8.71. | Example 3 |
| 45 | 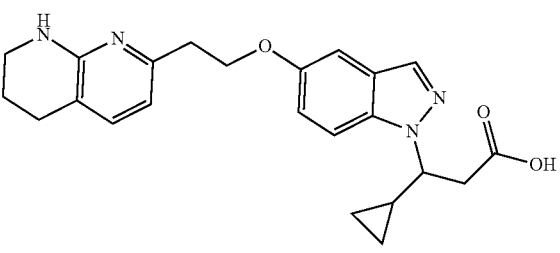 [SMILES: O=C(O)CC(C1CC1)n1ncc2cc(OCCc3ccc4c(n3)NCCC4)ccc21]<br>3-Cyclopropyl-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.92 (s, 1H), 7.56 (d, J = 7.3 Hz, 1H), 7.49 (d, J = 9.2 Hz, 1H), 7.13 (d, J = 2.1 Hz, 1H), 7.02 (dd, J = 9.1, 2.4 Hz, 1H), 6.72 (d, J = 7.3 Hz, 1H), 4.34 (td, J = 9.6, 4.6 Hz, 1H), 4.28 (td, J = 6.0, 1.4 Hz, 2H), 3.51-3.45 (m, 2H), 3.26 (dd, J = 16.2, 9.8 Hz, 1H), 3.14 (t, J = 6.0 Hz, 2H), 3.06 (dd, J = 16.0, 4.6 Hz, 1H), 2.80 (t, J = 6.2 Hz, 2H), 1.97-1.88 (m, 2H), 1.50-1.39 (m, 1H), 0.72-0.60 (m, 1H), 0.47-0.34 (m, 2H), 0.28 (dq, J = 9.6, 4.7 Hz, 1H). LC/MS (m/z) = 406.9 (M + H)$^+$. Human αVβ6 IC$_{50}$ (nM) = 2,300. | Example 3 |
| 46 | 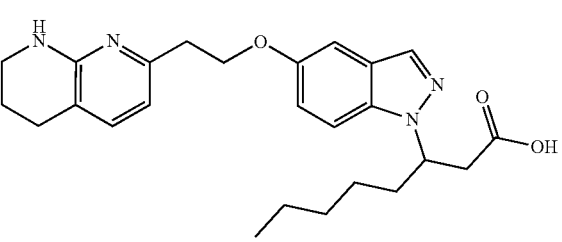 [SMILES: CCCCCC(CC(=O)O)n1ncc2cc(OCCc3ccc4c(n3)NCCC4)ccc21]<br>3-(5-(2-(5,6,7,8-Tetrahydro-1,8-naphthyridin-2-yl)ethoxy)-1H-indazol-1-yl)octanoic acid, TFA | $^1$H NMR (500 MHz, MeOH-$d_4$) δ 7.94 (s, 1H), 7.60-7.49 (m, 2H), 7.15 (d, J = 2.1 Hz, 1H), 7.04 (dd, J = 9.2, 2.4 Hz, 1H), 6.72 (d, J = 7.3 Hz, 1H), 4.29 (t, J = 6.0 Hz, 2H), 3.50-3.47 (m, 2H), 3.15 (t, J = 6.0 Hz, 2H), 3.03 (dd, J = 16.2, 9.2 Hz, 1H), 2.88 (dd, J = 16.2, 4.9 Hz, 1H), 2.81 (t, J = 6.2 Hz, 2H), 2.09-1.99 (m, 1H), 1.94 (dt, J = 11.7, 6.0 Hz, 2H), 1.90-1.80 (m, 1H), 1.27-1.04 (m, 6H), 0.88-0.80 (m, 1H), 0.79-0.73 (m, 3H). LC/MS (m/z) = 437.2 (M + H)$^+$. Human αVβ6 IC$_{50}$ (nM) = 330. | Example 3 |

| Example No. | Structure & Name | Analytical Data | Method |
|---|---|---|---|
| 47 | 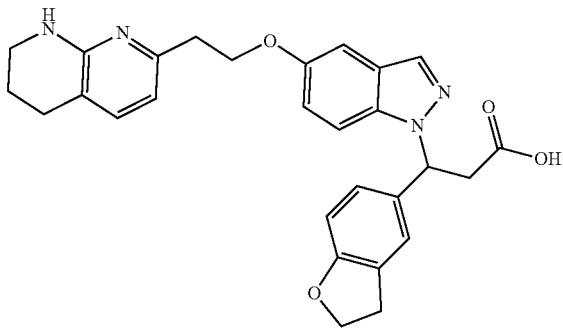 [SMILES: O=C(O)CC(c1ccc2c(c1)CCO2)n1ncc2cc(OCCc3ccc4c(n3)NCCC4)ccc21]<br>3-(2,3-Dihydrobenzofuran-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 7.90 (s, 1H), 7.48-7.41 (m, 2H), 7.17-7.09 (m, 2H), 7.05 (dd, J = 8.3, 1.8 Hz, 1H), 6.97 (dd, J = 9.2, 2.3 Hz, 1H), 6.67-6.57 (m, 2H), 6.08 (dd, J = 9.6, 5.2 Hz, 1H), 4.47 (td, J = 8.7, 1.0 Hz, 2H), 4.23 (t, J = 6.3 Hz, 2H), 3.62 (dd, J = 16.4, 9.7 Hz, 1H), 3.49-3.39 (m, 2H), 3.20-3.04 (m, 5H), 2.75 (t, J = 6.2 Hz, 2H), 1.89 (dt, J = 11.7, 6.1 Hz, 2H). LC/MS (m/z) = 485.0 (M + H)$^+$. Human αVβ6 IC$_{50}$ (nM) = 7.0. | Example 3 |
| 48 | 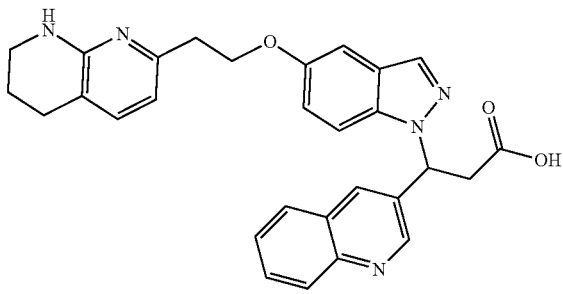 [SMILES: O=C(O)CC(c1cnc2ccccc2c1)n1ncc2cc(OCCc3ccc4c(n3)NCCC4)ccc21]<br>3-(Quinolin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 8.81 (d, J = 2.0 Hz, 1H), 8.34 (d, J = 2.0 Hz, 1H), 8.01 (s, 1H), 7.99-7.87 (m, 2H), 7.81-7.73 (m, 1H), 7.66-7.53 (m, 3H), 7.19 (d, J = 2.1 Hz, 1H), 7.05 (dd, J = 9.2, 2.3 Hz, 1H), 6.73 (d, J = 7.2 Hz, 1H), 6.47 (dd, J = 9.2, 5.4 Hz, 1H), 4.30 (t, J = 6.0 Hz, 2H), 3.79 (s, 1H), 3.52-3.41 (m, 3H), 3.21-3.11 (m, 2H), 2.77 (t, J = 6.0 Hz, 2H), 1.90 (dt, J = 11.7, 6.1 Hz, 2H). LC/MS (m/z) = 494.0 (M + H)$^+$. Human αVβ6 IC$_{50}$ (nM) = 5.5; Human αVβ1 IC$_{50}$ (nM) = 270; Human αVβ3 IC$_{50}$ (nM) = 3.8; Human αVβ5 IC$_{50}$ (nM) = 0.54; and Human αVβ8 IC$_{50}$ (nM) = 4,400. | Example 3 |
| 49 | 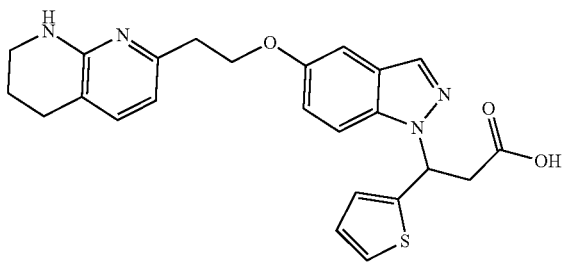 [SMILES: O=C(O)CC(c1cccs1)n1ncc2cc(OCCc3ccc4c(n3)NCCC4)ccc21]<br>3-(5-(2-(5,6,7,8-Tetrahydro-1,8-naphthyridin-2-yl)ethoxy)-1H-indazol-1-yl)-3-(thiophen-2-yl)propanoic acid, TFA | $^1$H NMR (500 MHz, DMSO-d$_6$) δ 7.96 (s, 1H), 7.69 (d, J = 9.3 Hz, 1H), 7.37 (dd, J = 5.0, 1.2 Hz, 1H), 7.16 (dd, J = 6.1, 2.9 Hz, 2H), 7.05 (d, J = 7.3 Hz, 1H), 7.00 (dd, J = 9.1, 2.4 Hz, 1H), 6.91 (dd, J = 5.0, 3.5 Hz, 1H), 6.46 (dd, J = 9.7, 5.1 Hz, 1H), 6.37 (d, J = 7.2 Hz, 1H), 6.31 (br. s., 1H), 4.24 (t, J = 6.9 Hz, 2H), 3.59 (dd, J = 16.3, 9.8 Hz, 1H), 3.26-3.20 (m, 3H), 2.90 (t, J = 6.8 Hz, 2H), 2.61 (t, J = 6.2 Hz, 2H), 1.75 (quin, J = 6.0 Hz, 2H). LC/MS (m/z) = 449.0 (M + H)$^+$. Human αVβ6 IC$_{50}$ (nM) = 33. | Example 3 |

| Example No. | Structure & Name | Analytical Data | Method |
|---|---|---|---|
| 50 | 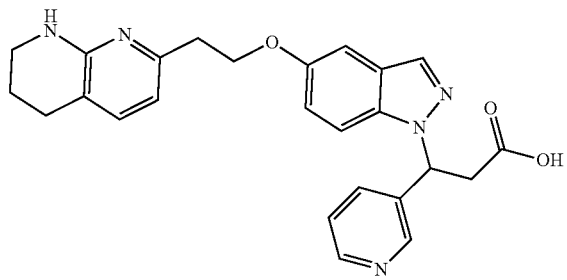 [SMILES: O=C(O)CC(c1cccnc1)n1ncc2cc(OCCc3ccc4c(n3)NCCC4)ccc21]<br>3-(Pyridin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 8.57 (s, 1H), 8.47 (d, J = 4.7 Hz, 1H), 7.98 (s, 1H), 7.94 (d, J = 7.7 Hz, 1H), 7.65-7.53 (m, 2H), 7.46 (dd, J = 7.7, 5.2 Hz, 1H), 7.19 (d, J = 2.2 Hz, 1H), 7.05 (dd, J = 9.1, 2.2 Hz, 1H), 6.74 (d, J = 7.4 Hz, 1H), 6.30 (dd, J = 9.1, 5.5 Hz, 1H), 4.31 (t, J = 5.9 Hz, 2H), 3.71 (dd, J = 16.8, 9.4 Hz, 1H), 3.54-3.46 (m, 2H), 3.38-3.33 (m, 1H), 3.17 (t, J = 5.8 Hz, 2H), 2.80 (t, J = 6.2 Hz, 2H), 1.93 (quin, J = 5.9 Hz, 2H).<br>LC/MS (m/z) = 444.1 (M + H)$^+$. Human αVβ6 IC$_{50}$ (nM) = 80. | Example 3 |
| 51 | 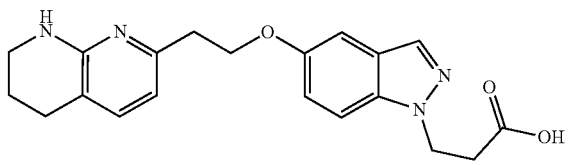 [SMILES: O=C(O)CCn1ncc2cc(OCCc3ccc4c(n3)NCCC4)ccc21]<br>3-(5-(2-(5,6,7,8-Tetrahydro-1,8-naphthyridin-2-yl)ethoxy)-1H-indazol-1-yl)propanoic acid | $^1$H NMR (500 MHz, DMSO-d$_6$) δ 7.90 (s, 1H), 7.55 (d, J = 9.0 Hz, 1H), 7.16 (s, 1H), 7.06 (d, J = 7.0 Hz, 1H), 6.98 (d, J = 9.3 Hz, 1H), 6.38 (d, J = 7.3 Hz, 1H), 6.27 (br. s., 1H), 4.52(t, J = 6.4 Hz, 2H), 4.23 (t, J = 6.6 Hz, 2H), 3.23 (br. s., 2H), 2.89 (t, J = 6.5 Hz, 2H), 2.80 (t, J = 6.4 Hz, 2H), 2.66-2.57 (m, 2H), 1.74 (br. s., 2H). LC/MS (m/z) = 367.1 (M + H)+.<br>Human αVβ6 IC$_{50}$ (nM) = 2,500. | Example 3 |
| 52 | 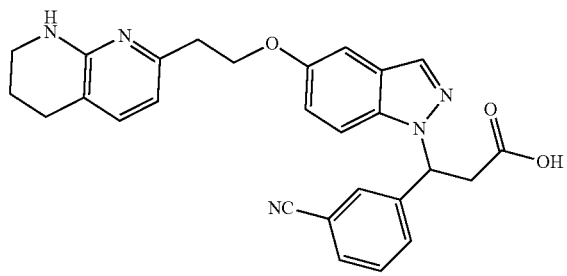 [SMILES: N#Cc1cccc(C(CC(=O)O)n2ncc3cc(OCCc4ccc5c(n4)NCCC5)ccc32)c1]<br>3-(3-Cyanophenyl)-3-(5-(2-(5,6,7,8-tetrahydro-1,8-naphthyridin-2-yl)ethoxy)-1H-indazol-1-yl)propanoic acid | $^1$H NMR (500 MHz, MeOH-d$_4$) δ 7.70-7.55 (m, 4H), 7.52-7.42 (m, 2H), 7.17 (s, 1H), 7.07 (d, J = 7.9 Hz, 1H), 6.73 (d, J = 7.3 Hz, 1H), 6.20 (br. s., 1H), 4.31 (t, J = 5.9 Hz, 2H), 3.54-3.43 (m, 2H), 3.16 (t, J = 5.7 Hz, 2H), 2.80 (t, J = 6.2 Hz, 2H), 1.93 (dt, J = 11.7, 6.1 Hz, 2H). LC/MS (m/z) = 468.0 (M + H)$^+$. | Example 3 |
| 53 | 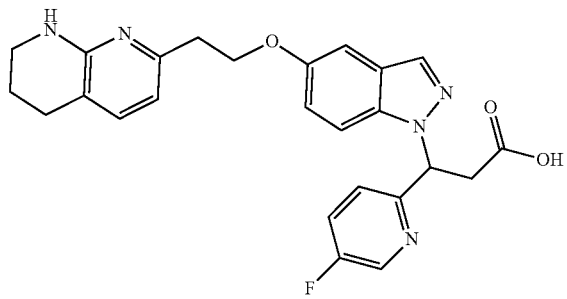 [SMILES: O=C(O)CC(c1ccc(F)cn1)n1ncc2cc(OCCc3ccc4c(n3)NCCC4)ccc21]<br>3-(5-Fluoropyridin-2-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 8.38 (d, J = 2.7 Hz, 1H), 7.91 (s, 1H), 7.54-7.37 (m, 2H), 7.16 (d, J = 7.3 Hz, 1H), 7.13 (d, J = 2.1 Hz, 1H), 7.05 (dd, J = 8.9, 4.3 Hz, 1H), 6.99 (d, J = 10.8 Hz, 1H), 6.48 (d, J = 7.3 Hz, 1H), 6.33 (t, J = 7.2 Hz, 1H), 4.24 (t, J = 6.7 Hz, 2H), 3.43-3.35 (m, 4H), 2.98 (t, J = 6.7 Hz, 2H), 2.70 (t, J = 6.2 Hz, 2H), 1.90-1.83 (m, 2H). LC/MS (m/z) = 462.0 (M + H)$^+$. Human αVβ6 IC$_{50}$ (nM) = 150. | Example 3 |

| Example No. | Structure & Name | Analytical Data | Method |
|---|---|---|---|
| 54 | 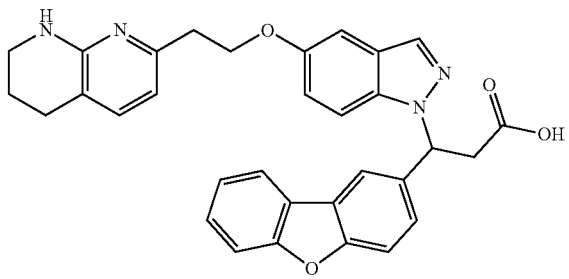 [SMILES: O=C(O)CC(c1ccc2oc3ccccc3c2c1)n1ncc2cc(OCCc3ccc4c(n3)NCCC4)ccc21]<br>3-(Dibenzo[b,d]furan-2-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 8.09-8.05 (m, 1H), 8.04-8.00 (m, 2H), 7.73-7.63 (m, 3H), 7.49 (ddd, J = 8.4, 7.2, 1.4 Hz, 1H), 7.42-7.34 (m, 2H), 7.17 (d, J = 2.3 Hz, 1H), 7.03 (d, J = 7.3 Hz, 1H), 6.96 (dd, J = 9.1, 2.4 Hz, 1H), 6.38-6.32 (m, 2H), 6.29 (s, 1H), 4.28-4.18 (m, 2H), 3.70 (dd, J = 16.6, 10.0 Hz, 1H), 3.24-3.18 (m, 2H), 2.88 (t, J = 6.9 Hz, 2H), 2.59 (t, J = 6.3 Hz, 2H), 1.78-1.68 (m, 2H). LC/MS (m/z) = 533.0 (M + H)$^+$. Human αVβ6 IC$_{50}$ (nM) = 30. | Example 3 |
| 55 | 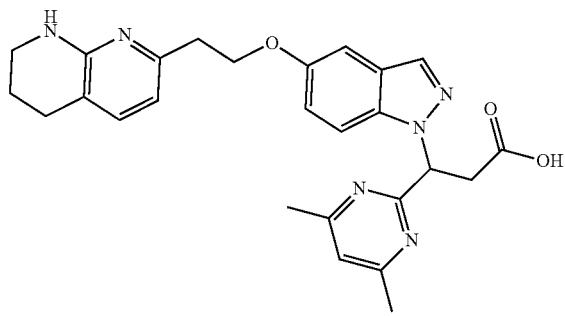 [SMILES: Cc1cc(C)nc(C(CC(=O)O)n2ncc3cc(OCCc4ccc5c(n4)NCCC5)ccc32)n1]<br>3-(4,6-Dimethylpyrimidin-2-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 7.87 (d, J = 0.6 Hz, 1H), 7.57 (d, J = 9.2 Hz, 1H), 7.18-7.11 (m, 2H), 7.06 (d, J = 7.3 Hz, 1H), 6.99 (dd, J = 9.1, 2.4 Hz, 1H), 6.38 (d, J = 7.3 Hz, 1H), 6.30 (s, 1H), 6.14 (dd, J = 8.0, 6.8 Hz, 1H), 4.24 (t, J = 6.9 Hz, 2H), 3.57 (dd, J = 16.7, 6.5 Hz, 1H), 3.38-3.34 (m, 1H), 3.26-3.19 (m, 2H), 2.90 (t, J = 6.8 Hz, 2H), 2.61 (t, J = 6.3 Hz, 2H), 2.33 (s, 6H), 1.81-1.69 (m, 2H). LC/MS (m/z) = 473.0 (M + H)$^+$. Human αVβ6 IC$_{50}$ (nM) = 920. | Example 3 |
| 56 | 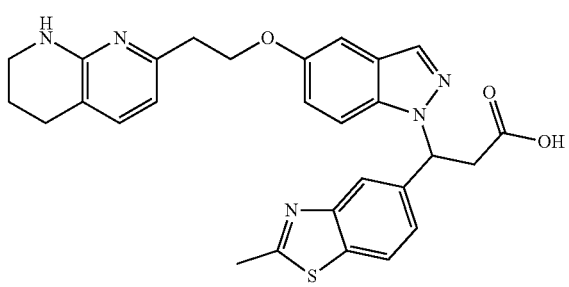 [SMILES: Cc1nc2cc(C(CC(=O)O)n3ncc4cc(OCCc5ccc6c(n5)NCCC6)ccc43)ccc2s1]<br>3-(2-Methylbenzo[d]thiazol-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, DMSO-d$_6$) δ 7.96 (s, 1H), 7.86 (d, J = 8.3 Hz, 1H), 7.78 (s, 1H), 7.58 (d, J = 9.2 Hz, 1H), 7.32 (d, J = 8.4 Hz, 1H), 7.14 (s, 1H), 7.04 (d, J = 7.2 Hz, 1H), 6.91 (d, J = 9.2 Hz, 1H), 6.35 (d, J = 7.2 Hz, 1H), 6.28 (t, J = 7.2 Hz, 1H), 6.18 (br. s., 1H), 4.19 (br. s., 2H), 3.21 (br. s., 2H), 3.06 (dd, J = 15.9, 5.8 Hz, 1H), 2.86 (t, J = 6.6 Hz, 2H), 2.72 (s, 3H), 2.58 (t, J = 5.9 Hz, 2H), 1.72 (br. s., 2H). LC/MS (m/z) = 514.0 (M + H)$^+$. Human αVβ6 IC$_{50}$ (nM) = 4.1. | Example 3 |
| 57 | 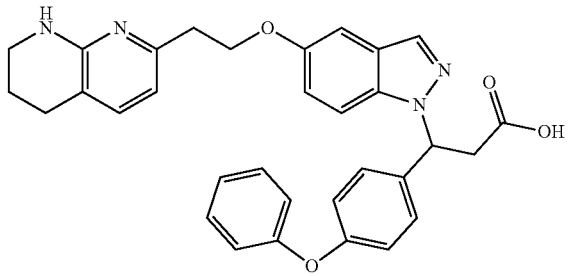 [SMILES: O=C(O)CC(c1ccc(Oc2ccccc2)cc1)n1ncc2cc(OCCc3ccc4c(n3)NCCC4)ccc21]<br>3-(4-Phenoxyphenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 7.90 (s, 1H), 7.59-7.51 (m, 1H), 7.42 (d, J = 9.0 Hz, 1H), 7.33-7.22 (m, 3H), 7.15 (s, 1H), 7.11-6.98 (m, 3H), 6.89-6.79 (m, 4H), 6.74-6.66 (m, 1H), 6.14 (dd, J = 9.6, 5.2 Hz, 1H), 4.29 (t, J = 6.0 Hz, 2H), 3.53-3.42 (m, 2H), 3.14 (d, J = 5.5 Hz, 2H), 2.78 (t, J = 6.2 Hz, 2H), 1.98-1.84 (m, 2H). LC/MS (m/z) = 535.0 (M + H)$^+$. Human αVβ6 IC$_{50}$ (nM) = 11. | Example 3 |

| Example No. | Structure & Name | Analytical Data | Method |
|---|---|---|---|
| 58 | 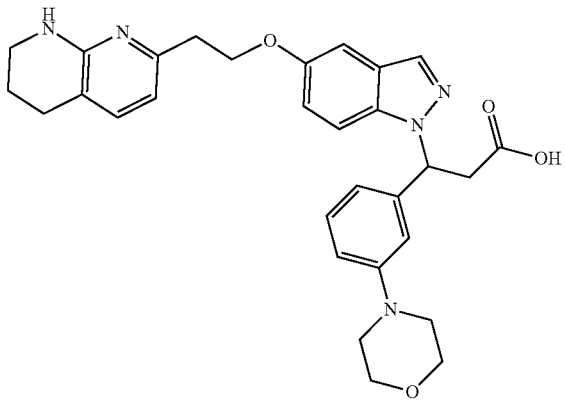 [SMILES: O=C(O)CC(c1cccc(N2CCOCC2)c1)n1ncc2cc(OCCc3ccc4c(n3)NCCC4)ccc21]<br>3-(3-Morpholinophenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.01 (s, 1H), 7.33 (d, J = 7.4 Hz, 1H), 7.22 (dd, J = 18.3, 8.7 Hz, 2H), 7.12 (d, J = 2.2 Hz, 1H), 6.99 (dd, J = 9.1, 2.2 Hz, 1H), 6.83 (dd, J = 8.3, 2.2 Hz, 1H), 6.80 (s, 1H), 6.72 (d, J = 7.4 Hz, 1H), 6.51 (d, J = 7.2 Hz, 1H), 6.00 (dd, J = 9.2, 4.3 Hz, 1H), 4.32 (t, J = 5.9 Hz, 2H), 3.85 (t, J = 4.8 Hz, 4H), 3.79 (dd, J = 16.4, 9.2 Hz, 1H), 3.50 (t, J = 4.8 Hz, 2H), 3.31 (dd, J = 16.4, 4.3 Hz, 1H), 3.24-3.17 (m, 2H), 3.11 (q, J = 4.5 Hz, 4H), 2.76 (t, J = 6.1 Hz, 2H), 1.98-1.88 (m, 2H). LC/MS (m/z) = 528.2 (M + H)$^+$. Human αVβ6 IC$_{50}$ (nM) = 1.7. | Example 3 |
| 59 | 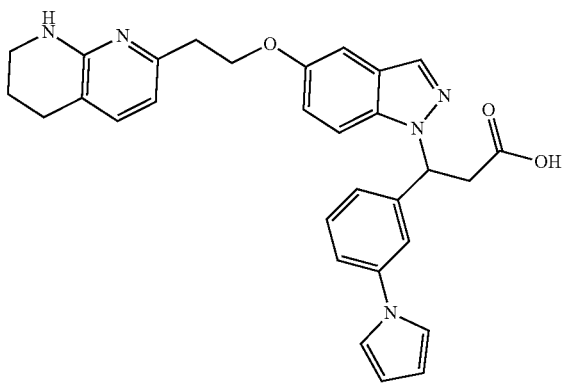 [SMILES: O=C(O)CC(c1cccc(-n2cccc2)c1)n1ncc2cc(OCCc3ccc4c(n3)NCCC4)ccc21]<br>3-(3-(1H-Pyrrol-1-yl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 7.92 (s, 1H), 7.50 (d, J = 9.3 Hz, 1H), 7.42 (s, 1H), 7.35-7.27 (m, 2H), 7.16 (d, J = 7.0 Hz, 2H), 7.13 (d, J = 2.4 Hz, 1H), 7.09 (t, J = 2.2 Hz, 2H), 6.99 (dd, J = 9.2, 2.3 Hz, 1H), 6.48 (d, J = 7.2 Hz, 1H), 6.28-6.19 (m, 3H), 4.24 (t, J = 6.7 Hz, 2H), 3.54-3.44 (m, 1H), 3.41-3.35 (m, 1H), 2.98 (t, J = 6.8 Hz, 2H), 2.69 (t, J = 6.3 Hz, 2H), 1.89-1.80 (m, 2H). LC/MS (m/z) = 508.0 (M + H)$^+$. Human αVβ6 IC$_{50}$ (nM) = 1.2. | Example 3 |
| 60 | 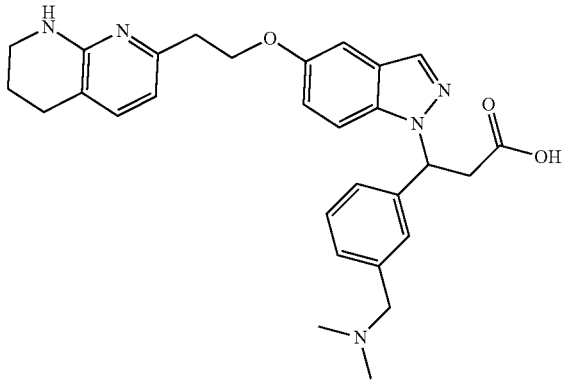 [SMILES: CN(C)Cc1cccc(C(CC(=O)O)n2ncc3cc(OCCc4ccc5c(n4)NCCC5)ccc32)c1]<br>3-(3-((Dimethylamino)methyl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 7.90 (d, J = 0.5 Hz, 1H), 7.52-7.44 (m, 2H), 7.39-7.30 (m, 2H), 7.29-7.24 (m, 1H), 7.18 (d, J = 7.3 Hz, 1H), 7.12 (d, J = 2.1 Hz, 1H), 6.97 (dd, J = 9.1, 2.4 Hz, 1H), 6.49 (d, J = 7.3 Hz, 1H), 6.22 (t, J = 7.6 Hz, 1H), 4.22 (t, J = 6.7 Hz, 2H), 4.05 (s, 2H), 3.39-3.35 (m, 3H), 2.97 (t, J = 6.7 Hz, 2H), 2.70 (t, J = 6.3 Hz, 2H), 2.65 (s, 6H), 1.90-1.81 (m, 2H). LC/MS (m/z) = 500.1 (M + H)$^+$. Human αVβ6 IC$_{50}$ (nM) = 5.1. | Example 3 |

| Example No. | Structure & Name | Analytical Data | Method |
|---|---|---|---|
| 61 | 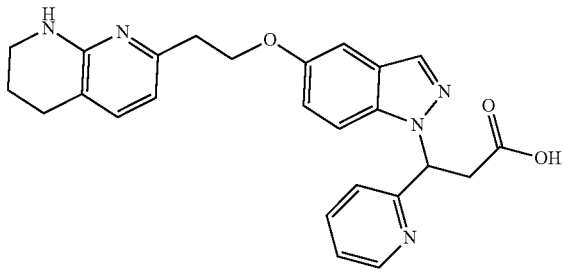 [SMILES: O=C(O)CC(c1ccccn1)n1ncc2cc(OCCc3ccc4c(n3)NCCC4)ccc21]<br>3-(Pyridin-2-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 8.51 (d, J = 4.0 Hz, 1H), 7.98 (s, 1H), 7.66 (t, J = 7.0 Hz, 1H), 7.53 (d, J = 8.9 Hz, 1H), 7.29-7.23 (m, 1H), 7.18 (s, 1H), 7.07 (d, J = 7.3 Hz, 1H), 6.97 (d, J = 7.3 Hz, 1H), 6.89 (d, J = 7.9 Hz, 1H), 6.38 (d, J = 7.3 Hz, 1H), 6.23-6.14 (m, 1H), 4.22 (t, J = 6.6 Hz, 2H), 3.56 (br. s., 1H), 3.50-3.40 (m, 1H), 3.23 (br. s., 2H), 2.89 (t, J = 6.6 Hz, 2H), 2.60 (t, J = 6.0 Hz, 2H), 1.81-1.66 (m, 2H). LC/MS (m/z) = 444.0 (M + H)$^+$. Human αVβ6 IC$_{50}$ (nM) = 80. | Example 3 |
| 62 | 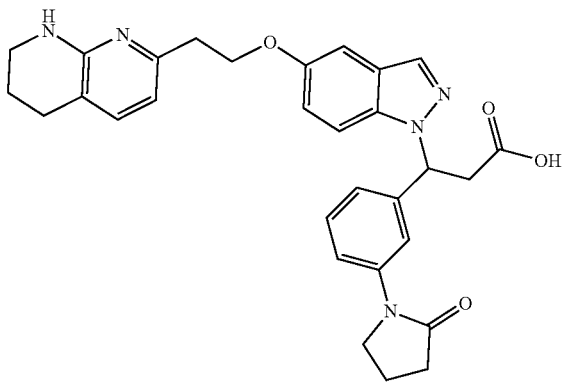 [SMILES: O=C(O)CC(c1cccc(N2CCCC2=O)c1)n1ncc2cc(OCCc3ccc4c(n3)NCCC4)ccc21]<br>3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.94 (d, J = 0.6 Hz, 1H), 7.63-7.56 (m, 2H), 7.51-7.43 (m, 2H), 7.29 (t, J = 7.9 Hz, 1H), 7.16 (d, J = 2.0 Hz, 1H), 7.08 (d, J = 7.6 Hz, 1H), 7.00 (dd, J = 9.2, 2.3 Hz, 1H), 6.74 (d, J = 7.3 Hz, 1H), 6.16 (dd, J = 9.9, 5.0 Hz, 1H), 4.31 (t, J = 6.0 Hz, 2H), 3.88-3.81 (m, 2H), 3.72 (dd, J = 16.6, 9.9 Hz, 1H), 3.52-3.44 (m, 2H), 3.25 (dd, J = 16.6, 5.0 Hz, 1H), 3.16 (t, J = 5.9 Hz, 2H), 2.79 (t, J = 6.2 Hz, 2H), 2.61-2.52 (m, 2H), 2.20-2.09 (m, 2H), 1.98-1.86 (m, 2H). LC/MS (m/z) = 526.2 (M + H)$^+$. Human αVβ6 IC$_{50}$ (nM) = 37. | Example 3 |
| 63 | 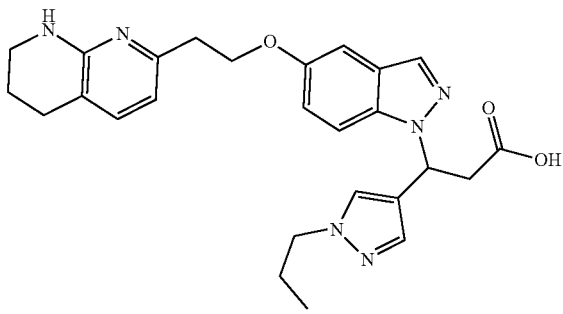 [SMILES: CCCn1cc(C(CC(=O)O)n2ncc3cc(OCCc4ccc5c(n4)NCCC5)ccc32)cn1]<br>3-(1-Propylpyrazol-4-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.89 (s, 1H), 7.56-7.51 (m, 2H), 7.34 (s, 1H), 7.24 (d, J = 7.0 Hz, 1H), 7.08 (d, J = 2.1 Hz, 1H), 6.99 (dd, J = 9.1, 2.4 Hz, 1H), 6.51 (d, J = 7.3 Hz, 1H), 6.21 (dd, J = 8.4, 6.4 Hz, 1H), 4.19 (q, J = 6.3 Hz, 2H), 3.99 (t, J = 7.0 Hz, 2H), 3.41-3.36 (m, 2H), 3.21-3.12 (m, 1H), 2.97 (t, J = 6.6 Hz, 2H), 2.71 (t, J = 6.3 Hz, 2H), 1.91-1.83 (m, 2H), 1.82-1.72 (m, 2H), 0.83 (t, J = 7.4 Hz, 3H). LC/MS (m/z) = 475.3 (M + H)$^+$. Human αVβ6 IC$_{50}$ (nM) = 55. | Example 3 |

| Example No. | Structure & Name | Analytical Data | Method |
|---|---|---|---|
| 64 | 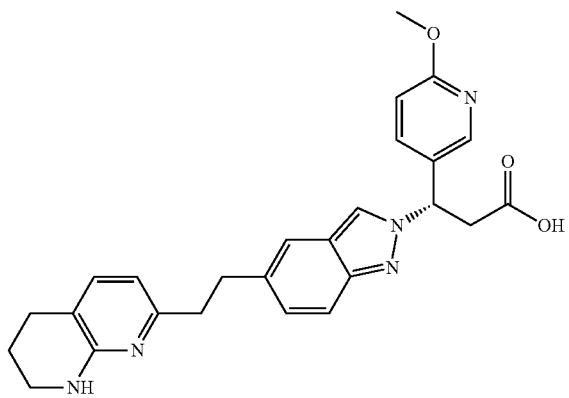 [SMILES: COc1ccc([C@H](CC(=O)O)n2cc3cc(CCc4ccc5c(n4)NCCC5)ccc3n2)cn1]<br>(S)-3-(6-Methoxypyridin-3-yl)-3-(5-(2-(5,6,7,8-tetrahydro-1,8-naphthyridin-2-yl)ethyl)-2H-indazol-2-yl)propanoic acid | $^1$H NMR (500 MHz, MeOH-$d_4$) δ 8.24 (d, J = 0.9 Hz, 1H), 8.16 (d, J = 2.5 Hz, 1H), 7.71 (dd, J = 8.7, 2.6 Hz, 1H), 7.46 (dt, J = 9.0, 0.9 Hz, 1H), 7.26-7.20 (m, 2H), 7.06 (dd, J = 8.9, 1.6 Hz, 1H), 6.73 (dd, J = 8.7, 0.7 Hz, 1H), 6.32 (d, J = 7.3 Hz, 1H), 6.14 (dd, J = 9.3, 5.9 Hz, 1H), 3.86 (s, 3H), 3.48 (dd, J = 15.8, 9.3 Hz, 1H), 3.39 (dd, J = 6.5, 4.7 Hz, 2H), 3.17 (dd, J = 15.8, 6.0 Hz, 1H), 2.91-2.78 (m, 4H), 2.69 (t, J = 6.3 Hz, 2H), 1.91-1.83 (m, 2H). LC/MS (m/z) = 458.3 (M + H)$^+$. Human αVβ6 IC$_{50}$ (nM) = 19. | Example 7 |
| 65 | 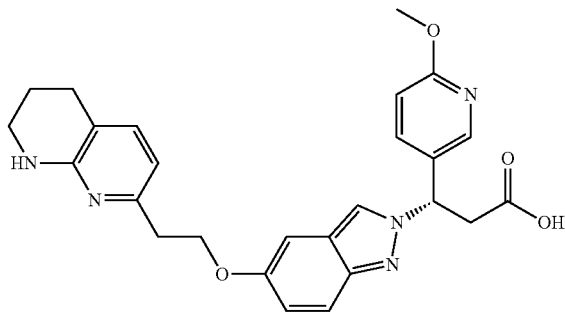 [SMILES: COc1ccc([C@H](CC(=O)O)n2cc3cc(OCCc4ccc5c(n4)NCCC5)ccc3n2)cn1]<br>(S)-3-(6-Methoxypyridin-3-yl)-3-(6-(2-(5,6,7,8-tetrahydro-1,8-naphthyridin-2-yl)ethoxy)-2H-indazol-2-yl)propanoic acid | $^1$H NMR (500 MHz, MeOH-$d_4$) δ 8.25 (s, 1H), 8.15 (d, J = 2.5 Hz, 1H), 7.71 (dd, J = 8.7, 2.6 Hz, 1H), 7.45 (d, J = 9.0 Hz, 1H), 7.34 (d, J = 7.3 Hz, 1H), 6.82 (d, J = 2.1 Hz, 1H), 6.72 (d, J = 8.7 Hz, 1H), 6.63 (dd, J = 9.1, 2.1 Hz, 1H), 6.55 (d, J = 7.3 Hz, 1H), 6.08 (dd, J = 9.2, 6.0 Hz, 1H), 4.16 (t, J = 6.4 Hz, 2H), 3.85 (s, 3H), 3.49 (dd, J = 16.0, 9.3 Hz, 1H), 3.40 (t, J = 5.7 Hz, 2H), 3.18 (dd, J = 15.9, 5.9 Hz, 1H), 3.05-2.96 (m, 2H), 2.72 (t, J = 6.3 Hz, 2H), 1.87 (p, 6.1 Hz, 2H). LC/MS (m/z) = 474.0 (m/z) = 474.0 (M + H)$^+$. Human αVβ6 IC$_{50}$ (nM) = 1.2; Human αVβ1 IC$_{50}$ (nM) = 2,300; Human αVβ3 IC$_{50}$ (nM) = 2.4; Human αVβ5 IC$_{50}$ (nM) = 1.0; and Human αVβ8 IC$_{50}$ (nM) = 2,300. | Example 6 |
| 66 | 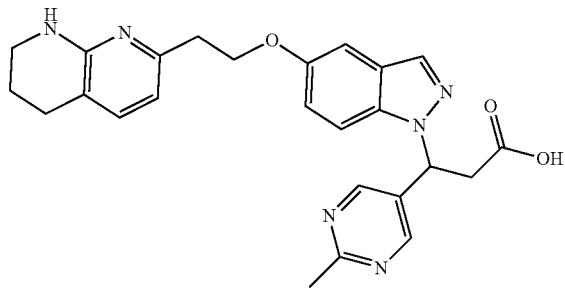 [SMILES: Cc1ncc(C(CC(=O)O)n2ncc3cc(OCCc4ccc5c(n4)NCCC5)ccc32)cn1]<br>3-(2-Methylpyrimidin-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 9.63 (br. s., 1H), 8.83 (s, 2H), 7.99 (s, 1H), 7.39-7.31 (m, 2H), 7.08 (s, 1H), 7.01 (d, J = 9.1 Hz, 1H), 6.51 (d, J = 7.4 Hz, 1H), 6.13 (t, J = 7.2 Hz, 1H), 4.29 (t, J = 5.6 Hz, 2H), 3.73 (dd, J = 16.8, 8.0 Hz, 1H), 3.48 (t, J = 5.4 Hz, 2H), 3.38 (dd, J = 16.9, 6.5 Hz, 1H), 3.17 (t, J = 5.8 Hz, 2H), 2.81-2.70 (m, 5H), 1.92 (quin, J = 5.9 Hz, 2H). LC/MS (m/z) 459.1 (M + H)$^+$. | Example 3 |

| Example No. | Structure & Name | Analytical Data | Method |
|---|---|---|---|
| 67 | 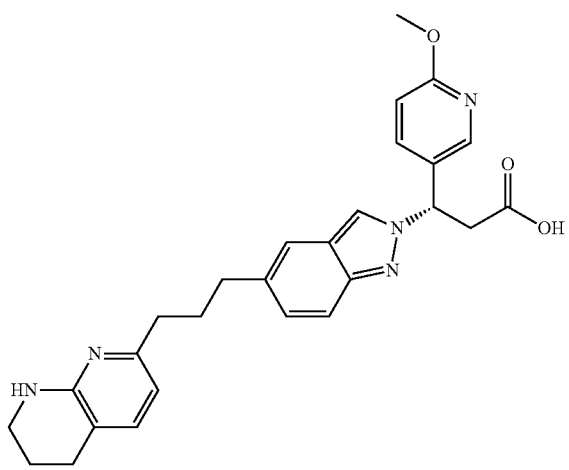 [SMILES: COc1ccc([C@H](CC(=O)O)n2cc3cc(CCCc4ccc5c(n4)NCCC5)ccc3n2)cn1]<br>(S)-3-(6-Methoxypyridin-3-yl)-3-(5-(3-(5,6,7,8-tetrahydro-1,8-naphthyridin-2-yl)propyl)-2H-indazol-2-yl)propanoic acid | $^1$H NMR (500 MHz, MeOH-$d_4$) δ 8.27 (s, 1H), 8.21 (d, J = 2.5 Hz, 1H), 7.79 (dd, J = 8.7, 2.6 Hz, 1H), 7.51 (d, J = 8.9 Hz, 1H), 7.43 (d, J = 7.4 Hz, 1H), 7.39 (s, 1H), 7.14 (dd, J = 8.9, 1.6 Hz, 1H), 6.76 (d, J = 8.7 Hz, 1H), 6.55 (d, J = 7.4 Hz, 1H), 6.14 (dd, J = 9.2, 6.0 Hz, 1H), 3.87 (s, 3H), 3.66 (dd, J = 16.7, 9.2 Hz, 1H), 3.38-3.33 (m, 2H), 2.77 (t, J = 7.1 Hz, 2H), 2.70 (t, J = 7.6 Hz, 2H), 2.61 (td, J = 6.1, 2.7 Hz, 2H), 2.13-2.01 (m, 2H), 1.80 (p, J = 6.2 Hz, 2H). LC/MS (m/z) = 472.3 (M + H)$^+$. Human αVβ6 IC$_{50}$ (nM) = 740. | Example 9 |
| 68 | 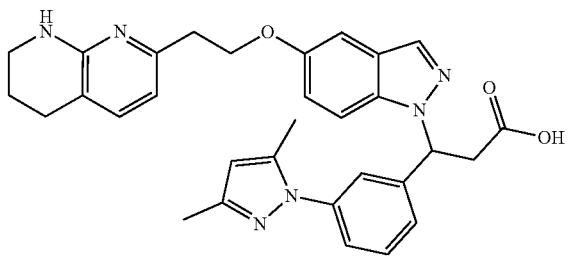 [SMILES: Cc1cc(C)n(-c2cccc(C(CC(=O)O)n3ncc4cc(OCCc5ccc6c(n5)NCCC6)ccc43)c2)n1]<br>3-(3-(3,5-Dimethylpyrazol-1-yl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.92 (s, 1H), 7.48 (d, J = 9.1 Hz, 1H), 7.45-7.37 (m, 2H), 7.32 (s, 1H), 7.28 (t, J = 6.5 Hz, 2H), 6.99 (s, 1H), 6.91 (dd, J = 9.1, 2.0 Hz, 1H), 6.47 (d, J = 7.3 Hz, 1H), 6.28 (dd, J = 9.7, 5.0 Hz, 1H), 6.02 (s, 1H), 4.12-4.04 (m, 1H), 4.04-3.96 (m, 1H), 3.66 (dd, J = 15.9, 9.8 Hz, 1H), 3.40-3.34 (m, 2H), 3.20 (dd, J = 15.9, 5.0 Hz, 1H), 2.95-2.80 (m, 2H), 2.21 (s, 3H), 2.12 (s, 3H), 1.88-1.77 (m, 2H). LC/MS (m/z) = 537.4 (M + H)$^+$. Human αVβ6 IC$_{50}$ (nM) = 1.5. | Example 3 |
| 69 | 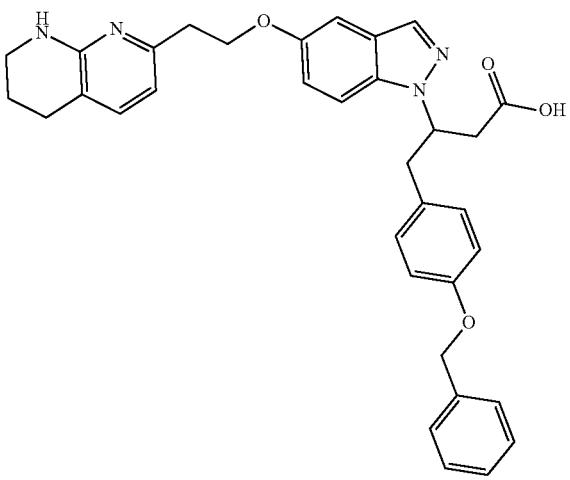 [SMILES: O=C(O)CC(Cc1ccc(OCc2ccccc2)cc1)n1ncc2cc(OCCc3ccc4c(n3)NCCC4)ccc21]<br>4-(4-(Benzyloxy)phenyl)-3-(5-(2-(5,6,7,8-tetrahydro-1,8-naphthyridin-2-yl)ethoxy)-1H-indazol-1-yl)butanoic acid, TFA | $^1$H NMR (500 MHz, MeOH-$d_4$) δ 7.91 (s, 1H), 7.39-7.32 (m, 4H), 7.32-7.26 (m, 2H), 7.08 (d, J = 2.0 Hz, 1H), 7.04 (d, J = 7.3 Hz, 1H), 6.88 (d, J = 8.5 Hz, 2H), 6.84 (dd, J = 9.1, 2.2 Hz, 1H), 6.72 (d, J = 8.5 Hz, 2H), 6.39-6.30 (m, 2H), 5.11 (d, J = 4.8 Hz, 1H), 4.95 (s, 2H), 4.20 (t, J = 6.8 Hz, 2H), 3.22 (br. s., 2H), 3.11-2.95 (m, 3H), 2.92-2.79 (m, 3H), 2.60 (t, J = 6.0 Hz, 2H), 1.81-1.66 (m, 2H). LC/MS (m/z) = 563.2 (M + H)$^+$. Human αVβ6 IC$_{50}$ (nM) = 400. | Example 3 |

| Example No. | Structure & Name | Analytical Data | Method |
|---|---|---|---|
| 70 | 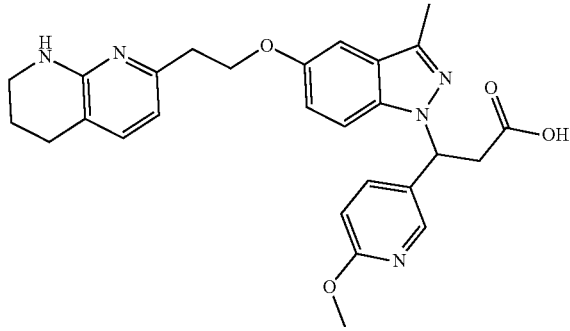 [SMILES: COc1ccc(C(CC(=O)O)n2nc(C)c3cc(OCCc4ccc5c(n4)NCCC5)ccc32)cn1]<br>3-(6-Methoxypyridin-3-yl)-3-(3-methyl-5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.22 (d, J = 2.5 Hz, 1H), 7.68-7.61 (m, 2H), 7.09 (d, J = 2.3 Hz, 1H), 7.06 (d, J = 7.3 Hz, 1H), 6.96 (dd, J = 9.0, 2.3 Hz, 1H), 6.72 (d, J = 8.6 Hz, 1H), 6.38 (d, J = 7.2 Hz, 1H), 6.34 (s, 1H), 6.08 (dd, J = 9.7, 5.4 Hz, 1H), 4.23 (td, J = 7.1, 2.6 Hz, 2H), 3.77 (s, 3H), 3.55 (dd, J = 16.4, 9.9 Hz, 1H), 3.23 (dq, J = 6.1, 2.8 Hz, 2H), 3.16 (dd, J = 16.4, 5.5 Hz, 1H), 2.90 (t, J = 6.9 Hz, 2H), 2.61 (t, J = 6.3 Hz, 2H), 2.44 (s, 3H), 1.75 (p, J = 6.0 Hz, 2H). LC/MS (m/z) = 488.0 (M + H)$^+$. Human αVβ6 IC$_{50}$ (nM) = 953. | Example 3 |
| 71 | 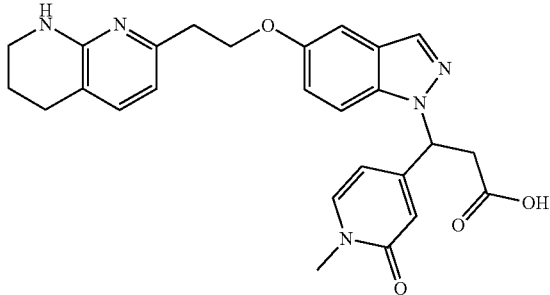 [SMILES: Cn1ccc(C(CC(=O)O)n2ncc3cc(OCCc4ccc5c(n4)NCCC5)ccc32)cc1=O]<br>3-(1-Methyl-2-oxo-1,2-dihydropyridin-4-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.93 (s, 1H), 7.52 (d, J = 7.0 Hz, 1H), 7.45 (d, J = 9.1 Hz, 1H), 7.23 (d, J = 7.3 Hz, 1H), 7.12 (s, 1H), 6.99 (dd, J = 9.0, 2.0 Hz, 1H), 6.51 (d, J = 7.3 Hz, 1H), 6.32 (d, J = 7.0 Hz, 1H), 6.27 (s, 1H), 6.07 (dd, J = 8.5, 5.8 Hz, 1H), 4.21 (t, J = 6.1 Hz, 2H), 3.52-3.42 (m, 4H), 3.41-3.37 (m, 2H), 3.11 (dd, J = 15.9, 5.7 Hz, 1H), 2.98 (t, J = 6.4 Hz, 2H), 2.71 (t, J = 6.2 Hz, 2H), 1.91-1.82 (m, 2H). LC/MS (m/z) = 474.3 (M + H)$^+$. Human αVβ6 IC$_{50}$ (nM) = 64. | Example 3 |
| 72 | 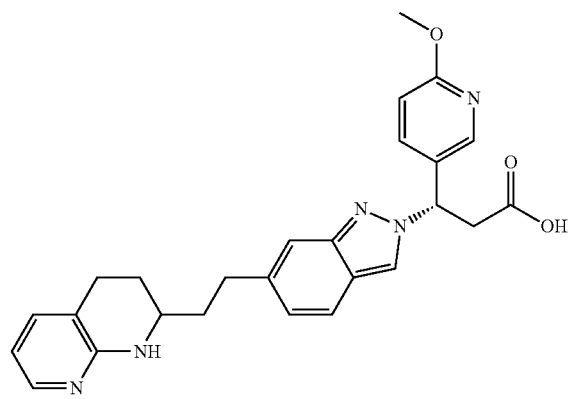 [SMILES: COc1ccc([C@H](CC(=O)O)n2cc3ccc(CCC4CCc5cccnc5N4)cc3n2)cn1]<br>(3S)-3-(6-Methoxypyridin-3-yl)-3-(6-(2-(1,2,3,4-tetrahydro-1,8-naphthyridin-2-yl)ethyl)-2H-indazol-2-yl)propanoic acid | $^1$H NMR (500 MHz, MeOH-$d_4$) δ 8.28 (s, 1H), 8.15 (d, J = 2.5 Hz, 1H), 7.72 (dd, J = 8.7, 2.6 Hz, 1H), 7.53 (d, J = 8.6 Hz, 1H), 7.30 (d, J = 7.3 Hz, 1H), 7.17 (s, 1H), 6.87 (dd, J = 8.6, 1.4 Hz, 1H), 6.73 (d, J = 8.6 Hz, 1H), 6.37 (d, J = 7.3 Hz, 1H), 6.13 (dd, J = 9.4, 5.9 Hz, 1H), 3.86 (s, 3H), 3.49 (dd, J = 15.8, 9.4 Hz, 1H), 3.39 (t, J = 5.7 Hz, 2H), 3.18 (dd, J = 15.8, 5.9 Hz, 1H), 2.88 (h, J = 6.1, 5.0 Hz, 4H), 2.70 (t, J = 6.3 Hz, 2H), 1.86 (p, J = 6.1 Hz, 2H). LC/MS (m/z) = 457.9 (M + H)$^+$. Human αVβ6 IC$_{50}$ (nM) = 8.2; Human αVβ1 IC$_{50}$ (nM) = 740; Human αVβ3 IC$_{50}$ (nM) = 4.4; Human αVβ5 IC$_{50}$ (nM) = 1.5; and Human αVβ8 IC$_{50}$ (nM) = 3,200. | Example 7 |

| Example No. | Structure & Name | Analytical Data | Method |
|---|---|---|---|
| 73 | 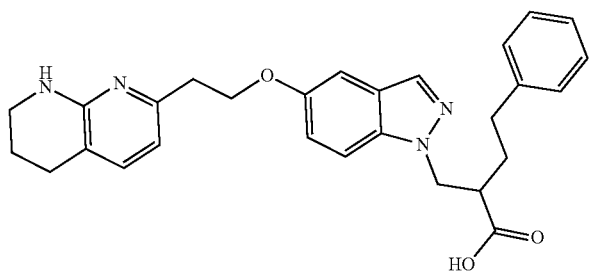 [SMILES: O=C(O)C(CCc1ccccc1)Cn1ncc2cc(OCCc3ccc4c(n3)NCCC4)ccc21]<br>4-Phenyl-2-((5-(2-(5,6,7,8-tetrahydro-1,8-naphthyridin-2-yl)ethoxy)-1H-indazol-1-yl)methyl)butanoic acid | $^1$H NMR (500 MHz, DMSO-$d_6$) δ 7.90 (s, 1H), 7.52 (d, J = 9.1 Hz, 1H), 7.28-7.21 (m, 2H), 7.19-7.13 (m, 2H), 7.10 (d, J = 7.3 Hz, 2H), 7.06 (d, J = 7.2 Hz, 1H), 6.97 (dd, J = 9.0, 1.9 Hz, 1H), 6.38 (d, J = 7.2 Hz, 1H), 6.31 (br. s., 1H), 4.60 (dd, J = 14.1, 8.1 Hz, 1H), 4.45 (dd, J = 14.1, 6.0 Hz, 1H), 4.23 (t, J = 6.7 Hz, 2H), 3.23 (br. s., 2H), 2.97-2.81 (m, 3H), 2.61 (t, J = 5.9 Hz, 3H), 1.87-1.63 (m, 4H). LC/MS (m/z) = 471.3 (M + H)$^+$. Human αVβ6 IC$_{50}$ (nM) = 1,800. | Example 3 |
| 74 | 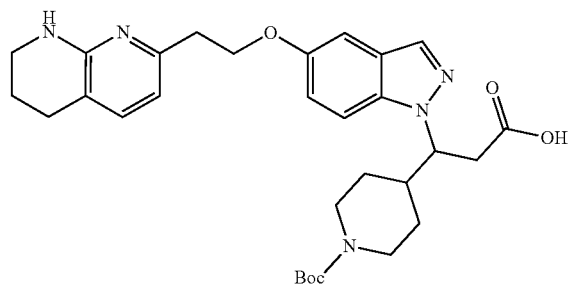 [SMILES: CC(C)(C)OC(=O)N1CCC(C(CC(=O)O)n2ncc3cc(OCCc4ccc5c(n4)NCCC5)ccc32)CC1]<br>3-(1-(tert-Butoxycarbonyl)piperidin-4-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 7.92 (s, 1H), 7.60 (d, J = 9.1 Hz, 1H), 7.13 (d, J = 1.9 Hz, 1H), 7.06 (d, J = 7.2 Hz, 1H), 6.97 (dd, J = 9.1, 2.1 Hz, 1H), 6.38 (d, J = 7.2 Hz, 1H), 6.34 (br. s., 1H), 4.84-4.73 (m, 1H), 4.24 (t, J = 6.8 Hz, 2H), 3.93 (br. s., 1H), 3.76 (br. s., 1H), 3.23 (br. s., 1H), 3.03-2.94 (m, 2H), 2.90 (t, J = 6.8 Hz, 2H), 2.61 (t, J = 6.1 Hz, 3H), 1.97 (d, J = 8.2 Hz, 1H), 1.83-1.66 (m, 3H), 1.34 (s, 9H), 1.13-0.87 (m, 2H), 0.78 (br. s., 1H). LC/MS (m/z) = 550.4 (M + H)$^+$.<br><br>Human αVβ6 IC$_{50}$ (nM) = 260. | Example 3 |
| 75 | 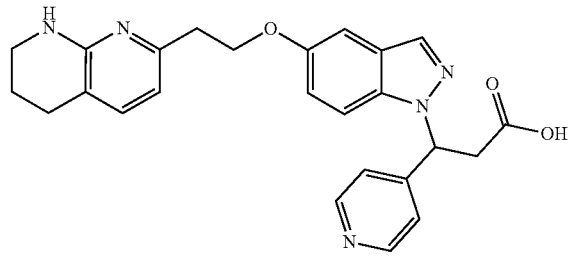 [SMILES: O=C(O)CC(c1ccncc1)n1ncc2cc(OCCc3ccc4c(n3)NCCC4)ccc21]<br>3-(Pyridin-4-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 8.77 (d, J = 6.9 Hz, 2H), 8.07 (s, 1H), 7.99 (d, J = 6.6 Hz, 2H), 7.60 (t, J = 8.9 Hz, 2H), 7.23 (d, J = 2.2 Hz, 1H), 7.08 (dd, J = 9.2, 2.3 Hz, 1H), 6.75 (d, J = 7.4 Hz, 1H), 6.54 (dd, J = 9.4, 5.2 Hz, 1H), 4.32 (td, J = 6.0, 2.6 Hz, 2H), 3.73 (dd, J = 17.1, 9.4 Hz, 1H), 3.53-3.44 (m, 3H), 3.19 (t, J = 5.8 Hz, 2H), 2.82 (t, J = 6.1 Hz, 2H), 2.02-1.89 (m, 2H). LC/MS (m/z) = 444.1 (M + H)$^+$. Human αVβ6 IC$_{50}$ (nM) = 23. | Example 3 |
| 76 | 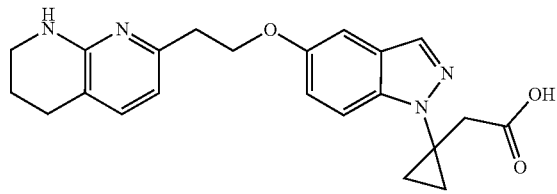 [SMILES: O=C(O)CC1(n2ncc3cc(OCCc4ccc5c(n4)NCCC5)ccc32)CC1]<br>2-(1-(5-(2-(5,6,7,8-tetrahydro-1,8-naphthyridin-2-yl)ethoxy)-1H-indazol-1-yl)cyclopropyl)acetic acid, TFA | $^1$H NMR (500 MHz, MeOH-$d_4$) δ 7.87 (s, 1H), 7.66 (d, J = 9.2 Hz, 1H), 7.50 (d, J = 7.3 Hz, 1H), 7.15 (d, J = 1.9 Hz, 1H), 7.05 (dd, J = 9.1, 2.1 Hz, 1H), 6.69 (d, J = 7.3 Hz, 1H), 4.29 (t, J = 6.1 Hz, 2H), 3.55-3.42 (m, 2H), 3.12 (t, J = 6.1 Hz, 2H), 2.87-2.73 (m, 4H), 1.93 (quin, J = 5.9 Hz, 2H), 1.35 (s, 4H). LC/MS (m/z) = 393.3 (M + H)$^+$. Human αVβ6 IC$_{50}$ (nM) = 3,400. | Example 3 |

| Example No. | Structure & Name | Analytical Data | Method |
|---|---|---|---|
| 77 | 3-(2-Ethoxypyrimidin-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.51 (s, 2H), 7.96 (s, 1H), 7.36-7.30 (m, 2H), 7.06 (d, J = 2.2 Hz, 1H), 7.02 (dd, J = 9.1, 2.2 Hz, 1H), 6.50 (d, J = 7.2 Hz, 1H), 6.01 (dd, J = 8.4, 5.9 Hz, 1H), 4.38 (q, J = 7.2 Hz, 2H), 4.27 (t, J = 5.8 Hz, 2H), 3.73 (dd, J = 16.6, 8.7 Hz, 1H), 3.47 (t, J = 5.4 Hz, 2H), 3.31 (dd, J = 16.5, 5.8 Hz, 1H), 3.16 (t, J = 5.8 Hz, 2H), 2.74 (t, J = 6.2 Hz, 2H), 1.96-1.86 (m, 2H), 1.43-1.34 (m, 3H). LC/MS (m/z) = 489.1 (M + H)$^+$. Human αVβ6 IC$_{50}$ (nM) = 5.8; Human αVβ1 IC$_{50}$ (nM) = 170; Human αVβ3 IC$_{50}$ (nM) = 2.8; Human αVβ5 IC$_{50}$ (nM) = 0.39; and Human αVβ8 IC$_{50}$ (nM) = 5,000. | Example 3 |
| 78 | 4-(4-Fluorophenyl)-3-(5-(2-(5,6,7,8-tetrahydro-1,8-naphthyridin-2-yl)ethoxy)-1H-indazol-1-yl)butanoic acid, TFA | $^1$H NMR (500 MHz, chloroform-d) δ 9.99 (br. s., 1H), 7.96 (s, 1H), 7.33 (d, J = 7.2 Hz, 1H), 7.01-6.92 (m, 2H), 6.89-6.81 (m, 3H), 6.80-6.73 (m, 2H), 6.49 (d, J = 7.2 Hz, 1H), 5.09-4.94 (m, 1H), 4.28 (d, J = 5.0 Hz, 2H), 3.48 (t, J = 5.4 Hz, 2H), 3.32-3.21 (m, 2H), 3.19-3.12 (m, 3H), 3.03 (dd, J = 16.4, 4.3 Hz, 1H), 2.75 (t, J = 6.2 Hz, 2H), 1.97-1.87 (m, 2H). LC/MS (m/z) = 475.1 (M + H)$^+$. Human αVβ6 IC$_{50}$ (nM) = 804.48. | Example 3 |
| 79 | 3-(5-Methoxypyrazin-2-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.17 (d, J = 1.1 Hz, 1H), 7.99 (s, 1H), 7.65 (s, 1H), 7.40-7.30 (m, 2H), 7.10 (d, J = 1.9 Hz, 1H), 7.02 (dd, J = 9.1, 2.2 Hz, 1H), 6.50 (d, J = 7.2 Hz, 1H), 6.20 (dd, J = 8.0, 5.5 Hz, 1H), 4.31 (t, J = 5.9 Hz, 2H), 3.90 (s, 3H), 3.75-3.56 (m, 2H), 3.49 (t, J = 5.5 Hz, 2H), 3.19 (t, J = 5.8 Hz, 2H), 2.75 (t, J = 6.2 Hz, 2H), 1.92 (quin, J = 5.9 Hz, 2H). LC/MS (m/z) = 475.1 (M + H)$^+$. Human αVβ6 IC$_{50}$ (nM) = 33. | Example 3 |

| Example No. | Structure & Name | Analytical Data | Method |
|---|---|---|---|
| 80 | 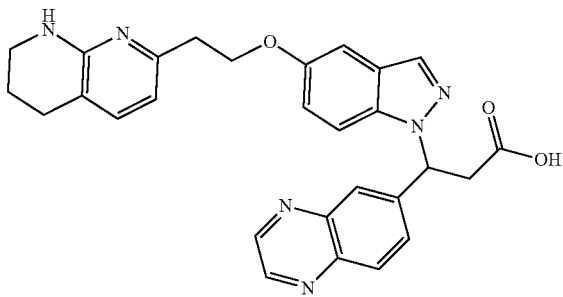 [SMILES: O=C(O)CC(c1ccc2nccnc2c1)n1ncc2cc(OCCc3ccc4c(n3)NCCC4)ccc21]<br>3-(Quinoxalin-6-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.85 (s, 2H), 8.08-8.01 (m, 2H), 7.97 (d, J = 1.7 Hz, 1H), 7.66 (dd, J = 8.8, 1.9 Hz, 1H), 7.34-7.28 (m, 2H), 7.10 (d, J = 1.9 Hz, 1H), 6.97 (dd, J = 9.1, 2.2 Hz, 1H), 6.48 (d, J = 7.2 Hz, 1H), 6.32 (dd, J = 8.9, 5.1 Hz, 1H), 4.28 (t, J = 5.8 Hz, 2H), 3.91 (dd, J = 16.5, 8.8 Hz, 1H), 3.52-3.41 (m, 3H), 3.16 (t, J = 5.8 Hz, 2H), 2.73 (t, J = 6.2 Hz, 2H), 1.96-1.85 (m, 2H). LC/MS(m/z) = 495.1 (M + H)$^+$. Human αVβ6 IC$_{50}$ (nM) = 13. | Example 3 |
| 81 | 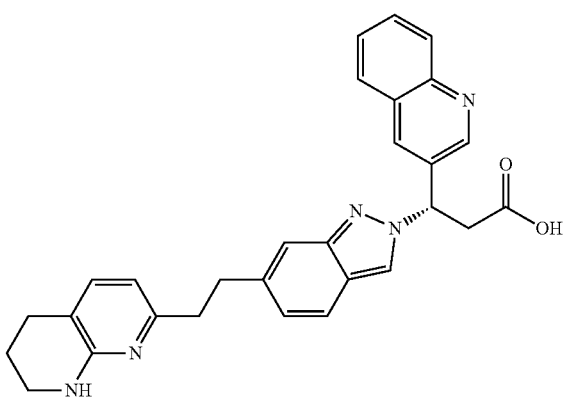 [SMILES: O=C(O)C[C@@H](c1cnc2ccccc2c1)n1cc2ccc(CCc3ccc4c(n3)NCCC4)cc2n1]<br>(S)-3-(Quinolin-3-yl)-3-(6-(2-(5,6,7,8-tetrahydro-1,8-naphthyridin-2-yl)ethyl)-2H-indazol-2-yl)propanoic acid | $^1$H NMR (500 MHz, DMSO-d$_6$) δ 8.99 (d, J = 2.3 Hz, 1H), 8.56 (s, 1H), 8.40 (d, J = 2.3 Hz, 1H), 7.97 (t, J = 8.1 Hz, 2H), 7.79-7.70 (m, 1H), 7.64-7.54 (m, 2H), 7.35 (s, 1H), 7.01 (d, J = 7.3 Hz, 1H), 6.91 (d, J = 8.6 Hz, 1H), 6.37 (t, J = 7.5 Hz, 1H), 6.28 (d, J = 7.2 Hz, 1H), 3.22 (s, 2H), 2.91 (dd, J = 17.9, 9.6 Hz, 2H), 2.78-2.70 (m, 2H), 2.58 (t, J = 6.3 Hz, 2H), 1.73 (t, J = 5.9 Hz, 2H). LC/MS (m/z) = 478.4 (M + H)$^+$. Human αVβ6 IC$_{50}$ (nM) = 3.2. | Example 7 |
| 82 | 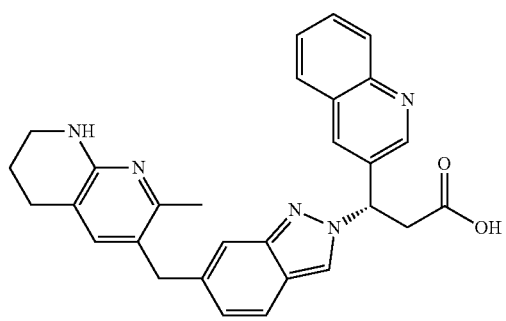 [SMILES: Cc1nc2c(cc1Cc1ccc3cn([C@@H](CC(=O)O)c4cnc5ccccc5c4)nc3c1)CCCN2]<br>(S)-3-(6-((2-Methyl-5,6,7,8-tetrahydro-1,8-naphthyridin-3-yl)methyl)-2H-indazol-2-yl)-3-(quinolin-3-yl)propanoic acid | $^1$H NMR (500 MHz, DMSO-d$_6$) δ 8.99 (s, 1H), 8.61 (s, 1H), 8.42 (d, J = 2.2 Hz, 1H), 8.02-7.94 (m, 2H), 7.75 (t, J = 7.7 Hz, 1H), 7.62 (d, J = 8.4 Hz, 2H), 7.50 (s, 1H), 7.28 (s, 1H), 6.88 (d, J = 8.6 Hz, 1H), 6.38 (t, J = 4.7 Hz, 1H), 3.87 (d, J = 11.5 Hz, 2H), 3.79-3.67 (m, 1H), 3.35 (s, 2H), 2.66 (d, J = 6.7 Hz, 2H), 2.34 (s, 3H), 1.77 (m, 2H). LC/MS (m/z) = 478.3 (M + H)$^+$. Human αVβ6 IC$_{50}$ (nM) = 150. | Example 8 |

| Example No. | Structure & Name | Analytical Data | Method |
|---|---|---|---|
| 83 | 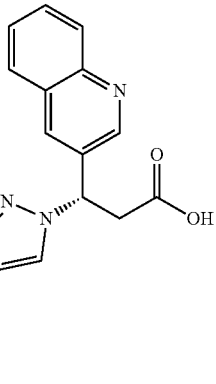<br>(3S)-3-(Quinolin-3-yl)-3-(6-(2-(1,2,3,4-tetrahydro-1,8-naphthyridin-2-yl)ethyl)-2H-indazol-2-yl)propanoic acid | $^1$H NMR (500 MHz, DMSO-$d_6$) δ 8.97 (s, 1H), 8.58 (s, 1H), 8.43 (s, 1H), 7.97 (t, J = 7.1 Hz, 2H), 7.81-7.69 (m, 2H), 7.63 (d, J = 8.1 Hz, 3H), 7.43 (s, 1H), 6.96 (d, J = 8.7 Hz, 1H), 6.72 (t, J = 6.8 Hz, 1H), 6.37 (dd, J = 9.4, 5.8 Hz, 1H), 3.56-3.45 (m, 2H), 3.16 (s, 2H), 2.83-2.66 (m, 4H), 2.00-1.85 (m, 2H), 1.85-1.74 (m, 1H), 1.62 (d, J = 8.6 Hz, 1H). LC/MS (m/z) = 478.4 (M + H)$^+$. Human αVβ6 IC$_{50}$ (nM) = 4.7; Human αVβ1 IC$_{50}$ (nM) = 360; Human αVβ3 IC$_{50}$ (nM) = 4.1; Human αVβ5 IC$_{50}$ (nM) = 2.2; and Human αVβ8 IC$_{50}$ (nM) = 5,000. | Example 7 |
| 84 | 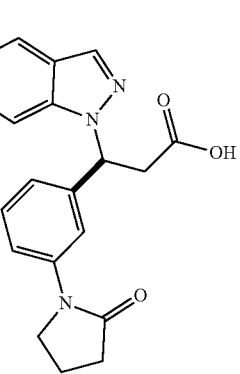<br>(S)-3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 7.98 (s, 1H), 7.61 (br. s., 1H), 7.44 (d, J = 8.3 Hz, 1H), 7.33 (d, J = 7.4 Hz, 1H), 7.28-7.22 (m, 2H), 7.09 (d, J = 1.9 Hz, 1H), 6.96 (dd, J = 8.9, 1.8 Hz, 2H), 6.50 (d, J = 7.2 Hz, 1H), 6.07 (dd, J = 8.5, 5.2 Hz, 1H), 4.28 (t, J = 5.6 Hz, 2H), 3.88-3.71 (m, 3H), 3.48 (t, J = 5.5 Hz, 2H), 3.32 (dd, J = 16.5, 4.7 Hz, 1H), 3.17 (t, J = 5.8 Hz, 2H), 2.74 (t, J = 6.2 Hz, 2H), 2.60 (t, J = 8.1 Hz, 2H), 2.14 (quin, J = 7.4 Hz, 2H), 1.97-1.87 (m, 2H). LC/MS (m/z) = 526.5 (M + H)$^+$. Human αVβ6 IC$_{50}$ (nM) = 120. | Example 16 and 17 |
| 85 | 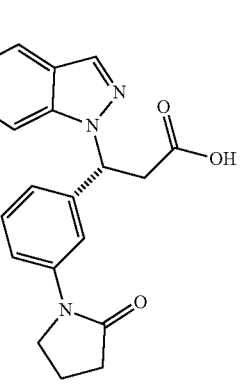<br>(R)-3-(3-(2-Oxopyrrolidin-1-yl)phenyl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 7.98 (s, 1H), 7.59 (s, 1H), 7.43 (d, J = 8.3 Hz, 1H), 7.32 (d, J = 7.2 Hz, 1H), 7.26-7.23 (m, 2H), 7.08 (s, 1H), 6.98-6.92 (m, 2H), 6.49 (d, J = 7.4 Hz, 1H), 6.06 (dd, J = 8.8, 5.0 Hz, 1H), 4.27 (t, J = 5.6 Hz, 2H), 3.86-3.70 (m, 3H), 3.53-3.43 (m, 2H), 3.32 (dd, J = 16.4, 4.5 Hz, 1H), 3.16 (t, J = 5.5 Hz, 2H), 2.74 (t, J = 5.9 Hz, 2H), 2.59 (t, J = 8.0 Hz, 2H), 2.20-2.08 (m, 2H), 1.96-1.85 (m, 2H). LC/MS (m/z) = 526.5 (M + H)+. Human αVβ6 IC$_{50}$ (nM) = 2.5. | Example 16 and 17 |

| Example No. | Structure & Name | Analytical Data | Method |
|---|---|---|---|
| 86 | 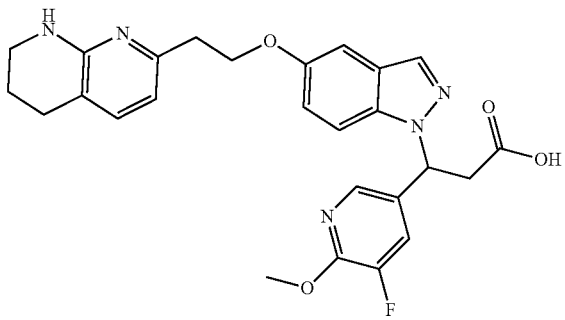 [SMILES: COc1ncc(C(CC(=O)O)n2ncc3cc(OCCc4ccc5c(n4)NCCC5)ccc32)cc1F]<br>3-(5-Fluoro-6-methoxypyridin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 7.95 (s, 1H), 7.90 (d, J = 1.9 Hz, 1H), 7.36-7.28 (m, 3H), 7.05 (d, J = 1.7 Hz, 1H), 6.99 (dd, J = 9.1, 2.2 Hz, 1H), 6.49 (d, J = 7.4 Hz, 1H), 6.01 (dd, J = 8.8, 5.5 Hz, 1H), 4.25 (t, J = 5.8 Hz, 2H), 3.97 (s, 3H), 3.74 (dd, J = 16.6, 8.9 Hz, 1H), 3.47 (t, J = 5.5 Hz, 2H), 3.25 (dd, J = 16.5, 5.2 Hz, 1H), 3.15 (t, J = 5.6 Hz, 2H), 2.74 (t, J = 6.1 Hz, 2H), 1.95-1.84 (m, 2H). LC/MS (m/z) = 492.4 (M + H)$^+$. Human αVβ6 IC$_{50}$ (nM) = 7.8. | Example 3 |
| 87 | 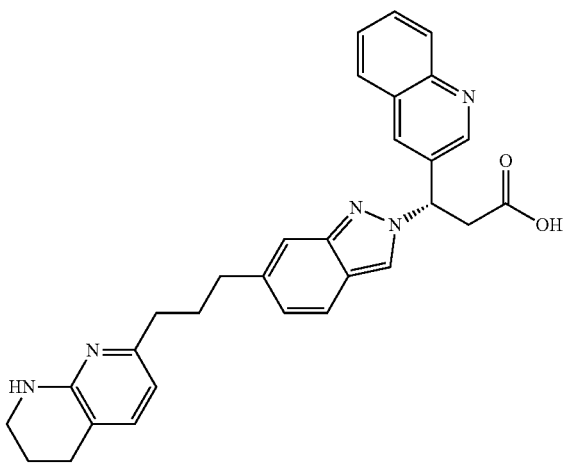 [SMILES: O=C(O)C[C@@H](c1cnc2ccccc2c1)n1cc2ccc(CCCc3ccc4c(n3)NCCC4)cc2n1]<br>(S)-3-(Quinolin-3-yl)-3-(6-(3-(5,6,7,8-tetrahydro-1,8-naphthyridin-2-yl)propyl)-2H-indazol-2-yl)propanoic acid | $^1$H NMR (500 MHz, DMSO-d$_6$) δ 9.02 (t, J = 2.4 Hz, 1H), 8.59 (s, 1H), 8.43 (s, 1H), 7.98 (t, J = 7.8 Hz, 2H), 7.76 (t, J = 7.7 Hz, 1H), 7.67-7.55 (m, 2H), 7.35 (s, 1H), 7.02 (d, J = 7.2 Hz, 1H), 6.89 (d, J = 8.6 Hz, 1H), 6.39 (s, 1H), 6.26 (d, J = 7.3 Hz, 1H), 3.74 (dd, J = 17.0, 9.4 Hz, 1H), 3.21 (s, 2H), 2.63 (t, J = 7.6 Hz, 2H), 2.57 (d, J = 6.2 Hz, 2H), 2.44 (t, J = 7.7 Hz, 2H), 1.89 (d, J = 8.3 Hz, 2H), 1.72 (s, 2H). LC/MS (m/z) = 1.30. (M + H)$^+$. Human αVβ6 IC$_{50}$ (nM) = 1.3; Human αVβ1 IC$_{50}$ (nM) = 10,000; Human αVβ3 IC$_{50}$ (nM) = 2.3; Human αVβ5 IC$_{50}$ (nM) = 3.2; and Human αVβ8 IC$_{50}$ (nM) = 3,300. | Example 9 |
| 88 | 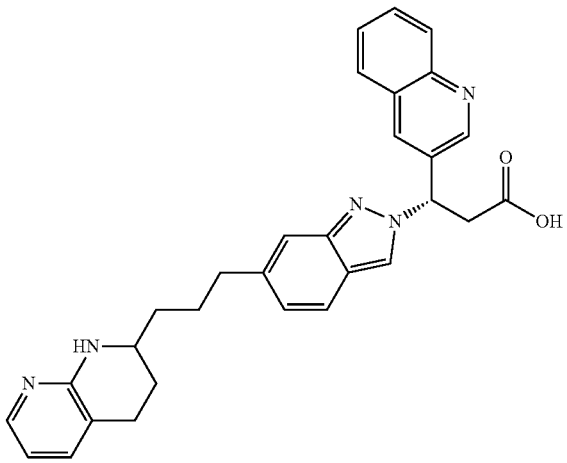 [SMILES: O=C(O)C[C@@H](c1cnc2ccccc2c1)n1cc2ccc(CCCC3CCc4cccnc4N3)cc2n1]<br>(3S)-3-(Quinolin-3-yl)-3-(6-(3-(1,2,3,4-tetrahydro-1,8-naphthyridin-2-yl)propyl)-2H-indazol-2-yl)propanoic acid | $^1$H NMR (500 MHz, MeOH-d$_4$) δ 8.86 (d, J = 2.2 Hz, 1H), 8.44 (s, 1H), 8.36 (d, J = 2.2 Hz, 1H), 7.99 (d, J = 8.5 Hz, 1H), 7.92 (d, J = 8.2 Hz, 1H), 7.76 (ddd, J = 8.4, 6.7, 1.4 Hz, 1H), 7.68-7.56 (m, 3H), 7.37 (s, 1H), 7.24 (d, J = 7.2 Hz, 1H), 6.98 (d, J = 8.6 Hz, 1H), 6.49 (dd, J = 7.2, 5.3 Hz, 1H), 6.43 (t, J = 7.6 Hz, 1H), 3.54 (dd, J = 15.9, 8.3 Hz, 1H), 3.45-3.36 (m, 2H), 2.74 (t, J = 7.5 Hz, 2H), 2.70 (t, J = 6.4 Hz, 2H), 1.79 (p, J = 8.1 Hz, 2H), 1.65-1.47 (m, 3H). LC/MS (m/z) = 492.2 (M + H)$^+$. Human αVβ6 IC$_{50}$ (nM) = 20. | Example 9 |

| Example No. | Structure & Name | Analytical Data | Method |
|---|---|---|---|
| 89 | 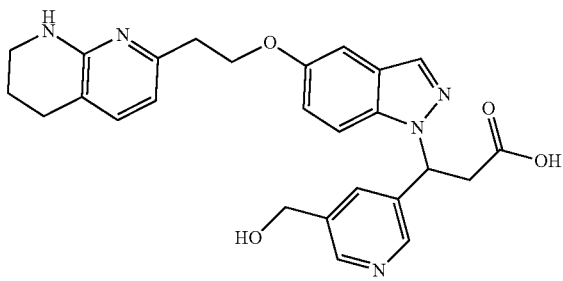 [SMILES: O=C(O)CC(c1cncc(CO)c1)n1ncc2cc(OCCc3ccc4c(n3)NCCC4)ccc21]<br>3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.54 (s, 1H), 8.43 (d, J = 2.2 Hz, 1H), 8.37 (s, 1H), 7.91 (s, 1H), 7.83 (s, 1H), 7.53 (d, J = 9.1 Hz, 1H), 7.17-7.10 (m, 2H), 7.00 (dd, J = 9.2, 2.4 Hz, 1H), 6.47 (d, J = 7.4 Hz, 1H), 6.27 (t, J = 7.4 Hz, 1H), 4.58 (s, 2H), 4.23 (t, J = 6.8 Hz, 2H), 3.08-2.91 (m, 4H), 2.69 (t, J = 6.3 Hz, 2H), 1.92-1.81 (m, 3H), 1.29 (t, J = 7.3 Hz, 3H). LC/MS (m/z) = 474.2 (M + H)$^+$. Human αVβ6 IC$_{50}$ (nM) = 19; Human αVβ1 IC$_{50}$ (nM) = 370; Human αVβ3 IC$_{50}$ (nM) = 3.1; Human αVβ5 IC$_{50}$ (nM) = 0.42; and Human αVβ8 IC$_{50}$(nM) = 5,000. | Example 3 |
| 90 | 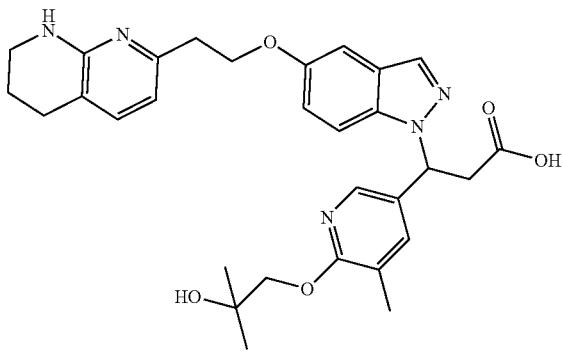 [SMILES: Cc1cc(C(CC(=O)O)n2ncc3cc(OCCc4ccc5c(n4)NCCC5)ccc32)cnc1OCC(C)(C)O]<br>3-(6-(2-Hydroxy-2-methylpropoxy)-5-methylpyridin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-$d_4$) δ 7.90 (s, 1H), 7.61 (s, 1H), 7.54 (d, J = 9.1 Hz, 1H), 7.39 (s, 1H), 7.24 (d, J = 7.2 Hz, 1H), 7.09 (d, J = 1.6 Hz, 1H), 6.99 (dd, J = 9.1, 2.0 Hz, 1H), 6.51 (d, J = 7.3 Hz, 1H), 6.02-5.93 (m, 1H), 4.26-4.12 (m, 2H), 4.09-3.95 (m, 2H), 3.38 (t, J = 5.5 Hz, 3H), 3.10 (dd, J = 15.5, 5.8 Hz, 1H), 2.97 (t, J = 6.4 Hz, 2H), 2.71 (t, J = 6.1 Hz, 2H), 2.02 (s, 3H), 1.90-1.81 (m, 2H), 1.14 (d, J = 12.0 Hz, 6H). LC/MS (m/z) = 546.5 (M + H)$^+$. Human αVβ6 IC$_{50}$ (nM) = 9.5. | Example 3 |
| 91 | 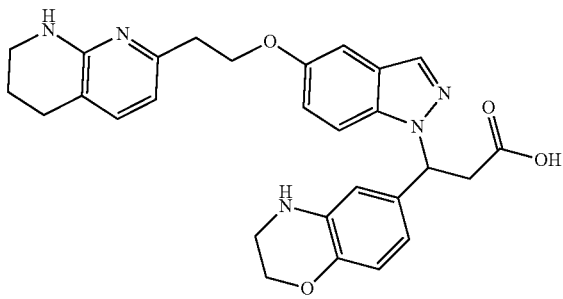 [SMILES: O=C(O)CC(c1ccc2c(c1)NCCO2)n1ncc2cc(OCCc3ccc4c(n3)NCCC4)ccc21]<br>3-(3,4-Dihydro-2H-pyrido[3,2-b][1,4]oxazin-6-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 7.94 (s, 1H), 7.66 (d, J = 9.1 Hz, 1H), 7.34 (d, J = 7.2 Hz, 1H), 7.12-7.03 (m, 2H), 6.99 (d, J = 9.1 Hz, 1H), 6.57 (d, J = 8.0 Hz, 1H), 6.50 (d, J = 7.2 Hz, 1H), 6.21 (t, J = 6.7 Hz, 1H), 4.28 (t, J = 5.6 Hz, 2H), 4.19 (dt, J = 8.5, 4.4 Hz, 2H), 3.69-3.52 (m, 3H), 3.51-3.39 (m, 3H), 3.16 (t, J = 5.6 Hz, 2H), 2.74 (t, J = 6.1 Hz, 2H), 1.97-1.85 (m, 2H). LC/MS (m/z) = 501.4 (M + H)$^+$. Human αVβ6 IC$_{50}$ (nM) = 31. | Example 3 |

| Example No. | Structure & Name | Analytical Data | Method |
|---|---|---|---|
| 92 | 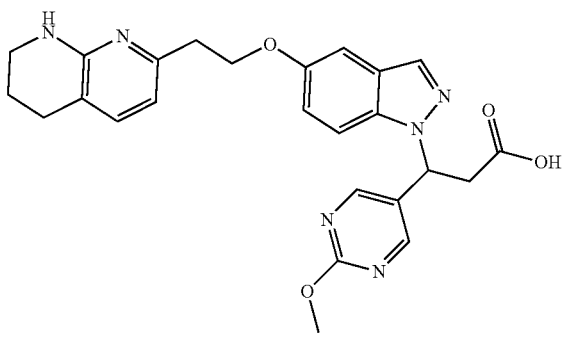 [SMILES: COc1ncc(C(CC(=O)O)n2ncc3cc(OCCc4ccc5c(n4)NCCC5)ccc32)cn1]<br>3-(2-Methoxypyrimidin-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.51 (s, 2H), 7.97 (s, 1H), 7.36-7.30 (m, 2H), 7.07 (d, J = 1.9 Hz, 1H), 7.03 (dd, J = 8.9, 2.3 Hz, 1H), 6.50 (d, J = 7.4 Hz, 1H), 6.02 (dd, J = 8.4, 5.9 Hz, 1H), 4.31 (t, J = 5.9 Hz, 2H), 3.97 (s, 3H), 3.74 (dd, J = 16.8, 8.5 Hz, 1H), 3.48 (t, J = 5.4 Hz, 2H), 3.33 (dd, J = 16.6, 5.9 Hz, 1H), 3.17 (t, J = 5.8 Hz, 2H), 2.74 (t, J = 6.1 Hz, 2H), 1.96-1.86 (m, 2H). LC/MS (m/z) = 475.5 (M + H)$^+$. Human αVβ6 IC$_{50}$ (nM) = 31; Human αVβ1 IC$_{50}$ (nM) = 210; Human αVβ3 IC$_{50}$ (nM) = 2.4; Human αVβ5 IC$_{50}$ (nM) = 0.39; and Human αVβ8 IC$_{50}$ (nM) = 5,000. | Example 3 |
| 93 | 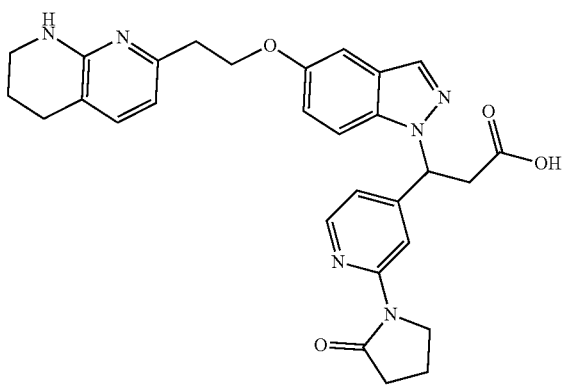 [SMILES: O=C(O)CC(c1ccnc(N2CCCC2=O)c1)n1ncc2cc(OCCc3ccc4c(n3)NCCC4)ccc21]<br>3-(2-(2-Oxopyrrolidin-1-yl)pyridin-4-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 9.82 (br. s., 1H), 8.41 (s, 1H), 8.25 (d, J = 5.2 Hz, 1H), 8.03 (s, 1H), 7.35 (d, J = 7.2 Hz, 1H), 7.12 (d, J = 1.9 Hz, 1H), 7.01 (dd, J = 9.2, 2.3 Hz, 1H), 6.76 (d, J= 5.5 Hz, 1H), 6.52 (d, J = 7.4 Hz, 1H), 6.10 (dd, J = 8.9, 4.8 Hz, 1H), 4.31 (t, J = 5.8 Hz, 2H), 4.08 (t, J = 7.2 Hz, 2H), 3.79 (dd, J = 16.5, 8.8 Hz, 1H), 3.51 (t, J = 5.5 Hz, 2H), 3.37 (dd, J = 16.5, 4.7 Hz, 1H), 3.19 (t, J = 5.8 Hz, 2H), 2.77 (t, J = 6.1 Hz, 2H), 2.71-2.66 (m, 2H), 2.22-2.09 (m, 2H), 2.00-1.89 (m, 2H). LC/MS (m/z) = 527.5 (M + H)$^+$. Human αVβ6 IC$_{50}$ (nM) = 8.1. | Example 3 |
| 94 | 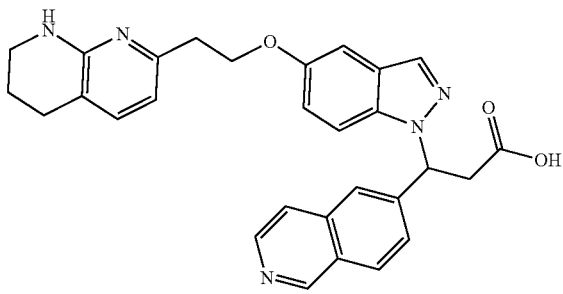 [SMILES: O=C(O)CC(c1ccc2cnccc2c1)n1ncc2cc(OCCc3ccc4c(n3)NCCC4)ccc21]<br>3-(Isoquinolin-6-yl)-3-(5-(2-(5,6,7,8-tetrahydro-1,8-naphthyridin-2-yl)ethoxy)-1H-indazol-1-yl) propanoic acid, 2 TFA | $^1$H NMR (500 MHz, MeOH-d$_4$) δ 9.57 (br. s., 1H), 8.51 (d, J = 6.3 Hz, 1H), 8.34 (d, J = 8.5 Hz, 1H), 8.26 (d, J = 3.6 Hz, 1H), 8.14 (s, 1H), 8.03 (s, 1H), 7.91 (d, J = 8.5 Hz, 1H), 7.64-7.53 (m, 2H), 7.21 (d, J = 1.9 Hz, 1H), 7.03 (dd, J = 9.1, 2.2 Hz, 1H), 6.73 (d, J = 7.2 Hz, 1H), 6.51 (dd, J = 9.5, 5.1 Hz, 1H), 4.31 (td, J = 5.9, 2.8 Hz, 2H), 3.81 (dd, J = 16.8, 9.6 Hz, 1H), 3.51-3.42 (m, 3H), 3.17 (t, J = 5.9 Hz, 2H), 2.80 (t, J = 6.2 Hz, 2H), 1.93 (quin, J = 5.9 Hz, 2H). LC/MS (m/z) = 494.2 (M + H)$^+$. Human αVβ6 IC$_{50}$ (nM) = 13. | Example 3 |

-continued

| Example No. | Structure & Name | Analytical Data | Method |
|---|---|---|---|
| 95 | 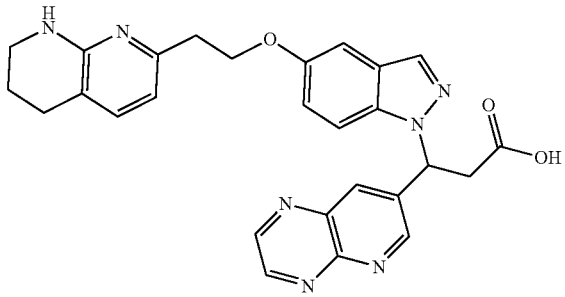 [SMILES: O=C(O)CC(c1cnc2nccnc2c1)n1ncc2cc(OCCc3ccc4c(n3)NCCC4)ccc21]<br>3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 9.26 (br. s., 1H), 9.07 (d, J = 1.4 Hz, 1H), 8.98 (d, J = 1.7 Hz, 1H), 8.47 (d, J = 1.9 Hz, 1H), 8.04 (s, 1H), 7.42-7.31 (m, 2H), 7.09 (d, J = 1.9 Hz, 1H), 7.02 (dd, J = 9.1, 2.2 Hz, 1H), 6.51 (d, J = 7.2 Hz, 1H), 6.45-6.36 (m, 1H), 4.32-4.24 (m, 2H), 3.58-3.52 (m, 1H), 3.49 (t, J = 5.5 Hz, 2H), 3.16 (t, J = 5.8 Hz, 2H), 2.75 (t, J = 6.2 Hz, 2H), 1.97-1.87 (m, 2H). LC/MS (m/z) = 496.2 (M + H)$^+$. Human αVβ6 IC$_{50}$ (nM) = 30: Hmnan αVβ1 IC$_{50}$ (nM) = 210; Human αVβ3 IC$_{50}$ (nM) = 2.4; and Human αVβ8 IC$_{50}$ (nM) = 7,600. | Example 3 |
| 96 | 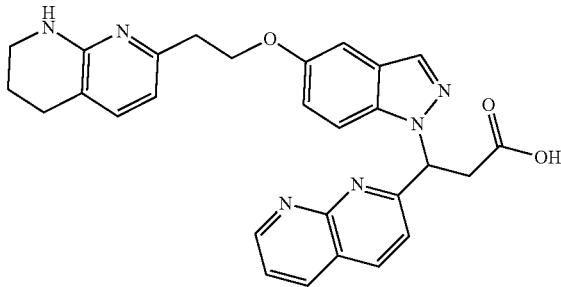 [SMILES: O=C(O)CC(c1ccc2cccnc2n1)n1ncc2cc(OCCc3ccc4c(n3)NCCC4)ccc21]<br>3-(1,8-Naphthyridin-2-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 10.09 (br. s., 1H), 9.21 (br. s., 1H), 8.33 (d, J = 7.7 Hz, 1H), 8.12 (d, J = 8.5 Hz, 1H), 8.01 (s, 1H), 7.65 (dd, J = 7.8, 4.0 Hz, 1H), 7.42 (d, J = 9.1 Hz, 1H), 7.33 (d, J = 7.2 Hz, 1H), 7.13 (s, 1H), 7.08 (d, J = 8.3 Hz, 1H), 6.98 (d, J = 7.4 Hz, 1H), 6.58 (t, J = 6.6 Hz, 1H), 6.50 (d, J = 7.2 Hz, 1H), 4.32 (t, J = 5.8 Hz, 2H), 3.99 (dd, J = 16.2, 6.9 Hz, 1H), 3.57-3.44 (m, 3H), 3.19 (t, J = 5.8 Hz, 2H), 2.75 (t, J = 6.1 Hz, 2H), 1.92 (quin, J = 5.8 Hz, 2H). LC/MS (m/z) = 495.2 (M + H)$^+$. Human αVβ6 IC$_{50}$ (nM) = 7.2. | Example 3 |
| 97 | 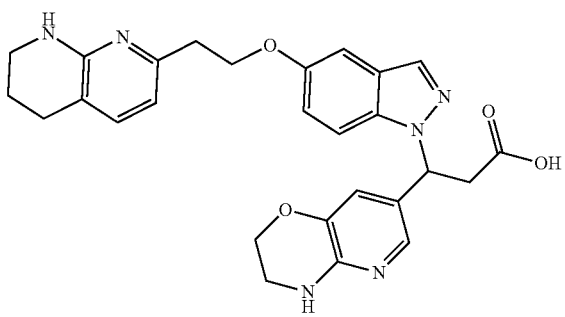 [SMILES: O=C(O)CC(c1cnc2c(c1)OCCN2)n1ncc2cc(OCCc3ccc4c(n3)NCCC4)ccc21]<br>3-(3,4-Dihydro-2H-pyrido[3,2-b][1,4]oxazin-3-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 10.61 (br. s., 1H), 10.12 (br. s., 1H), 7.96 (s, 1H), 7.76 (s, 1H), 7.37-7.28 (m, 2H), 7.11 (d, J = 1.9 Hz, 1H), 7.01 (dd, J = 8.9, 1.8 Hz, 1H), 6.49 (d, J = 7.2 Hz, 1H), 5.95 (t, J = 7.0 Hz, 1H), 4.29 (t, J = 4,8 Hz, 2H), 4.24-4.09 (m, 2H), 3.67-3.53 (m, 3H), 3.51-3.36 (m, 3H), 3.17 (t, J = 5.8 Hz, 2H), 2.74 (t, J = 6.1 Hz, 2H), 1.97-1.86 (m, 2H). LC/MS (m/z) = 501.2 (M + H)$^+$. Human αVβ6 IC$_{50}$ (nM) = 10; Human αVβ1 IC$_{50}$ (nM) = 100; Human αVβ3 IC$_{50}$ (nM) = 2.6; Human αVβ5 IC$_{50}$ (nM) = 0.59; and Human αVβ8 IC$_{50}$ (nM) = 5,000. | Example 3 |

-continued

| Example No. | Structure & Name | Analytical Data | Method |
|---|---|---|---|
| 98 | 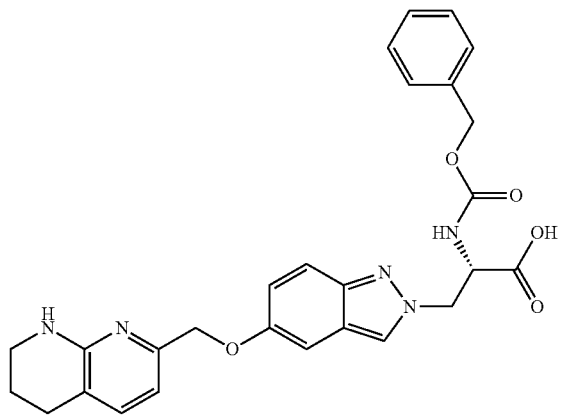 [SMILES: O=C(N[C@@H](Cn1cc2cc(OCc3ccc4c(n3)NCCC4)ccc2n1)C(=O)O)OCc1ccccc1](S)-2-(((Benzyloxy)carbonyl)amino)-3-(5-((5,6,7,8-tetrahydro-1,8-naphthyridin-2-yl)methoxy)-2H-indazol-2-yl)propanoic acid | $^1$H NMR (500 MHz, MeOH-$d_4$) δ 7.84 (s, 1H), 7.46 (dd, J = 12.5, 9.2 Hz, 1H), 7.36 (d, J = 7.3 Hz, 1H), 7.31-7.22 (m, 4H), 7.22-7.17 (m, 1H), 7.12 (d, J = 2.3 Hz, 1H), 7.03 (dd, J = 9.1, 2.4 Hz, 1H), 6.75-6.69 (m, 1H), 4.79 (dd, J = 14.5, 4.3 Hz, 1H), 4.68 (dd, J = 14.4, 7.4 Hz, 1H), 4.61-4.46 (m, 1H), 3.78 (s, 2H), 3.43 (q, J = 5.4 Hz, 2H), 2.77 (t, J = 6.2 Hz, 3H), 1.90 (q, J = 5.9 Hz, 2H). LC/MS (m/z) = 502.1 (M + H)$^+$. Human αVβ6 IC$_{50}$ (nM) = 160. | Example 4 |
| 99 | 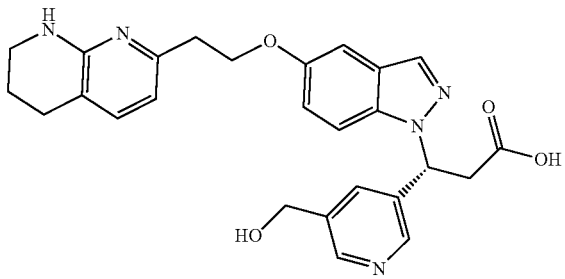 [SMILES: O=C(O)C[C@H](c1cncc(CO)c1)n1ncc2cc(OCCc3ccc4c(n3)NCCC4)ccc21](R)-3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.54 (s, 1H), 8.43 (d, J = 2.2 Hz, 1H), 8.37 (s, 1H), 7.91 (s, 1H), 7.83 (s, 1H), 7.53 (d, J = 9.1 Hz, 1H), 7.17-7.10 (m, 2H), 7.00 (dd, J = 9.2, 2.4 Hz, 1H), 6.47 (d, J = 7.4 Hz, 1H), 6.27 (t, J = 7.4 Hz, 1H), 4.58 (s, 2H), 4.23 (t, J = 6.8 Hz, 2H), 3.08-2.91 (m, 4H), 2.69 (t, J = 6.3 Hz, 2H), 1.92-1.81 (m, 3H), 1.29 (t, J = 7.3 Hz, 3H). LC/MS (m/z) = 474.2 (M + H)$^+$. Human αVβ6 IC$_{50}$ (nM) = 340. | Example 16 and 17 |
| 100 | 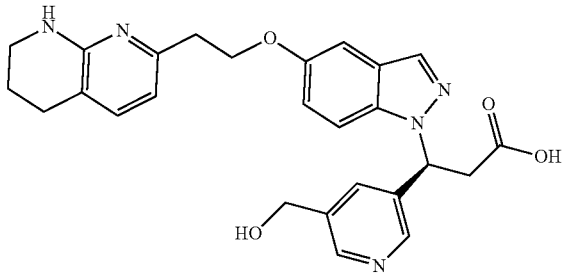 [SMILES: O=C(O)C[C@@H](c1cncc(CO)c1)n1ncc2cc(OCCc3ccc4c(n3)NCCC4)ccc21](S)-3-(5-(Hydroxymethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.54 (s, 1H), 8.43 (d, J = 2.2 Hz, 1H), 8.37 (s, 1H), 7.91 (s, 1H), 7.83 (s, 1H), 7.53 (d, J = 9.1 Hz, 1H), 7.17-7.10 (m, 2H), 7.00 (dd, J = 9.2, 2.4 Hz, 1H), 6.47 (d, J = 7.4 Hz, 1H), 6.27 (t, J = 7.4 Hz, 1H), 4.58 (s, 2H), 4.23 (t, J = 6.8 Hz, 2H), 3.08-2.91 (m, 4H), 2.69 (t, J = 6.3 Hz, 2H), 1.92-1.81 (m, 3H), 1.29 (t, J = 7.3 Hz, 3H). LC/MS (m/z) = 474.2 (M + H)$^+$. Human αVβ6 IC$_{50}$ (nM) = 14; Human αVβ1 IC$_{50}$ (nM) = 140; Human αVβ3 IC$_{50}$ (nM) = 2.9; Human αVβ5 IC$_{50}$ (nM) = 0.41; and Human αVβ8 IC$_{50}$ (nM) = 4,400. | Example 16 and 17 |

-continued

| Example No. | Structure & Name | Analytical Data | Method |
|---|---|---|---|
| 101 | 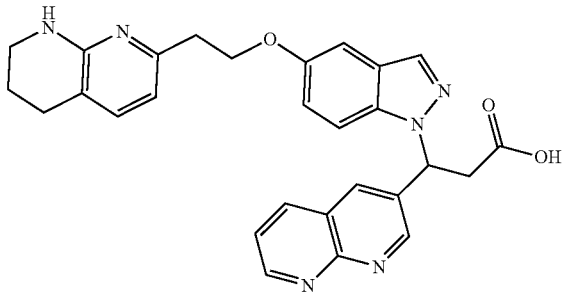 [SMILES: O=C(O)CC(c1cnc2ncccc2c1)n1ncc2cc(OCCc3ccc4c(n3)NCCC4)ccc21]<br>3-(1,8-Naphthyridin-3-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 10.03 (br s, 1H), 9.29 (d, J = 2.2 Hz, 1H), 9.18 (dd, J = 4.3, 1.8 Hz, 1H), 8.31-8.23 (m, 2H), 8.03 (s, 1H), 7.60 (dd, J = 8.1, 4.3 Hz, 1H), 7.40-7.31 (m, 2H), 7.11 (d, J = 1.9 Hz, 1H), 7.00 (dd, J = 9.1, 2.2 Hz, 1H), 6.50 (d, J = 7.4 Hz, 1H), 6.41 (t, J = 7.2 Hz, 1H), 4.36-4.27 (m, 2H), 3.84 (dd, J = 16.5, 7.7 Hz, 1H), 3.54 (dd, J = 16.8, 6.6 Hz, 1H), 3.48 (br t, J = 5.4 Hz, 2H), 3.18 (t, J = 5.8 Hz, 2H), 2.75 (br t, J = 6.1 Hz, 2H), 1.96-1.88 (m, 2H). LC/MS (m/z) = 495.4 (M + H)$^+$. Human αVβ6 IC$_{50}$ (nM) = 5.7; Human αVβ1 IC$_{50}$ (nM) = 100; Human αVβ3 IC$_{50}$ (nM) = 1.6; and Human αVβ8 IC$_{50}$ (nM) = 2,300. | Example 3 |
| 102 | 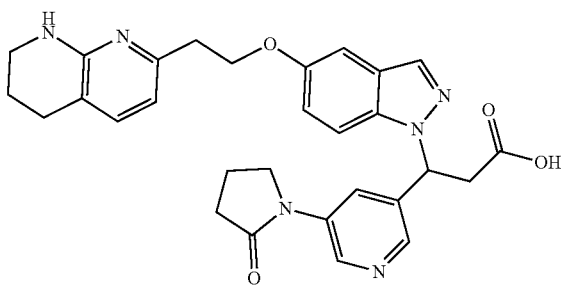 [SMILES: O=C(O)CC(c1cncc(N2CCCC2=O)c1)n1ncc2cc(OCCc3ccc4c(n3)NCCC4)ccc21]<br>3-(5-(2-Oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 9.98 (br s, 1H), 9.16 (d, J = 1.9 Hz, 1H), 8.80 (s, 1H), 8.47 (s, 1H), 8.00 (s, 1H), 7.37-7.33 (m, 2H), 7.10 (d, J = 2.2 Hz, 1H), 6.88 (dd, J = 9.1, 2.2 Hz, 1H), 6.50 (d, J = 7.4 Hz, 1H), 6.41 (t, J = 7.0 Hz, 1H), 4.37-4.22 (m, 2H), 3.87-3.81 (m, 2H), 3.81-3.72 (m, 2H), 3.41 (br dd, J = 17.1, 6.3 Hz, 1H), 3.17 (br t, J = 5.9 Hz, 2H), 2.76 (br t, J = 6.1 Hz, 2H), 2.68-2.59 (m, 2H), 2.23 (br t, J = 7.7 Hz, 2H), 1.99-1.88 (m, 2H). LC/MS (m/z) = 527.5 (M + H)$^+$. Human αVβ6 IC$_{50}$ (nM) = 4.3; Human αVβ1 IC$_{50}$ (nM) = 39; Human αVβ3 IC$_{50}$ (nM) = 2.2; and Human αVβ8 IC$_{50}$ (nM) = 1,300. | Example 3 |
| 103 | 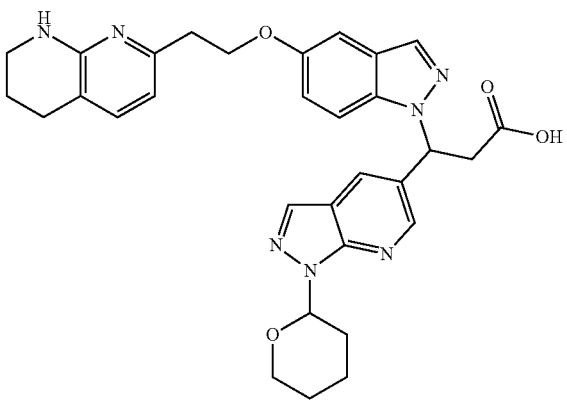 [SMILES: O=C(O)CC(c1cnc2c(cnn2C2CCCCO2)c1)n1ncc2cc(OCCc3ccc4c(n3)NCCC4)ccc21]<br>3-(5-(2-(5,6,7,8-tetrahydro-1,8-naphthyridin-2-yl)ethoxy)-1H-indazol-1-yl)-3-(1-(tetrahydro-2H-pyran-2-yl)pyrazolo[3,4-b]pyridin-5-yl)propanoic acid, TFA | $^1$H NMR (500 MHz, chloroform-d) δ 9.84 (br s, 1H), 8.66-8.55 (m, 1H), 8.07-7.96 (m, 2H), 7.37-7.30 (m, 2H), 7.08 (s, 1H), 6.98 (br d, J = 9.1 Hz, 1H), 6.49 (d, J = 7.4 Hz, 1H), 6.24 (br dd, J = 8.3, 5.8 Hz, 1H), 6.05 (ddd, J = 10.2, 5.1, 2.1 Hz, 1H), 4.28 (br t, J = 5.4 Hz, 2H), 4.09 (br d, J = 10.5 Hz, 1H), 3.90-3.75 (m, 2H), 3.48 (br t, J = 5.1 Hz, 2H), 3.39 (dt, J = 16.4, 4.7 Hz, 1H), 3.21-3.13 (m, 2H), 2.74 (br t, J = 6.1 Hz, 2H), 2.68-2.56 (m, 1H), 2.23-2.09 (m, 1H), 2.01-1.87 (m, 3H), 1.78 (br t, J = 9.1 Hz, 2H), 1.63 (br d, J = 7.2 Hz, 1H). LC/MS (m/z) = 568.6 (M + H)$^+$. Human αVβ6 IC$_{50}$ (nM) = 5.4. | Example 3 |

| Example No. | Structure & Name | Analytical Data | Method |
|---|---|---|---|
| 104 | 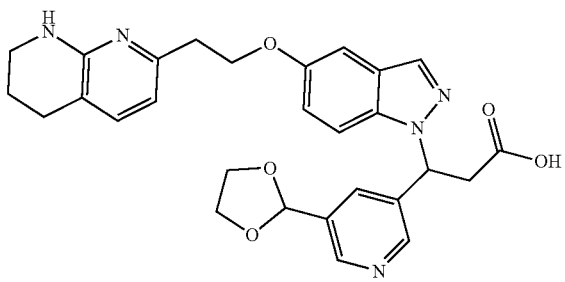 [SMILES: O=C(O)CC(c1cncc(C2OCCO2)c1)n1ncc2cc(OCCc3ccc4c(n3)NCCC4)ccc21]<br>3-(5-(1,3-Dioxolan-2-yl)pyridin-3-yl)-3-(5-(2-(5,6,7,8-tetrahydro-1,8-naphthyridin-2-yl)ethoxy)-1H-indazol-1yl)propanoic acid | $^1$H NMR (500 MHz, DMSO-$d_6$) δ 8.61 (s, 1H), 8.47 (s, 1H), 8.00 (s, 1H), 7.75 (s, 1H), 7.67 (d, J = 9.2 Hz, 1H), 7.17 (d, J = 2.4 Hz, 1H), 7.06 (d, J = 7.3 Hz, 1H), 7.01-6.92 (m, 1H), 6.37 (d, J = 7.3 Hz, 1H), 6.25 (d, J = 8.9 Hz, 1H), 5.72 (s, 1H), 4.22 (d, J = 7.3 Hz, 2H), 3.99 (d, J = 6.4 Hz, 1H), 3.92 (d, J = 6.2 Hz, 1H), 3.68 (d, J = 12.0 Hz, 1H), 3.55-3.42 (m, 1H), 3.26-3.13 (m, 4H), 2.87 (t, J = 6.7 Hz, 2H), 2.59 (t, J = 6.3 Hz, 2H), 1.78-1.63 (m, 2H). LC/MS (m/z) = 516.3 (M + H)$^+$. Human αVβ6 IC$_{50}$ (nM) = 12; Human αVβ1 IC$_{50}$ (nM) = 30; Human αVβ3 IC$_{50}$ (nM) = 2.61; Human αVβ5 IC$_{50}$ (nM) = 0.28: and Human αVβ8 IC$_{50}$ (nM) = 1,800. | Example 3 |
| 105 | 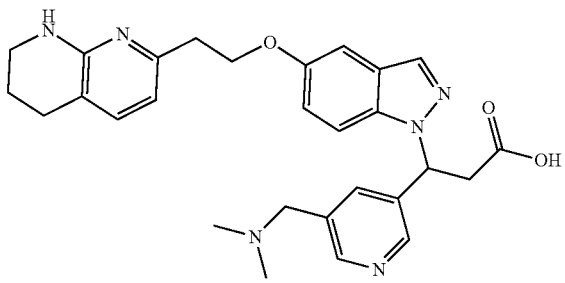 [SMILES: CN(C)Cc1cncc(C(CC(=O)O)n2ncc3cc(OCCc4ccc5c(n4)NCCC5)ccc32)c1]<br>3-(5-((Dimethylamino)methyl)pyridin-3-yl)-3-(5-(2-(5,6,7,8-tetrahydro-1,8-naphthyridin-2-yl)ethoxy)-1H-indazol-1-yl)propanoic acid | $^1$H NMR (400 MHz, MeCN-$d_3$) δ 9.51 (s, 1H), 8.67 (d, J = 2.1 Hz, 1H), 8.58 (d, J = 2.0 Hz, 1H), 8.07 (t, J = 2.1 Hz, 1H), 7.96 (d, J = 0.8 Hz, 1H), 7.51 (d, J = 9.1 Hz, 1H), 7.44 (d, J = 7.4 Hz, 1H), 7.17 (d, J = 2.4 Hz, 1H), 7.01 (dd, J = 9.1, 2.3 Hz, 1H), 6.58 (d, J = 7.3 Hz, 1H), 6.22 (dd, J = 9.2, 5.6 Hz, 1H), 4.32-4.24 (m, 3H), 4.23-4.13 (m, 2H), 3.69 (dd, J = 16.8, 9.2 Hz, 1H), 3.41 (t, J = 5.7 Hz, 2H), 3.34 (dd, J = 16.8, 5.6 Hz, 1H), 3.11 (t, J = 6.2 Hz, 2H), 2.72 (d, J = 7.7 Hz, 2H), 2.70 (s, 6H), 1.86 (dq, J = 7.0, 5.6 Hz, 2H). LC/MS (m/z) = 501.1 (M + H)$^+$. Human αVβ6 IC$_{50}$ (nM) = 10. | Example 3 |
| 106 | 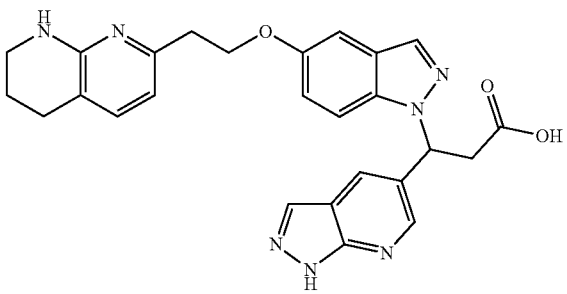 [SMILES: O=C(O)CC(c1cnc2[nH]ncc2c1)n1ncc2cc(OCCc3ccc4c(n3)NCCC4)ccc21]<br>3-(1H-Pyrazolo[3,4-b]pyridin-5-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 8.59 (d, J = 1.9 Hz, 1H), 8.27 (d, J = 1.9 Hz, 1H), 8.08 (s, 1H), 8.00 (s, 1H), 7.66-7.58 (m, 2H), 7.20 (d, J = 1.9 Hz, 1H), 7.06 (dd, J = 9.2, 2.3 Hz, 1H), 6.76 (d, J = 7.2 Hz, 1H), 6.41 (dd, J = 9.4, 5.5 Hz, 1H), 4.33 (br t, J = 5.6 Hz, 2H), 3.80 (dd, J = 16.8, 9.4 Hz, 1H), 3.51-3.46 (m, 2H), 3.45-3.38 (m, 1H), 3.18 (t, J = 5.8 Hz, 2H), 2.80 (br t, J = 6.1 Hz, 2H), 2.01-1.89 (m, 2H). LC/MS (m/z) = 484.5 (M + H)$^+$. Human αVβ6 IC$_{50}$ (nM) = 23; Human αVβ1 IC$_{50}$ (nM) = 78; Human αVβ3 IC$_{50}$ (nM) = 1.3; Human αVβ5 IC$_{50}$ (nM) = 2.6; and Human αVβ8 IC$_{50}$ (nM) = 3,000. | Example 3 |

| Example No. | Structure & Name | Analytical Data | Method |
|---|---|---|---|
| 107 | 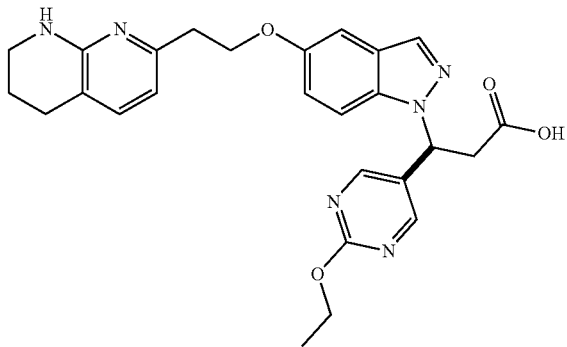<br>(S)-3-(2-Ethoxypyrimidin-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, MeOH-d$_4$) δ 8.58 (s, 2H), 8.00 (s, 1H), 7.67-7.61 (m, 2H), 7.21 (d, J = 2.2 Hz, 1H), 7.09 (dd, J = 9.1, 2.5 Hz, 1H), 6.77 (d, J = 7.4 Hz, 1H), 6.24 (dd, J = 9.1, 5.8 Hz, 1H), 4.40 (q, J = 7.0 Hz, 2H), 4.34 (t, J = 5.9 Hz, 2H), 3.68 (dd, J = 16.6, 9.2 Hz, 1H), 3.55-3.49 (m, 2H), 3.20 (t, J = 5.8 Hz, 2H), 2.83 (t, J = 6.2 Hz, 2H), 1.96 (br dd, J = 6.3, 5.2 Hz, 2H), 1.38 (t, J = 7.2 Hz, 3H). LC/MS (m/z) = 489.5 (M + H)$^+$. Human αVβ6 IC$_{50}$ (nM) = 15; Human αVβ1 IC$_{50}$ (nM) = 64; Human αVβ3 IC$_{50}$ (nM) = 2.4; Human αVβ5 IC$_{50}$ (nM) = 0.32; and Human αVβ8 IC$_{50}$ (nM) = 300. | Example 16 and 17 |
| 108 | 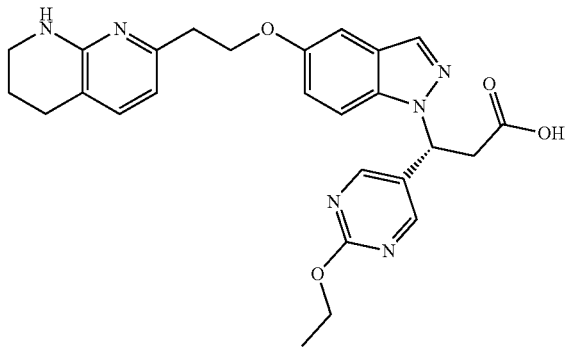<br>(R)-3-(2-Ethoxypyrimidin-5-yl)-3-(5-(2-(5,6,7,8-tetrahydro-1,8-naphthyridin-2-yl)ethoxy)-1H-indazol-1-yl) propanoic acid, TFA | $^1$H NMR (500 MHz, MeOH-d$_4$) δ 8.58 (s, 2H), 8.00 (s, 1H), 7.67-7.61 (m, 2H), 7.21 (d, J = 2.2 Hz, 1H), 7.09 (dd, J = 9.1, 2.5 Hz, 1H), 6.77 (d, J = 7.4 Hz, 1H), 6.24 (dd, J = 9.1, 5.8 Hz, 1H), 4.40 (q, J = 7.0 Hz, 2H), 4.34 (t, J = 5.9 Hz, 2H), 3.68 (dd, J = 16.6, 9.2 Hz, 1H), 3.55-3.49 (m, 2H), 3.20 (t, J = 5.8 Hz, 2H), 2.83 (t, J = 6.2 Hz, 2H), 1.96 (br dd, J = 6.3, 5.2 Hz, 2H), 1.38 (t, J = 7.2 Hz, 3H). LC/MS (m/z) = 489.5 (M + H)$^+$. Human αVβ6 IC$_{50}$ (nM) = 390. | Example 16 and 17 |
| 109 | 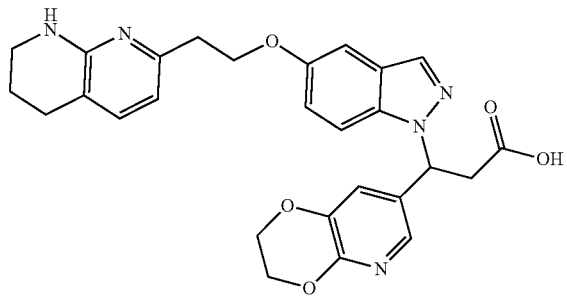 [SMILES: O=C(O)CC(c1cnc2c(c1)OCCO2)n1ncc2cc(OCCc3ccc4c(n3)NCCC4)ccc21]<br>3-(2,3-Dihydro-[1,4]dioxino[2,3-b]pyridin-7-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-d$_4$) δ 7.99 (s, 1H), 7.95 (s, 1H), 7.38-7.30 (m, 2H), 7.28-7.25 (m, 1H), 7.09 (d, J = 2.2 Hz, 1H), 7.00 (dd, J = 9.1, 1.9 Hz, 1H), 6.53 (d, J = 7.2 Hz, 1H), 6.06 (t, J = 7.2 Hz, 1H), 4.48-4.40 (m, 2H), 4.34-4.27 (m, 2H), 4.27-4.20 (m, 2H), 3.74 (dd, J = 16.5, 8.5 Hz, 1H), 3.51 (br t, J = 5.5 Hz, 2H), 3.31 (br dd, J = 16.5, 5.5 Hz, 1H), 3.22-3.15 (m, 2H), 2.77 (br t, J = 6.1 Hz, 2H), 1.99-1.91 (m, 2H). LC/MS (m/z) = 502.2 (M + H)$^+$ Human αVβ6 IC$_{50}$ (nM) = 15; Human αVβ1 IC$_{50}$ (nM) = 62; Human αVβ3 IC$_{50}$ (nM) = 1.3; and Human αVβ8 IC$_{50}$ (nM) = 9,300. | Example 3 |

| Example No. | Structure & Name | Analytical Data | Method |
|---|---|---|---|
| 110 | 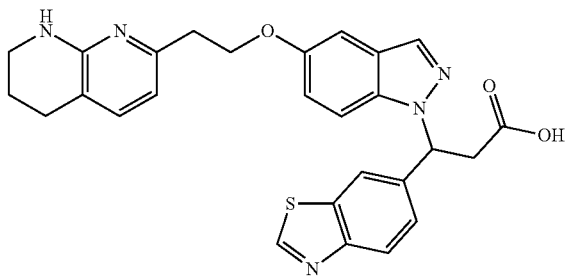 [SMILES: O=C(O)CC(c1ccc2ncsc2c1)n1ncc2cc(OCCc3ccc4c(n3)NCCC4)ccc21]<br>3-(Benzo[d]thiazol-6-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.98 (s, 1H), 8.06 (d, J = 8.5 Hz, 1H), 8.04 (s, 1H), 7.79 (s, 1H), 7.44 (dd, J = 8.5, 1.4 Hz, 1H), 7.34-7.30 (m, 1H), 7.26 (s, 1H), 7.12 (d, J = 1.7 Hz, 1H), 6.98 (dd, J = 8.9, 2.1 Hz, 1H), 6.48 (d, J = 7.4 Hz, 1H), 6.23 (dd, J = 9.1, 4.7 Hz, 1H), 4.30 (br t, J = 5.8 Hz, 2H), 3.87 (dd, J = 16.4, 9.2 Hz, 1H), 3.48 (br t, J = 5.2 Hz, 2H), 3.40 (dd, J = 16.2, 4.7 Hz, 1H), 3.18 (br t, J = 5.6 Hz, 2H), 2.74 (br t, J = 6.2 Hz, 2H), 1.95-1.89 (m, 2H). LC/MS (m/z) = 500.2 (M + H)$^+$. Human αVβ6 IC$_{50}$ (nM) = 19 | Example 3 |
| 111 | 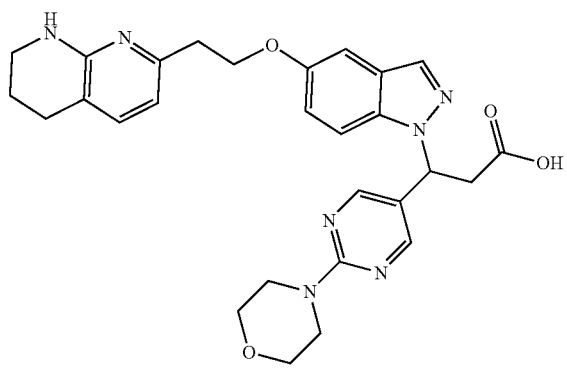 [SMILES: O=C(O)CC(c1cnc(N2CCOCC2)nc1)n1ncc2cc(OCCc3ccc4c(n3)NCCC4)ccc21]<br>3-(2-Morpholinopyrimidin-5-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 8.60 (s, 2H), 7.99 (s, 1H), 7.40-7.33 (m, 2H), 7.10 (d, J = 1.9 Hz, 1H), 6.99 (d, J = 8.4 Hz, 1H), 6.54 (d, J = 7.2 Hz, 1H), 6.05 (t, J = 7.3 Hz, 1H), 4.31 (br t, J = 5.5 Hz, 2H), 3.89-3.81 (m, 4H), 3.81-3.75 (m, 4H), 3.66 (br d, J = 7.4 Hz, 1H), 3.52 (br t, J = 5.5 Hz, 2H), 3.39 (br dd, J = 16.6, 7.0 Hz, 1H), 3.22-3.15 (m, 2H), 2.78 (br t, J = 6.1 Hz, 2H), 2.00-1.91 (m, 2H). LC/MS (m/z) = 530.3 (M + H)$^+$. Human αVβ6 IC$_{50}$ (nM) = 24. | Example 3 |
| 112 | 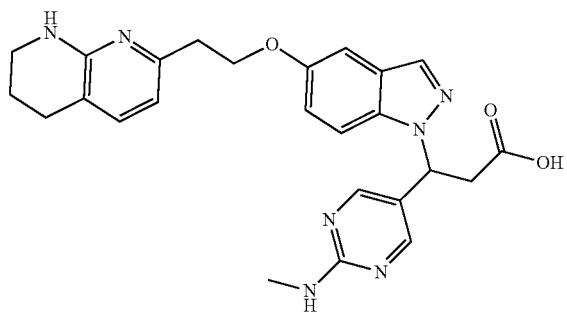 [SMILES: CNc1ncc(C(CC(=O)O)n2ncc3cc(OCCc4ccc5c(n4)NCCC5)ccc32)cn1]<br>3-(2-(Methylamino)pyrimidin-5-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-d$_4$) δ 8.43 (s, 2H), 7.98 (s, 1H), 7.67-7.58 (m, 2H), 7.20 (d, J = 2.2 Hz, 1H), 7.09 (dd, J = 9.1, 2.2 Hz, 1H), 6.75 (d, J = 7.4 Hz, 1H), 6.13 (dd, J = 9.1, 6.1 Hz, 1H), 4.34 (t, J = 5.9 Hz, 2H), 3.62 (dd, J = 16.6, 8.9 Hz, 1H), 3.54-3.47 (m, 2H), 3.31-3.25 (m, 1H), 3.20 (t, J = 5.9 Hz, 2H), 2.93 (s, 3H), 2.82 (br t, J = 6.2 Hz, 2H), 2.01-1.90 (m, 2H). LC/MS (m/z) = 474.2 (M + H)$^+$. Human αVβ6 IC$_{50}$ (nM) = 21; Human αVβ1 IC$_{50}$ (nM) = 93; Human αVβ3 IC$_{50}$ (nM) = 2.9; and Human αVβ8 IC$_{50}$ (nM) = 5,000. | Example 3 |

| Example No. | Structure & Name | Analytical Data | Method |
|---|---|---|---|
| 113 | 3-(6-Methoxypyridin-3-yl)-3-(5-(3-(5,6,7,8-tetrahydro-1,8-naphthyridin-2-yl)propyl)-1H-pyrazolo[4,3-6]pyridin-1-yl)propanoic acid | $^1$H NMR (500 MHz, DMSO-$d_6$) δ 8.27 (d, J = 2.5 Hz, 1H), 8.21 (d, J = 10.4 Hz, 2H), 7.71 (dd, J = 8.7.2.4 Hz, 1H), 7.28 (d, J = 8.7 Hz, 1H), 7.02 (d, J = 7.1 Hz, 1H), 6.74 (d, J = 8.6 Hz, 1H), 6.30-6.19 (m, 2H), 3.78 (s, 3H), 3.54 (s, 1H), 3.19 (d, J = 23.9 Hz, 3H), 2.81 (t, J = 7.6 Hz, 2H), 2.58 (t, J = 6.3 Hz, 2H), 2.45 (t, J = 7.6 Hz, 2H), 1.98 (t, J = 7.5 Hz, 2H), 1.77-1.68 (m, 2H). Human αVβ6 IC$_{50}$ (nM) = 890. | Example 1 |
| 114 | 3-(6-Methoxypyridazin-3-yl)-3-(5-(2-(5,6,7,8-tetrahydro-1,8-naphthyridin-2-yl)ethoxy)-1H-indazol-1-yl)propanoic acid, TFA | $^1$H NMR (500 MHz, chloroform-d) δ 7.98 (s, 1H), 7.44 (br d, J = 9.1 Hz, 1H), 7.37 (d, J = 7.4 Hz, 1H), 7.30 (d, J = 9.1 Hz, 1H), 7.12-7.05 (m, 1H), 7.01 (d, J = 9.1 Hz, 2H), 6.60-6.47 (m, 2H), 4.28 (br t, J = 5.8 Hz, 2H), 4.12 (s, 3H), 3.75-3.57 (m, 2H), 3.51 (br t, J = 5.4 Hz, 2H), 3.17 (br t, J = 5.6 Hz, 2H), 2.77 (br t, J = 6.1 Hz, 2H), 1.99-1.90 (m, 2H). LC/MS (m/z) = 475.2 (M + H)$^+$. Human αVβ6 IC$_{50}$ (nM) = 2.6. | Example 3 |
| 115 | 3-([1,2,4]Triazolo[4,3-a]pyridin-6-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 9.23 (s, 1H), 8.66 (s, 1H), 8.03 (s, 1H), 7.93 (s, 1H), 7.73 (d, J = 9.1 Hz, 1H), 7.69 (d, J = 9.7 Hz, 1H), 7.59 (d, J = 7.4 Hz, 1H), 7.39-7.32 (m, 1H), 7.29 (s, 1H), 7.23-7.16 (m, 2H), 7.09 (s, 1H), 7.01 (dd, J = 9.1,2.3 Hz, 1H), 6.70 (d, J = 7.4 Hz, 1H), 6.24 (dd, J = 10.1, 4.7 Hz, 1H), 4.26 (q, J = 5.6 Hz, 2H), 3.38 (t, J = 5.6 Hz, 2H), 3.26 (dd, J = 16.7, 4.7 Hz, 1H), 3.11 (t, J = 6.1 Hz, 2H), 2.70 (d, J = 6.4 Hz, 2H), 1.79 (t, J = 5.8 Hz, 2H). LC/MS (m/z) = 484.4 (M + H)$^+$. Human αVβ6 IC$_{50}$ (nM) = 60. | Example 3 |
| 116 | 3-(5,6,7,8-Tetrahydro-1,8-naphthyridin-2-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 8.04 (s, 1H), 7.68-7.56 (m, 2H), 7.51 (d, J = 7.4 Hz, 1H), 7.23 (d, J = 2.1 Hz, 1H), 7.10 (dd, J = 9.1, 2.5 Hz, 1H), 6.77 (d, J = 7.2 Hz, 1H), 6.62 (d, J = 7.2 Hz, 1H), 6.22 (dd, J = 8.9, 5.6 Hz, 1H), 4.34 (br t, J = 5.9 Hz, 2H), 3.62 (dd, J = 17.1, 9.1 Hz, 1H), 3.55-3.46 (m, 4H), 3.41 (br dd, J = 16.9, 5.6 Hz, 1H), 3.25-3.18 (m, 2H), 2.84 (br t, J = 6.1 Hz, 2H), 2.80 (br t, J = 6.1 Hz, 2H), 2.00-1.88 (m, 4H). LC/MS (m/z) = 499.2 (M + H)$^+$. Human αVβ6 IC$_{50}$ (nM) = 5.9. | Example 3 |

| Example No. | Structure & Name | Analytical Data | Method |
| --- | --- | --- | --- |
| 117 | 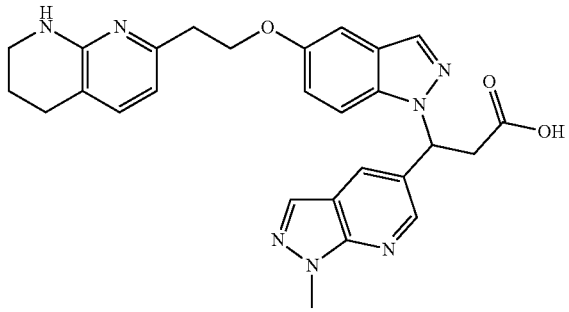 [SMILES: Cn1ncc2cc(C(CC(=O)O)n3ncc4cc(OCCc5ccc6c(n5)NCCC6)ccc43)cnc21]<br>3-(1-Methyl-1H-pyrazolo[3,4-b]pyridin5-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 8.61 (d, J = 1.9 Hz, 1H), 8.23 (d, J = 2.2 Hz, 1H), 8.04 (s, 1H), 8.00 (s, 1H), 7.64-7.58 (m, 2H), 7.19 (d, J = 2.2 Hz, 1H), 7.05 (dd, J = 9.1, 2.2 Hz, 1H), 6.76 (d, J = 7.4 Hz, 1H), 6.41 (dd, J = 9.2, 5.6 Hz, 1H), 4.38-4.28 (m, 2H), 4.08 (s, 3H), 3.80 (dd, J = 16.8, 9.4 Hz, 1H), 3.52-3.48 (m, 2H), 3.44-3.38 (m, 1H), 3.21-3.16(m, 2H), 2.81 (br t, J = 6.1 Hz, 2H), 1.97-1.91 (m, 2H). LC/MS (m/z) = 498.2 (M + H)+. Human αVβ6 IC$_{50}$ (nM) = 19; Human αVβ1 IC$_{50}$ (nM) = 63; Human αVβ3 IC$_{50}$ (nM) = 1.6; Human αVβ5 IC$_{50}$ (nM) = 0.46; and Human αVβ8 IC$_{50}$ (nM) = 2,200. | Example 3 |
| 118 | 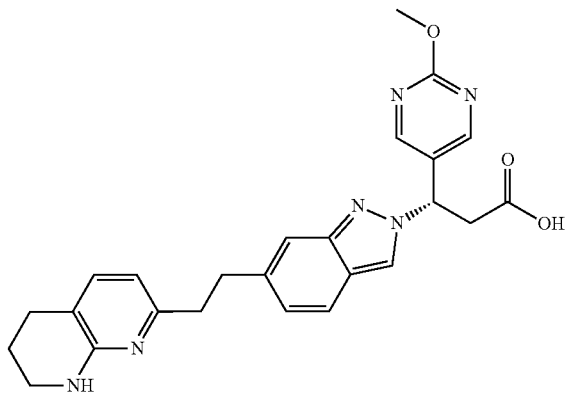 [SMILES: COc1ncc([C@H](CC(=O)O)n2cc3ccc(CCc4ccc5c(n4)NCCC5)cc3n2)cn1]<br>(S)-3-(2-Methoxypyrimidin-5-yl)-3-(6-(2-(5,6,7,8-tetrahydro-1,8-naphthyridin-2-yl)ethyl)-2H-indazol-2-yl)propanoic acid | $^1$H NMR (500 MHz, DMSO-$d_6$) δ 8.74 (s, 2H), 8.50 (s, 1H), 7.95 (s, 1H), 7.61 (d, J = 8.6 Hz, 1H), 7.40 (s, 1H), 7.37 (d, J = 7.3 Hz, 1H), 6.95 (d, J = 8.6 Hz, 1H), 6.50 (d, J = 7.3 Hz, 1H), 6.18 (dd, J = 9.2, 5.7 Hz, 1H), 3.88 (s, 3H), 3.64 (dd, J = 16.9, 9.4 Hz, 1H), 3.40-3.31 (m, 1H), 3.02-2.95 (m, 2H), 2.92 (d, J = 7.8 Hz, 2H), 2.67 (t, J = 6.2 Hz, 2H), 1.83-1.73 (m, 2H).<br>LC/MS (m/z) = 459.0 (M + H)$^+$. Human αVβ6 IC$_{50}$ (nM) = 12; Human αVβ1 IC$_{50}$ (nM) = 4,300; Human αVβ3 IC$_{50}$ (nM) = 2.0; Human αVβ5 IC$_{50}$ (nM) = 1.1; and Human αVβ8 IC$_{50}$ (nM) = 3,100. | Example 7 |
| 119 | 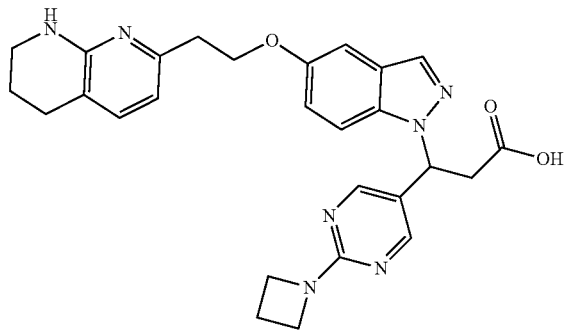 [SMILES: O=C(O)CC(c1cnc(N2CCC2)nc1)n1ncc2cc(OCCc3ccc4c(n3)NCCC4)ccc21]<br>3-(2-(Azetidin-1-yl)pyrimidin-5-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, chloroform-d) δ 10.05 (br s, 1H), 8.60 (s, 2H), 7.94 (s, 1H), 7.38-7.29 (m, 2H), 7.07 (d, J = 2.2 Hz, 1H), 6.85 (d, J = 8.6 Hz, 1H), 6.48 (d, J = 7.2 Hz, 1H), 6.11 (br t, J = 7.2 Hz, 1H), 4.32-4.19 (m, 6H), 3.81-3.59 (m, 1H), 3.47 (br t, J = 5.2 Hz, 2H), 3.26 (br dd, J = 16.5, 6.3 Hz, 1H), 3.16 (br t, J = 5.9 Hz, 2H), 2.74 (br t, J = 6.1 Hz, 2H), 2.42 (br t, J = 7.7 Hz, 2H), 1.98-1.88 (m, 2H). LC/MS (m/z) = 500.2 (M + H)$^+$. Human αVβ6 IC$_{50}$ (nM) = 10.55; Human αVβ1 IC$_{50}$ (nM) = 98; Human αVβ IC$_{50}$ (nM) = 1.4; Human αVβ5 IC$_{50}$ (nM) = 0.60; and Human αVβ8 IC$_{50}$ (nM) = 4,400. | Example 3 |

| Example No. | Structure & Name | Analytical Data | Method |
|---|---|---|---|
| 120 | 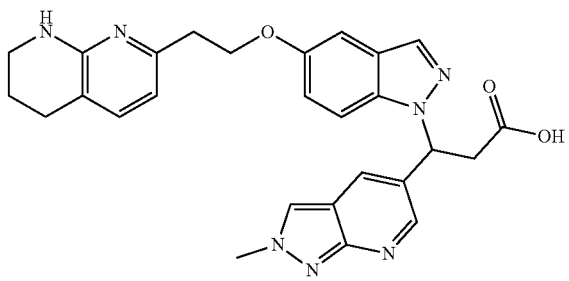 [SMILES: Cn1cc2cc(C(CC(=O)O)n3ncc4cc(OCCc5ccc6c(n5)NCCC6)ccc43)cnc2n1]<br>3-(2-Methyl-2H-pyrazolo[3,4-b]pyridin-5-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 8.63 (br s, 1H), 8.33-8.25 (m, 2H), 8.00 (s, 1H), 7.66-7.58 (m, 2H), 7.19 (d, J = 2.2 Hz, 1H), 7.06 (dd, J = 9.2, 2.3 Hz, 1H), 6.76 (d, J = 7.2 Hz, 1H), 6.38 (dd, J = 9.4, 5.5 Hz, 1H), 4.33 (br t, J = 5.8 Hz, 2H), 4.24 (s, 3H), 3.77 (dd, J = 16.6, 9.2 Hz, 1H), 3.52-3.46 (m, 2H), 3.41 (br dd, J = 16.6, 5.6 Hz, 1H), 3.18 (t, J = 5.9 Hz, 2H), 2.81 (br t, J = 6.1 Hz, 2H), 1.99-1.90 (m, 2H). LC/MS (m/z) = 498.2 (M + H)$^+$. Human αVβ6 IC$_{50}$ (nM) = 16; Human αVβ1 IC$_{50}$ (nM) = 200; Human αVβ3 IC$_{50}$ (nM) = 1.5; Human αVβ5 IC$_{50}$ (nM) = 0.20; and Human αVβ8 IC$_{50}$ (nM) = 7,500. | Example 3 |
| 121 | 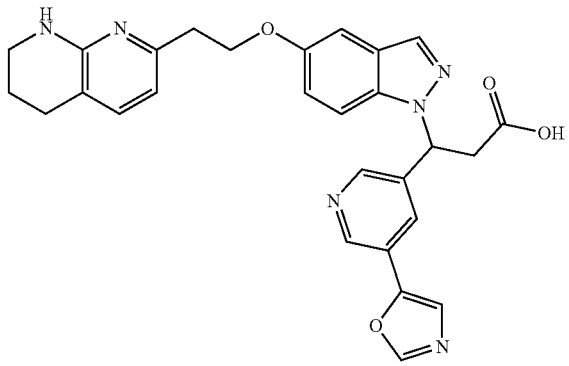 [SMILES: O=C(O)CC(c1cncc(-c2cnco2)c1)n1ncc2cc(OCCc3ccc4c(n3)NCCC4)ccc21]<br>3-(5-(Oxazol-5-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.86 (d, J = 2.1 Hz, 1H), 8.58 (d, J = 2.1 Hz, 1H), 8.51 (s, 1H), 8.08 (t, J = 2.2 Hz, 1H), 8.04 (s, 1H), 7.82 (s, 1H), 7.75 (d, J = 9.2 Hz, 1H), 7.19 (d, J = 2.3 Hz, 1H), 7.12 (d, J = 7.2 Hz, 1H), 7.00 (dd, J = 9.1, 2.4 Hz, 1H), 6.41 (d, J = 7.3 Hz, 1H), 6.33 (dd, J = 10.0, 5.1 Hz, 1H), 4.29-4.16 (m, 2H), 3.66 (dd, J = 16.6, 9.9 Hz, 1H), 3.33 (dd, J = 16.7, 5.1 Hz, 1H), 3.25 (s, 2H), 2.92 (t, J = 6.7 Hz, 2H), 2.62 (t, J = 6.2 Hz, 2H), 1.81-1.68 (m, 2H). LC/MS (m/z) = 511.1 (M + H)$^+$. Human αVβ6 IC$_{50}$ (nM) = 8.8; Human αVβ1 IC$_{50}$ (nM) = 71; Human αVβ3 IC$_{50}$ (nM) = 3.1; Human αVβ5 IC$_{50}$ (nM) = 0.46; and Human αVβ8 IC$_{50}$ (nM) = 2,600. | Example 3 |
| 122 | 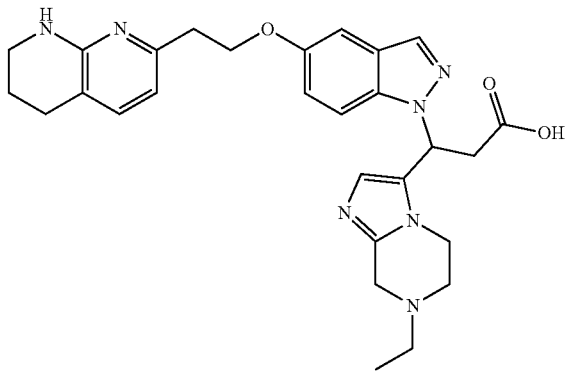 [SMILES: CCN1CCn2c(C(CC(=O)O)n3ncc4cc(OCCc5ccc6c(n5)NCCC6)ccc43)cnc2C1]<br>3-(7-Ethyl-5,6,7,8-tetrahydroimidazo[1,2-a]pyrazin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 7.96 (s, 1H), 7.68 (d, J = 9.3 Hz, 1H), 7.34 (d, J = 7.3 Hz, 1H), 7.23-7.13 (m, 2H), 7.02 (dd, J = 9.2, 2.4 Hz, 1H), 6.56 (d, J = 7.4 Hz, 1H), 6.29 (t, J = 7.3 Hz, 1H), 4.26 (t, J = 6.5 Hz, 2H), 4.02 (s, 1H), 3.33 (d, J = 7.0 Hz, 2H), 3.02 (t, J = 6.5 Hz, 2H), 2.96-2.61 (m, 4H), 1.94 (d, J = 23.9 Hz, 2H), 1.84-1.71 (m, 2H), 1.24 (s, 2H), 1.02 (t, J = 7.1 Hz, 4H). LC/MS (m/z) = 516.5 (M + H)$^+$. Human αVβ6 IC$_{50}$ (nM) = 14. | Example 3 |

| Example No. | Structure & Name | Analytical Data | Method |
|---|---|---|---|
| 123 | 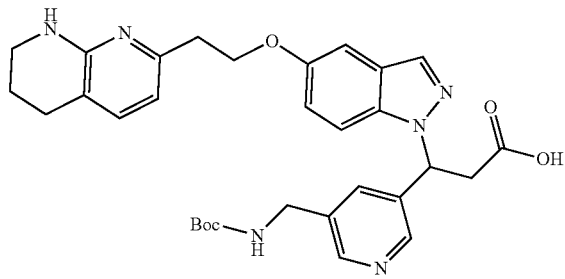 [SMILES: CC(C)(C)OC(=O)NCc1cncc(C(CC(=O)O)n2ncc3cc(OCCc4ccc5c(n4)NCCC5)ccc32)c1]<br>3-(5-(((tert-Butoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, MeOH-$d_4$) δ 8.83-8.65 (m, 1H), 8.65-8.52 (m, 1H), 8.42-8.16 (m, 1H), 8.03 (s, 1H), 7.62 (br d, J = 8.5 Hz, 2H), 7.21 (d, J = 1.9 Hz, 1H), 7.08 (br d, J = 9.1 Hz, 1H), 6.76 (br dd, J = 6.9, 2.8 Hz, 1H), 6.43 (br s, 1H), 4.33 (br d, J = 3.6 Hz, 4H), 3.72 (br dd, J = 16.9, 9.2 Hz, 1H), 3.55-3.48 (m, 2H), 3.48-3.37 (m, 1H), 3.24-3.16 (m, 2H), 2.83 (br t, J = 5.9 Hz, 2H), 1.96 (quin, J = 5.7 Hz, 2H), 1.43 (br s, 9H). LC/MS (m/z) = 573.3 (M + H)$^+$. Human αVβ6 IC$_{50}$ (nM) = 5.5. | Example 3 |
| 124 | 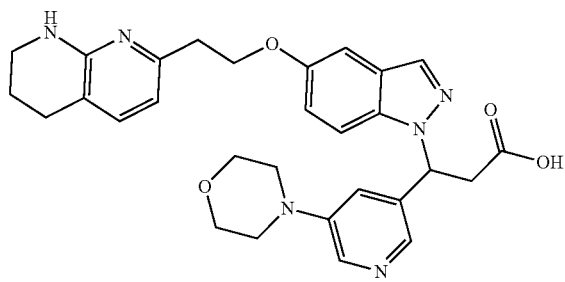 [SMILES: O=C(O)CC(c1cncc(N2CCOCC2)c1)n1ncc2cc(OCCc3ccc4c(n3)NCCC4)ccc21]<br>3-(5-Morpholinopyridin-3-yl)-3-(5-(2-(5,6,7,8-tetrahydro-1,8-naphthyridin-2-yl)ethoxy)-1H-indazol-1-yl)propanoic acid, 3 TFA | $^1$H NMR (500 MHz, MeOH-$d_4$) δ 8.27 (br s, 1H), 8.13 (s, 1H), 8.11-8.02 (m, 2H), 7.68-7.56 (m, 2H), 7.22 (d, J = 1.9 Hz, 1H), 7.10 (dd, J = 9.1, 2.2 Hz, 1H), 6.76 (d, J = 7.1 Hz, 1H), 6.38 (br s, 1H), 4.38-4.28 (m, 2H), 3.85 (t, J = 5.0 Hz, 4H), 3.72 (br dd, J = 16.9, 9.2 Hz, 1H), 3.56-3.48 (m, 2H), 3.46-3.39 (m, 1H), 3.39-3.35 (m, 4H), 3.24-3.16 (m, 2H), 2.83 (br t, J = 6.1 Hz, 2H), 1.96 (quin, J = 5.8 Hz, 2H). LC/MS (m/z) = 529.2 (M + H)$^+$ Human αVβ6 IC$_{50}$ (nM) = 1.9. | Example 3 |
| 125 | 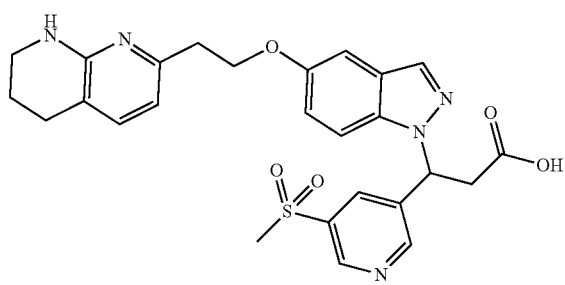 [SMILES: CS(=O)(=O)c1cncc(C(CC(=O)O)n2ncc3cc(OCCc4ccc5c(n4)NCCC5)ccc32)c1]<br>3-(5-(Methylsulfonyl)pyridin-3-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 9.00 (br d, J = 2.2 Hz, 1H), 8.92-8.82 (m, 1H), 8.34 (br s, 1H), 8.05-8.00 (m, 1H), 7.65-7.53 (m, 2H), 7.23-7.17 (m, 1H), 7.08 (br dd, J = 9.1, 2.2 Hz, 1H), 6.79-6.68 (m, 1H), 6.43 (br dd, J = 9.2, 5.6 Hz, 1H), 4.38-4.28 (m, 2H), 3.74 (br dd, 16.6, 9.2 Hz, 1H), 3.53-3.47 (m, 2H), 3.42 (br dd, J = 16.8, 5.5 Hz, 1H), 3.25-3.12 (m, 5H), 2.81 (br d, 5.8 Hz, 2H), 2.01-1.86 (m, 2H). LC/MS (m/z) = 522.2 (M + H)$^+$. Human αVβ6 IC$_{50}$ (nM) = 4.7. | Example 3 |
| 126 | 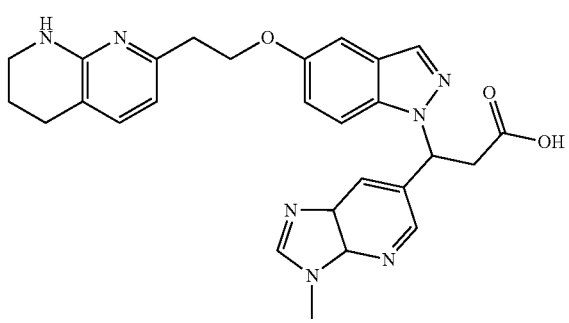 [SMILES: CN1C=NC2C=C(C(CC(=O)O)n3ncc4cc(OCCc5ccc6c(n5)NCCC6)ccc43)C=NC21]<br>3-(3-Methyl-3H-imidazo[4,5-b]pyridin-6-yl)-3-(5-(2-(5,6,7,8-tetrahydro-1,8-naphthyridin-2-yl)ethoxy)-1H-indazol-1-yl)propanoic acid, 2 TFA | $^1$H NMR (500 MHz, MeOH-$d_4$) δ 9.07-8.78 (m, 1H), 8.68 (br s, 1H), 8.20 (br s, 1H), 8.01 (s, 1H), 7.64-7.55 (m, 2H), 7.22-7.15 (m, 1H), 7.05 (br d, J = 9.1 Hz, 1H), 6.77-6.70 (m, 1H), 6.47 (br dd, J = 8.4, 5.4 Hz, 1H), 4.36-4.27 (m, 2H), 4.04-3.96 (m, 3H), 3.80 (dd, J = 16.6, 9.2 Hz, 1H), 3.49 (br t, J = 5.2 Hz, 2H), 3.43 (br dd, J = 16.5, 5.8 Hz, 1H), 3.18 (br t, J = 5.8 Hz, 2H), 2.80 (br s, 2H), 2.01-1.85 (m, 2H). LC/MS (m/z) = 498.2 (M + H)$^+$. Human αVβ6 IC$_{50}$ (nM) = 21. | Example 3 |

| Example No. | Structure & Name | Analytical Data | Method |
|---|---|---|---|
| 127 | 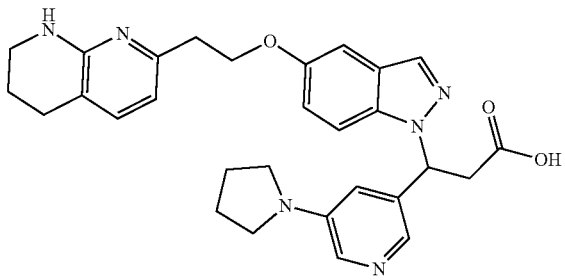<br>3-(5-(Pyrrolidin-1-yl)pyridin-3-yl)-3-(5-(2-(5,6,7,8-tetrahydro-1,8-naphthyridin-2-yl)ethoxy)-1H-indazol-1-yl)propanoic acid, 3 TFA | $^1$H NMR (500 MHz, MeOH-$d_4$) δ 8.05 (s, 1H), 7.94 (s, 1H), 7.89 (d, J = 2.2 Hz, 1H), 7.68-7.59 (m, 3H), 7.23 (d, J = 1.9 Hz, 1H), 7.10 (dd, J = 9.1, 2.2 Hz, 1H), 6.76 (d, J = 7.4 Hz, 1H), 6.38 (dd, J = 9.2, 5.6 Hz, 1H), 4.38-4.28 (m, 2H), 3.73 (dd, J = 16.9, 9.2 Hz, 1H), 3.56-3.48 (m, 2H), 3.46-3.39 (m, 1H), 3.39-3.35 (m, 4H), 3.24-3.16 (m, 2H), 2.84 (br t, J = 6.1 Hz, 2H), 2.10 (br t, J = 6.5 Hz, 4H), 1.96 (dt, J = 11.7, 6.0 Hz, 2H). LC/MS (m/z) = 513.2 (M + H)$^+$. Human αVβ6 IC$_{50}$ (nM) = 6.2. | Example 3 |
| 128 | 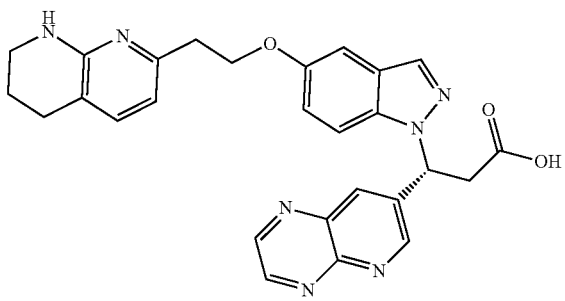 [SMILES: O=C(O)C[C@H](c1cnc2nccnc2c1)n1ncc2cc(OCCc3ccc4c(n3)NCCC4)ccc21]<br>(R)-3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid | $^1$H NMR (500 MHz, chloroform-d) δ 9.26 (br. s., 1H), 9.07 (d, J = 1.4 Hz, 1H), 8.98 (d, J = 1.7 Hz, 1H), 8.47 (d, J = 1.9 Hz, 1H), 8.04 (s, 1H), 7.42-7.31 (m, 2H), 7.09 (d, J = 1.9 Hz, 1H), 7.02 (dd, J = 9.1, 2.2 Hz, 1H), 6.51 (d, J = 7.2 Hz, 1H), 6.45-6.36 (m, 1H), 4.32-4.24 (m, 2H), 3.58-3.52 (m, 1H), 3.49 (t, J = 5.5 Hz, 2H), 3.16 (t, J = 5.8 Hz, 2H), 2.75 (t, J = 6.2 Hz, 2H), 1.97-1.87 (m, 2H). LC/MS (m/z) = 496.2 (M + H)$^+$. Human αVβ6 IC$_{50}$ (nM) = 25. | Example 16 and 17 |
| 129 | 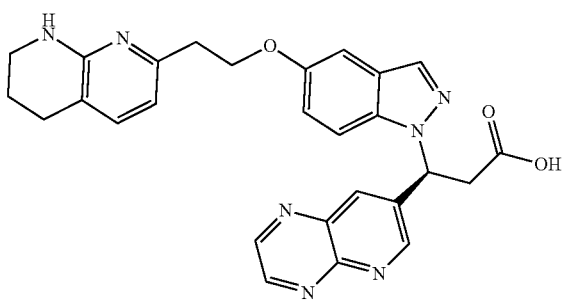 [SMILES: O=C(O)C[C@@H](c1cnc2nccnc2c1)n1ncc2cc(OCCc3ccc4c(n3)NCCC4)ccc21]<br>(S)-3-(Pyrido[2,3-b]pyrazin-7-yl)-3-(5-(2-(5,6,7,8-tetrahydro-1,8-naphthyridin-2-yl)ethoxy)-1H-indazol-1-yl)propanoic acid | $^1$H NMR (500 MHz, chloroform-d) δ 9.26 (br. s., 1H), 9.07 (d, J = 1.4 Hz, 1H), 8.98 (d, J = 1.7 Hz, 1H), 8.47 (d, J = 1.9 Hz, 1H), 8.04 (s, 1H), 7.42-7.31 (m, 2H), 7.09 (d, J = 1.9 Hz, 1H), 7.02 (dd, J = 9.1, 2.2 Hz, 1H), 6.51 (d, J = 7.2 Hz, 1H), 6.45-6.36 (m, 1H), 4.32-4.24 (m, 2H), 3.58-3.52 (m, 1H), 3.49 (t, J = 5.5 Hz, 2H), 3.16 (t, J = 5.8 Hz, 2H), 2.75 (t, J = 6.2 Hz, 2H), 1.97-1.87 (m, 2H). LC/MS (m/z) = 496.2 (M + H)$^+$. Human αVβ6 IC$_{50}$ (nM) = 480. | Example 16 and 17 |
| 130 | 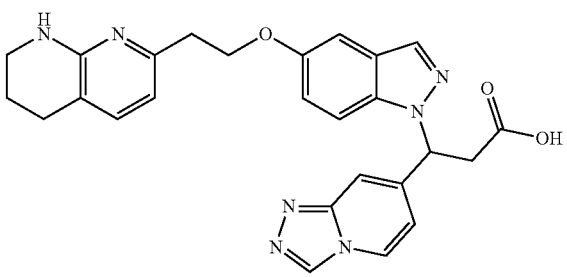 [SMILES: O=C(O)CC(c1ccn2cnnc2c1)n1ncc2cc(OCCc3ccc4c(n3)NCCC4)ccc21]<br>3-([1,2,4]Triazolo[4,3-a]pyridin-7-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 9.17 (s, 1H), 8.44 (d, J = 7.3 Hz, 1H), 8.05 (s, 1H), 7.73 (d, J = 9.1 Hz, 1H), 7.68 (s, 1H), 7.44 (d, J = 7.2 Hz, 1H), 7.22 (d, J = 2.4 Hz, 1H), 7.01 (dd, J = 9.1, 2.4 Hz, 1H), 6.87 (d, J = 7.4 Hz, 1H), 6.61 (d, J = 7.2 Hz, 1H), 6.28 (d, J = 8.1 Hz, 1H), 4.26 (q, J = 5.6 Hz, 2H), 3.63 (dd, J = 17.1, 9.8 Hz, 1H), 3.40-3.24 (m, 2H), 3.05 (t, J = 6.5 Hz, 2H), 2.93 (s, 2H), 2.68 (t, J = 6.2 Hz, 2H), 1.78 (d, J = 6.4 Hz, 3H), 1.17(1, J = 7.3 Hz, 2H). LC/MS (m/z) = 484.1 (M + H)$^+$. Human αVβ6 IC$_{50}$ (nM) = 57. | Example 3 |

| Example No. | Structure & Name | Analytical Data | Method |
|---|---|---|---|
| 131 | 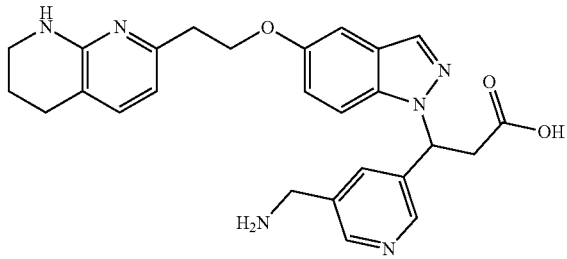 [SMILES: NCc1cncc(C(CC(=O)O)n2ncc3cc(OCCc4ccc5c(n4)NCCC5)ccc32)c1]<br>3-(5-(Aminomethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.63 (s, 1H), 8.54 (s, 1H), 8.02-7.95 (m, 2H), 7.63-7.55 (m, 2H), 7.18 (d, J = 2.3 Hz, 1H), 7.06 (dd, J = 9.1,2.3 Hz, 1H), 6.73 (d, J = 7.4 Hz, 1H), 6.32 (dd, J = 9.3, 5.6 Hz, 1H), 4.30 (tt, J = 6.2, 3.1 Hz, 2H), 4.14 (s, 2H), 3.70 (dd, J = 16.7, 9.3 Hz, 1H), 3.49 (t, J = 5.7 Hz, 2H), 3.38-3.32 (m, 1H), 3.17 (t, J = 5.9 Hz, 2H), 2.81 (t, J = 6.3 Hz, 2H), 1.97-1.89 (m, 2H). LC/MS(m/z) = 473.1 (M + H)$^+$. Human αVβ6 IC$_{50}$ (nM) = 30. | Deprotection of Boc-in Example 126 with TFA |
| 132 | 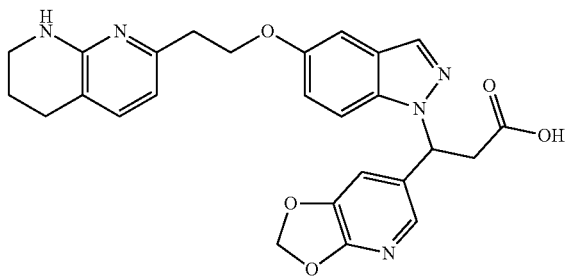 [SMILES: O=C(O)CC(c1cnc2c(c1)OCO2)n1ncc2cc(OCCc3ccc4c(n3)NCCC4)ccc21]<br>3-([1,3]Dioxolo[4,5-b]pyridin-6-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.01 (d, J = 14.3 Hz, 1H), 1.72 (d, J = 9.1 Hz, 1H), 7.68 (d, J = 1.9 Hz, 1H), 7.61 (d, J = 7.3 Hz, 1H), 7.30-7.13 (m, 3H), 7.09-6.96 (m, 2H), 6.73 (dd, J = 7.2, 3.3 Hz, 1H), 6.23-6.11 (m, 1H), 6.09 (s, 1H), 6.05 (s, 1H), 4.28 (d, J = 8.6 Hz, 3H), 3.61 (dd, J = 16.7, 10.0 Hz, 1H), 3.22-3.09 (m, 3H), 2.73 (s, 2H), 1.82 (s, 3H). LC/MS (m/z) = 487.9 (M + H)$^+$. Human αVβ6 IC$_{50}$ (nM) = 22. | Example 3 |
| 133 | 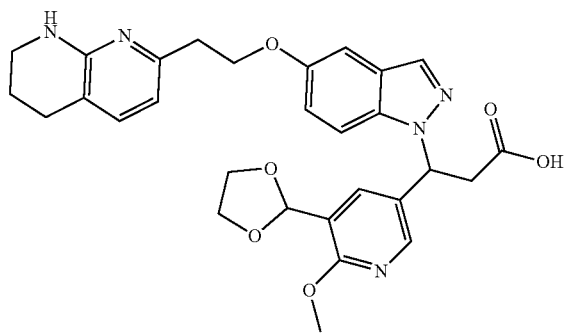 [SMILES: COc1ncc(C(CC(=O)O)n2ncc3cc(OCCc4ccc5c(n4)NCCC5)ccc32)cc1C1OCCO1]<br>3-(5-(1,3-Dioxolan-2-yl)-6-methoxypyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 7.99 (s, 1H), 7.88 (s, 1H), 7.61 (d, J = 7.4 Hz, 1H), 7.49 (d, J = 9.1 Hz, 1H), 7.19 (d, J = 2.4 Hz, 1H), 7.00 (dd, J = 9.1, 2.4 Hz, 1H), 6.93 (s, 1H), 6.76 (d, J = 7.3 Hz, 1H), 6.63 (dd, J = 10.9, 3.6 Hz, 1H), 5.93 (s, 1H), 4.33 (q, J = 5.0, 4.0 Hz, 3H), 4.27-4.20 (m, 1H), 4.20-4.09 (m, 2H), 3.85 (s, 3H), 3.72 (dd, J = 16.8, 10.8 Hz, 1H), 3.50 (t, J = 5.7 Hz, 2H), 3.27-3.14 (m, 3H), 2.81 (t, J = 6.3 Hz, 2H), 1.94 (p, J = 5.8 Hz, 2H). LC/MS (m/z) = 546.1 (M + H)$^+$. Human αVβ6 IC$_{50}$ (nM) = 400. | Example 3 |
| 134 | 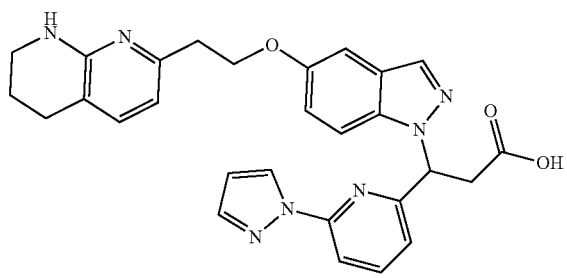 [SMILES: O=C(O)CC(c1cccc(-n2cccn2)n1)n1ncc2cc(OCCc3ccc4c(n3)NCCC4)ccc21]<br>3-(6-(1H-Pyrazol-1-yl)pyridin-2-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.59 (d, J = 2.4 Hz, 1H), 8.03 (s, 1H), 7.88-7.75 (m, 3H), 7.66 (d, J = 9.1 Hz, 1H), 7.51 (d, J = 7.4 Hz, 1H), 7.23 (d, J = 2.3 Hz, 1H), 7.03 (dd, J = 9.0, 2.3 Hz, 1H), 6.77 (d, J = 7.6 Hz, 1H), 6.66 (d, J = 7.4 Hz, 1H), 6.59 (t, J = 2.1 Hz, 1H), 6.33-6.24 (m, 1H), 4.27 (t, J = 6.1 Hz, 2H), 3.47 (dd, J = 17.3, 8.8 Hz, 1H), 3.37 (t, J = 5.6 Hz, 2H), 3.09 (t, J = 6.2 Hz, 2H), 2.70 (t, J = 6.2 Hz, 2H), 1.79 (s, 2H), 1.22 (s, 2H). LC/MS (m/z) = 510.3 (M + H)$^+$. Human αVβ6 IC$_{50}$ (nM) = 17. | Example 3 |

-continued

| Example No. | Structure & Name | Analytical Data | Method |
|---|---|---|---|
| 135 | 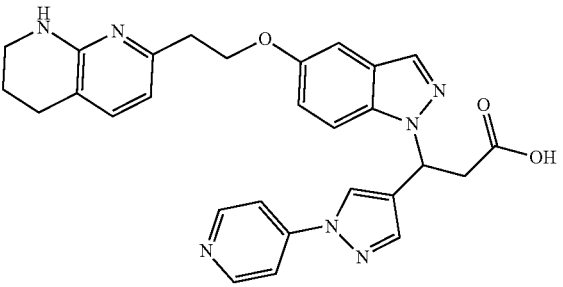 [SMILES: O=C(O)CC(c1cnn(-c2ccncc2)c1)n1ncc2cc(OCCc3ccc4c(n3)NCCC4)ccc21]<br>3-(1-(Pyridin-4-yl)-1H-pyrazol-4-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.76 (s, 1H), 8.68 (d, J = 5.6 Hz, 2H), 7.99 (s, 1H), 7.91 (d, J = 5.6 Hz, 2H), 7.74 (d, J = 9.1 Hz, 1H), 7.61 (d, J = 7.4 Hz, 1H), 7.29 (s, 1H), 7.23-7.13 (m, 2H), 7.12-7.00 (m, 2H), 6.72 (d, J = 7.3 Hz, 1H), 6.28-6.16 (m, 1H), 4.27 (s, 2H), 3.39 (t, J = 5.6 Hz, 2H), 3.28 (dd, J = 16.9, 5.0 Hz, 1H), 3.12 (t, J = 6.2 Hz, 2H), 2.72 (t, J = 5.9 Hz, 2H), 1.80 (s, 2H), 1.22 (s, 2H). LC/MS (m/z) = 510.4 (M + H)$^+$. Human αVβ6 IC$_{50}$ (nM) = 3.8. | Example 3 |
| 136 | 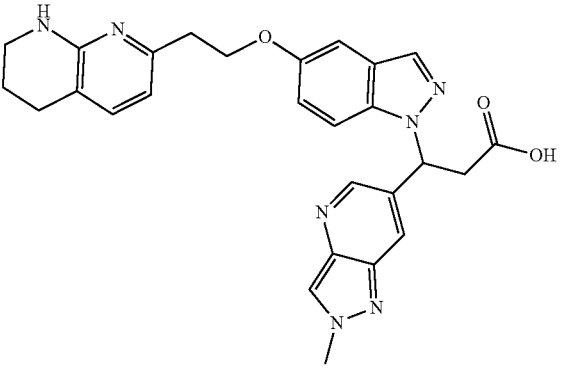 [SMILES: Cn1cc2ncc(C(CC(=O)O)n3ncc4cc(OCCc5ccc6c(n5)NCCC6)ccc43)cc2n1]<br>3-(2-Methyl-2H-pyrazolo[4,3-b]pyridin-6-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.60-8.48 (m, 2H), 8.00 (br d, J = 17.9 Hz, 2H), 7.75-7.66 (m, 1H), 7.23-7.15 (m, 1H), 7.14-7.06 (m, 1H), 7.03-6.96 (m, 1H), 6.45-6.38 (m, 1H), 6.38-6.31 (m, 1H), 4.31-4.23 (m, 2H), 4.22-4.13 (m, 3H), 3.74-3.58 (m, 2H), 2.97-2.86 (m, 2H), 2.66-2.60 (m, 2H), 2.29 (br t, J = 7.4 Hz, 1H), 1.83-1.72 (m, 2H), 1.60-1.48 (m, 1H), 0.87 (s, 1H) LC/MS (m/z) = 497.9 (M + H)$^+$. Human αVβ6 IC$_{50}$ (nM) = 41. | Example 3 |
| 137 | 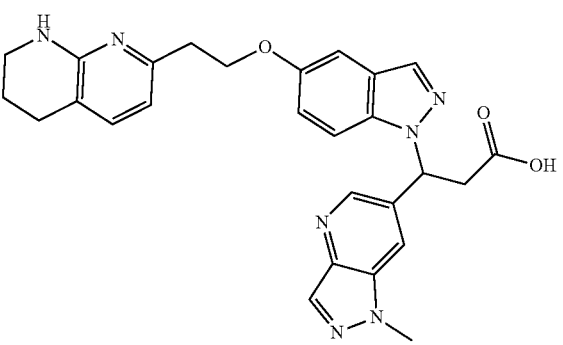 [SMILES: Cn1ncc2ncc(C(CC(=O)O)n3ncc4cc(OCCc5ccc6c(n5)NCCC6)ccc43)cc21]<br>3-(1-Methyl-1H-pyrazolo[4,3-b]pyridin-6-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.60-8.48 (m, 1H), 8.21-8.15 (m, 2H), 8.03 (s, 1H), 7.74 (d, J = 9.1 Hz, 1H), 7.62-7.53 (m, 1H), 7.26-7.18 (m, 1H), 7.07-6.98 (m, 1H), 6.73-6.66 (m, 1H), 6.44-6.35 (m, 1H), 4.35-4.21 (m, 2H), 4.08-3.97 (m, 3H), 3.79-3.68 (m, 1H), 3.44-3.37 (m, 1H), 3.17-3.07 (m, 1H), 2.77-2.68 (m, 2H), 1.87-1.76 (m, 2H). LC/MS (m/z) = 497.9 (M + H)$^+$. Human αVβ6 IC$_{50}$ (nM) = 7.0. | Example 3 |
| 138 | 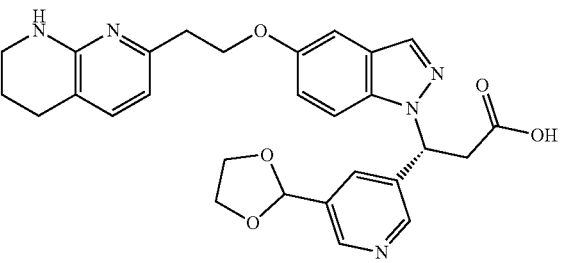 [SMILES: O=C(O)C[C@H](c1cncc(C2OCCO2)c1)n1ncc2cc(OCCc3ccc4c(n3)NCCC4)ccc21]<br>(R)-3-(5-(1,3-dioxolan-2-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (400 MHz, methanol-$d_4$) δ 8.54 (d, J = 8.6 Hz, 2H), 7.98 (s, 1H), 7.95 (s, 1H), 7.64-7.51 (m, 2H), 7.18 (d, J = 2.3 Hz, 1H), 7.05 (dd, J = 9.1, 2.4 Hz, 1H), 6.74 (d, J = 7.4 Hz, 1H), 6.31 (dd, J = 9.4, 5.3 Hz, 1H), 5.79 (s, 1H), 4.31 (t, J = 5.9 Hz, 2H), 4.10-3.95 (m, 4H), 3.77-3.62 (m, 1H), 3.48 (dd, J = 6.5, 4.8 Hz, 2H), 3.17 (t, J = 5.9 Hz, 2H), 2.79 (t, J = 6.2 Hz, 2H), 1.97-1.87 (m, 3H). LC/MS (m/z) = 516.2 (M + H)$^+$. Human αVβ6 IC$_{50}$ (nM) = 43. | Examples 104, 16, and 17. |

| Example No. | Structure & Name | Analytical Data | Method |
|---|---|---|---|
| 139 | 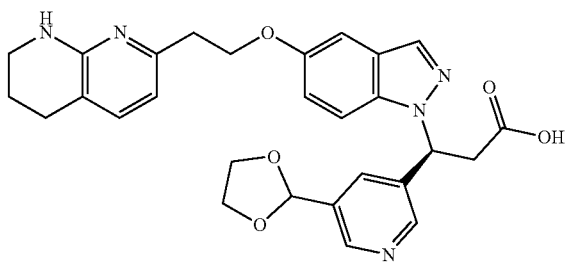 [SMILES: O=C(O)C[C@@H](c1cncc(C2OCCO2)c1)n1ncc2cc(OCCc3ccc4c(n3)NCCC4)ccc21]<br>(S)-3-(5-(1,3-dioxolan-2-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (400 MHz, methanol-d$_4$) δ 8.55 (s, 3H), 7.99 (s, 1H), 7.63-7.53 (m, 2H), 7.18 (s, 1H), 7.05 (d, J = 8.4 Hz, 1H), 6.75 (d, J = 7.5 Hz, 1H), 6.32 (s, 1H), 5.80 (s, 1H), 4.31 (t, J = 5.9 Hz, 2H), 4.12-3.94 (m, 4H), 3.71 (dd, J = 16.8,9.4 Hz, 1H), 3.48 (td, J = 4.9, 3.2 Hz, 3H), 3.17 (t, J = 5.9 Hz, 2H), 3.13 (p, J = 1.7 Hz, 1H), 2.80 (t, J = 6.2 Hz, 3H), 1.97-1.88 (m, 2H). LC/MS (m/z) = 516.1 (M + H)$^+$. Human αVβ6 IC$_{50}$ (nM) = 4.7. | Example 104, 16, and 17. |
| 140 | 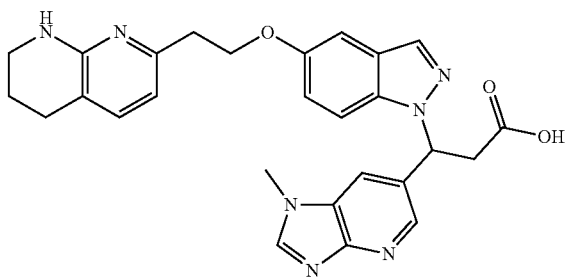 [SMILES: Cn1cnc2ncc(C(CC(=O)O)n3ncc4cc(OCCc5ccc6c(n5)NCCC6)ccc43)cc21]<br>3-(1-methyl-1H-imidazo[4,5-b]pyridin-6-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.58-8.48 (m, 2H), 8.21 (s, 1H), 8.01 (s, 1H), 7.68-7.59 (m, 2H), 7.20 (d, J = 2.2 Hz, 1H), 7.06 (dd, J = 9.1, 2.2 Hz, 1H), 6.76 (d, J = 7.4 Hz, 1H), 6.46 (dd, J = 9.4, 5.5 Hz, 1H), 4.38-4.29 (m, 2H), 3.95 (s, 3H), 3.83 (dd, J = 16.5, 9.4 Hz, 1H), 3.52-3.47 (m, 2H), 3.43 (br dd, J = 16.9, 5.6 Hz, 1H), 3.21-3.15 (m, 2H), 2.81 (br t, J = 6.1 Hz, 2H), 1.99-1.90 (m, 2H). LC/MS (m/z) = 498.3 (M + H)$^+$. Human αVβ6 IC$_{50}$ (nM) = 5.7. | Example 3 |
| 141 | 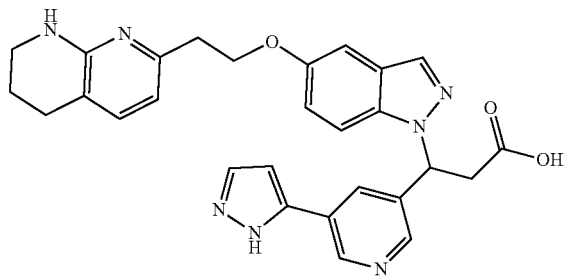 [SMILES: O=C(O)CC(c1cncc(-c2ccn[nH]2)c1)n1ncc2cc(OCCc3ccc4c(n3)NCCC4)ccc21]<br>3-(5-(1H-pyrazol-5-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-d$_6$) δ 8.91-8.82 (m, 1H), 8.56-8.49 (m, 1H), 8.17-8.09 (m, 1H), 8.07-8.00 (m, 1H), 7.84-7.70 (m, 2H), 7.51-7.42 (m, 1H), 7.24-7.18 (m, 1H), 7.04-6.97 (m, 1H), 6.82-6.75 (m, 1H), 6.68-6.59 (m, 1H), 6.35-6.26 (m, 1H), 4.35-4.18 (m, 2H), 3.76-3.51 (m, 2H), 3.40-3.29 (m, 2H), 3.06 (br t, J = 5.8 Hz, 2H), 2.73-2.64 (m, 2H), 1.84-1.73 (m, 2H). LC/MS (m/z) = 510.3 (M + H)$^+$. Human αVβ6 IC$_{50}$ (nM) = 8.2. | Example 3 |
| 142 | 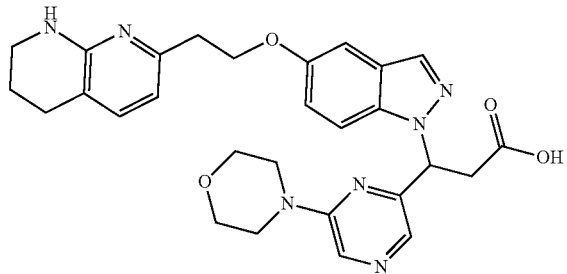 [SMILES: O=C(O)CC(c1cncc(N2CCOCC2)n1)n1ncc2cc(OCCc3ccc4c(n3)NCCC4)ccc21]<br>3-(6-morpholinopyrazin-2-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-d$_6$) δ 8.19-8.11 (m, 1H), 8.02-7.94 (m, 1H), 7.67-7.60 (m, 1H), 7.43-7.33 (m, 1H), 7.23-7.18 (m, 1H), 7.18-7.10 (m, 1H), 7.04-6.96 (m, 1H), 6.48-6.40 (m, 1H), 6.17-6.10 (m, 1H), 4.30-4.20 (m, 2H), 3.73-3.62 (m, 3H), 3.52-3.46 (m, 1H), 3.31-3.22 (m, 1H), 2.97-2.88 (m, 2H), 2.67-2.58 (m, 2H), 2.56-2.52 (m, 2H), 2.50 (br s, 5H), 1.82-1.70 (m, 2H). LC/MS (m/z) = 530.3 (M + H)$^+$. Human αVβ6 IC$_{50}$ (nM) = 36. | Example 3 |

-continued

| Example No. | Structure & Name | Analytical Data | Method |
|---|---|---|---|
| 143 | 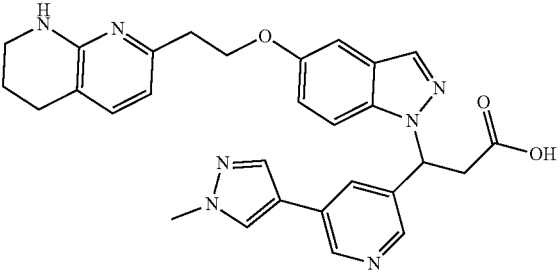 [SMILES: Cn1cc(-c2cncc(C(CC(=O)O)n3ncc4cc(OCCc5ccc6c(n5)NCCC6)ccc43)c2)cn1]<br>3-(5-(1-methyl-1H-pyrazol-4-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.76-8.62 (m, 1H), 8.39-8.29 (m, 1H), 8.24-8.17 (m, 1H), 8.07-8.00 (m, 2H), 7.93-7.88 (m, 1H), 7.78-7.70 (m, 1H), 7.62-7.55 (m, 1H), 7.35-7.26 (m, 1H), 7.26-7.16 (m, 1H), 7.14-7.06 (m, 1H), 7.06-6.97 (m, 1H), 6.74-6.66 (m, 1H), 6.29-6.17 (m, 1H), 4.26 (br d, J = 3.7 Hz, 2H), 3.86 (s, 3H), 3.73-3.52 (m, 1H), 3.43-3.36 (m, 2H), 3.35-3.27 (m, 1H), 3.15-3.07 (m, 2H), 2.75-2.67 (m, 2H), 1.86-1.73 (m, 2H). LC/MS (m/z) = 524.3 (M + H)$^+$. Human αVβ6 IC$_{50}$ (nM) = 9.8. | Example 3 |
| 144 | 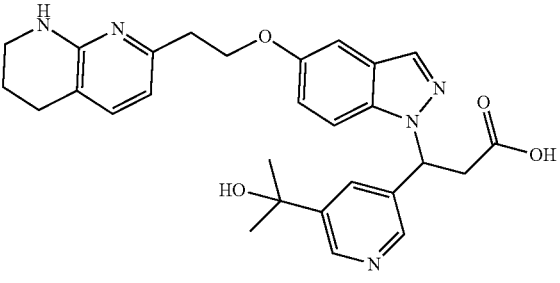 [SMILES: CC(C)(O)c1cncc(C(CC(=O)O)n2ncc3cc(OCCc4ccc5c(n4)NCCC5)ccc32)c1]<br>3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.61-8.49 (m, 1H), 8.48-8.37 (m, 1H), 8.09-7.99 (m, 1H), 7.99-7.90 (m, 1H), 7.75-7.66 (m, 1H), 7.64-7.56 (m, 1H), 7.36-7.28 (m, 1H), 7.25-7.17 (m, 2H), 7.15-7.07 (m, 1H), 7.06-6.97 (m, 1H), 6.75-6.65 (m, 1H), 6.31-6.19 (m, 1H), 4.25 (br d, J = 2.4 Hz, 2H), 3.68-3.55 (m, 1H), 3.43-3.33 (m, 2H), 3.31-3.21 (m, 1H), 3.15-3.06 (m, 2H), 2.75-2.66 (m, 2H), 1.84-1.74 (m, 2H), 1.43-1.31 (m,6H). LC/MS (m/z) = 502.1 (M + H)$^+$. Human αVβ6 IC$_{50}$ (nM) = 5.0. | Example 3 |
| 145 | 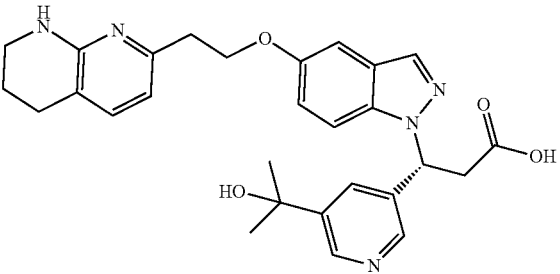 [SMILES: CC(C)(O)c1cncc([C@@H](CC(=O)O)n2ncc3cc(OCCc4ccc5c(n4)NCCC5)ccc32)c1]<br>(R)-3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.56 (d, J = 2.0 Hz, 1H), 8.40 (d, J = 2.0 Hz, 1H), 7.99 (s, 1H), 7.98 (s, 1H), 7.53 (d, J = 9.0 Hz, 1H), 7.32 (d, J = 7.3 Hz, 1H), 7.00 (s, 1H), 6.95 (d, J = 8.9 Hz, 1H), 6.52 (d, J = 7.3 Hz, 1H), 6.31 (dd, J = 9.5, 5.5 Hz, 1H), 4.13-3.99 (m, 2H), 3.63 (dd, J = 15.9, 9.5 Hz, 1H), 3.41-3.37 (m, 2H), 3.24-3.18 (m, 1H), 2.94 (t, J = 6.3 Hz, 2H), 2.70 (t, J = 6.2 Hz, 2H), 1.90-1.82 (m, 2H), 1.54-1.48 (m, 6H). LC/MS (m/z) = 502.3 (M + H)$^+$. Human αVβ6 IC$_{50}$ (nM) = 1,900. | Examples 144, 16, and 17 |
| 146 | 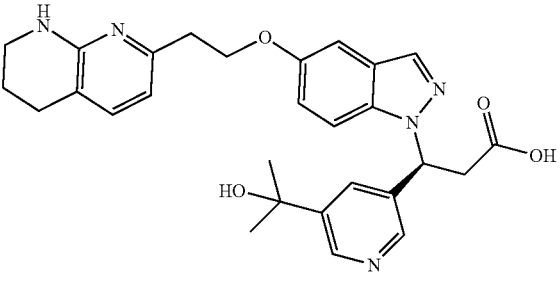 [SMILES: CC(C)(O)c1cncc([C@H](CC(=O)O)n2ncc3cc(OCCc4ccc5c(n4)NCCC5)ccc32)c1]<br>(S)-3-(5-(2-hydroxypropan-2-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.61-8.51 (m, 1H), 8.43-8.33 (m, 1H), 8.02-7.92 (m, 2H), 7.55-7.48 (m, 1H), 7.39-7.31 (m, 1H), 7.05-6.99 (m, 1H), 6.99-6.91 (m, 1H), 6.58-6.51 (m, 1H), 6.34-6.24 (m, 1H), 4.13-4.02 (m, 2H), 3.62 (dd, J = 15.9, 9.5 Hz, 1H), 3.40-3.36 (m, 2H), 3.25-3.18 (m, 1H), 2.96 (t, J = 6.1 Hz, 2H), 2.70 (t, J = 6.2 Hz, 2H), 1.50-1.47 (m, 6H). LC/MS (m/z) = 502.3 (M + H)$^+$. Human αVβ6 IC$_{50}$ (nM) = 5.2. | Examples 144, 16, and 17 |

| Example No. | Structure & Name | Analytical Data | Method |
|---|---|---|---|
| 147 | 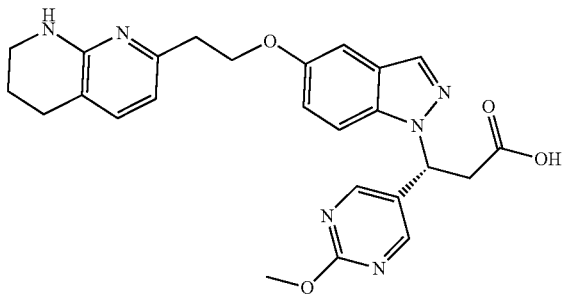 [SMILES: COc1ncc([C@@H](CC(=O)O)n2ncc3cc(OCCc4ccc5c(n4)NCCC5)ccc32)cn1]<br>(R)-3-(2-methoxypyrimidin-5-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.71-8.47 (m, 2H), 8.09-7.90 (m, 1H), 7.84-7.72 (m, 1H), 7.65-7.54 (m, 1H), 7.25-7.17 (m, 1H), 7.07-6.99 (m, 1H), 6.80-6.60 (m, 1H), 6.36-6.16 (m, 1H), 4.28 (br s, 2H), 3.85 (s, 3H), 3.68-3.55 (m, 1H), 3.30 (dd, J = 16.6, 5.0 Hz, 1H), 3.18-3.07 (m, 2H), 2.75-2.68 (m, 2H), 1.86-1.74 (m, 2H), 1.19 (s, 1H). LC/MS (m/z) = 475.2 (M + H)$^+$. Human αVβ6 IC$_{50}$ (nM) = 620. | Examples 92, 16, and 17 |
| 148 | 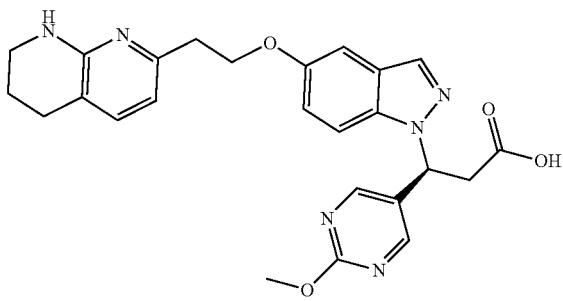 [SMILES: COc1ncc([C@H](CC(=O)O)n2ncc3cc(OCCc4ccc5c(n4)NCCC5)ccc32)cn1]<br>(S)-3-(2-methoxypyrimidin-5-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.70-8.54 (m, 2H), 8.08-7.92 (m, 1H), 7.85-7.71 (m, 1H), 7.69-7.53 (m, 1H), 7.25-7.15 (m, 1H), 7.12-6.93 (m, 1H), 6.79-6.62 (m, 1H), 6.30-6.17 (m, 1H), 4.34-4.18(m, 2H), 3.85 (s, 3H), 3.66-3.53 (m, 1H), 3.35-3.22 (m, 1H), 3.19-3.07 (m, 2H), 2.80-2.66 (m, 2H), 1.88-1.74 (m, 2H), 1.30-1.14 (m, 1H). LC/MS (m/z) = 475.2 (M + H)$^+$. Human αVβ6 IC$_{50}$ (nM) = 18. | Examples 92, 16, and 17 |
| 149 | 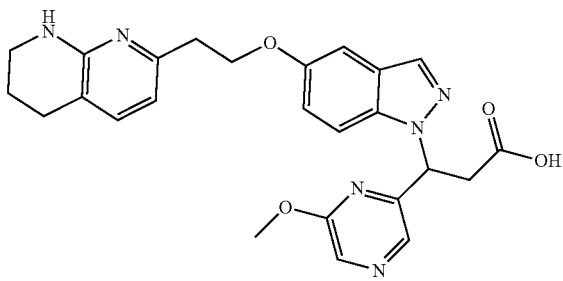 [SMILES: COc1cncc(C(CC(=O)O)n2ncc3cc(OCCc4ccc5c(n4)NCCC5)ccc32)n1]<br>3-(6-methoxypyrazin-2-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.09 (s, 1H), 8.01 (s, 1H), 7.66-7.56 (m, 3H), 7.24 (s, 1H), 7.11 (dd, J = 9.1, 1.4 Hz, 1H), 6.77 (br s, 1H), 6.34 (t, J = 7.4 Hz, 1H), 4.36 (br t, J = 5.8 Hz, 2H), 4.02-3.95 (m, 3H), 3.63 (d, J = 6.1 Hz, 1H), 3.57 (br d, J = 8.5 Hz, 1H), 3.53-3.46 (m, 2H), 3.21 (br t, J = 5.8 Hz, 2H), 2.86-2.79 (m, 2H), 2.01-1.90 (m, 2H). LC/MS(m/z) = 475.1 (M + H)$^+$. Human αVβ6 IC$_{50}$ (nM) = 2,300. | Example 3 |
| 150 | 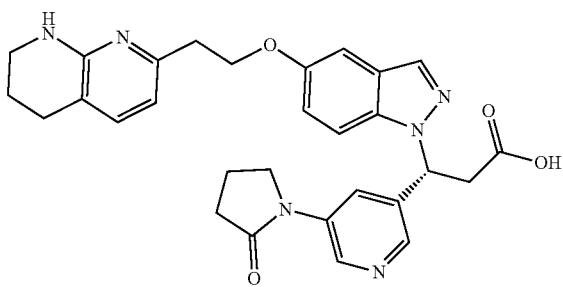 [SMILES: O=C(O)C[C@H](c1cncc(N2CCCC2=O)c1)n1ncc2cc(OCCc3ccc4c(n3)NCCC4)ccc21]<br>(R)-3-(5-(2-oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.94-8.83 (m, 1H), 8.39-8.33 (m, 1H), 8.33-8.23 (m, 1H), 8.04-7.96 (m, 1H), 7.55 (br s, 2H), 7.24-7.15 (m, 1H), 7.12-7.00 (m, 1H), 6.70 (br s, 1H), 6.36-6.26 (m, 1H), 4.38-4.22 (m, 2H), 3.99-3.82 (m, 2H), 3.78-3.66 (m, 1H), 3.54-3.46 (m, 2H), 3.38-3.33 (m, 1H), 3.21-3.12 (m, 2H), 2.86-2.77 (m, 2H), 2.66-2.50 (m, 2H), 2.26-2.13 (m, 2H), 1.93 (dt, J = 11.7, 6.0 Hz, 2H). LC/MS (m/z) = 527.2 (M + H)$^+$. Human αVβ6 IC$_{50}$ (nM) = 110. | Examples 102, 16, and 17 |

| Example No. | Structure & Name | Analytical Data | Method |
|---|---|---|---|
| 151 | 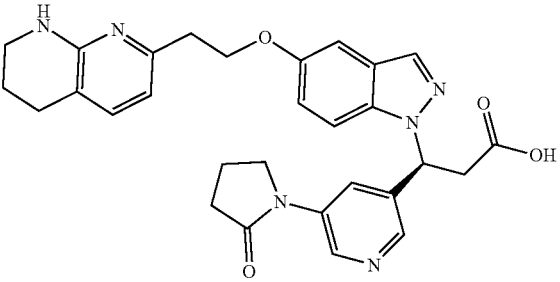 [SMILES: O=C(O)C[C@@H](c1cncc(N2CCCC2=O)c1)n1ncc2cc(OCCc3ccc4c(n3)NCCC4)ccc21]<br>(5)-3-(5-(2-oxopyrrolidin-1-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.94-8.83 (m, 1H), 8.39-8.33 (m, 1H), 8.33-8.23 (m, 1H), 8.04-7.96 (m, 1H), 7.55 (br s, 2H), 7.24-7.15 (m, 1H), 7.12-7.00 (m, 1H), 6.70 (br s, 1H), 6.36-6.26 (m, 1H), 4.38-4.22 (m, 2H), 3.99-3.82 (m, 2H), 3.78-3.66 (m, 1H), 3.54-3.46 (m, 2H), 3.38-3.33 (m, 1H), 3.21-3.12 (m, 2H), 2.86-2.77 (m, 2H), 2.66-2.50 (m, 2H), 2.26-2.13 (m, 2H), 1.93 (dt, J = 11.7, 6.0 Hz, 2H). LC/MS (m/z) = 527.2 (M + H)$^+$. Human αVβ6 IC$_{50}$ (nM) = 1. | Examples 102, 16, and 17 |
| 152 | 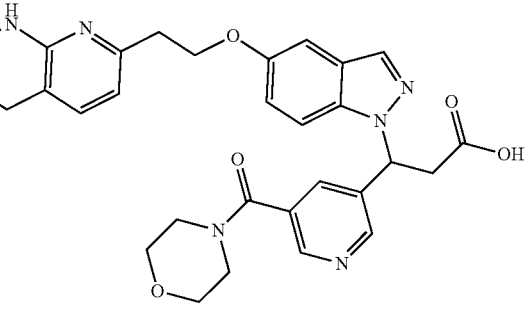<br>3-(5-(morpholine-4-carbonyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.76-8.64 (m, 1H), 8.54 (s, 1H), 8.02 (s, 1H), 7.82 (t, J = 1.8 Hz, 1H), 7.66-7.56 (m, 2H), 7.21 (d, J = 1.9 Hz, 1H), 7.07 (dd, J = 9.1, 2.2 Hz, 1H), 6.76 (d, J = 7.2 Hz, 1H), 6.35 (dd, J = 9.1, 5.8 Hz, 1H), 4.34 (td, J = 5.8, 2.1 Hz, 2H), 3.73 (br dd, J = 16.8, 9.1 Hz, 5H), 3.55 (br s, 2H), 3.53-3.47 (m, 2H), 3.46-3.36 (m, 1H), 3.20 (br t, J = 5.9 Hz, 2H), 2.83 (br t, J = 6.1 Hz, 2H), 1.95 (dt, J = 11.6, 6.1 Hz, 2H). LC/MS(m/z) = 557.1 (M + H)$^+$. Human αVβ6 IC$_{50}$ (nM) = 22. | Example 3 |
| 153 | 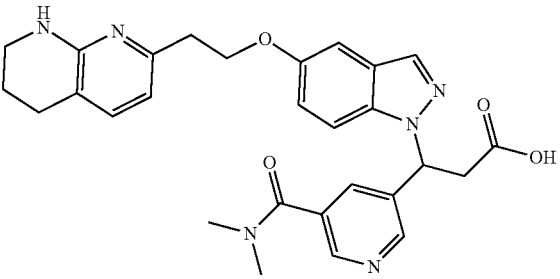 [SMILES: CN(C)C(=O)c1cncc(C(CC(=O)O)n2ncc3cc(OCCc4ccc5c(n4)NCCC5)ccc32)c1]<br>3-(5-(dimethylcarbamoyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.67 (s, 1H), 8.55 (s, 1H), 8.01 (s, 1H), 7.93 (s, 1H), 7.60 (d, J = 8.5 Hz, 2H), 7.20 (d, J = 2.2 Hz, 1H), 7.07 (dd, J = 9.1, 2.2 Hz, 1H), 6.75 (d, J = 7.4 Hz, 1H), 6.35 (dd, J = 9.1, 5.8 Hz, 1H), 4.33 (t, J = 5.8 Hz, 2H), 3.73 (dd, J = 16.6,9.2 Hz, 1H), 3.53-3.47 (m, 2H), 3.45-3.35 (m, 1H), 3.19 (t, J = 5.8 Hz, 2H), 3.10 (s, 3H), 2.93 (s, 3H), 2.81 (br t, J = 6.1 Hz, 2H), 1.99-1.90 (m, 2H). LC/MS (m/z) = 515.1 (M + H)$^+$. Human αVβ6 IC$_{50}$ (nM) = 17. | Example 3 |
| 154 | 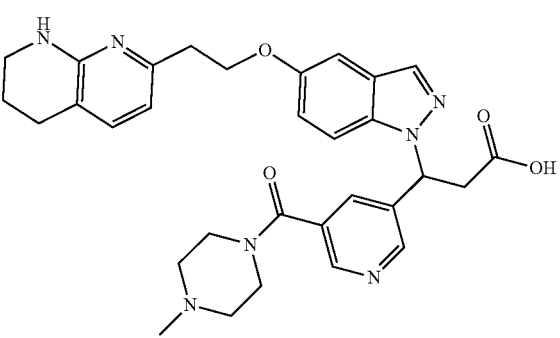 [SMILES: CN1CCN(C(=O)c2cncc(C(CC(=O)O)n3ncc4cc(OCCc5ccc6c(n5)NCCC6)ccc43)c2)CC1]<br>3-(5-(4-methylpiperazine-1-carbonyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.73 (s, 1H), 8.61 (s, 1H), 8.01 (s, 2H), 7.64-7.57 (m, 2H), 7.20 (d, J = 1.9 Hz, 1H), 7.08 (dd, J = 9.1, 2.2 Hz, 1H), 6.74 (d, J = 7.4 Hz, 1H), 6.36 (dd, J = 8.9, 5.9 Hz, 1H), 4.33 (br t, J = 5.5 Hz, 2H), 3.72 (br dd, J = 16.6, 9.2 Hz, 3H), 3.55-3.47 (m, 3H), 3.46-3.35 (m, 2H), 3.24-3.15 (m, 3H), 2.96 (s, 3H), 2.81 (t, J = 6.2 Hz, 2H), 2.01-1.88 (m, 2H). LC/MS (m/z) = 570.2 (M + H)$^+$. Human αVβ6 IC$_{50}$ (nM) = 29. | Example 3 |

-continued

| Example No. | Structure & Name | Analytical Data | Method |
|---|---|---|---|
| 155 | 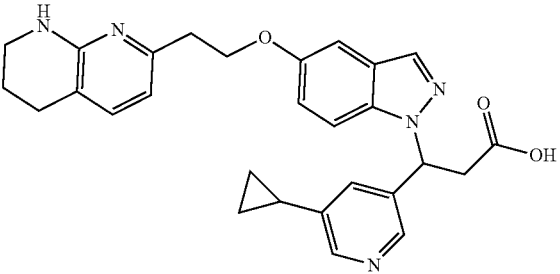 [SMILES: O=C(O)CC(c1cncc(C2CC2)c1)n1ncc2cc(OCCc3ccc4c(n3)NCCC4)ccc21]<br>3-(5-cyclopropylpyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.52 (br s, 1H), 8.44 (br s, 1H), 8.02 (br d, J = 9.6 Hz, 2H), 7.66-7.55 (m, 2H), 7.27-7.13 (m, 1H), 7.07 (dd, J = 9.1, 1.9 Hz, 1H), 6.72 (d, J = 7.4 Hz, 1H), 6.36 (br dd, J = 8.9, 5.6 Hz, 1H), 4.31 (br t, J = 5.6 Hz, 2H), 3.68 (br dd, J = 16.8, 9.1 Hz, 1H), 3.48 (br t, J = 5.5 Hz, 2H), 3.39 (br dd, J = 16.8, 5.5 Hz, 1H), 3.18 (br t, J = 5.8 Hz, 2H), 2.80 (br t, J = 6.1 Hz, 2H), 2.15-2.00 (m, 1H), 1.93 (quin, J = 5.8 Hz, 2H), 1.25-1.12 (m, 2H), 0.95-0.77 (m, 2H). LC/MS (m/z) = 484.1 (M + H)$^+$. Human αVβ6 IC$_{50}$ (nM) = 5.3. | Example 3 |
| 156 | 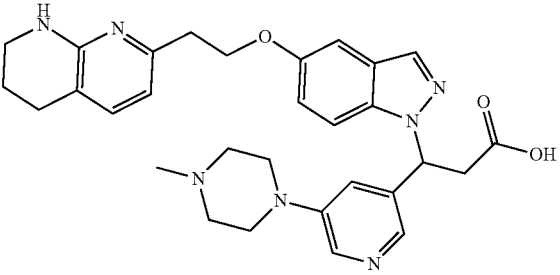 [SMILES: CN1CCN(c2cncc(C(CC(=O)O)n3ncc4cc(OCCc5ccc6c(n5)NCCC6)ccc43)c2)CC1]<br>3-(5-(4-methylpiperazin-1-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.42-8.33 (m, 1H), 8.21 (s, 1H), 8.07-8.01 (m, 2H), 7.67-7.57 (m, 2H), 7.21 (d, J = 2.2 Hz, 1H), 7.09 (dd, J = 9.1, 2.2 Hz, 1H), 6.74 (d, J = 7.2 Hz, 1H), 6.37 (dd, J = 9.2, 5.6 Hz, 1H), 4.33 (br t, J = 5.1 Hz, 2H), 3.73 (br dd, J = 16.8, 9.4 Hz, 2H), 3.55-3.48 (m, 3H), 3.42 (br dd, J = 16.9, 5.6 Hz, 2H), 3.24-3.17 (m, 2H), 2.99 (s, 3H), 2.82 (br t, J = 6.1 Hz, 2H), 1.99-1.88 (m, 2H). LC/MS (m/z) = 542.2 (M + H)$^+$. Human αVβ6 IC$_{50}$ (nM) = 8.8. | Example 3 |
| 157 | 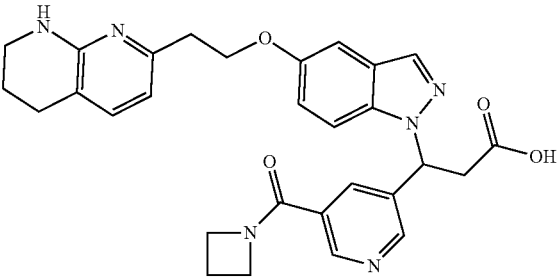 [SMILES: O=C(O)CC(c1cncc(C(=O)N2CCC2)c1)n1ncc2cc(OCCc3ccc4c(n3)NCCC4)ccc21]<br>3-(5-(azetidine-1-carbonyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.82-8.72 (m, 2H), 8.18-8.06 (m, 1H), 8.02 (s, 1H), 7.64-7.57 (m, 2H), 7.20 (d, J = 2.2 Hz, 1H), 7.07 (dd, J = 9.1, 2.2 Hz, 1H), 6.74 (d, J = 7.4 Hz, 1H), 6.38 (dd, J = 8.8, 5.8 Hz, 1H), 4.39-4.23 (m, 4H), 4.19 (br t, J = 7.7 Hz, 2H), 3.72 (dd, J = 16.8, 9.1 Hz, 1H), 3.55-3.46 (m, 2H), 3.45-3.36 (m, 1H), 3.19 (br t, J = 5.8 Hz, 2H), 2.81 (br t, J = 5.9 Hz, 2H), 2.43-2.31 (m, 2H), 2.00-1.89 (m, 2H). LC/MS (m/z) = 527.0 (M + H)$^+$. Human αVβ6 IC$_{50}$ (nM) = 32. | Example 3 |
| 158 | 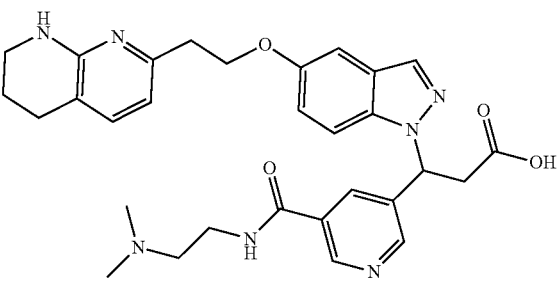 [SMILES: CN(C)CCNC(=O)c1cncc(C(CC(=O)O)n2ncc3cc(OCCc4ccc5c(n4)NCCC5)ccc32)c1]<br>3-(5-((2-(dimethylamino)ethyl)carbamoyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.93 (br s, 1H), 8.75 (br s, 1H), 8.36 (br s, 1H), 8.00 (s, 1H), 7.68-7.57 (m, 2H), 7.20 (s, 1H), 7.07 (br d, J = 8.5 Hz, 1H), 6.74 (br d, J = 7.2 Hz, 1H), 6.37 (br dd, J = 8.3, 5.8 Hz, 1H), 4.33 (br s, 2H), 3.85-3.69 (m, 3H), 3.50 (br s, 2H), 3.45-3.36 (m, 3H), 3.23-3.13 (m, 2H), 2.99 (s, 6H), 2.81 (br t, J = 5.5 Hz, 2H), 2.00-1.89 (m, 2H). LC/MS (m/z) = 558.2 (M + H)$^+$. Human αVβ6 IC$_{50}$ (nM) = 13. | Example 3 |

| Example No. | Structure & Name | Analytical Data | Method |
|---|---|---|---|
| 159 | 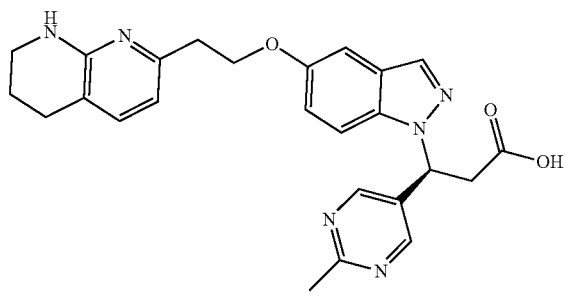 [SMILES: Cc1ncc([C@H](CC(=O)O)n2ncc3cc(OCCc4ccc5c(n4)NCCC5)ccc32)cn1]<br>(S)-3-(2-methylpyrimidin-5-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.70 (s, 2H), 8.05-7.98 (m, 1H), 7.67-7.56 (m, 2H), 7.24-7.17 (m, 1H), 7.13-7.04 (m, 1H), 6.81-6.69 (m, 1H), 6.34-6.25 (m, 1H), 4.38-4.30 (m, 2H), 3.75-3.65 (m, 1H), 3.55-3.48 (m, 2H), 3.42-3.35 (m, 1H), 3.23-3.16 (m, 2H), 2.86-2.77 (m, 2H), 2.69-2.57 (m, 3H), 1.98-1.91 (m, 2H). LC/MS (m/z) = 459.2 (M + H)$^+$. Human αVβ6 IC$_{50}$ (nM) = 47. | Examples 66, 16, and 17 |
| 160 | 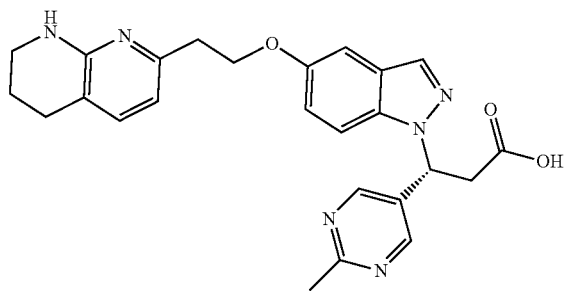 [SMILES: Cc1ncc([C@@H](CC(=O)O)n2ncc3cc(OCCc4ccc5c(n4)NCCC5)ccc32)cn1]<br>(R)-3-(2-methylpyrimidin-5-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.70 (s, 2H), 8.05-7.98 (m, 1H), 7.67-7.56 (m, 2H), 7.24-7.17 (m, 1H), 7.13-7.04 (m, 1H), 6.81-6.69 (m, 1H), 6.34-6.25 (m, 1H), 4.38-4.30 (m, 2H), 3.75-3.65 (m, 1H), 3.55-3.48 (m, 2H), 3.42-3.35 (m, 1H), 3.23-3.16 (m, 2H), 2.86-2.77 (m, 2H), 2.69-2.57 (m, 3H), 1.98-1.91 (m, 2H). LC/MS (m/z) = 459.2 (M + H)$^+$. Human αVβ6 IC$_{50}$ (nM) = 2,600. | Example 3 |
| 161 | 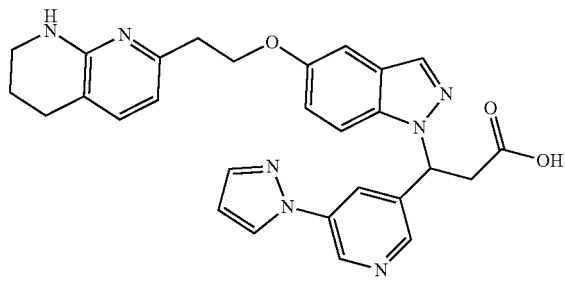 [SMILES: O=C(O)CC(c1cncc(-n2cccn2)c1)n1ncc2cc(OCCc3ccc4c(n3)NCCC4)ccc21]<br>3-(5-(1H-pyrazol-1-yl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, chloroform-d) δ 9.58-9.40 (m, 1H), 9.08-9.01 (m, 1H), 8.83-8.75 (m, 1H), 8.51-8.42 (m, 1H), 8.02-7.96 (m, 2H), 7.81-7.76 (m, 1H), 7.39-7.33 (m, 2H), 7.07 (br d, J = 2.1 Hz, 1H), 6.97-6.94 (m, 1H), 6.57-6.54 (m, 1H), 6.52-6.49 (m, 1H), 6.37-6.29 (m, 1H), 4.31-4.22 (m, 2H), 4.01-3.99 (m, 1H), 3.84-3.77 (m, 1H), 3.51-3.46 (m, 3H), 3.19-3.13 (m, 2H), 2.78-2.72 (m, 2H), 1.96-1.89 (m, 2H). LC/MS (m/z) = 510.2 (M + H)$^+$. Human αVβ6 IC$_{50}$ (nM) = 5.5. | Example 3 |
| 162 | 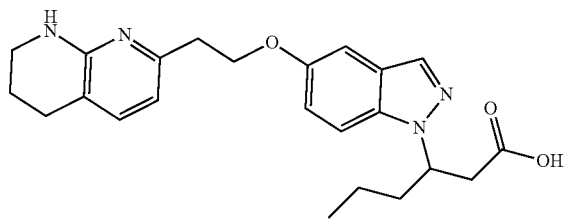 [SMILES: CCCC(CC(=O)O)n1ncc2cc(OCCc3ccc4c(n3)NCCC4)ccc21]<br>3-(5-(2-(5,6,7,8-tetrahydro-1,8-naphthyridin-2-yl)ethoxy)-1H-indazol-1-yl)hexanoic acid | $^1$H NMR (500 MHz, DMSO-$d_6$) δ 8.25-8.09 (m, 1H), 7.51-7.44 (m, 1H), 7.12-7.06 (m, 1H), 7.02-6.97 (m, 1H), 6.87-6.81 (m, 1H), 6.42-6.36 (m, 1H), 4.80 (dt, J = 9.0, 4.7 Hz, 1H), 4.24-4.15 (m, 2H), 3.28-3.19 (m, 2H), 3.03-2.84 (in, 4H), 2.65-2.57 (m, 2H), 1.95-1.85 (m, 2H), 1.81-1.69 (m, 3H), 1.14-1.01 (m, 1H), 0.94-0.81 (m, 1H), 0.82-0.74 (m, 3H). LC/MS (m/z) = 409.2 (M + H)$^+$. Human αVβ6 IC$_{50}$ (nM) = 730. | Example 3 |

| Example No. | Structure & Name | Analytical Data | Method |
|---|---|---|---|
| 163 | 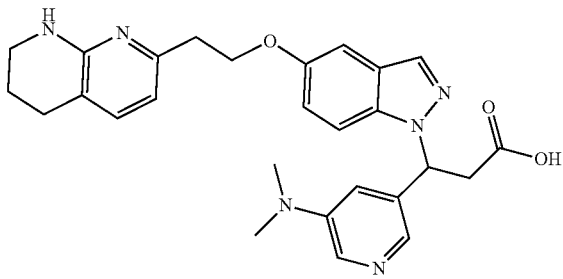 [SMILES: CN(C)c1cncc(C(CC(=O)O)n2ncc3cc(OCCc4ccc5c(n4)NCCC5)ccc32)c1]<br>3-(5-(dimethylamino)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 8.01-7.96 (m, 1H), 7.95-7.93 (m, 1H), 7.85-7.78(m, 1H), 7.68-7.63 (in, 1H), 7.19-7.14 (m, 1H), 7.08-7.04 (m, 2H), 6.99-6.93 (m, 1H), 6.39-6.31 (m, 2H), 6.17-6.10 (m, 1H), 4.28-4.17 (m, 2H), 3.64-3.55 (m, 1H), 3.26-3.20 (m, 1H), 2.92-2.83 (m, 8H), 2.64-2.58 (m, 2H), 1.77-1.71 (m, 2H). LC/MS (m/z) = 487.2 (M + H)$^+$. Human αVβ6 IC$_{50}$ (nM) = 3.8. | Example 3 |
| 164 | 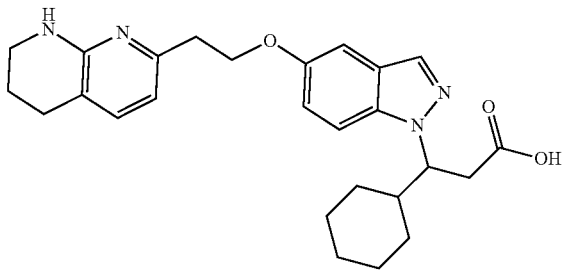 [SMILES: O=C(O)CC(C1CCCCC1)n1ncc2cc(OCCc3ccc4c(n3)NCCC4)ccc21]<br>3-cyclohexyl-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 7.73-7.67 (m, 1H), 7.36-7.30 (m, 1H), 6.92 (s, 1H), 6.86 (d, J = 7.0 Hz, 1H), 6.78-6.72 (m, 1H), 6.18 (d, J = 7.3 Hz, 1H), 6.12-6.06 (m, 1H), 4.55-4.45 (m, 1H), 4.07-3.99 (m, 2H), 3.07-2.99 (m, 1H), 2.81-2.66 (m, 3H), 2.47-2.37 (m, 2H), 1.67-1.42 (m, 5H), 1.37-1.23 (m, 2H), 1.05-0.89 (m, 2H), 0.86-0.52 (m, 5H). LC/MS (m/z) = 449.1 (M + H)$^+$. Human αVβ6 IC$_{50}$ (nM) = 3,200. | Example 3 |
| 165 | 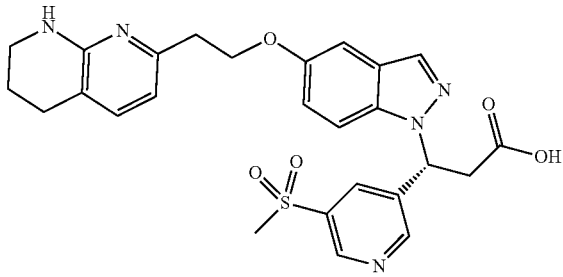 [SMILES: CS(=O)(=O)c1cncc([C@@H](CC(=O)O)n2ncc3cc(OCCc4ccc5c(n4)NCCC5)ccc32)c1]<br>(R)-3-(5-(methylsulfonyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 9.00-8.91 (m, 2H), 8.30-8.23 (m, 1H), 8.11-8.03 (m, 1H), 7.83-7.75 (m, 1H), 7.65-7.57 (m, 1H), 7.26-7.19 (m, 1H), 7.07-6.99 (m, 1H), 6.76-6.69 (m, 1H), 6.49-6.40 (m, 1H), 4.33-4.22 (m, 2H), 3.93-3.86 (m, 1H), 3.71-3.60 (m, 1H), 3.32-3.28 (m, 1H), 3.19-3.08 (m, 2H), 2.76-2.68 (m, 1H), 2.54-2.52 (m, 3H), 1.86-1.75 (m, 2H), 1.29-1.19 (m, 1H). LC/MS (m/z) = 522.2 (M + H)$^+$. Human αVβ6 IC$_{50}$ (nM) = 540. | Examples 125, 16, and 17 |
| 166 | 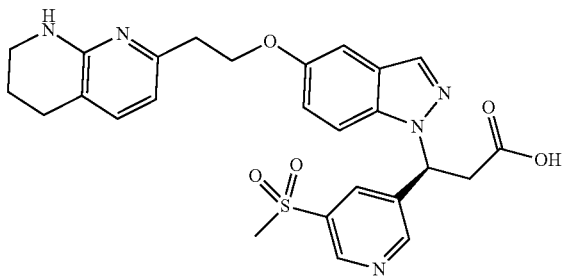 [SMILES: CS(=O)(=O)c1cncc([C@H](CC(=O)O)n2ncc3cc(OCCc4ccc5c(n4)NCCC5)ccc32)c1]<br>(S)-3-(5-(methylsulfonyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, DMSO-$d_6$) δ 9.00-8.91 (m, 2H), 8.30-8.23 (m, 1H), 8.11-8.03 (m, 1H), 7.83-7.75 (m, 1H), 7.65-7.57 (m, 1H), 7.26-7.19 (m, 1H), 7.07-6.99 (m, 1H), 6.76-6.69 (m, 1H), 6.49-6.40 (m, 1H), 4.33-4.22 (m, 2H), 3.93-3.86 (m, 1H), 3.71-3.60 (m, 1H), 3.32-3.28 (m, 1H), 3.19-3.08 (m, 2H), 2.76-2.68 (m, 2H), 2.54-2.52 (m, 3H), 1.86-1.75 (m, 2H), 1.29-1.19 (m, 1H). LC/MS (m/z) = 522.2 (M + H)$^+$. Human αVβ6 IC$_{50}$ (nM) = 5.2. | Examples 125, 16, and 17 |

Example 167

3-(5-((((Methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid, 2 TFA

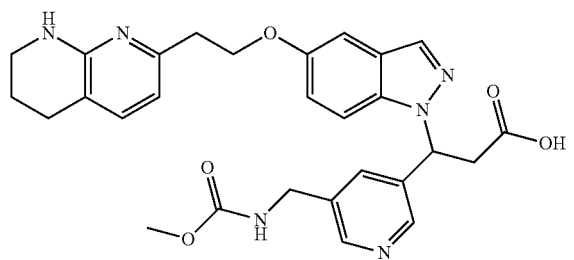

Example 167

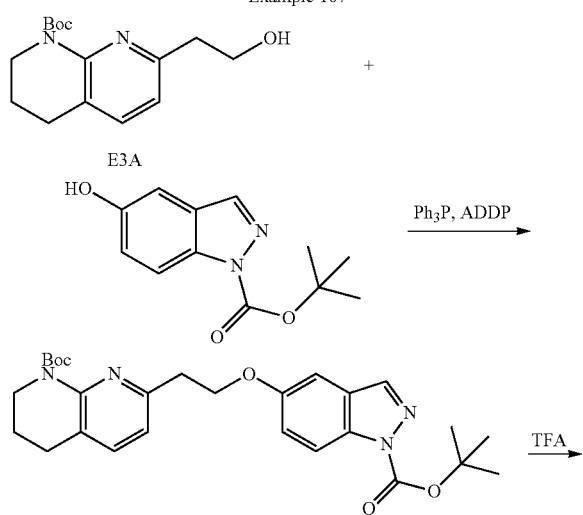

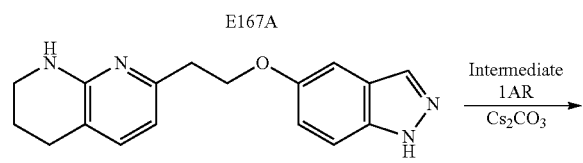

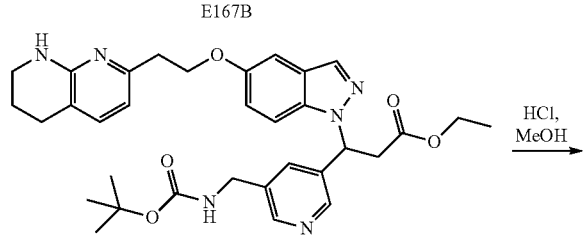

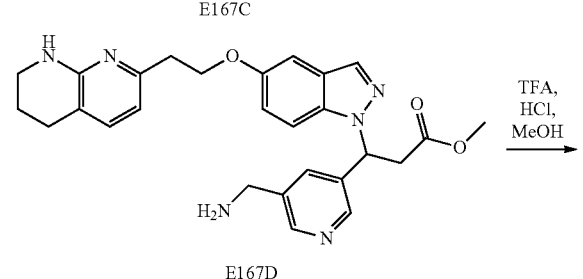

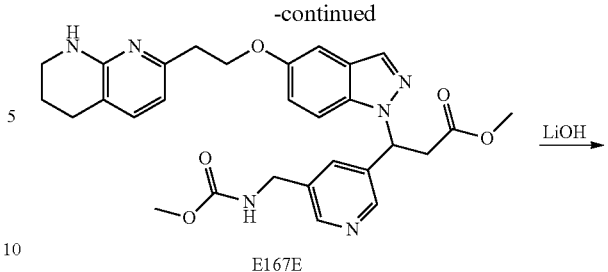

E167E

Example 167

Intermediate E167A: To a solution of Intermediate E3A (3.53 g, 12.7 mmol), tert-butyl 5-hydroxy-1H-indazole-1-carboxylate [(WO 2016/21043), 2.7 g, 11.5 mmol] and Ph$_3$P (3.78 g, 14.4 mmol) in THF (70 mL), maintained in an ice-water bath, was added (E)-diazene-1,2-diylbis(piperidin-1-ylmethanone) (3.64 g, 14.41 mmol) dropwise over 5 min. The reaction mixture was allowed to warm to rt and stir for 16 h. The reaction was diluted with NaHCO$_3$ solution (aqueous, saturated, 30 mL), the resulting aqueous mixture was extracted with EtOAc (3×50 mL). The combine organic layers were washed with brine (10 mL), and then dried over Na$_2$SO$_4$. The mixture was filtered and concentrated under reduced pressure. The residue was purified via flash chromatography (hexanes/ethyl acetate, 0-100% gradient) to give Intermediate E167A (3.94 g, 69%). $^1$H NMR (500 MHz, chloroform-d) δ 8.09-8.01 (m, 2H), 7.37-7.32 (m, 1H), 7.20-7.15 (m, 2H), 6.98-6.93 (m, 1H), 4.44 (t, J=6.9 Hz, 2H), 3.81-3.76 (m, 2H), 3.29-3.20 (m, 2H), 2.80-2.74 (m, 2H), 1.98-1.92 (m, 2H), 1.76-1.75 (m, 1H), 1.75-1.73 (m, 9H), 1.53 (s, 9H). LCMS (ES): m/z 495.1 [M+H]$^+$.

Intermediate E167B: To a solution of Intermediate E167A (3.94 g, 7.97 mmol) in DCM (40 mL) was added TFA (8 mL, 104 mmol) and the mixture was stirred at rt for 16 hrs. It was concentrated and the crude product was purified using medium pressure reverse phase chromatography (10-90% water 0.1% TFA/acetonitrile gradient) to afford Intermediate E167B, TFA salt (2.63 g, 6.44 mmol, 81% yield). $^1$H NMR (500 MHz, chloroform-d) δ 10.39-10.23 (m, 1H), 8.17-7.88 (m, 1H), 7.45-7.38 (m, 1H), 7.37-7.31 (m, 1H), 7.19-7.12 (m, 1H), 7.11-6.96 (m, 1H), 6.59-6.48 (m, 1H), 4.48-4.23 (m, 2H), 3.63-3.41 (m, 2H), 3.31-3.09 (m, 2H), 2.84-2.61 (m, 2H), 2.04-1.83 (m, 2H). LCMS (ES): m/z 295.2 [M+H]$^+$.

Intermediate E167C: To a solution of Intermediate E167B, TFA salt (100 mg, 0.245 mmol) in acetonitrile (2 mL) was added cesium carbonate (239 mg, 0.735 mmol). After stirring at rt for 5 min, Intermediate 1AR (75 mg, 0.245 mmol) was added and the resulting mixture was stirred at 80° C. for 8 hrs. The mixture was cooled to rt, filtered, and concentrated. The residue purified via preparative HPLC (Phenomenex Luna Axia 5μ C18 30×100 mm; 10 min gradient from 75% A: 25% B to 0% A:100% B (A=90% H$_2$O/10% MeOH+0.1% TFA); (B=90% MeOH/10% H$_2$O+ 0.1% TFA); detection at 220 nm) to give Intermediate E167C, bis TFA salt (95 mg, 0.115 mmol, 47% yield). LCMS (ES): m/z 601.3 [M+H]$^+$.

Intermediate E167D: To a solution of Intermediate E167C, bis TFA salt (95 mg, 0.115 mmol) in methanol (1 mL) was added a 4 M solution of HCl in dioxane (0.115 mL, 0.459 mmol). The reaction mixture was stirred at rt for 3 days. The mixture was diluted with acetonitrile and purified using reverse phase preparative HPLC (Phenomenex Luna Axia 5μ C18 30×100 mm; 10 min gradient from 75% A:

25% B to 0% A:100% B (A=90% H$_2$O/10% MeOH+0.1% TFA); (B=90% MeOH/10% H$_2$O+0.1% TFA); detection at 220 nm) to give Intermediate E167D, 3 TFA salt (50 mg, 0.060 mmol, 53% yield). LCMS (ES): m/z 487.1 [M+H]$^+$.

Intermediate E167E: To a solution of E167D, 3 TFA (16 mg, 0.019 mmol) in DCM (0.5 mL) was added triethylamine (0.013 mL, 0.097 mmol). The mixture was stirred at rt for 10 min and then methyl carbonochloridate (2.74 mg, 0.029 mmol) was added and stirred at rt for 4 hrs. After 4 hrs, the reaction mixture was diluted with sat aqueous NaHCO$_3$ solution and then extracted with dichloromethane. The combine organics layers were washed with brine, dried over sodium sulfate, filtered, and concentrated in vacuo. The mixture was diluted with acetonitrile and purified using reverse phase preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+0.1% TFA); detection at 220 nm) to give Intermediate E167E, bis TFA salt (13 mg, 0.017 mmol, 87% yield). LCMS (ES): m/z 545.1 [M+H]$^+$.

Example 167

To a solution of Intermediate E167E, bis TFA salt (13 mg, 0.017 mmol) in THF (0.5 mL) was added a solution of aqueous 1 M LiOH (0.067 mL, 0.067 mmol). The reaction mixture was stirred at rt for 3 hrs. The reaction mixture was neutralized with TFA, filtered, and concentrated under reduced pressure. The residue was diluted purified using reverse phase preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+0.1% TFA); detection at 220 nm) to give Intermediate E167, bis TFA salt (12 mg, 0.016 mmol, 94% yield). $^1$H NMR (500 MHz, methanol-d$_4$) δ 8.55 (br s, 1H), 8.47 (br s, 1H), 8.10-7.91 (m, 2H), 7.59 (br t, J=9.4 Hz, 2H), 7.20 (d, J=2.2 Hz, 1H), 7.07 (dd, J=9.1, 2.2 Hz, 1H), 6.77-6.72 (m, 1H), 6.34 (br dd, J=9.2, 5.4 Hz, 1H), 4.37-4.28 (m, 4H), 3.72 (br dd, J=16.8, 9.4 Hz, 1H), 3.65 (s, 3H), 3.54-3.46 (m, 2H), 3.43-3.35 (m, 1H), 3.19 (br t, J=5.9 Hz, 2H), 2.82 (br t, J=6.1 Hz, 2H), 1.99-1.91 (m, 2H). LC/MS (m/z)=531.1 (M+H)$^+$. Human αVβ6 IC$_{50}$ (nM)=15.

The following examples were prepared using methods analogous to the ones indicated in the table below.

| Example No. | Structure & Name | Analytical Data | Method |
|---|---|---|---|
| 168 | 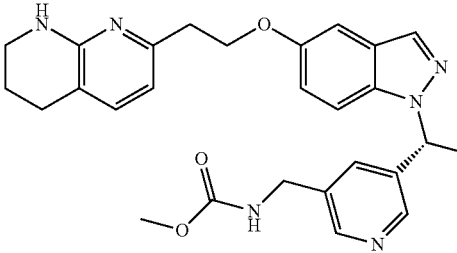<br>(R)-3-(5-(((methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.48-8.41 (m, 1H), 8.39-8.33 (m, 1H), 8.00-7.94 (m, 1H), 7.81-7.75 (m, 1H), 7.54-7.49 (m, 1H), 7.32-7.28 (m, 1H), 7.04-7.00 (m, 1H), 6.99-6.93 (m, 1H), 6.55-6.50 (m, 1H), 6.33-6.27 (m, 1H), 4.30-4.25 (m, 2H), 4.16-4.03 (m, 2H), 3.66-3.56 (m, 4H), 3.40-3.36 (m, 5H), 3.25-3.19 (m, 1H), 2.97-2.93 (m, 2H), 2.73-2.68 (m, 2H), 1.90-1.83 (m, 2H). LC/MS (m/z) = 531.4 (M + H)$^+$. Human αVβ6 IC$_{50}$ (nM) = 740. | Examples 167, 16, and 17 |
| 169 | 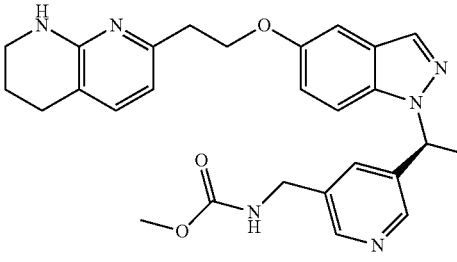<br>(S)-3-(5-(((methoxycarbonyl)amino)methyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-d$_4$) δ 8.52-8.30 (m, 2H), 8.00-7.93 (m, 1H), 7.80-7.76 (m, 1H), 7.56-7.49 (m, 1H), 7.32-7.27 (m, 1H), 7.05-7.01 (m, 1H), 6.99-6.94 (m, 1H), 6.55-6.50 (m, 1H), 6.33-6.26 (m, 1H), 4.28 (s, 2H), 4.16-4.04 (m, 2H), 3.66-3.55 (m, 4H), 3.41-3.36 (m, 3H), 3.24-3.18 (m, 1H), 2.98-2.93 (m, 2H), 2.73-2.68 (m, 2H), 1.90-1.84 (m, 2H). LC/MS (m/z) = 515.1 (M + H)$^+$. Human αVβ6 IC$_{50}$ (nM) = 3.7. | Examples 167, 16, and 17 |

-continued

| Example No. | Structure & Name | Analytical Data | Method |
|---|---|---|---|
| 170 | 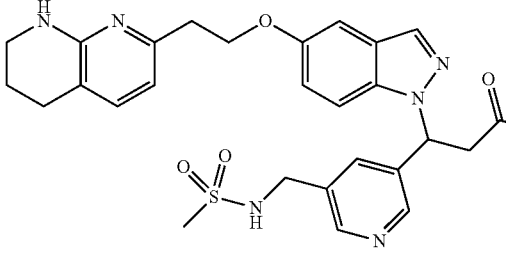<br>3-(5-(methylsulfonamidomethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.59-8.45 (m, 2H), 8.07-7.93 (m, 2H), 7.68-7.55 (m, 2H), 7.20 (d, J = 1.9 Hz, 1H), 7.06 (dd, J = 9.4, 2.2 Hz, 1H), 6.77 (br d, J = 7.4 Hz, 1H), 6.40-6.25 (m, 1H), 4.43-4.22 (m, 4H), 3.74 (br dd, J = 16.8, 9.4 Hz, 1H), 3.51 (br t, J = 5.6 Hz, 3H), 3.23-3.15 (m, 2H), 2.90-2.78 (m, 4H), 2.00-1.88 (m, 2H). LC/MS (m/z) = 552.1 (M + H)$^+$. Human αVβ6 IC$_{50}$ (nM) = 18. | Example 167 |
| 171 | 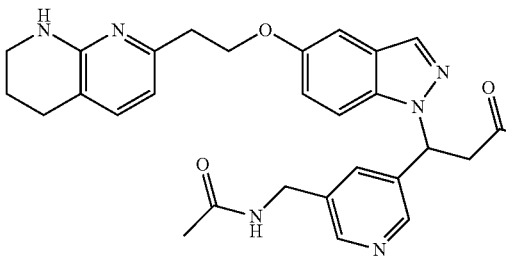<br>3-(5-(acetamidomethyl)pyridin-3-yl)-3-(5-(2-(5,6,7,8-tetrahydro-1,8-naphthyridin-2-yl)ethoxy)-1H-indazol-1-yl)propanoic acid | $^1$H NMR (500 MHz, methanol-$d_4$) δ 8.63-8.49 (m, 1H), 8.49-8.43 (m, 1H), 8.07-7.84 (m, 2H), 7.65-7.55 (m, 2H), 7.21 (d, J = 1.9 Hz, 1H), 7.07 (dd, J = 9.2, 2.1 Hz, 1H), 6.77 (br d, J = 6.1 Hz, 1H), 6.38-6.30 (m, 1H), 4.44-4.36 (m, 2H), 4.33 (br t, J = 5.1 Hz, 2H), 3.97-3.89 (m, 1H), 3.72 (dd, J = 16.8, 9.4 Hz, 1H), 3.54-3.48 (m, 2H), 3.23-3.15 (m, 2H), 2.83 (br t, J = 6.2 Hz, 2H), 2.00-1.91 (m, 5H). LC/MS (m/z) = 515.1 (M + H)$^+$. Human αVβ6 IC$_{50}$ (nM) = 46. | Example 167 |

Example 172

3-(5-(2-(5,6,7,8-Tetrahydro-1,8-naphthyridin-2-yl)ethoxy)-1H-indazol-1-yl)-3-(5,6,7,8-tetrahydro-1,8-naphthyridin-3-yl)propanoic acid, 2 TFA

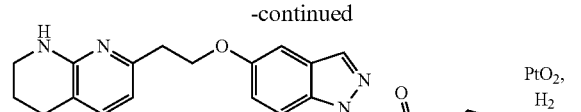

Example 172

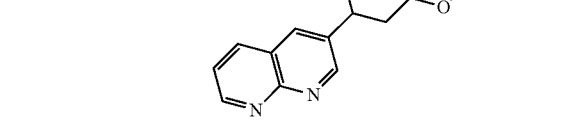

E167B intermediate 1BW, Cs$_2$CO$_3$

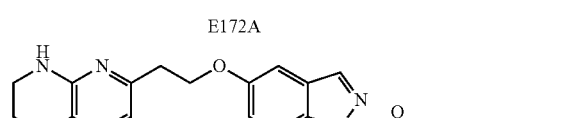

E172A

PtO$_2$, H$_2$

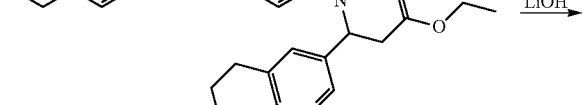

E172B

LiOH

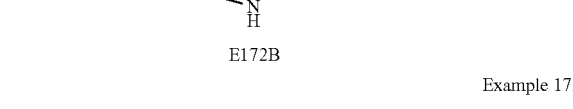

Example 172

Intermediate E172A: To a solution of Intermediate E167B, TFA salt (55 mg, 0.135 mmol) in acetonitrile (1.2 mL) was added cesium carbonate (132 mg, 0.404 mmol). After stirring at rt for 5 min, Intermediate 1BW (30.7 mg, 0.135) was added and the resulting mixture was stirred at 80° C. for 6 hrs. The mixture was cooled to rt, filtered, and concentrated. The residue purified via preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+ 0.1% TFA); detection at 220 nm) to give Intermediate E172A, bis TFA salt (62 mg, 0.083 mmol, 61.3% yield). LCMS (ES): m/z 523.1 [M+H]$^+$.

Intermediate E172B: To a degassed solution of E172A in EtOH (0.7 mL) was added platinum(IV) oxide (3 mg, 0.013 mmol). The reaction was stirred at rt for 4 hrs with under an atmosphere of hydrogen (balloon). The reaction was purged with nitrogen, filtered, and concentrated in vacuo. The crude product was diluted with MeCN, filtered, and purified using reverse phase preparative HPLC (Phenomenex Luna Axia 5μ C18 30×100 mm; 10 min gradient from 75% A: 25% B to 0% A:100% B (A=90% H$_2$O/10% MeOH+0.1% TFA); (B=90% MeOH/10% H$_2$O+0.1% TFA); detection at 220 nm) to give Intermediate E172B, bis TFA salt (22 mg, 0.029 mmol, 35.3% yield). LCMS (ES): m/z 527.1 [M+H]$^+$.

Example 172

To a solution of Intermediate E172B, bis TFA salt (22 mg, 0.029 mmol) in THF (0.5 mL) was added a solution of aqueous 1 M LiOH (0.117 mL, 0.117 mmol). The reaction mixture was stirred at rt overnight. The reaction mixture was neutralized with TFA, filtered, and concentrated under reduced pressure. The residue was diluted purified using reverse phase preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+0.1% TFA); detection at 220 nm) to give Intermediate E172, bis TFA salt (11 mg, 0.014 mmol, 46.7% yield). $^1$H NMR (500 MHz, methanol-d$_4$) δ 7.96 (s, 1H), 7.72 (s, 1H), 7.70 (br s, 1H), 7.65-7.52 (m, 2H), 7.18 (s, 1H), 7.06 (br d, J=9.1 Hz, 1H), 6.73 (d, J=7.4 Hz, 1H), 6.10 (br dd, J=8.8, 6.1 Hz, 1H), 4.31 (br t, J=5.6 Hz, 2H), 3.59 (br dd, J=16.5, 9.1 Hz, 1H), 3.53-3.39 (m, 4H), 3.30-3.22 (m, 1H), 3.18 (br t, J=5.5 Hz, 2H), 2.87-2.72 (m, 4H), 2.01-1.85 (m, 4H). LC/MS (m/z)=499.1 (M+H)$^+$. Human α$_v$β6 IC$_{50}$ (nM)=12.

Example 173

4-((6-(2-Carboxy-1-(5-(2-(5,6,7,8-tetrahydro-1,8-naphthyridin-2-yl)ethoxy)-1H-indazol-1-yl)ethyl)pyrazin-2-yl)amino)butanoic acid, TFA

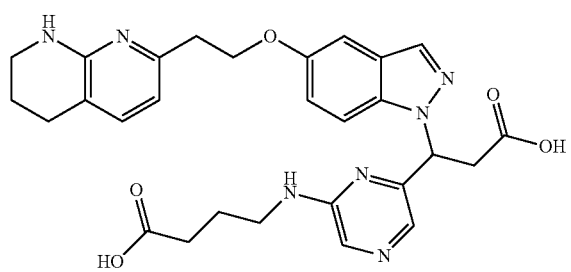

Example 173

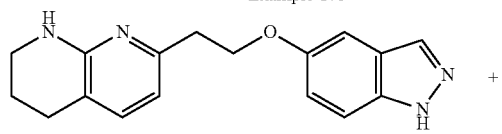

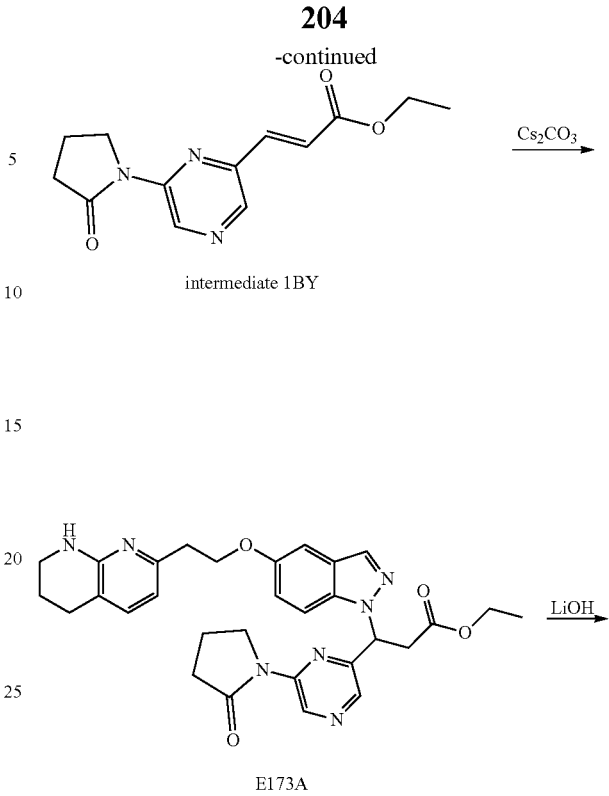

Intermediate E173A: To a solution of Intermediate E167B, TFA salt (136 mg, 0.463 mmol) in acetonitrile (2.5 mL) was added cesium carbonate (453 mg, 1.389 mmol). After stirring at rt for 5 min, Intermediate 1BY (121 mg, 0.463 mmol) was added and the resulting mixture was stirred at 80° C. for 16 hrs. The mixture was cooled to rt, filtered, and concentrated. The residue purified via preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+ 0.1% TFA); detection at 220 nm) to give Intermediate E173A, bis TFA salt (19.6 mg, 0.035 mmol, 7% yield). LCMS (ES): m/z 556.3 [M+H]$^+$.

Example 173

To a solution of Intermediate E173A, bis TFA salt (19.6 mg, 0.035 mmol) in THF (1 mL) was added a solution of aqueous 1 M LiOH (0.106 mL, 0.106 mmol). The reaction mixture was stirred at rt overnight. The reaction mixture was concentrated under reduced pressure, diluted with acetonitrile and filtered. The product was purified using reverse phase preparative HPLC (Phenomenex Luna Axia 5μ C18 30×100 mm; 10 min gradient from 20% A: 80% B to 0% A:100% B (A=90% H$_2$O/10% MeOH+0.1% TFA); (B=90% MeOH/10% H$_2$O+0.1% TFA); detection at 220 nm) to give Example 173, TFA salt (8.1 mg, 0.011 mmol, 32% yield). $^1$H NMR (500 MHz, methanol-d$_4$) δ 8.00-7.97 (m, 1H), 7.64-7.61 (m, 2H), 7.59-7.55 (m, 1H), 7.24-7.21 (m, 1H), 7.10-7.09 (m, 1H), 7.09-7.07 (m, 1H), 6.80-6.77 (m, 1H), 6.21-6.16 (m, 1H), 4.37-4.31 (m, 3H), 3.54-3.50 (m, 4H), 3.42-3.39 (m, 2H), 3.23-3.19 (m, 3H), 2.85-2.81 (m, 3H), 2.36 (t, J=7.4 Hz, 2H), 1.98-1.94 (m, 3H), 1.86 (t, J=7.2 Hz, 2H). LC/MS (m/z)=546.3 (M+H)$^+$. Human α$_v$β6 IC$_{50}$ (nM)=370.

Example 174

3-(6-Methoxypyridin-3-yl)-3-(4-(2-(5,6,7,8-tetrahydro-1,8-naphthyridin-2-yl)ethyl)-1H-indazol-1-yl) propanoic acid, TFA

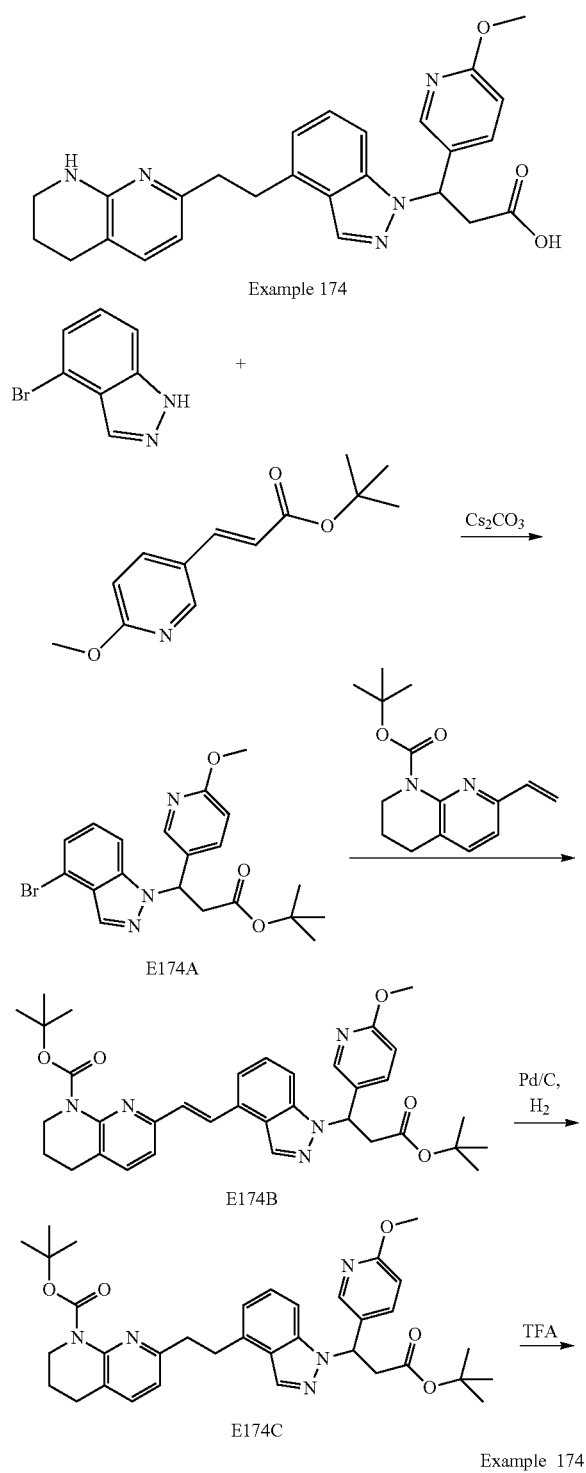

Intermediate E174A: To a mixture of tert-butyl (E)-3-(6-methoxypyridin-3-yl)acrylate [(*J. Org. Chem.* 2004, 69, 1959) 0.746 g, 3.17 mmol] and 4-bromo-1H-indazole (0.500 g, 2.54 mmol) in acetonitrile (20 mL) at room temperature was added DBU (0.383 mL, 2.54 mmol). The reaction mixture was heated at 50° C. for 48 h. The mixture was diluted with water and extracted with ethyl acetate. The combined organic layers were washed with brine, dried over magnesium sulfate, filtered and concentrated in vacuo. The crude residue was purified using silica gel column chromatography (2% MeOH/dichloromethane) to afford E174A (447 mg, 1.034 mmol, 41% yield). 1H NMR (400 MHz, chloroform-d) δ 8.18 (d, J=2.3 Hz, 1H), 8.04 (s, 1H), 7.58 (dd, J=8.8, 2.5 Hz, 1H), 7.41 (d, J=8.5 Hz, 1H), 7.31-7.27 (m, 1H), 7.25-7.16 (m, 1H), 6.67 (d, J=8.5 Hz, 1H), 6.00 (dd, J=9.2, 5.9 Hz, 1H), 3.89 (s, 3H), 3.64 (dd, J=16.1, 9.3 Hz, 1H), 3.16 (dd, J=16.1, 6.0 Hz, 1H), 1.28 (s, 9H). LCMS (ES): m/z 432.2, 434.2 [M+H]$^+$.

Intermediate E174B: Palladium(II) acetate (8.62 mg, 0.038 mmol) was added to a vial charged with a degassed mixture of tert-butyl 7-vinyl-3,4-dihydro-1,8-naphthyridine-1(2H)-carboxylate [(*Eur. J. Med. Chem.* 2007, 42, 334), 0.100 g, 0.384 mmol], intermediate E174A (0.166 g, 0.384 mmol), tri-o-tolylphosphine (0.023 g, 0.077 mmol), and triethylamine (0.107 mL, 0.768 mmol) in DMF (3 mL). The vessel's headspace was purged with nitrogen and the vial was sealed. The mixture was heated at 100° C. for 20 h. After cooling to rt, the vessel was uncapped and its contents were diluted with water and extracted with ethyl acetate. The combined organic layers were washed with brine, dried over magnesium sulfate, filtered and concentrated in vacuo. The residue was purified using silica gel column chromatography (5% methanol/dichloromethane) to afford E174B (238 mg, 0.389 mmol, 101% yield). The product was a mixture of cis/trans isomers and was contaminated with minor impurities. The material was used for subsequent chemistry without further purification. LC/MS (m/z)=612.43 (M+H)$^+$.

Intermediate E174C: To a flask charged with a solution of E174B (238 mg, 0.389 mmol) in methanol under a nitrogen atmosphere was added 10% palladium on carbon (41.4 mg, 0.389 mmol). The vessel was partially evacuated and flushed repeatedly with hydrogen gas. The reaction was left to stir under a hydrogen atmosphere (double balloon). After 24 h, the reaction mixture was purged with nitrogen and filtered through celite. The concentrated filtrate was purified using silica gel column chromatography (5-10% MeOH/dichloromethane) to afford E174C (25 mg, 0.040 mmol, 10% yield). LC/MS (m/z)=614.4 (M+H)$^+$.

Example 174

Triflouroacetic acid (0.5 mL) was added to a solution containing E174C (41.8 mg, 0.068 mmol) in dichloromethane (2.5 mL). The resulting mixture was heated at 40° C. for 2 h. The mixture was concentrated under a stream of dry nitrogen. The residue was dissolved in methanol and purified via preparative LC/MS with the following conditions: Column: XBridge C18, 19×200 mm, 5-µm particles, Mobile Phase A: 5:95 acetonitrile: water with 10-mM ammonium acetate; Mobile Phase B: 95:5 acetonitrile: water with 10-mM ammonium acetate; Gradient: 0-40% B over 20 minutes, then a 5-minute hold at 100% B; Flow: 20 mL/min. Fractions containing the desired product were combined and dried via centrifugal evaporation to afford example 172 (29.4 mg, 0.062 mmol, 91% yield). $^1$H NMR (500 MHz, DMSO-d$_6$) δ 8.30-8.22 (m, 1H), 8.22-8.15 (m, 1H), 7.74-7.65 (m, 1H), 7.65-7.56 (m, 1H), 7.31-7.22 (m, 1H), 7.07-6.99 (m, 1H), 6.97-6.90 (m, 1H), 6.77-6.69 (m, 1H), 6.38-6.27 (m, 2H), 6.25-6.13 (m, 1H), 3.82-3.73 (m, 3H), 3.63 (br s, 1H), 3.31-3.12 (m, 5H), 2.88-2.77 (m, 2H), 2.64-2.56 (m, 2H), 1.80-1.70 (m, 2H). LC/MS (m/z)=458.2 (M+H)$^+$. Human αVβ6 IC$_{50}$ (nM)=540.

Examples 175-178

(R)-3-(5-(2-((R)-7-methyl-5,6,7,8-tetrahydro-1,8-naphthyridin-2-yl)ethoxy)-1H-indazol-1-yl)-3-(2-methylpyrimidin-5-yl)propanoic acid (S)-3-(5-(2-((R)-7-methyl-5,6,7,8-tetrahydro-1,8-naphthyridin-2-yl)ethoxy)-1H-indazol-1-yl)-3-(2-methylpyrimidin-5-yl)propanoic acid (R)-3-(5-(2-((S)-7-methyl-5,6,7,8-tetrahydro-1,8-naphthyridin-2-yl)ethoxy)-1H-indazol-1-yl)-3-(2-methylpyrimidin-5-yl)propanoic acid (S)-3-(5-(2-((S)-7-methyl-5,6,7,8-tetrahydro-1,8-naphthyridin-2-yl)ethoxy)-1H-indazol-1-yl)-3-(2-methylpyrimidin-5-yl)propanoic acid

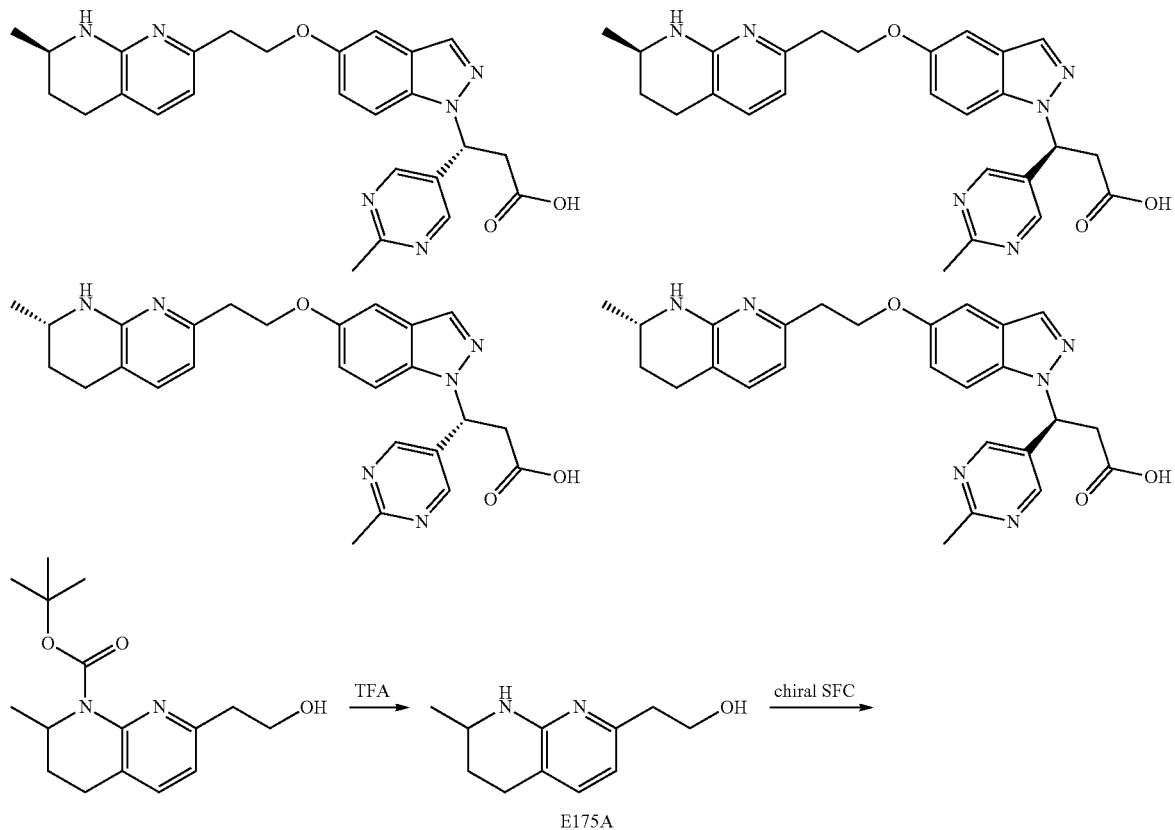

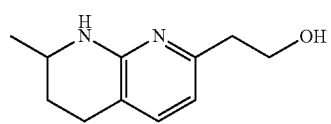

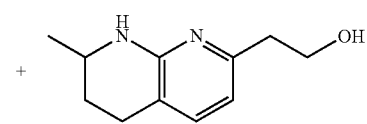

-continued

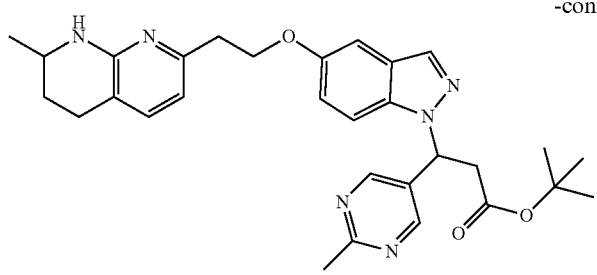

E175A-Diastereomers A & B

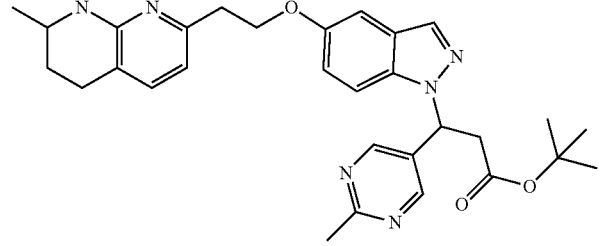

E175B-Diastereomers C & D

```
              |                                        |
         chiral HPLC                              chiral HPLC
         ↙        ↘                              ↙        ↘
E175B-Diastereomers A   E175B-Diastereomers B   E175B-Diastereomers C   E175B-Diastereomers D
         ↓                       ↓                       ↓                       ↓
     Example 175            Example 176            Example 177            Example 178
```

Intermediate E175A: To a solution of tert-butyl 7-(2-hydroxyethyl)-2-methyl-3,4-dihydro-1,8-naphthyridine-1(2H)-carboxylate [(WO 2007/141473), 2.509 g, 8.58 mmol) in DCM (20 mL) was added trifluoroacetic acid (5 mL). The resulting mixture was allowed to stir at rt for 24 h. The reaction was concentrated in vacuo and diluted with aqueous saturated sodium bicarbonate solution. The aqueous mixture was extracted with ethyl acetate. The combined organic layers were washed with brine, dried over magnesium sulfate, filtered and concentrated in vacuo. The crude product was purified using silica gel column chromatography (ISCO system, prepacked ISCO silica cartridge, 90:10 dichloromethane/methanol) to afford E175A (2.509 g, 8.58 mmol). $^1$H NMR (500 MHz, chloroform-d) δ 7.38-7.31 (m, 1H), 6.45-6.37 (m, 1H), 3.93 (s, 2H), 3.74-3.61 (m, 1H), 2.93 (t, J=5.9 Hz, 2H), 2.84-2.69 (m, 2H), 2.06-1.97 (m, 1H), 1.65-1.55 (m, 1H), 1.37 (d, J=6.6 Hz, 3H). LCMS (ES): m/z 193.1 [M+H]$^+$.

Intermediates E175B-Enantiomers A and B. A sample of E175A (1.3 g) was subjected to preparative chiral SFC purification (Column: Chiralpak AD-H, 30×250 mm, 5 micron, BPR pressure: 120 bar, temperature 35° C., flow rate: 70.0 mL/min, mobile phase: 50% MeCN w/0.1% DEA in C02, detector wavelength: 314 nm, stacked injections: 0.5 mL of 110 mg/mL solution) to afford E175A-Enantiomer A (374 mg) and E175A-Enantiomer B (391 mg). LCMS data for each enantiomer was identical to the racemate. The absolute configuration of the separated enantiomers was not determined.

Intermediates E175B-Diastereomers A & B. A sample of E175A-Enantiomer A was subjected to the Mitsunobu coupling (with tert-butyl 5-hydroxy-1H-indazole-1-carboxylate, WO 2016/21043), BOC deprotection, and Michael addition (with intermediate CC) employing the methods outlined in Example 152 to afford a mixture of E175B-Diastereomers A & B (106 mg, 11% yield over 3 steps). LCMS (ES): m/z 529.4 [M+H]$^+$. A sample of E175B-Diastereomers A & B (106 mg) was subjected to preparative chiral HPLC purification (Column: Chiralpak OD, 21×250 mm, 10 micron, flow rate: 15 mL/min, mobile phase: 20% ethanol/80% heptane, detector wavelength: 220 nm, injection: 1 mL of 40 mg/mL solution) to afford E175B-Diastereomer A (44.6 mg) and E175B-Diastereomer B (47.5 mg). LCMS data for the separated diastereomers was identical to the diastereomeric mixture. The relative and absolute stereochemistry of the individual diastereomers was not determined.

Intermediates E175B-Diastereomers C & D. A sample of E175A-Enantiomer B was subjected to the Mitsunobu coupling (with tert-butyl 5-hydroxy-1H-indazole-1-carboxylate, WO 2016/21043), BOC deprotection, and Michael addition (with intermediate CC) employing the methods outlined in Example 152 to afford a mixture of E175B-Diastereomers C & D (121 mg, 12% yield over 3 steps). LCMS (ES): m/z 529.4 [M+H]$^+$. A sample of E175B-Diastereomers C & D (121 mg) was subjected to preparative chiral HPLC purification (Column: Chiralpak OD, 21×250 mm, 10 micron, flow rate: 15 mL/min, mobile phase: 20% ethanol/80% heptane, detector wavelength: 220 nm, injection: 1 mL of 40 mg/mL solution) to afford E175B-Diastereomer C (49 mg) and E175B-Diastereomer D (47 mg). LCMS data for the separated diastereomers was identical to the diastereomeric mixture. The relative and absolute stereochemistry of the individual diastereomers was not determined.

Example 175

Trifluoroacetic acid (0.5 mL) was added to a flask charged with a stirred solution of E175B-Diastereomer A (34.6 mg, 0.065 mmol) in dichloromethane (2.0 mL). The reaction vessel was placed in a 50° C. oil bath for 2 h. The reaction contents were concentrated under a stream of dry nitrogen. The residue was dissolved in a mixture of 1 mL of 28-30% aqueous ammonium hydroxide solution/1 mL DMSO/1 mL 95:5 water (containing 0.5% of 30% aqueous ammonium hydroxide solution):acetonitrile. The clear solution was loaded onto a Waters Sep-Pak C18 Plus Short Cartridge, 360 mg Sorbent per cartridge, 55-105 uM particle size (WAT020515) that had been preconditioned with 10 mL of 2 M ammonia in methanol, then equilibrated with 20 mL of 95:5 water (containing 0.5% of 30% aqueous ammonium hydroxide solution):acetonitrile. After loading, the cartridge was flushed with 40 mL of 95:5 water (containing 0.5% of 30% aqueous ammonium hydroxide solution):acetonitrile at a flow rate equal to a fast drip. The cartridge was next eluted with 5 mL of 2 M ammonia in methanol at the same rate. The salt free product eluted in the first 2.5 mL of methanolic ammonia. The desired fraction was concentrated in vacuo to afford Example 175 (30.9 mg, 92% yield). $^1$H NMR (500 MHz, methanol-$d_4$) δ 8.76-8.65 (m, 2H), 8.02-7.95 (m, 1H), 7.57-7.48 (m, 1H), 7.35-7.29 (m, 1H), 6.96-6.88 (m, 2H), 6.53-6.47 (m, 1H), 6.32-6.23 (m, 1H), 4.09-3.99 (m, 1H), 3.96-3.88 (m, 1H), 3.63-3.48 (m, 2H), 3.25-3.15 (m, 1H), 2.95-2.87 (m, 2H), 2.76-2.64 (m, 2H), 2.64-2.58 (m, 3H), 1.98-1.86 (m, 1H), 1.49-1.37 (m, 1H), 1.26-1.19 (m, 1H). LC/MS (m/z)=473.2 (M+H)$^+$.

Human α$_V$β6 IC$_{50}$ (nM)=6,000.

Example 176

A sample of E175B-Diastereomer B (37.5 mg, 0.071 mmol) was subjected to the deprotection and desalting methods outlined for Example 175 to afford Example 176 (33.5 mg, 92% yield). $^1$H NMR (500 MHz, methanol-$d_4$) δ 8.80-8.63 (m, 2H), 8.04-7.95 (m, 1H), 7.61-7.51 (m, 1H), 7.38-7.29 (m, 1H), 7.00-6.88 (m, 2H), 6.57-6.47 (m, 1H), 6.34-6.23 (m, 1H), 4.12-4.01 (m, 1H), 4.00-3.90 (m, 1H), 3.65-3.51 (m, 2H), 3.27-3.18 (m, 1H), 2.97-2.89 (m, 2H), 2.80-2.67 (m, 2H), 2.66-2.60 (m, 3H), 1.98-1.89 (m, 1H), 1.54-1.41 (m, 1H), 1.29-1.23 (m, 3H). LC/MS (m/z)=473.2 (M+H)$^+$. Human αVβ6 IC$_{50}$ (nM)=33.

Example 177

A sample of E175B-Diastereomer C (39 mg, 0.074 mmol) was subjected to the deprotection and desalting methods outlined for Example 175 to afford Example 177 (32.9 mg, 93% yield). $^1$H NMR (500 MHz, methanol-$d_4$) δ 8.75-8.64 (m, 2H), 8.02-7.92 (m, 1H), 7.58-7.51 (m, 1H), 7.33-7.27 (m, 1H), 6.98-6.91 (m, 2H), 6.54-6.47 (m, 1H), 6.32-6.22 (m, 1H), 4.13-4.02 (m, 1H), 4.02-3.92 (m, 1H), 3.58-3.47 (m, 2H), 3.26-3.15 (m, 1H), 2.97-2.87 (m, 2H), 2.74-2.65 (m, 2H), 2.62 (s, 3H), 1.97-1.88 (m, 1H), 1.45 (dtd, J=13.1, 9.4, 6.0 Hz, 1H), 1.27-1.21 (m, 3H). LC/MS (m/z)=473.2 (M+H)$^+$. Human αVβ6 IC$_{50}$ (nM)=5,000.

Example 178

A sample of E175B-Diastereomer D (37 mg, 0.070 mmol) was subjected to the deprotection and desalting methods outlined for Example 175 to afford Example 178 (31.9 mg, 95% yield). $^1$H NMR (500 MHz, methanol-$d_4$) δ 8.77-8.66 (m, 2H), 8.02-7.95 (m, 1H), 7.58-7.49 (m, 1H), 7.36-7.28 (m, 1H), 6.99-6.91 (m, 2H), 6.54-6.48 (m, 1H), 6.31-6.23 (m, 1H), 4.11-4.01 (m, 1H), 4.00-3.92 (m, 1H), 3.62-3.50 (m, 2H), 3.25-3.18 (m, 1H), 2.97-2.87 (m, 2H), 2.76-2.66 (m, 2H), 1.97-1.87 (m, 1H), 1.51-1.38 (m, 1H), 1.27-1.20 (m, 3H). LC/MS (m/z)=473.2 (M+H)$^+$. Human α$_V$β6 IC$_{50}$ (nM)=110.

Example 179

3-(6-Methoxypyridin-3-yl)-3-(5-(2-(1-methyl-1,2,3,4-tetrahydropyrido[2,3-b]pyrazin-6-yl)ethoxy)-1H-indazol-1-yl)propanoic acid

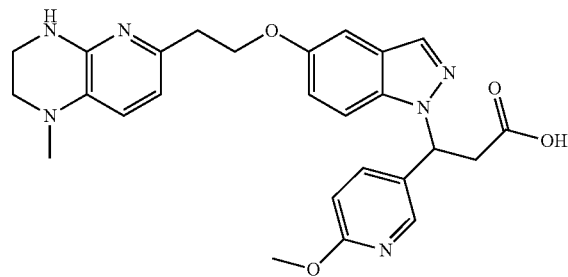

Example 179

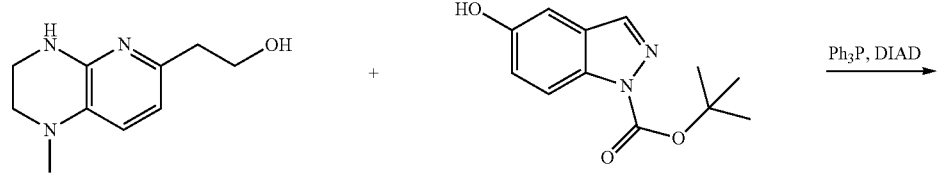

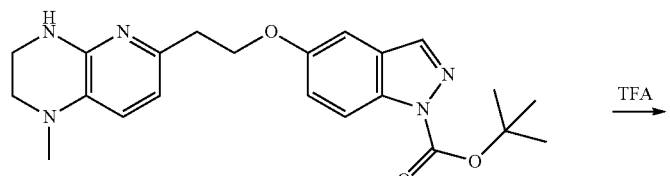

E179A

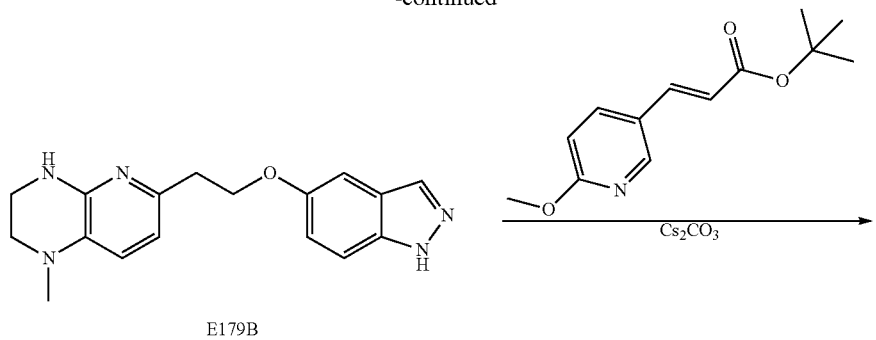

E179B

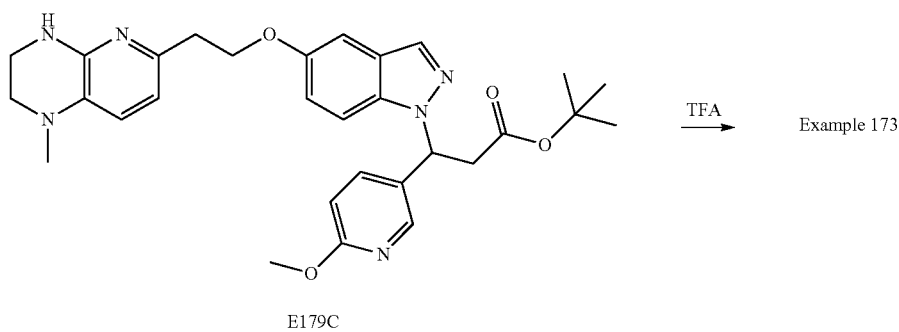

E179C

Intermediate E179A: To a solution of 2-(1-methyl-1,2,3,4-tetrahydropyrido[2,3-b]pyrazin-6-yl)ethan-1-ol [(US 2004/0092538) 50 mg, 0.259 mmol), tert-butyl 5-hydroxy-1H-indazole-1-carboxylate [(WO 2016/21043), 60.6 mg, 0.259 mmol] and Ph$_3$P (71.3 mg, 0.272 mmol) in THF (2270 µl) was added DIAD (52.8 µl, 0.272 mmol); the reaction was stirred at rt overnight. The reaction was diluted with aqueous saturated NaHCO$_3$ solution. The resulting mixture extracted 3 times with EtOAc. The combine organic layers were washed with water, then with brine, and dried over sodium sulfate. The mixture was filtered and concentrated under reduced pressure. The crude product was purified by silica gel column chromatography using a gradient of 20-100% EtOAc/hexanes). The fractions containing the desired product were collected and the solvent was removed under vacuo to afford E179A (52 mg, 49% yield) which was contaminated with a small amount of triphenylphospine oxide. The material was carried on without further purification. LCMS (ES): m/z 410.0 [M+H]$^+$.

Intermediate E179B: To a solution of intermediate E179A (52 mg, 0.127 mmol) in DCM (2 mL) was added TFA (0.5 mL, 6.5 mmol) and the mixture was stirred at rt for 4 hrs. The reaction mixture was concentrated in vacuo to afford E179B, TFA salt (30 mg, 52% yield). LCMS (ES): m/z 310.0 [M+H]$^+$.

Intermediate E179C: To a solution of Intermediate E179B, TFA salt (30 mg, 0.071 mmol) in acetonitrile (0.6 mL) was added cesium carbonate (69.3 mg, 0.213 mmol). After stirring at rt for 5 min, tert-butyl (E)-3-(6-methoxypyridin-3-yl)acrylate [(J. Org. Chem. 2004, 69, 1959), 25.1 mg, 0.106 mmol] was added and the resulting mixture was stirred at 80° C. for 16 hrs. The mixture was cooled to rt, filtered, and concentrated. The residue was purified by silica-gel column chromatography (ISCO column, 40 g, 30-100% EtOAc/hexanes). The pure fractions were concentrated in vacuo to afford E179C (30 mg, 0.055 mmol, 78% yield). LCMS (ES): m/z 545.2 [M+H]$^+$.

Example 179

Triflouroacetic acid (1 mL) was added to a solution containing E179C (40 mg, 0.073 mmol) in dichloromethane (2 mL). The resulting mixture was stirred at rt for 4 h. The mixture was concentrated in vacuo. The residue was dissolved in methanol and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile: water with 10-mM ammonium acetate; Gradient: 10-100% B over 17 minutes, then a 5-minute hold at 100% B; Flow: 20 mL/min. Fractions containing the desired product were combined and dried via centrifugal evaporation to afford example 179 (29.4 mg, 0.062 mmol, 91% yield). $^1$H NMR (500 MHz, DMSO-d$_6$) δ 8.28-8.22 (m, 1H), 8.00-7.92 (m, 1H), 7.74-7.68 (m, 1H), 7.68-7.63 (m, 1H), 7.20-7.13 (m, 1H), 7.01-6.96 (m, 1H), 6.75-6.70 (m, 1H), 6.58-6.52 (m, 1H), 6.40-6.31 (m, 2H), 6.22-6.12 (m, 1H), 4.23-4.14 (m, 2H), 3.79-3.74 (m, 3H), 3.66-3.53 (m, 1H), 3.46-3.37 (m, 3H), 3.23-3.13 (m, 1H), 3.09-3.02 (m, 2H), 2.87-2.80 (m, 2H), 2.75-2.68 (m, 3H). LC/MS (m/z)=489.1 (M+H)$^+$. Human αVβ6 IC$_{50}$ (nM)=47.

Examples 180
(S)-3-(5-(2-(3,4-dihydro-2H-pyrido[3,2-b][1,4]ox-azin-6-yl)ethoxy)-1H-indazol-1-yl)-3-(6-methoxy-pyridin-3-yl)propanoic acid
and
Example 181
(R)-3-(5-(2-(3,4-dihydro-2H-pyrido[3,2-b][1,4]ox-azin-6-yl)ethoxy)-1H-indazol-1-yl)-3-(6-methoxy-pyridin-3-yl)propanoic acid
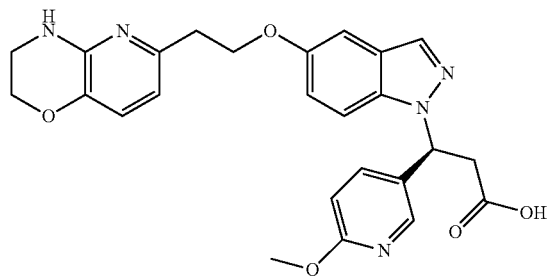
Example 180
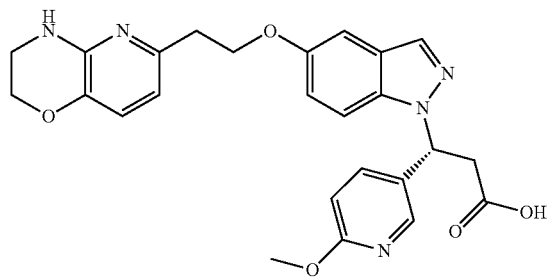
Example 181
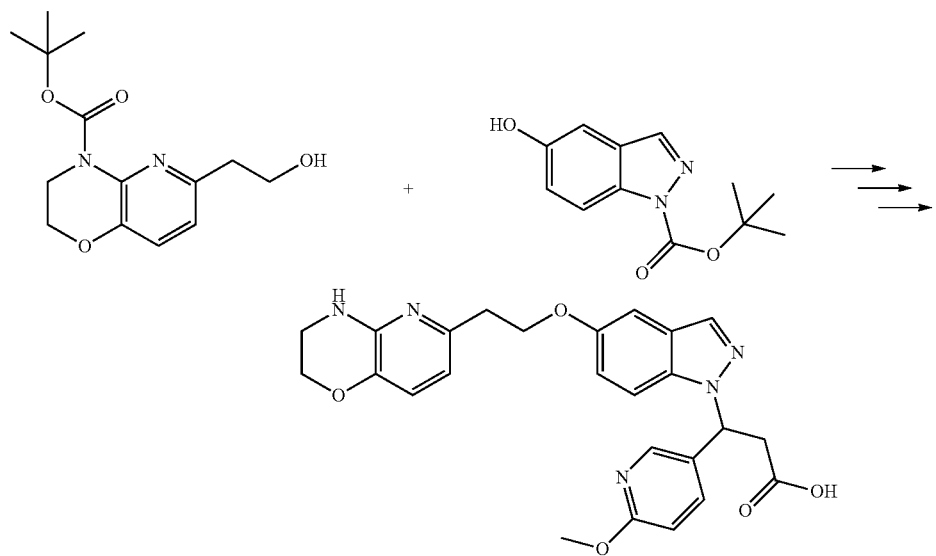

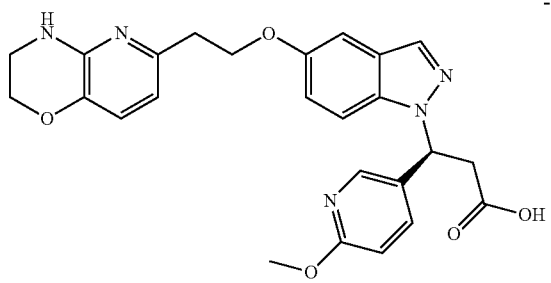

Example 180

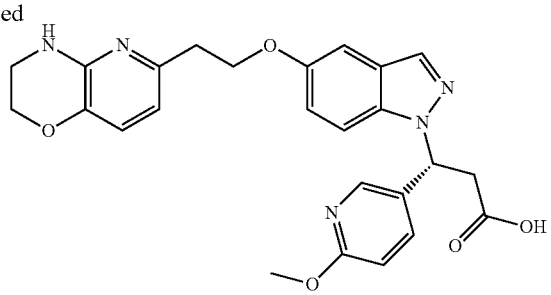

Example 181

Intermediate E180A: A sample of tert-butyl 6-(2-hydroxyethyl)-2,3-dihydro-4H-pyrido[3,2-b][1,4]oxazine-4-carboxylate (*Bioorg. Med. Chem. Lett.* 2005, 15, 2679) was converted in 4 steps using the methods outlined in Example 3 into E173A. LCMS (ES): m/z 476.0 [M+H]$^+$.

Examples 180 and Example 181

A sample of E180A (143 mg) was subjected to chiral SFC purification (Column: Chiralpak OJ-H, 30×250 mm, 5 micron, BPR pressure: 150 bar, temperature 35° C., flow rate: 70.0 mL/min, mobile phase: 20% MeOH w/0.1% NH$_4$OH in CO$_2$, detector wavelength: 254 nm, stacked injections: 0.5 mL of 24 mg/mL solution) to afford Example 180 (29 mg) and E181 (32 mg).

Data for Example 180: $^1$H NMR (400 MHz, DMSO-d$_6$) δ 8.23 (d, J=2.3 Hz, 1H), 7.96 (s, 1H), 7.72-7.67 (m, 1H), 7.67-7.62 (m, 1H), 7.17-7.15 (m, 1H), 7.00-6.95 (m, 1H), 6.84 (d, J=7.8 Hz, 1H), 6.71 (d, J=8.5 Hz, 1H), 6.67-6.60 (m, 1H), 6.41 (d, J=7.8 Hz, 1H), 6.16 (dd, J=9.7, 5.4 Hz, 1H), 4.21 (br t, J=6.7 Hz, 2H), 4.13-3.95 (m, 2H), 3.77 (s, 3H), 3.56 (br dd, J=16.2, 9.7 Hz, 1H), 3.35 (br s, 1H), 3.16 (br dd, J=16.6, 5.3 Hz, 1H), 2.90 (t, J=6.8 Hz, 2H). LC/MS (m/z)=476.1 (M+H)$^+$. Human αVβ6 IC$_{50}$ (nM)=15.

Data for Example 181: $^1$H NMR (400 MHz, DMSO-d$_6$) δ 8.24 (d, J=2.3 Hz, 1H), 7.96 (s, 1H), 7.69 (d, J=9.0 Hz, 1H), 7.65 (dd, J=8.5, 2.5 Hz, 1H), 7.16 (d, J=2.3 Hz, 1H), 6.98 (dd, J=9.0, 2.3 Hz, 1H), 6.84 (d, J=7.8 Hz, 1H), 6.71 (d, J=8.5 Hz, 1H), 6.67-6.61 (m, 1H), 6.41 (d, J=7.8 Hz, 1H), 6.16 (dd, J=9.5, 5.3 Hz, 1H), 4.21 (br t, J=6.8 Hz, 2H), 4.09-4.02 (m, 2H), 3.77 (s, 3H), 3.57 (br dd, J=16.6, 9.8 Hz, 1H), 3.35 (br d, J=2.8 Hz, 2H), 3.18 (br dd, J=16.4, 5.1 Hz, 1H), 2.90 (br t, J=6.9 Hz, 2H). LC/MS (m/z)=476.1 (M+H)$^+$. Human αVβ6 IC$_{50}$ (nM)=5,000.

Biological Evaluation

All binding assays used the HTRF (homogeneous time resolved fluorescence) technology from Cisbio International, therefore all assays are described as HTRF binding assays. The assay results for the Examples are listed above together with the characterization data. The HTRF binding assays are established for the following integrins: human αVβ6, human αVβ1, human αVβ3, human αVβ5, and human αVβ8. All assays used the following assay buffer: 20 mM Tris, pH 7.4, 1 mM MgCl$_2$, 1 mM MnCl$_2$, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at room temperature for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" *Anal Biochem.* 1995 Sep. 1; 230(1):101-7.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula (Ia) or (Ib):

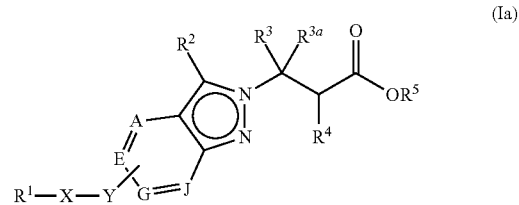

(Ia)

219

-continued (Ib)

[Chemical structure showing: R¹—X—Y connected to a bicyclic pyrazole system with substituents R², R³, R³ᵃ, R⁴, and ending in C(O)OR⁵, with atoms labeled A, E, G, J]

wherein:
A, E, G, and J are independently C or CH with the proviso that only one of A, E, G, and J is C attached to Y;
$L^1$ and $L^2$ are each independently $C_{1-4}$ alkylene;
X is a $C_{1-4}$ alkylene substituted with 0, 1, or 2 $R^{8a}$;
Y is a covalent bond;
m is an integer of 1 or 2;
r is an integer of 0, 1, 2, or 3;
$R^1$ is an Arginine mimetic moiety selected from the group consisting of

[Chemical structures showing various arginine mimetic moieties including tetrahydronaphthyridines with $(R^e)_f$ and OR^f, OCOR^g substituents; tetrahydronaphthyridines with $(R^e)_r$ and NH; oxazine and pyrazine variants; and imidazole-containing bicyclic systems]

and wherein one of the asterisks in each of the arginine mimetics moiety is an attachment point to X and the other two asterisks are hydrogen;
$R^2$ is hydrogen, halo, or $C_{1-6}$ alkyl;
$R^3$ is hydrogen, $C_{1-6}$ alkyl, 3- to 10-membered carbocyclyl, carbocyclylalkyl, 6- to 10-membered aryl, arylalkyl, 3- to 14-membered heterocyclyl, heterocyclylalkyl, 5- to 14-membered heteroaryl, or heteroarylalkyl, wherein the alkyl, carbocyclyl, heterocyclyl, aryl, and heteroaryl, by themselves or as part of another group, are each independently substituted with 0, 1, 2, or 3 $R^6$;

220

$R^{3a}$ is hydrogen;
$R^4$ is hydrogen, $C_{1-6}$ alkyl, 3- to 10-membered carbocyclyl, carbocyclylalkyl, 3- to 10-membered heterocyclyl, heterocyclylalkyl, 6- to 10-membered aryl, arylalkyl, 5- to 14-membered heteroaryl, heteroarylalkyl, $-S(O)_mR^7$, $-C(O)NR^aR^b$, $-NHC(O)OR^a$, $-NHC(O)NR^aR^b$, $-OC(O)NR^aR^b$, $-OC(O)R^7$, $-NHS(O)_mNR^aR^b$, or
$NHS(O)_mR^7$; wherein the alkyl, carbocyclyl, heterocyclyl, aryl, and heteroaryl, by themselves or as part of another group, are each independently substituted with 0, 1, 2, or 3 $R^9$;
$R^5$ is hydrogen, $R^{5a}$, or a structural moiety selected from

[Two structural moieties shown: one with $L^2$ connected to $R^{5b}$, and one with $L^2$—O—C(O)—$R^{5c}$]

$R^{5a}$ and $R^{5b}$ are each independently $C_{1-6}$ alkyl, phenyl, benzyl, or 5- to 7-membered heterocyclyl; wherein the alkyl, phenyl, and heterocyclyl are each independently substituted with 0 to 3 $R^{5d}$;
$R^{5c}$ is $C_{1-6}$ alkyl or 5- to 7-membered carbocyclyl; wherein the $C_{1-6}$ alkyl, and heterocyclyl are each independently substituted with 0 to 3 $R^{5d}$; and
$R^{5d}$, at each occurrence, is independently halo, OH, alkoxy, oxo, or alkyl; or alternatively, two adjacent $R^{5d}$, together with the atoms to which they are attached, form a carbocyclyl moiety;
$R^6$ is halo, cyano, hydroxyl, amino, oxo, nitro, $-S(O)_m R^{12}$, $C_{1-6}$ alkyl, alkoxy, haloalkyl, haloalkoxy, haloaminoalkyl, hydroxyalkyl, aminoalkyl, alkoxycarbonyl, 6- to 10-membered aryl, aryloxy, arylalkoxy, 5- to 10-membered heteroaryl, 3- to 6-membered carbocyclyl, or 3- to 7-membered heterocyclyl; wherein the alkyl, aryl, heteroaryl, carbocyclyl, or heterocyclyl, by themselves or as part of another group, are each independently substituted with 0, 1, or 2 $R^{10}$;
$R^7$ is each independently $C_{1-6}$ alkyl, $C_{1-6}$ alkoxy, $C_{1-6}$ aminoalkyl, $C_{1-6}$ haloalkyl, 6- to 10-membered aryl, arylalkyl, 5- to 10-membered heteroaryl, cycloalkyl, or heterocycloalkyl; wherein the alkyl, aryl, heteroaryl, cycloalkyl, and heterocycloalkyl, by themselves or as part of another group, are each independently substituted with 0, 1, 2, or 3 $R^{11}$;
$R^{8a}$ and $R^{8b}$, at each occurrence, are independently halo, cyano, hydroxyl, amino, oxo, $C_{1-6}$ alkyl, haloalkyl, hydroxyalkyl, aminoalkyl, alkoxy, or haloalkoxy;
$R^9$ is each independently halo, cyano, hydroxyl, amino, oxo, nitro, $C_{1-6}$ alkyl, alkoxy, haloalkyl, haloalkoxy, haloaminoalkyl, hydroxyalkyl, aminoalkyl, alkoxycarbonyl, 6- to 10-membered aryl, aryloxy, arylalkoxy, 5- to 10-membered heteroaryl, 3- to 6-membered carbocyclyl, or 3- to 7-membered heterocyclyl; wherein the alkyl, aryl, heteroaryl, carbocyclyl, or heterocyclyl, by themselves or as part of another group, are each independently substituted with 0, 1, or 2 $R^{13}$;
$R^{10}$ is halo, cyano, hydroxyl, amino, oxo, $C_{1-6}$ alkyl, haloalkyl, hydroxyalkyl, aminoalkyl, alkoxy, haloalkoxy, amido, carbamate, or sulfonamide;
$R^{11}$, at each occurrence, is independently halo, cyano, hydroxyl, amino, oxo, $C_{1-6}$ alkyl, haloalkyl, hydroxyalkyl, aminoalkyl, alkoxy, or haloalkoxy; $R^{12}$ is —N(R$^x$R$^y$), C$_{1-6}$ alkyl, C$_{1-6}$ haloalkyl, C$_{1-6}$ alkoxy, C$_{1-6}$ haloalkoxy, C$_{1-6}$ hydroxyalkyl, or C$_{1-6}$ aminoalkyl;

R$^{13}$ is halo, cyano, hydroxyl, amino, oxo, C$_{1-6}$ alkyl, haloalkyl, hydroxyalkyl, aminoalkyl, alkoxy, haloalkoxy, amido, carbamate, or sulfonamide;

R$^a$ and R$^b$, at each occurrence, are independently hydrogen, C$_{1-6}$ alkyl, C$_{1-6}$ haloalkyl, C$_{3-6}$ cycloalkyl, 6- to 10-membered aryl, 5- to 10-membered heteroaryl, cycloalkylalkyl, arylalkyl, heteroarylalkyl, or alkoxyalkyl; or alternatively, R$^a$ and R$^b$, taken together with the atoms to which they are attached, form a 3- to 8-membered carbocyclic or heterocyclic ring; wherein the aryl and heteroaryl, by themselves or as part of another group, are each independently substituted with one or more groups independently selected from halo, cyano, hydroxyl, amino, C$_{1-6}$ alkyl, haloalkyl, hydroxyalkyl, aminoalkyl, alkoxy, haloalkoxy, amido, carbamate, and sulfonamide; and the carbocyclyl and heterocyclyl, by themselves or as part of another group, are each independently substituted with one or more groups independently selected from halo, cyano, hydroxyl, amino, oxo, C$_{1-6}$ alkyl, haloalkyl, hydroxyalkyl, aminoalkyl, alkoxy, haloalkoxy, amido, carbamate, and sulfonamide;

R$^e$ is OH, amino, amido, carbamate, sulfonamide, C$_{1-4}$ alkyl, halo, C$_{1-4}$ haloalkyl, or C$_{3-6}$ cycloalkyl;

R$^f$ is hydrogen, CH$_3$, CH$_2$CH$_3$, or C(O)OCH$_2$CH$_3$;

R$^g$ is selected from CH$_3$, CH$_2$CCl$_3$, phenyl, 4-fluorophenyl, 4-methoxyphenyl, benzyl,

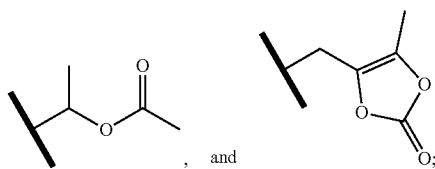

, and and

R$^x$ and R$^y$ are each independently hydrogen or C$_{1-6}$ alkyl; or a pharmaceutically acceptable salt thereof.

2. The compound of claim 1 or a pharmaceutically acceptable salt thereof, wherein the compound of Formula (Ia) or Formula (Ib) is represented by structural Formula (IIa), Formula (IIb), Formula (IIc), or Formula (IId):

(IIa)

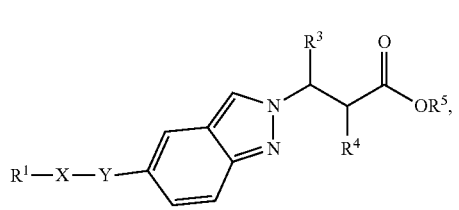

(IIb)

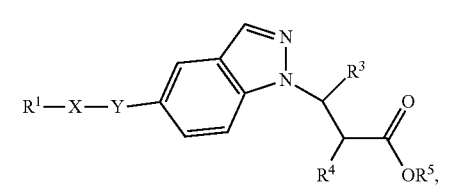

(IIc)

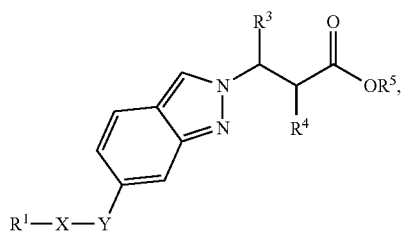

(IId)

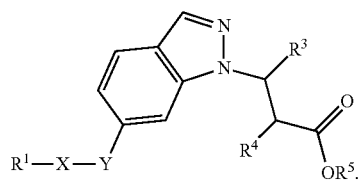

3. The compound of claim 1 or a pharmaceutically acceptable salt thereof, wherein the compound of Formula (Ia) or Formula (Ib) is represented by structural Formula (IIIa), Formula (IIIb), Formula (IIIc), or Formula (IIId):

(IIIa)

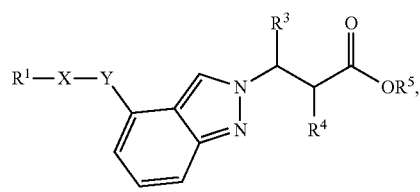

(IIIb)

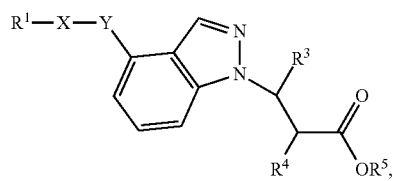

(IIIc)

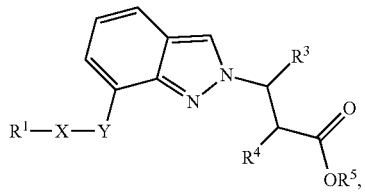

(IIId)

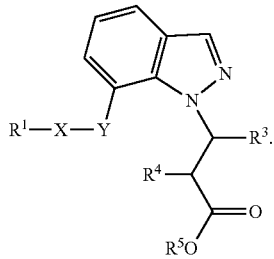

4. The compound of claim 1 or a pharmaceutically acceptable salt thereof, wherein R$^1$ is selected from the group consisting of

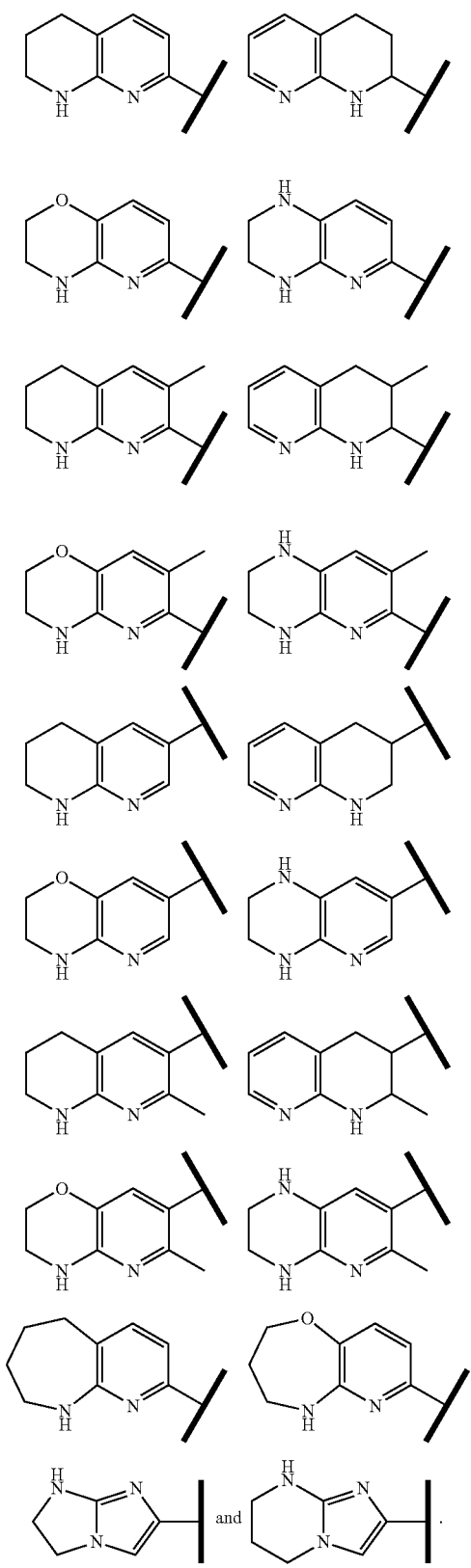
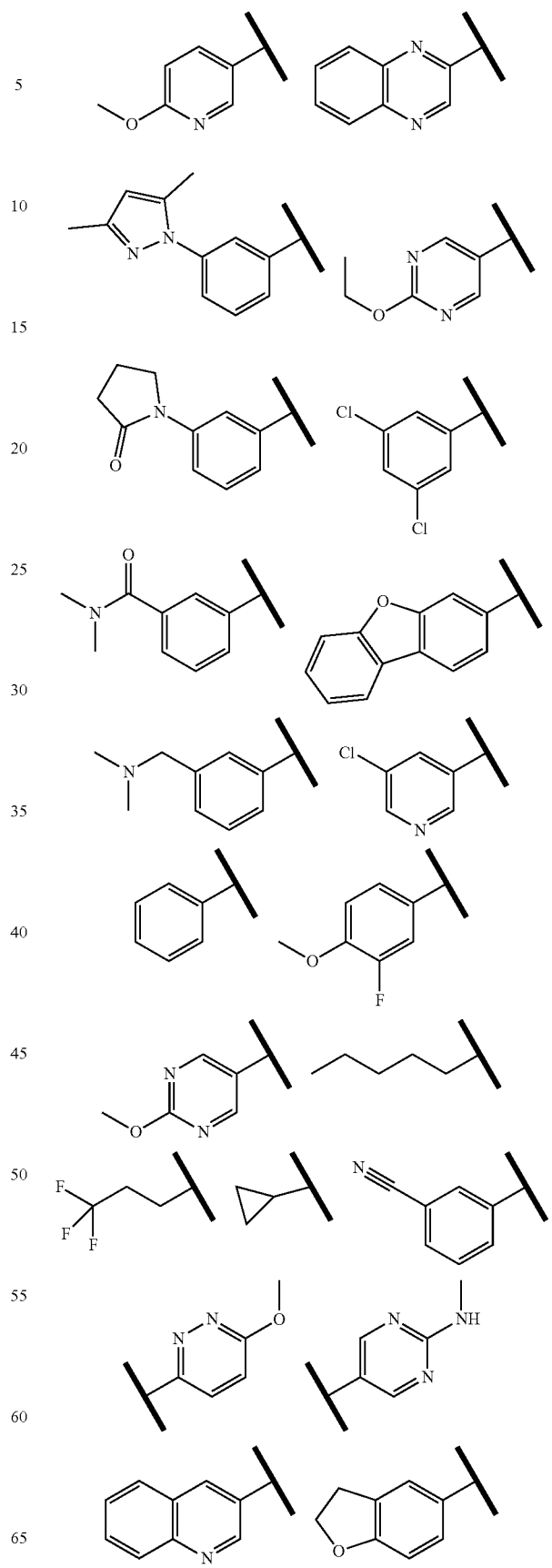
5. The compound of claim 1 or a pharmaceutically acceptable salt thereof, wherein R³ is hydrogen or a structural moiety selected from the group consisting of 225
-continued
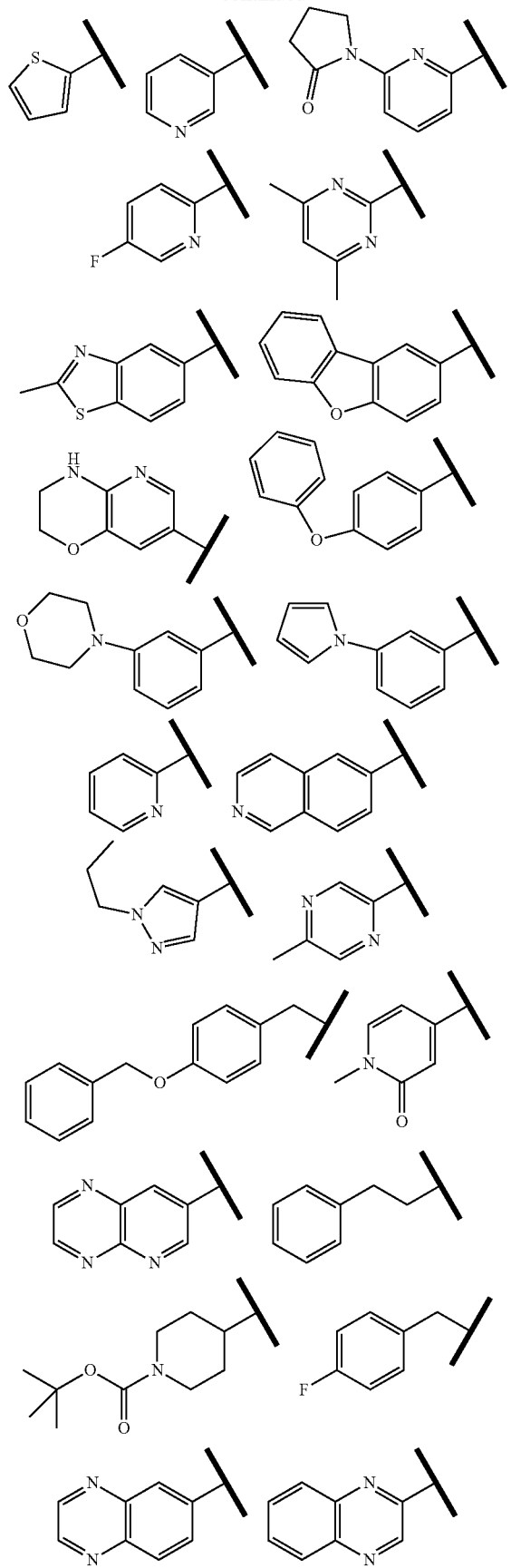
226
-continued
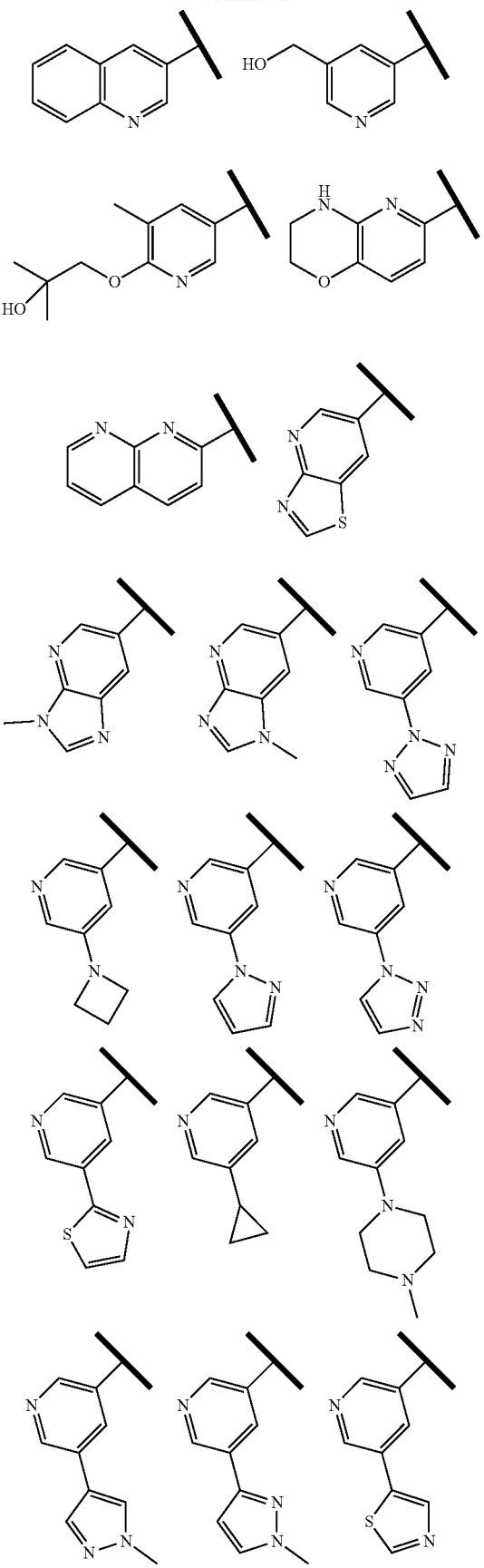

-continued
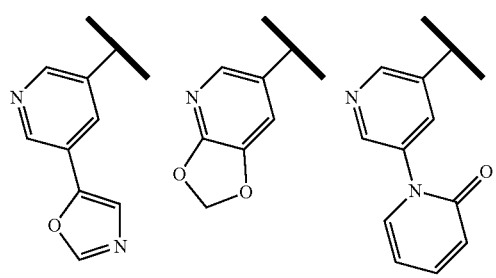
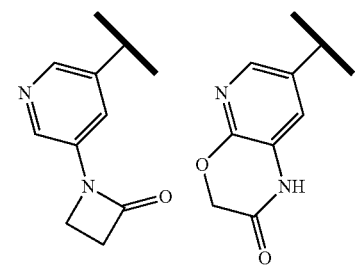
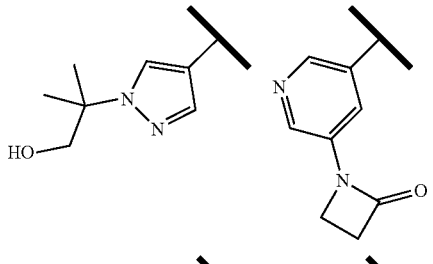
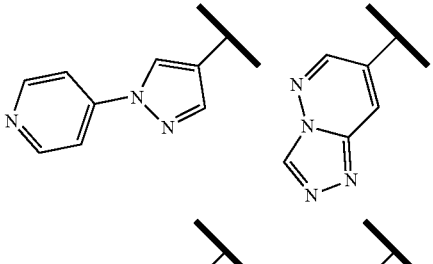
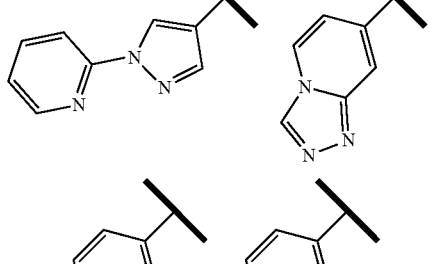
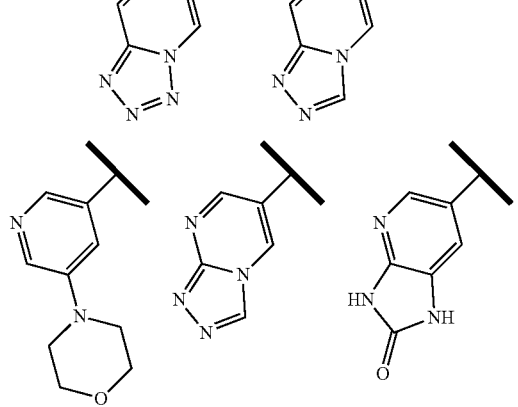
-continued
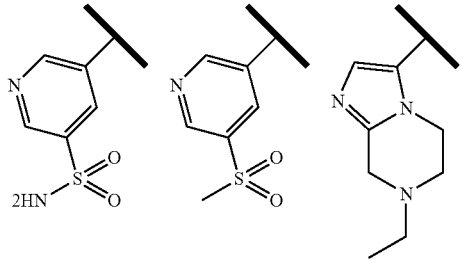
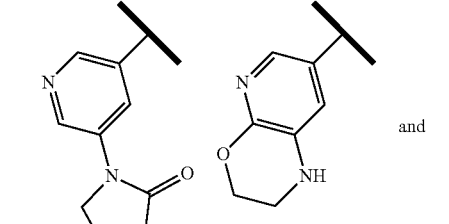
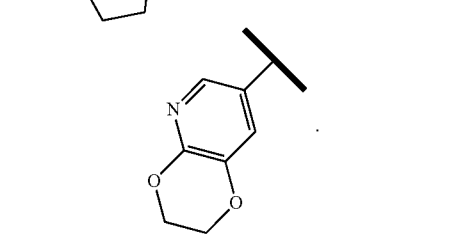
and
6. The compound of claim 1 or a pharmaceutically acceptable salt thereof, wherein $R^5$ is hydrogen or $R^{5a}$; and $R^{5a}$ is methyl, ethyl, isopropyl, n-butyl, isopentyl, or a structural moiety selected from
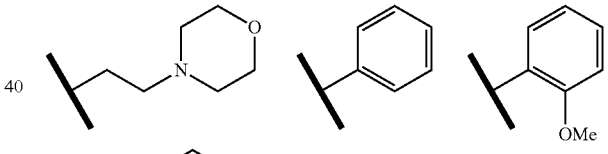
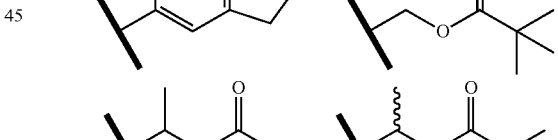
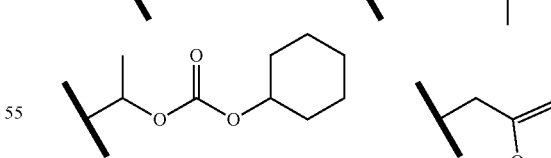
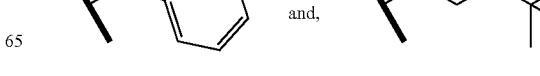
and, 7. The compound of claim 1 or a pharmaceutically acceptable salt thereof, wherein X is $C_{1-3}$ alkylene.

8. The compound of claim 1 or a pharmaceutically acceptable salt thereof, wherein said compound is selected from the group consisting of:
3-(6-Methoxypyridin-3-yl)-3-(4-(3-(5,6,7,8-tetrahydro-1,8-naphthyridin-2-yl)propyl)-1H-indazol-1-yl)propanoic acid;
3-(6-Methoxypyridin-3-yl)-3-(5-(2-(5,6,7,8-tetrahydro-1,8-naphthyridin-2-yl)ethyl)-1H-indazol-1-yl)propanoic acid;
(S)-3-(6-Methoxypyridin-3-yl)-3-(6-(2(5,6,7,8-tetrahydro-1,8 naphthyridin-2-yl)ethyl)-2H-indazol-2-yl) propanoic acid;
(S)-3-(6-Methoxypyridin-3-yl)-3-(6-(2-methyl-5,6,7,8-tetrahydro-1,8-naphthyridin-2-(S)-3-(6-Methoxypyridin-3-yl)-3-(6-((2-methyl-5,6,7,8-tetrahydro-1,8-naphthyridin-3-yl)methyl)-2H-indazol-2-yl)propanoic acid;
(S)-3-(6-Methoxypyridin-3-yl)-3-(6-(3-(5,6,7,8-tetrahydro-1,8-naphthyridin-2-yl)propyl)-2H-indazol-2-yl) propanoic acid;
(S)-3-(6-Methoxypyridin-3-yl)-3-(6-(2-(2-methyl-5,6,7,8-tetrahydro-1,8-naphthyridin-3-yl)ethyl)-2H-indazol-2-yl)propanoic acid;
(3-(3,5-Dichlorophenyl)-3-(4-(3-(5,6,7,8-tetrahydro-1,8-naphthyridin-2-yl)propyl)-1H-indazol-1-yl)propanoic acid;
3-(Quinoxalin-2-yl)-3-(4-(3-(5,6,7,8-tetrahydro-1,8-naphthyridin-2-yl)propyl)-1H-indazol-1-yl)propanoic acid;
3-(6-Methoxypyridin-3-yl)-3-(5-(3-(5,6,7,8-tetrahydro-1,8-naphthyridin-2-yl)propyl)-1H-indazol-1-yl)propanoic acid;
3-(3,5-Dichlorophenyl)-3-(5-(3-(5,6,7,8-tetrahydro-1,8-naphthyridin-2-yl)propyl)-1H-indazol-1-yl)propanoic acid;
3-(Quinoxalin-2-yl)-3-(5-(3-(5,6,7,8-tetrahydro-1,8-naphthyridin-2-yl)propyl)-1H-indazol-1-yl)propanoic acid;
3-(3-(Dimethylcarbamoyl)phenyl)-3-(5-(3-(5,6,7,8-tetrahydro-1,8-naphthyridin-2-yl)propyl)-1H-indazol-1-yl)propanoic acid;
3-(3-(Dimethylcarbamoyl)phenyl)-3-(5-(2-(5,6,7,8-tetrahydro-1,8-naphthyridin-2-yl)ethyl)-1H-indazol-1-yl) propanoic acid;
3-(Dibenzo[b,d]furan-3-yl)-3-(5-(2-(5,6,7,8-tetrahydro-1,8-naphthyridin-2-yl)ethyl)-1H-indazol-1-yl)propanoic acid;
3-(3-((Dimethylamino)methyl)phenyl)-3-(5-(2-(5,6,7,8-tetrahydro-1,8-naphthyridin-2-yl)ethyl)-1H-indazol-1-yl)propanoic acid;
3-(Quinoxalin-2-yl)-3-(5-(2-(5,6,7,8-tetrahydro-1,8-naphthyridin-2-yl)ethyl)-1H-indazol-1-yl)propanoic acid;
3-(3,5-Dichlorophenyl)-3-(5-(2-(5,6,7,8-tetrahydro-1,8-naphthyridin-2-yl)ethyl)-1H-indazol-1-yl)propanoic acid;
6,6,6-Trifluoro-3-(4-(3-(5,6,7,8-tetrahydro-1,8-naphthyridin-2-yl)propyl)-1H-indazol-1-yl)hexanoic acid;
3-(Quinoxalin-2-yl)-3-(4-(2-(5,6,7,8-tetrahydro-1,8-naphthyridin-2-yl)ethoxy)-1H-indazol-1-yl)propanoic acid;
(S)-2-(((Benzyloxy)carbonyl)amino)-3-(5-(3-(5,6,7,8-tetrahydro-1,8-naphthyridin-2-yl)propyl)-1H-indazol-1-yl)propanoic acid;
(S)-3-(6-Methoxypyridin-3-yl)-3-(5-(2-(5,6,7,8-tetrahydro-1,8-naphthyridin-2-yl)ethyl)-2H-indazol-2-yl) propanoic acid;
(S)-3-(6-Methoxypyridin-3-yl)-3-(5-(3-(5,6,7,8-tetrahydro-1,8-naphthyridin-2-yl)propyl)-2H-indazol-2-yl) propanoic acid;
(3S)-3-(6-Methoxypyridin-3-yl)-3-(6-(2-(1,2,3,4-tetrahydro-1,8-naphthyridin-2-yl)ethyl)-2H-indazol-2-yl) propanoic acid;
(S)-3-(Quinolin-3-yl)-3-(6-(2-(5,6,7,8-tetrahydro-1,8-naphthyridin-2-yl)ethyl)-2H-indazol-2-yl)propanoic acid;
(S)-3-(6-((2-Methyl-5,6,7,8-tetrahydro-1,8-naphthyridin-3-yl)methyl)-2H-indazol-2-yl)-3-(quinolin-3-yl)propanoic acid;
(3S)-3-(Quinolin-3-yl)-3-(6-(2-(1,2,3,4-tetrahydro-1,8-naphthyridin-2-yl)ethyl)-2H-indazol-2-yl)propanoic acid;
(S)-3-(Quinolin-3-yl)-3-(6-(3-(5,6,7,8-tetrahydro-1,8-naphthyridin-2-yl)propyl)-2H-indazol-2-yl)propanoic acid;
(3S)-3-(Quinolin-3-yl)-3-(6-(3-(1,2,3,4-tetrahydro-1,8-naphthyridin-2-yl)propyl)-2H-indazol-2-yl)propanoic acid;
3-(6-Methoxypyridin-3-yl)-3-(5-(3-(5,6,7,8-tetrahydro-1,8-naphthyridin-2-yl)propyl)-1H-pyrazolo[4,3-b]pyridin-1-yl)propanoic acid;
(S)-3-(2-Methoxypyrimidin-5-yl)-3-(6-(2-(5,6,7,8-tetrahydro-1,8-naphthyridin-2-yl)ethyl)-2H-indazol-2-yl) propanoic acid; and
3-(6-Methoxypyridin-3-yl)-3-(4-(2-(5,6,7,8-tetrahydro-1,8-naphthyridin-2-yl)ethyl)-1H-indazol-1-yl)propanoic acid;
or a pharmaceutically acceptable salt thereof.

9. The compound of claim 1 or a pharmaceutically acceptable salt thereof, wherein:
Y is a covalent bond or O;
X is a $C_{1-3}$ alkylene;
$R^1$ is:

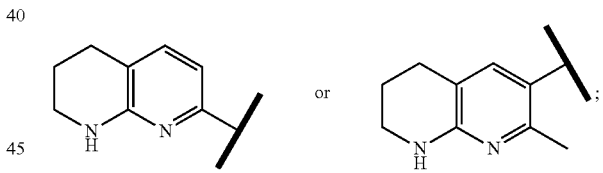

$R^2$ is hydrogen or methyl;
$R^3$ is:

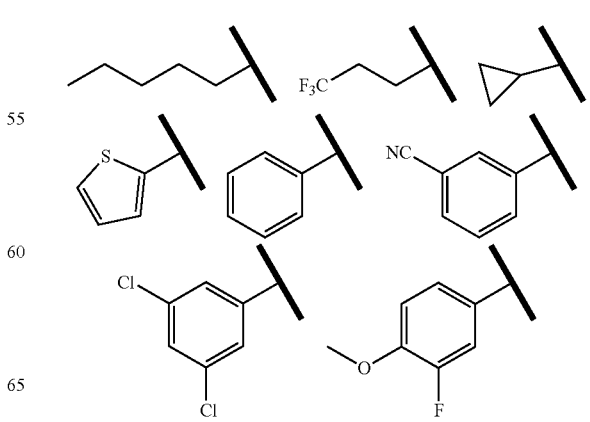

-continued

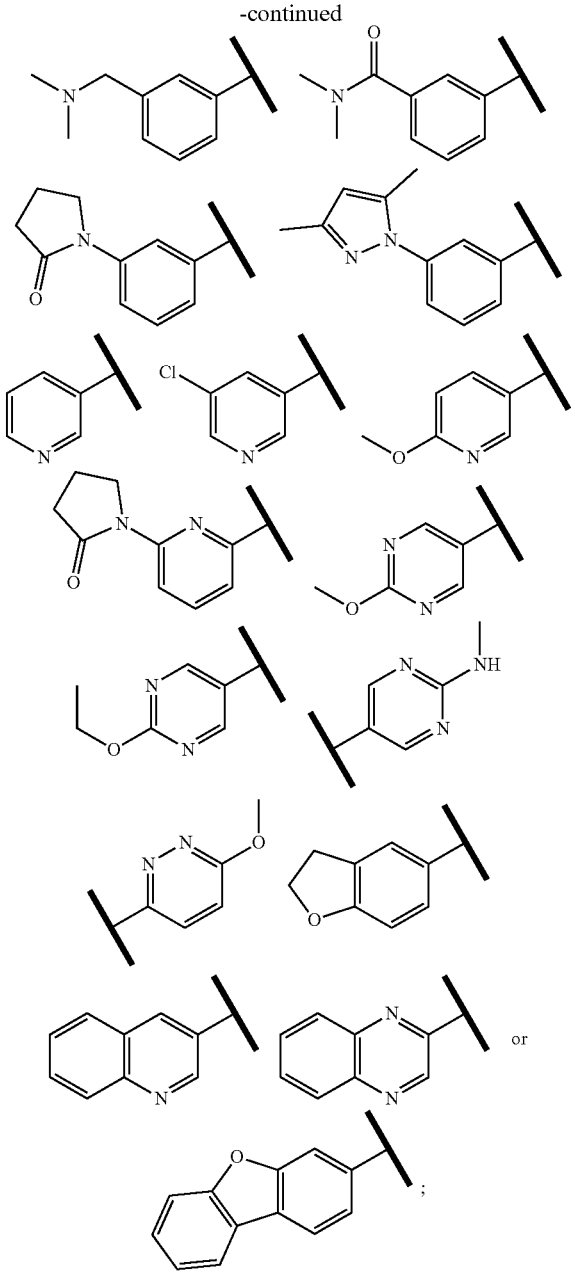

R⁴ is hydrogen; and
R⁵ is hydrogen.

10. The compound of claim 1 or a pharmaceutically acceptable salt thereof, wherein:
Y is a covalent bond;
X is a $C_{1-3}$ alkylene;
R¹ is:

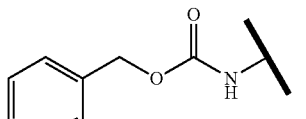

$R^2$ is hydrogen or methyl;
$R^3$ is hydrogen;
$R^4$ is

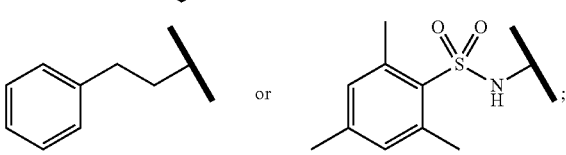

and
$R^5$ is hydrogen.

11. The compound of claim 1 having the structure of Formula (IIb):

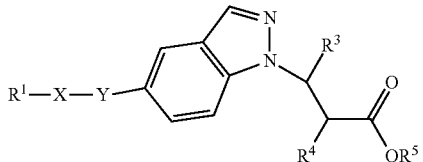

(IIb)

or a pharmaceutically acceptable salt thereof.

12. The compound of claim 1 having the structure of Formula (IIb):

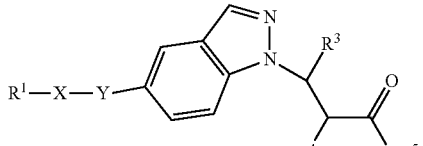

(IIb)

or a pharmaceutically acceptable salt thereof, wherein $R^3$ is a structural moiety selected from the group consisting of

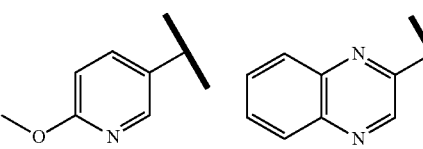

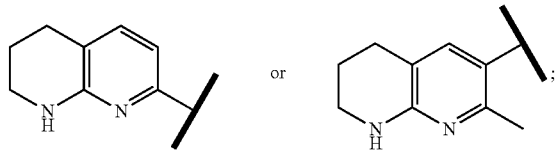

-continued
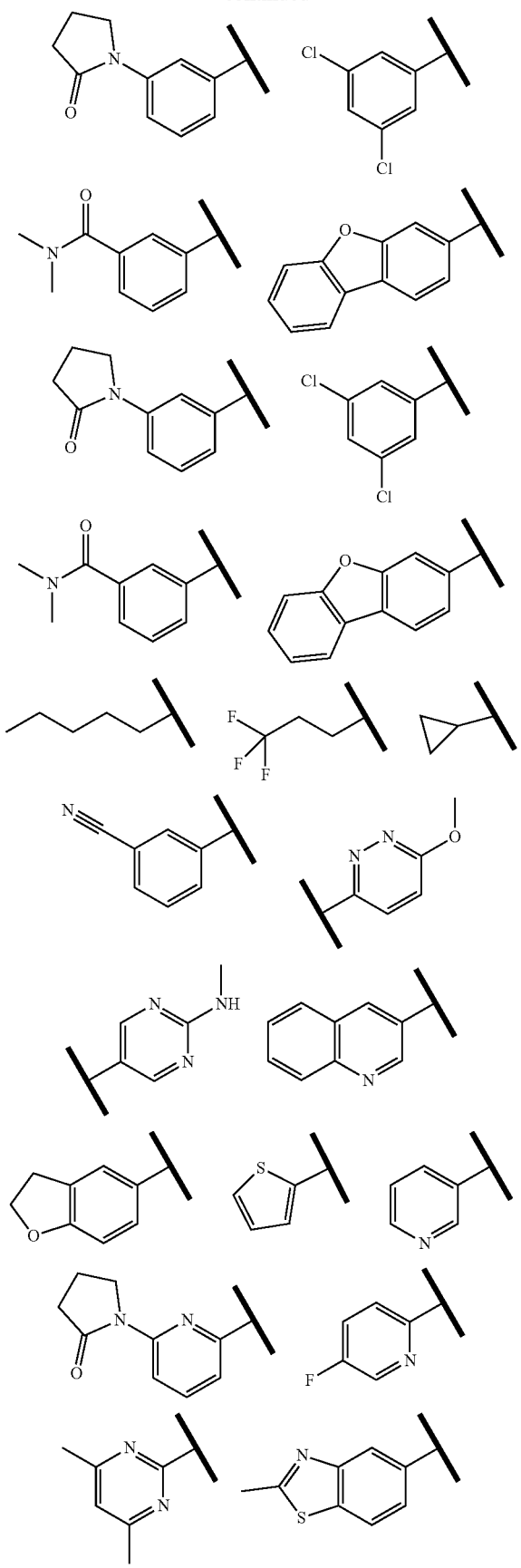
-continued
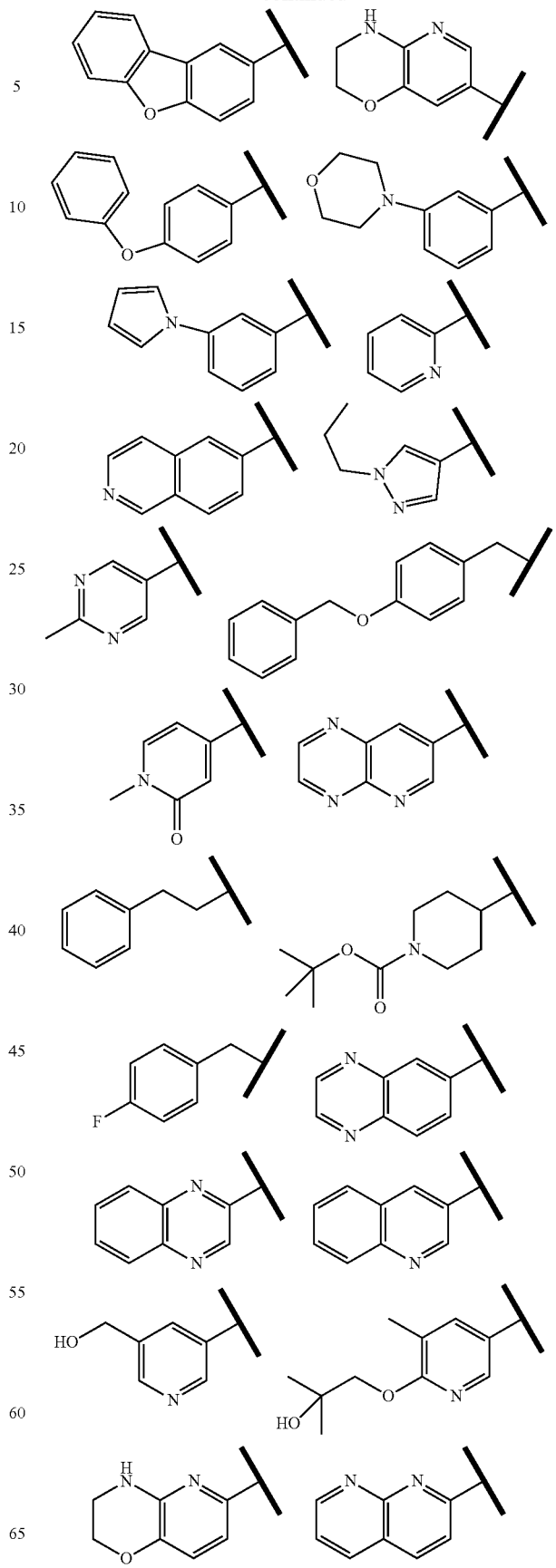

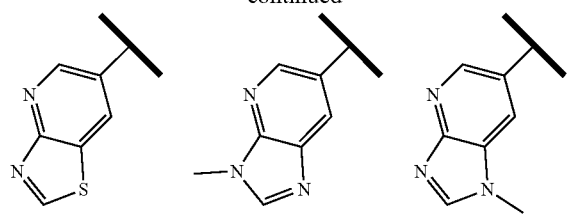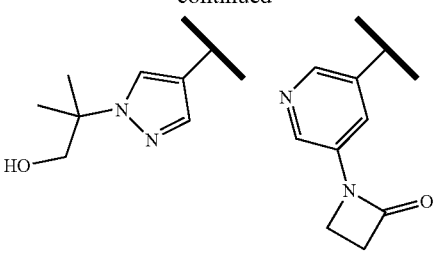

13. The compound of claim 9 the structure of Formula (IIb):

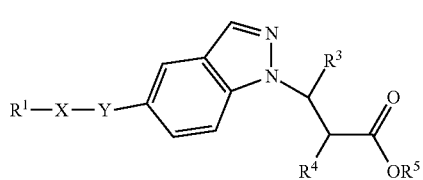

or a pharmaceutically acceptable salt thereof.

14. The compound of claim 1 or a pharmaceutically acceptable salt thereof, having the structure of Formula (Ia):

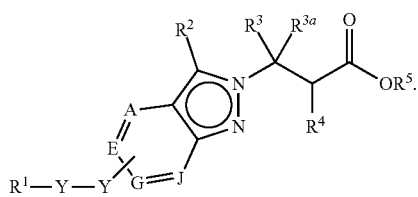

15. The compound of claim 1 or a pharmaceutically acceptable salt thereof, wherein the compound of Formula (Ia) or Formula (Ib) is represented by structural Formula (IIa), Formula (IIc), or Formula (IIIc):

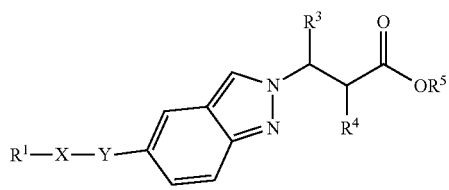

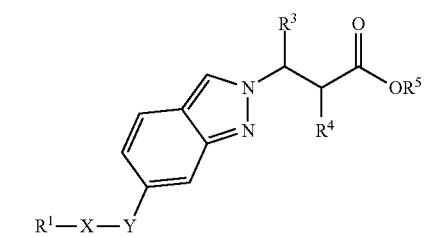

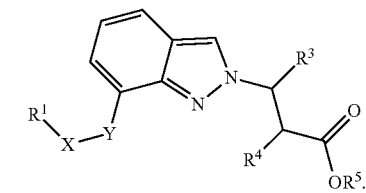
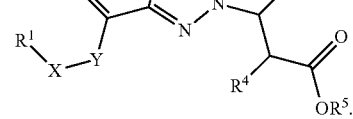

16. The compound of claim 1 or a pharmaceutically acceptable salt thereof, having the structure of Formula (Ib):

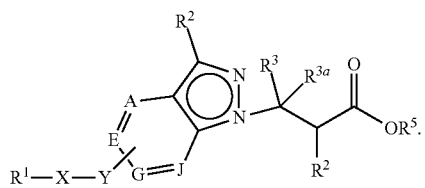

17. The compound of claim 1 or a pharmaceutically acceptable salt thereof, wherein the compound of Formula (Ia) or Formula (Ib) is represented by structural Formula (IIb), Formula (IId), or Formula (IIId):

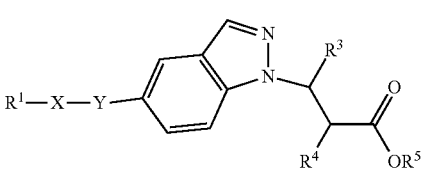

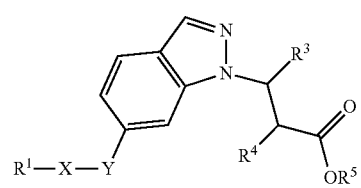

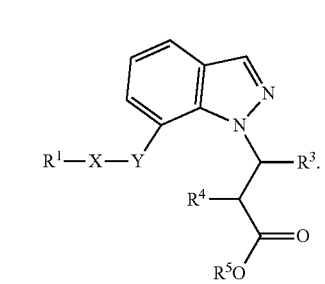

18. A pharmaceutical composition comprising a compound of claim 1, or a pharmaceutically acceptable salt thereof, and a carrier.

\* \* \* \* \*

UNITED STATES PATENT AND TRADEMARK OFFICE
CERTIFICATE OF CORRECTION

PATENT NO. : 10,745,384 B2
APPLICATION NO. : 16/347831
DATED : August 18, 2020
INVENTOR(S) : Xiang-Yang Ye et al.

Page 1 of 4

It is certified that error appears in the above-identified patent and that said Letters Patent is hereby corrected as shown below:

On the Title Page

Column 2, item (57) Abstract, Line 2, After "(Ib):" insert

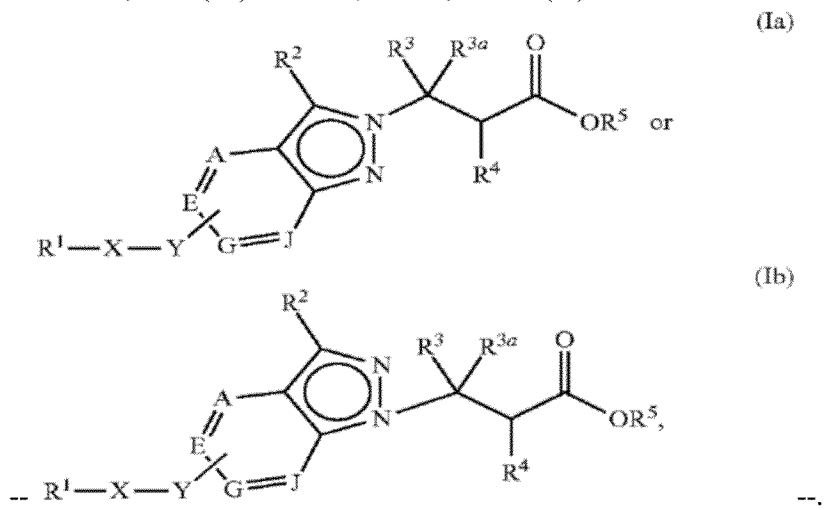

Signed and Sealed this
Fifth Day of October, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,745,384 B2

Column 2, item (57) Abstract, Line 12-13 (Approx.) (Structures), After "compositions." delete

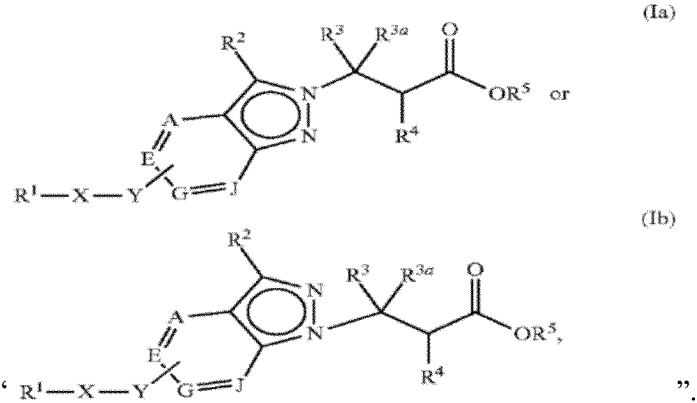

".

In the Claims

In Claim 1, Column 219, Line 22-27 (Approx.), delete " 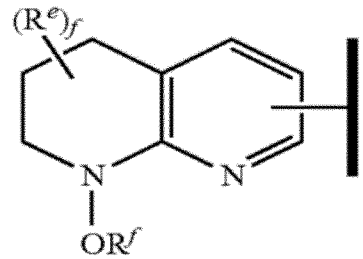 " and insert

-- 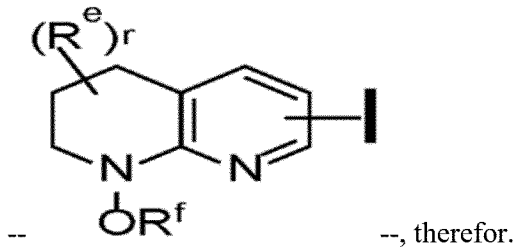 --, therefor.

In Claim 1, Column 219, Line 22-27 (Approx.), delete " 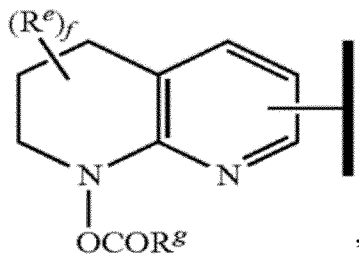 " and insert

-- 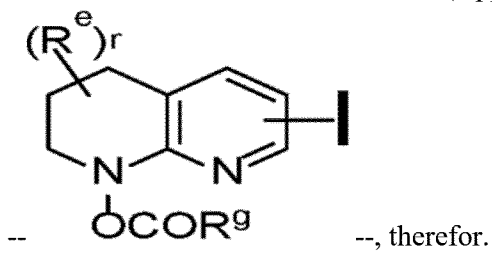 --, therefor.

CERTIFICATE OF CORRECTION (continued)
U.S. Pat. No. 10,745,384 B2

In Claim 1, Column 220, Line 17-20 (Approx.), delete " 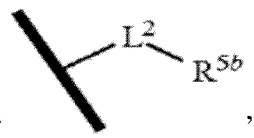 " and insert

-- 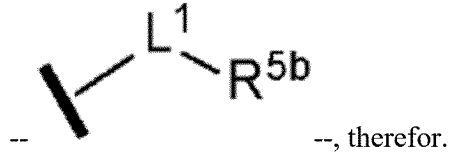 --, therefor.

In Claim 5, Column 227, Line 13-22 (Approx.), delete " 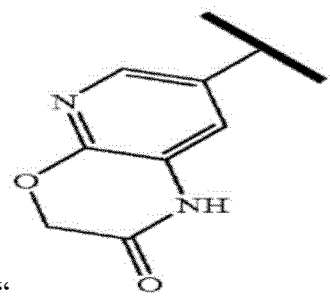 " and insert

-- 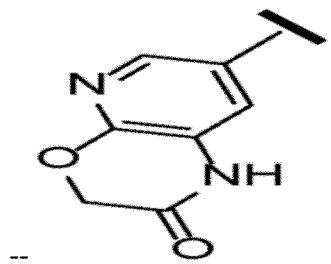 --, therefor.

In Claim 8, Column 229, Line 13 (Approx.), delete "-(2(" and insert -- -(2-( --, therefor.

In Claim 8, Column 229, Line 14 (Approx.), delete "-1,8 naphthyridin-" and insert -- -1,8-naphthyridin- --, therefor.

In Claim 8, Column 229, Line 16-17 (Approx.), below "acid;" delete "(S)-3-(6-Methoxypyridin-3-yl)-3-(6-(2-methyl-5,6,7,8-tetrahydro-1,8-naphthyridin-2-".

In Claim 8, Column 229, Line 26 (Approx.), delete "(3-" and insert -- 3- --, therefor.

In Claim 13, Column 237, Line 1, after "9" insert -- having --.

CERTIFICATE OF CORRECTION (continued)
U.S. Pat. No. 10,745,384 B2

In Claim 14, Column 237, Line 18-25 (Approx.), delete "

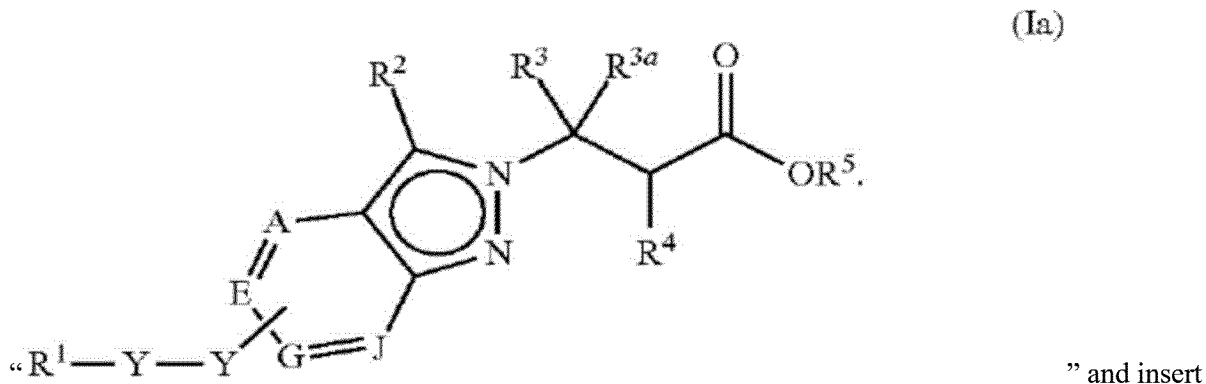

(Ia)

" and insert

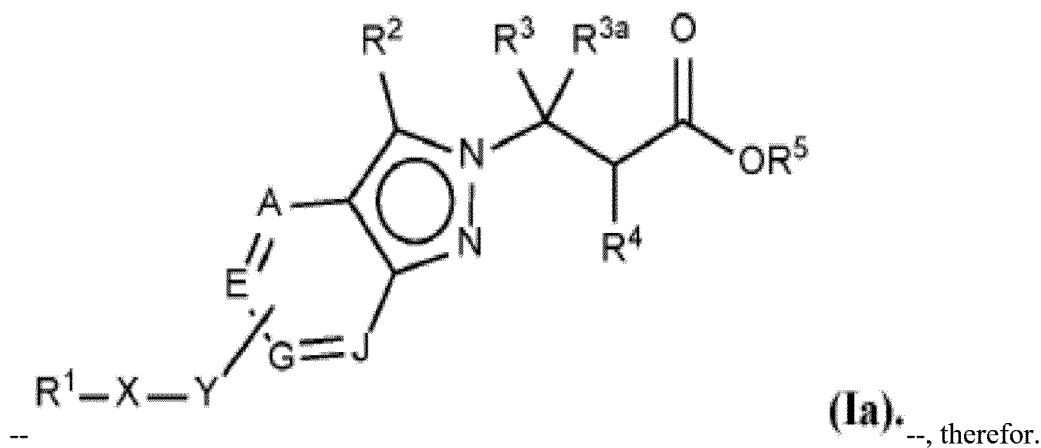

(Ia). --, therefor.

In Claim 16, Column 238, Line 5-12 (Approx.), delete "

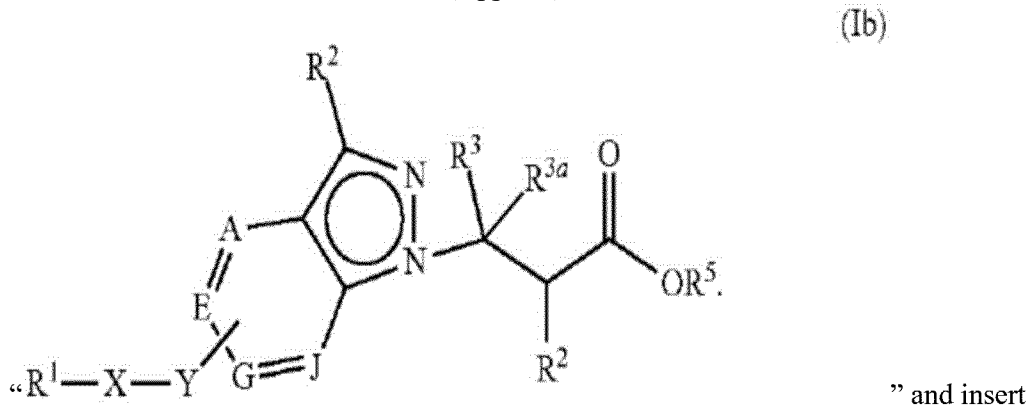

(Ib)

" and insert

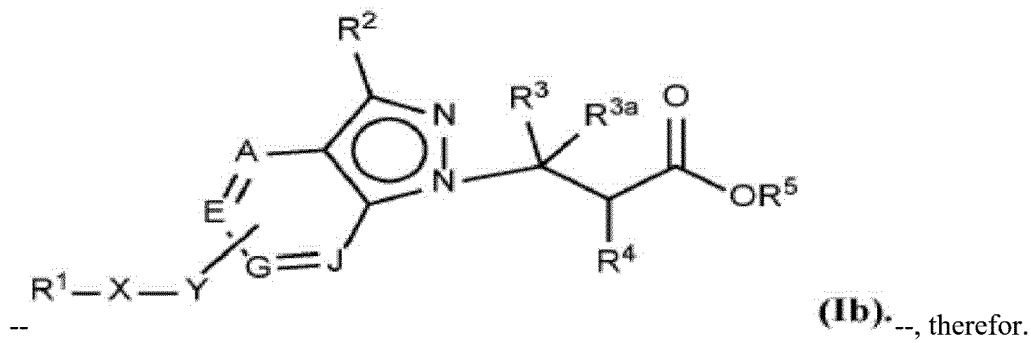

(Ib). --, therefor.